US012315601B2

(12) United States Patent
Aiden et al.

(10) Patent No.: US 12,315,601 B2
(45) Date of Patent: May 27, 2025

(54) LINEAR GENOME ASSEMBLY FROM THREE DIMENSIONAL GENOME STRUCTURE

(71) Applicants: THE BROAD INSTITUTE, INC., Cambridge, MA (US); BAYLOR COLLEGE OF MEDICINE, Houston, TX (US)

(72) Inventors: Erez Aiden, Houston, TX (US); Olga Dudchenko, Houston, GA (US); Aviva Aiden, Houston, TX (US); Elena Stamenova, Cambridge, MA (US); Sanjit Singh Batra, Houston, TX (US); Arina Omer, Houston, TX (US); Per Aspera Adastra, Houston, TX (US); Neva Durand, Houston, TX (US); Maxim Massenkoff, Cambridge, MA (US); Sarah Nyquist, Cambridge, MA (US); Anthony Tzen, Houston, TX (US); Christopher Lui, Houston, TX (US); Melanie Pham, Houston, TX (US); Eric Lander, Cambridge, MA (US)

(73) Assignees: THE BROAD INSTITUTE, INC., Cambridge, MA (US); BAYLOR COLLEGE OF MEDICINE, Houston, TX (US)

(*) Notice: Subject to any disclaimer, the term of this patent is extended or adjusted under 35 U.S.C. 154(b) by 1177 days.

(21) Appl. No.: 16/308,386

(22) PCT Filed: Jun. 8, 2017

(86) PCT No.: PCT/US2017/036649
§ 371 (c)(1),
(2) Date: Dec. 7, 2018

(87) PCT Pub. No.: WO2017/214461
PCT Pub. Date: Dec. 14, 2017

(65) Prior Publication Data
US 2019/0385703 A1 Dec. 19, 2019

Related U.S. Application Data

(60) Provisional application No. 62/347,605, filed on Jun. 8, 2016, provisional application No. 62/475,808, filed on Mar. 23, 2017, provisional application No. 62/471,777, filed on Mar. 15, 2017, provisional application No. 62/374,475, filed on Aug. 12, 2016.

(51) Int. Cl.
| G01N 33/48 | (2006.01) |
| C12Q 1/6869 | (2018.01) |
| G01N 33/50 | (2006.01) |
| G16B 5/10 | (2019.01) |
| G16B 15/10 | (2019.01) |
| G16B 30/20 | (2019.01) |

(52) U.S. Cl.
CPC ............ G16B 5/10 (2019.02); C12Q 1/6869 (2013.01); G16B 15/10 (2019.02); G16B 30/20 (2019.02)

(58) Field of Classification Search
CPC .......... G16B 5/10; G16B 15/10; G16B 30/20; C12Q 1/6869
USPC ........................................................ 702/20
See application file for complete search history.

(56) References Cited

U.S. PATENT DOCUMENTS

| 2016/0246922 A1* | 8/2016 | Putnam | ................. G16B 30/00 |
| 2023/0002823 A1* | 1/2023 | Porreca | ................ C12Q 1/6869 |

FOREIGN PATENT DOCUMENTS

| WO | WO-2010036323 A1 * | 4/2010 | ............... C12Q 1/68 |
| WO | WO-2014127414 A1 * | 8/2014 | ............... A01H 1/00 |
| WO | 2015010051 A1 | 1/2015 | |
| WO | 2015197711 A1 | 12/2015 | |
| WO | WO-2017011710 A2 * | 1/2017 | ............... C12Q 1/68 |
| WO | 2017031370 A1 | 2/2017 | |

OTHER PUBLICATIONS

Barutcu et al. C-ing the Genome: A Compendium of Chromosome Conformation Capture Methods to Study Higher-Order Chromatin Organization Journal of Cellular Physiology vol. 231, pp. 31-35 (Year: 2015).*
Myers et al. A Whole-Genome Assembly of Drosophila Science vol. 287, pp. 2196-2204 (Year: 2000).*
Burton et al. Chromosome-scale scaffolding of de novo genome assemblies based on chromatin interactions Nature Biotechnology vol. 31, pp. 1119-1125 and online methods and supplementary material (Year: 2013).*
Sanborn et al. Chromatin extrusion explains key features of loop and domain formation in wild-type and engineered genomes Proceedings of the National Academy of Sciences USA vol. 112, pp. E6456-E6465 (Year: 2015).*

(Continued)

Primary Examiner — Russell S Negin
(74) Attorney, Agent, or Firm — F. Brent Nix, Esq.; Johnson, Marcou, Isaacs & Nix, LLC

(57) ABSTRACT

Embodiments provide a method for sequencing and assembling long DNA genomes comprising generating a 3D contact map of chromatin loop structures in a target genome, the 3D contact map of chromatin loop structures defining spatial proximity relationships between genomic loci in the genome, and deriving a linear genomic nucleic acid sequence from the 3D map of chromatin loop structures.

25 Claims, 60 Drawing Sheets

(56) References Cited

OTHER PUBLICATIONS

Seitan et al. Cohsesin-based chromatin interactions enable regulated gene expression within preexisting architectural compartments Genome Research vol. 23 pp. 2066-2077 (Year: 2013).*
Lun et al. diffHic: a Bioconductor package to detect differential genomic interactions in Hi—C data BMC Bioinformatics vol. 16 article 258 (Year: 2015).*
Pop et al. Bioinformatics challenges of new sequencing technology Trends in Genetics vol. 24 pp. 142-149 (Year: 2008).*
Gnerre et al. High-quality draft assemblies of mammalian genomes from massively parallel sequence data Proceedings of the National Academy of Sciences USA vol. 108 pp. 1513-1518 (Year: 2011).*
Varoquaux et al. Accurate identification of centromere locations in yeast genomes using Hi—C Nucleic Acids Research vol. 43 pp. 5331-5339 (Year: 2015).*
Naumova et al. Organization of the Mitotic Chromosome Sciennce vol. 342 pp. 948-953 (Year: 2013).*
Fraser, James, et al. "An overview of genome organization and how we got there: from FISH to Hi—C." Microbiology and Molecular Biology Reviews 79.3 (2015): 347-372. (Year: 2015).*
Wang, Jingjing, et al. "Exploring the mechanisms of genome-wide long-range interactions: interpreting chromosome organization." Briefings in functional genomics 15.5 (2016): 385-395. (Year: 2015).*
Schwartzman, Omer, and Amos Tanay. "Single-cell epigenomics: techniques and emerging applications." Nature Reviews Genetics 16.12 (2015): 716-726. (Year: 2015).*
Silva, GZ, et al., "Combining de novo and reference-guided assembly with scaffold_builder", Source Code for Biology and Medicine, vol. 8, No. 1, pp. 1-5, Published: Nov. 22, 2013.
Williamson, Iain, et al., "Spatial genome organization: contrasting views from chromosome conformation capture and fluorescence in situ hybridization", Genes and Development, vol. 28, No. 24, pp. 2778-2791, Revised version accepted: Oct. 30, 2014.
Berkum, NL, et al., "Hi—C: A Method to Study the Three-dimensional Architecture of Genomes.", Journal of Visualized Experiments, vol. 39, e1869, pp. 1-7, May 6, 2010.
Sato, Yukuto, et al., "SUGAR: graphical user interface-based data refiner for high-throughput DNA sequencing", BMC Genomics, vol. No. 15: No. 664, pp. 1-5, Aug. 8, 2014.
Duvick, Jon, et al., "xGDBvm: A Web GUI-Driven Workflow for Annotating Eukaryotic Genomes in the Cloud", Plant Cell, vol. No. 25 : No. 4, pp. 840-854, Published Mar. 28, 2016.
Jiang, Yanliang, et al., "Generation of Physical Map Contig-Specific Sequences Useful for Whole Genome Sequence Scaffolding", PLOS One, vol. 8 : Issue 10, e78872, pp. 1-9, Published: Oct. 24, 2013.
Li, Heng, "FermiKit: assembly-based variant calling for Illumina resequencing data", Bioinformatics, vol. No. 31 : No. 22, pp. 3694-3696, Accepted on Jul. 22, 2015.
Ramani, Vijay, et al., "High-throughput determination of rNA structure by proximity ligation", Nature Biotechnology, vol. 33 : No. 9, pp. 1-18, Sep. 2015.
Nguyen, Richard, et al., "Quantifying Spillover Spreading for Comparing Instrument Performance and Aiding in Multicolor Panel Design", Cytometry Part A, vol. No. 83A : No. 3, pp. 1-17, Feb. 6, 2013.
International Search Report issued by the United States Patent and Trademark Office for PCT/US2017/036649 on Nov. 8, 2017.
Written Opinion of the International Searching Authority issued by the United States Patent and Trademark Office for PCT/US2017/036649 on Nov. 8, 2017.
Invitation to Pay Additional Fees for PCT International Application No. PCT/US2017/036649.
International Preliminary Report on Patentability, issued by the U.S. Patent Office for PCT/US2017/036649 on Nov. 8, 2017.
Barutcu et al., "C-ing the Genome: A Compendium of Chromosome Conformation Capture Methods to Study Higher-Order Chromatin Organization", J Cell Physiol. Jan. 2016 vol. 231(1), pp. 31-35. doi: 10.1002/jcp.25062. PMID: 26059817; PMCID: PMC4586368.
Bickhart et al., "Single-molecule sequencing and conformational capture enable de novo mammalian reference genomes", bioRxiv, 064352, pp. 1-31, Published: Jul. 18, 2016.
Burton et al., "chromosome-scale scaffolding of de novo genome assemblies based on chromatin interactions", Nature Biotechnology, vol. 31, No. 2, pp. 1119-1127, Published online: Nov. 3, 2013.
Love et al., "Evaluation of DISCOVAR de novo using a mosquito sample for cost-effective short-read genome assembly", BMC Genomics, vol. 17, No. 187, 2016.
Marie-Nelly et al., "High-quality genome (re)assembly using chromosomal contact data", Nature Communication, vol. 5, No. 5695, pp. 1-10, Published: Dec. 17, 2014.
Myers et al., "A Whole-Genome Assembly of *Drosophila*", Science, vol. 287, pp. 2196-2204, Mar. 24, 2000.
Pendleton et al., "Assembly and diploid architecture of an individual human genome via single-molecule technologies", Nat Methods, vol. 12, No. 8, pp. 780-786, Aug. 2015.
Putnam et al., "Chromosome-scale shotgun assembly using an in vitro method for long-range linkage", Genome Research, vol. 26, pp. 342-350, 2016.
Sessions et al., "Genome evolution in the allotetraploid frog *Xenopus laevis*", Nature, vol. 538, No. 7625, pp. 336-343, Oct. 20, 2016.

* cited by examiner

210

305
Calculate an exepected model for contact frequency

310
Detect misjoins

315
Localize mijsoins

320
Scaffold during misjoin detection

Return to 215, FIG. 2

FIG. 3

Aedes aegypti assembly AaegL2

Assisted assembly of the Squirrel monkey genome from the common marmoset genome and comparison to a de novo assembly of the same species Meta Hi-C maps can be used to assemble all members of the community at the same time Human chromosome X Using a loop call to identify relative orientation of two genomic sequences.

LINEAR GENOME ASSEMBLY FROM THREE DIMENSIONAL GENOME STRUCTURE

CROSS-REFERENCE TO RELATED APPLICATIONS

This application claims the benefit of U.S. Provisional Application No. 62/347,605 filed Jun. 8, 2016, U.S. Provisional Application No. 62/374,475 filed Aug. 12, 2016, U.S. Provisional Application No. 62/471,777 filed Mar. 15, 2017, and U.S. Provisional Application No. 62/475,808 filed Mar. 23, 2017. The entire contents of the above-identified priority applications are hereby fully incorporated herein by reference.

STATEMENT REGARDING FEDERALLY SPONSORED RESEARCH

This invention was made with government support under Grant Nos. HG003067, OD008540, HG009375, and HL130010 awarded by the National Institutes of Health, and Grant No. PHY1427654 awarded by the National Science Foundation. The government has certain rights in the invention.

BACKGROUND

Generating a high-quality genome sequence is a critical foundation for the analysis of any organism. Yet it remains a challenge, especially for genomes containing substantial repetitive sequence, such as *Aedes aegypti*, the principal vector of the Zika virus. Recently, an international consortium was organized to better understand Zika's principal vector by improving the quality of the *A. aegypti* genome (1).

Currently, most genomes are assembled from a deep collection of short DNA sequence reads. This data is combined with linking information, which makes it possible to estimate the distance between individual sequences; such linking information is typically obtained by sequencing paired ends from a DNA clone library with a characteristic insert size. On the basis of sequence overlap, the reads are assembled into contiguous sequences (contigs); by means of the linking information, the contigs are ordered and oriented with respect to one another into larger scaffolds (2). Within scaffolds, adjacent contigs are often separated by a gap, which corresponds to a region that is hard to assemble from the available sequence reads (for example, due to repetitive sequence or low coverage), but that can nevertheless be spanned by using the linking information to determine the contigs at either end of the gap. Long links, from large-insert clones such as Fosmids, have been especially valuable (3). Such clone libraries provide physical coverage (defined as the average number of clones spanning a point in the genome), often in the range of 1000-fold. With this strategy, it has been possible to produce mammalian genome assemblies with scaffolds ranging from 1-15 megabases (2, 3). However, it has generally not been feasible to achieve scaffolds that span entire chromosomes, because some repetitive regions are too large and difficult to be spanned by the available clone libraries.

SUMMARY OF THE INVENTION

In one aspect, the invention provides a method for assembly of one or more long DNA molecules comprising generating contigs and scaffolds from input sequencing reads obtained, at least in part, from a DNA proximity ligation assay, conducted on one or more samples and assembling one or more larger sequences corresponding to the one or more DNA molecules by overlapping, ordering, orienting, and merging the contigs and scaffolds to generate a final assembly. In certain example embodiments, the assembling step may be done visually using a contact map generated from the DNA proximity ligation assay, the contact map providing a frequency of contacts between different sequencing reads.

In another aspect, the invention provides a method for de novo genome assembly comprising: combining reads from a DNA proximity ligation assay on a test sample with reads from a DNA proximity ligation assay of a reference sample to generate a combined 3D contact map; determining chromosomal breakpoints and/or fusions between the test sample and the reference sample from the combined contact map; realigning the test sample reads according to the determined breakpoints and/or fusions; and variant calling to replace one or more single nucleotide polymorphisms between the realigned test sample and the reference sample to derive a test sample reference genome. In one embodiment, the test sample. and the reference sample are from the same species. In another embodiment, the test sample and the reference sample are from closely related species.

In another aspect, the invention provides a method for de novo genome assembly comprising: generating a 3D contact map from sequencing reads derived from a DNA proximity ligation assay; ordering a set of genomic contigs based on the 3D contact map to generate a genome assembly. In one embodiment, the 3D contact map defines one or more contact domains. In another embodiment, the 3D contact map further defines centromere and telomere regions. In another embodiment, the method further comprises a correction step to remove undercollapsed heterozygosity. In another embodiment, aligning a set of genomic contigs comprises determining a proper orientation of the genomic sequence contigs. In another embodiment, the proper orientation of the genomic sequence contigs is determined based on identifying a proper orientation of CTCF motifs defining one or more contact domains in the 3D contact map. In another embodiment, the proper orientation of the genomic sequence is determined, at least in part, based on a frequency an end of a given contig forms contacts with an end of other contigs. In another embodiment, the frequency is determined, at least in part, by application of a greedy algorithm.

In another aspect, the invention provides a computer implemented method for de novo genome assembly comprising: receiving, using one or more computing devices a set of input scaffolds; correcting, using the one or more computing device, misjoined sequencing reads in the set of input scaffolds; generating, using the one or more computing devices, chromosome length scaffolds (megascaffold) from the corrected input scaffolds; and splitting, using the one or more computing device, the megascaffold into individual chromosome scaffolds. In one embodiment, the input scaffolds comprise contact frequencies as determined using a DNA proximity ligation assay. In another embodiment, the DNA proximity ligation assay is Hi-C. In another embodiment, the method further comprises removing tiny scaffolds prior to the correcting step. In another embodiment, a tiny scaffold is less than 15 kb and/or has a N50 length of less than 6.1 kb. In another embodiment, the method further comprises merging, by the one or more computing devices, assembly errors due to undercollapsed heterozygosity.

In another aspect, the invention provides a method for de novo genome assembly comprising generating a set of input sequencing reads derived from DNA proximity ligation assays conducted on one or more samples and ordering an orienting the input. The ordering an orienting of input sequencing reads may be based in part on frequency an end of a given sequencing read forms contact with other sequencing reads in the set. The frequency may be determined, at least in part, by application of a greedy algorithm or an optimization algorithm. The input sequencing reads may be contigs, scaffolds, or a combination thereof. The input sequencing reads may be generated using short-read sequencing technology, long-read sequencing technology, insert clones, linkage mapping data, physical mapping data, optical mapping date, sequencing reads from DNA proximity ligation assays, or a combination thereof. The input sequencing reads may be from a single species or multiple species.

In another aspect, the invention comprises a method for misassembly detection in genome assemblies comprising detecting errors in one or more genome assemblies based, at least in part, on the frequency of contacts between one part of a contig or scaffold and other parts of the same contig or scaffold, or based on the frequency of contact between one part of a contig or scaffold and other contigs and scaffolds, or a combination thereof. The errors may be misjoins, rearrangements, translocations, inversions, insertion, deletions, repeats, alignment errors, due to features of how the genome folds in three dimensions, cyclic permutations of the chromosomes, or a combination thereof. The translocations may be balanced translocations, unbalanced translocations, or a combination thereof. The repeats may be tandem repeats. In certain example embodiments, the frequency of contact is determined based on a contact matrix derived from a DNA proximity ligation assay, wherein reads are represented as pixels in the contact map and wherein the contact frequency is a function of distance from a diagonal of the contact matrix. The contact matrix may be used to derive an expected model to determine the contact frequency. The contigs and scaffolds may be first ordered and oriented using the methods disclosed to generate a draft assembly prior to detecting any errors. The draft assembly may then be further reordered and reoriented based on the detected errors to improve the overall genome assembly.

In another aspect, the invention comprises a method for merging assembly errors due to undercollapsed heterozygosity comprising identifying alternative haplotypes in a genome assembly based at least in part on a frequency of contact between a sequence and other loci in the genome, and removing or merging the alternative haplotypes to produce a single consensus sequence. The frequency of contact may also be used in combination with sequence identity analysis, coverage analysis, or both to identify alternative haplotypes. The frequency of contact may be determined based on a contact matrix derived from a DNA proximity ligation assay, wherein reads are represented as pixels in the contact map and wherein contact frequency is a function of distance from the diagonal of the contact matrix. In certain example embodiments, the alternative haplotype may be merged to increase contiguity of the genome assembly or otherwise removed. The identification of alternative haplotypes may be done simultaneously on multiple genome assemblies.

In another aspect, the invention provides a method for phasing different haplotypes comprising calculating a frequency of contact between loci containing particular variants, wherein the frequency of contact is determined using sequencing reads derived from a DNA proximity ligation assay, wherein the frequency of contact between two variants indicates if two variants are on the same molecule. In certain example embodiments, the frequency of contact between two variants is compared to an expected model to determine whether the two variants are on the same molecule. The expected model may be determined based on a contact matrix derived from a DNA proximity ligation assay, wherein reads are represented as pixels in the contact map and wherein contact frequency is a function of distance from a diagonal of the contact matrix. In certain example embodiments, the analysis may be done in an iterative fashion and wherein in data from DNA proximity ligation experiments is used to go from one possible phasing of a variant set to another possible phasing of a variant set. The analysis of the data from the DNA proximity ligation experiments is performed using gradient descent, hill-climbing, a genetic algorithm, reducing to an instance of the Boolean satisfiability problem (SAT) and solving, or using any combinatorial optimization algorithm.

In another aspect, the invention provides a method for reference-assisted genome assembly. Reads from DNA proximity ligation reads on a test sample may be aligned to a reference sequence derived from a control sample to generate a combined 3D contact map. The chromosomal breakpoints and/or fusions are identified between the test sample and the reference sample to create a proxy genome assembly. Variant calling may then be used to identify one or more small-scale changes, such as indels and singe nucleotide polymorphisms, between the realigned test sample and the control reference sequence. Local reassembly is then performed on the identified variants to address the one or more small-scale changes to generate a final output genome assembly. The test sample and the reference sample may be from the same or different species, or from closely related or distantly related species. The breakpoints and fusions may be identified using one of the embodiments disclosed above. In certain example embodiments, the breakage and fusion points are examined to determine regions of synteny between the test and reference samples and/or polymorphisms. The test sample may be aligned to the same or different reference sample, or multiple test samples may be aligned to may different reference sample sequences. The breakage and fusion points may be examined to infer phylogenetic relationships between samples. In certain example embodiment, multiple reference-assisted assemblies may be prepared at the same time.

In another aspect, the invention provides a method for genome assembly, wherein proper orientation of contigs and/or scaffolds is determined, at least in part, by the relative orientation of certain DNA motifs. The motif may be a CTCF mediated loop. The proper orientation may be determined, at least in part, from DNA proximity ligation assays, which may used to generate a 3D contact map defining one or more contact domains, loops, compartment domains, links, compartment loops, superloops, one or more compartment interactions. The 3D contact map may also define centromere and telomere regions. In certain example embodiment, the DNA proximity ligation assay is Hi-C. In certain example embodiments, wherein massively multiplex single cell Hi-C is used to identify different subpopulations with differences in scaling and long range behavior. The DNA proximity ligation assay may be performed on synchronized populations of cells. In certain example embodiments, the cells may be synchronized in metaphase. The method may be performed on one or more cell treated to modify genome folding. Modifications may include gene editing, degradation of proteins that play a role in genome folding (such as HDAc inhibitors, Degron that target CTCF, Cohesin etc.), and/or modification of transcriptional machinery. The methods may be used to assemble transcriptomes. In certain example embodiments bisulfate treatment is applied to ligation junctions derived from a proximity ligation experiment and used to analyze proximity between DNA loci in sample, including the frequency of methylation for one or more basis in a sample.

In another aspect, the invention provides a method for genome assembly wherein the proper orientation of contigs and/or scaffolds is determined, at least in part, by the relative orientation of certain DNA motifs. In certain example embodiments, the motif is a CTCF motif. In certain example embodiments, the proper orientation of the motifs is determined, at least in part, by data from a DNA proximity ligation assay.

In another aspect, the invention provides a method for estimating the linear genomic distance between sequences in a gene comprising sequencing reads derived from DNA proximity ligation assay. The distance may be determined, at least in part, based on the frequency a given sequence forms contacts with another sequence in the set. The distance may also be determined based on the relative orientation with which a given sequence forms contacts with other sequences in the set. In certain example embodiments, the contact features are determined from DNA proximity ligation assays. In certain example embodiments, a contact map generated from the DNA proximity ligation assays may be used to derive an expected model for the linear genomic distance between sequences in a genome.

In another example embodiment, the invention provides a method for quality control analysis of genome assemblies by visually examining a contact map derived from a DNA proximity ligations. In certain example embodiments, the visual examination may be facilitated by a computer implemented graphical user interface, wherein the graphical user interface facilitates annotation of the genome assembly. In certain example embodiments, the contig map may span a single contig or scaffold.

These and other aspects, objects, features, and advantages of the example embodiments will become apparent to those having ordinary skill in the art upon consideration of the following detailed description of illustrated example embodiments.

BRIEF DESCRIPTION OF DRAWINGS

FIG. 3—Shows a block flow diagram depicting a method for detecting misjoins in input scaffolds, in accordance with certain example embodiments.

DETAILED DESCRIPTION

General Definitions

Figure 1:
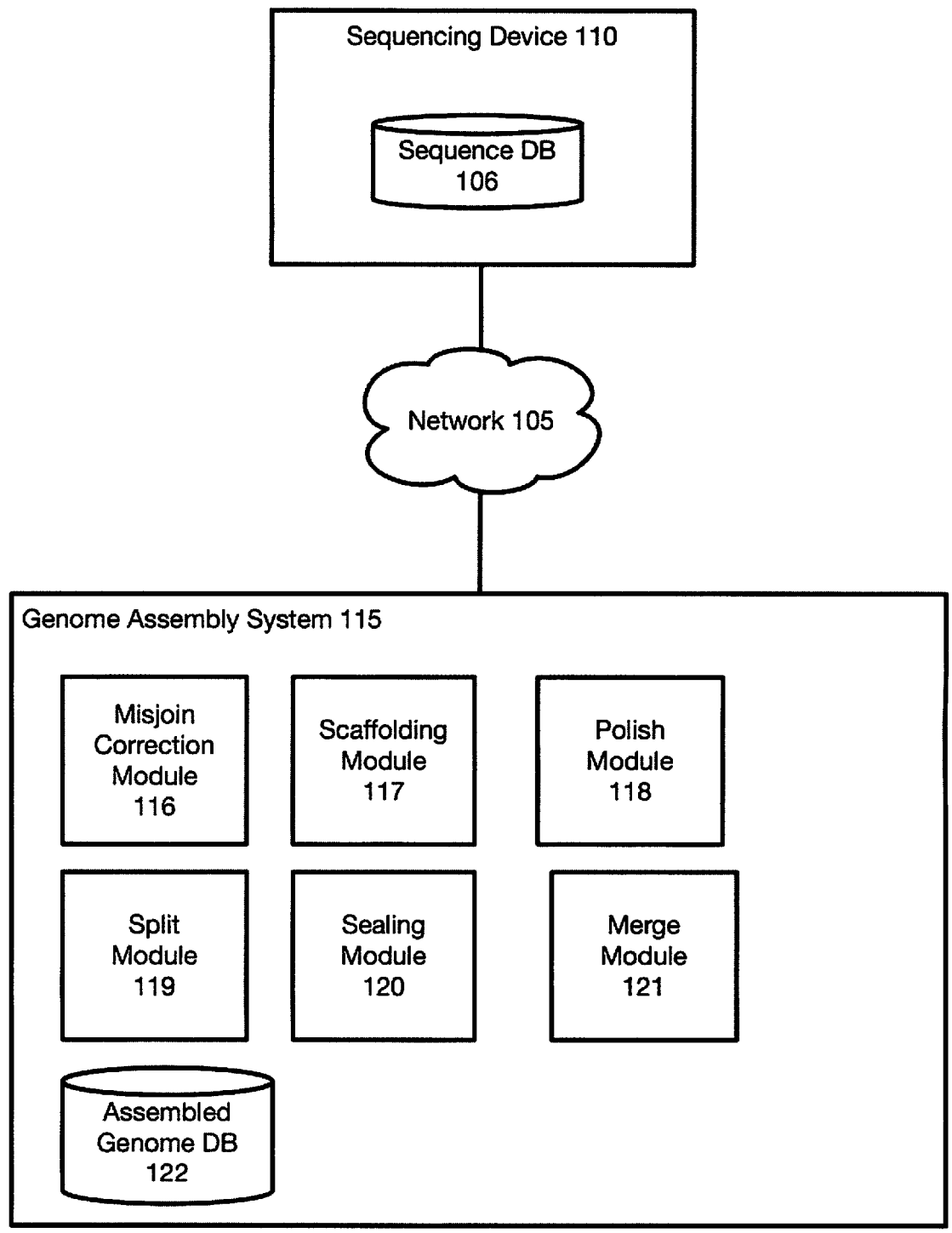
FIG. 1—Shows a block diagram depicting a system for generating genome assemblies, in accordance with certain example embodiments.

Unless defined otherwise, technical and scientific terms used herein have the same meaning as commonly understood by one of ordinary skill in the art to which this disclosure pertains. Definitions of common terms and techniques in molecular biology may be found in MOLECULAR CLONING: A LABORATORY MANUAL, $2^{nd}$ edition (1989) (Sambrook, Fritsch, and Maniatis); MOLECULAR CLONING: A LABORATORY MANUAL, $4^{th}$ edition (2012) (Green and Sambrook); CURRENT PROTOCOLS IN MOLECULAR BIOLOGY (1987) (F. M. Ausubel et al. eds.); the series METHODS IN ENZYMOLOGY (Academic Press, Inc.): PCR 2: A PRACTICAL APPROACH (1995) (M. J. MacPherson, B. D. Hames, and G. R. Taylor eds.): ANTIBODIES, A LABORATORY MANUAL (1988) (Harlow and Lane, eds.): ANTIBODIES A LABORATORY MANUAL, $2^{nd}$ edition 2013 (E. A. Greenfield ed.); ANIMAL CELL CULTURE (1987) (R. I. Freshney, ed.); Benjamin Lewin, Genes IX, published by Jones and Bartlet, 2008 (ISBN 0763752223); Kendrew et al. (eds.), THE ENCYCLOPEDIA OF MOLECULAR BIOLOGY, published by Blackwell Science Ltd., 1994 (ISBN 0632021829); Robert A. Meyers (ed.), MOLECULAR BIOLOGY AND BIOTECHNOLOGY: A COMPREHENSIVE DESK REFERENCE, published by VCH Publishers, Inc., 1995 (ISBN 9780471185710); Singleton et al., DICTIONARY OF MICROBIOLOGY AND MOLECULAR BIOLOGY 2nd ed., J. Wiley & Sons (New York, N.Y. 1994), March, ADVANCED ORGANIC CHEMISTRY REACTIONS, MECHANISMS AND STRUCTURE 4th ed., John Wiley & Sons (New York, N.Y. 1992); Marten H. Hofker and Jan van Deursen, TRANSGENIC MOUSE METHODS AND PROTOCOLS, $2^{nd}$ edition (2011), Richard C. Deonier et al. COMPUTATIONAL GENOME ANALYSIS: INTRODUCTION, published by Springer (New York, N.Y. 2005), and Veli Mäkinen et al. GENOME-SCALE ALGORITHM DESIGN: BIOLOGICAL SEQUENCE ANALYSIS IN THE ERA OF HIGH-THROUGHPUT SEQUENCING, Cambridge University Press (Cambridge, U.K. 2015).

As used herein, the singular forms "a", "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

As used herein the term "contig" refers to input sequences that are gap free and the term "scaffold" refers to input sequences that are permitted to contain gaps.

All publications, published patent documents, and patent applications cited in this application are indicative of the level of skill in the art(s) to which the application pertains. All publications, published patent documents, and patent applications cited herein are hereby incorporated by reference to the same extent as though each individual publication, published patent document, or patent application was specifically and individually indicated as being incorporated by reference.

Overview

Embodiments disclosed herein provide method for the assembly of one or more DNA sequences, in particular long DNA sequences exceeding 1 kb. In certain example embodiments, the long DNA sequences may be between 1 kb and 1 Mb, 1 kb and 1 Gb, 1mb and 1 Gb, or greater than 1 Gb. The methods disclosed herein may rely, in part, on contact maps derived from DNA proximity ligation assays.

In one example embodiment, the present invention provides a method for sequencing and assembling long DNA genomes comprising generating a 3D contact map of chromatin loop structures in a target genome, the 3D contact map of chromatin loop structures defining spatial proximity relationships between genomic loci in the genome, and deriving a linear genomic nucleic acid sequence from the 3D map of chromatin loop structures.

Figure 27:
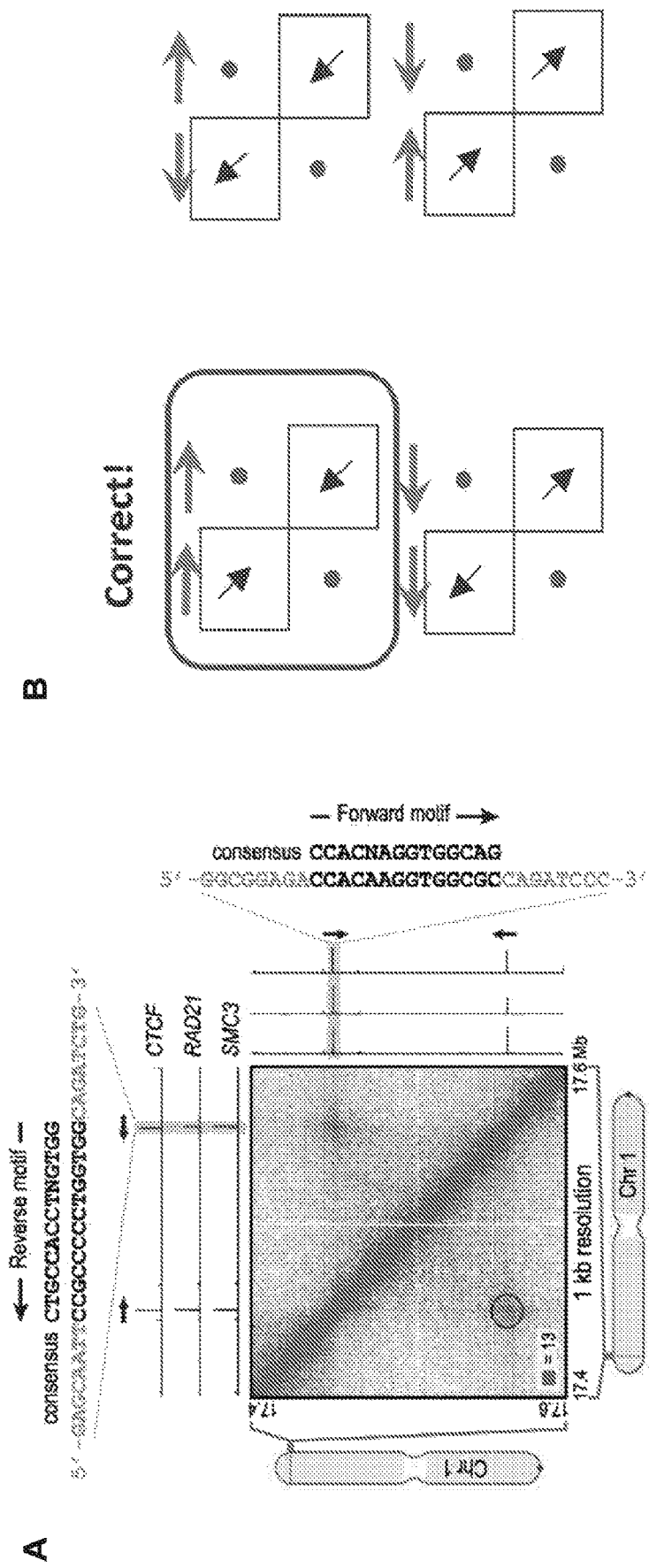
FIG. 27—Shows a schematic of how 3D features associated with oriented motifs can be used for genome assembly.

In one embodiment, the method of long DNA molecule assembly comprises generating a 3D contact map for a sample to be sequenced. A 3D contact map is a list of DNA-DNA contacts produced by a DNA proximity ligation assay, such as the in situ Hi-C assays described in WO 2016/089920. By partitioning the linear genome into "loci" of fixed sized (e.g. binds of 1 MB or 1 Kb), the 3D contact map can be represented as a "contact matrix" M, where the entry $M_{ij}$ is the number of contacts observed between locus $L_i$ and $L_j$. A "contact" is a read pair that remains after exclusion of reads that do not align to a reference genome, that correspond to un-ligated fragments, or that are duplicates. The contact map can be visualized as a heatmap whose entries are calls "pixels." An "interval" refers to a one-dimensional set of consecutive loci. The contacts between two intervals thus may form a "rectangle" or "square: in the contact matrix. "Matrix resolution" is the locus size used to construct a particular contact matrix and "map resolution" is the smallest locus size such that 80% of loci have at least 1,000 contacts. The map resolution describes the finest scale at which one can reliably discern local features. The 3D contact maps may be used to discern contact domains which are contiguous genomic intervals in which there is an enhanced probability of contact among all loci (which manifest as bright spots off the diagonal of the contact map), as well as the location of centromeres and telomeres. See FIG. 1 and FIG. 27. These features, and the ability to discern distances between loci relative and/or contig orientation relative to said features provides a basis for the de novo sequencing approaches disclosed herein.

In certain example embodiments, the DNA proximity ligation assay is Hi-C. Hi-C is a sequencing-based approach for determining how a genome is folded by measuring the frequency of contact between pairs of loci (4, 5). Contact frequency depends strongly on the one-dimensional distance, in base pairs, between a pair of loci. For instance, loci separated by 10 kb in the human genome form contacts 8 times more often than those at a distance of 100 kb. In absolute terms, a typical distribution of Hi-C contacts from a given locus is 15% to loci within 10 kb; 15% to loci 10 kb-100 kb away; 18% to loci 100 kb-1 Mb away; 13% to loci 1 Mb-10 Mb away; 16% to loci 10 Mb-100 Mb away; 2% to loci on the same chromosome, but more than 100 Mb away; and 21% to loci on a different chromosome. Hi-C data can provide links across a variety of length scales, spanning even whole chromosomes. However, unlike paired-end reads from clone libraries, any given Hi-C contact spans an unknown length and may connect loci on different chromosomes. This challenge may be mitigated, in part, by the physical coverage achieved by Hi-C datasets. For the maps reported in (4, 5), summing the span of each individual contact reveals that 1× of sequence coverage of the target genome translates, on average, into 23,000× of physical coverage. This suggests that a statistical approach analyzing the pattern of Hi-C contacts as a whole could generate extremely long scaffolds.

Chromatin loop formation is the result of the presence of a pair of CTCF binding motifs in the convergent orientation on opposite strands of the DNA. The inventors have shown that a genome is partitioned into domains that are associated with particular patterns of histone marks that segregates into sub-compartments, distinguished by unique long-range contact patterns. Domain includes reference to superdomain and loop domain. A loop domain is a domain whose endpoints are anchored to form a chromatin loop. Loops are anchored at DNA sites bound by higher-order "loop anchor complexes" containing loop anchor proteins, including CTCF and cohesin, and other factors. Many loops demarcate domains; the vast majority of loops are anchored at a pair of convergent CTCF/RAD21/SMC3 binding sites. The pairs of CTCF motifs that anchor a loop are nearly all found in the convergent orientation. The inactive X chromosome (Xi) is found to be partitioned into two large "superdomains" whose boundary lies near the locus of the lncRNA DXZ4 (Chadwick, 2008). A network of extremely long-range (7-74 Mb) "superloops," has also been detected, the strongest of which are anchored at locations containing lncRNA genes (loc550643, XIST, DXZ4, and FIRRE). With the exception of XIST, all of these lncRNAs contain CTCF-binding tandem repeats that bind CTCF only on the inactive X.

In one embodiment the sequencing method comprises generating a 3D contact map from sequencing reads derived from DNA proximity ligation assays conducted on a sample, such as the in situ Hi-C assays described herein, wherein the 3D contact maps identify genomic loci that define one or more contact domains. Genomic sequencing contigs are then generated using known methods in the art. The sequencing contigs may be prepared from a new sample to be sequenced or obtained from a database of previously sequenced contigs. In characterizing sets of input scaffolds, it is also useful to define the "effective N50 length" of the input scaffolds. This is simply the N50 of the scaffolds after all misjoins they contain have been corrected. Of course, for a typical published set of scaffolds, the effective N50 is not known, since it may contain misjoins and other scaffolding errors that the authors were unaware of. Naturally, the actual N50 of the scaffold set furnishes an upper bound for the effective N50—but the two are often not equal in practice. The embodiment disclosed herein provide a way to remove misjoins until the underlying scaffold set is largely free of misjoins. If there is a disparity between the actual N50 length of the input scaffolds and their effective N50 length, it will be greatly reduced by this step. After misjoin detection, the resulting input scaffolds are used to create the final ordered-and-oriented chromosome-length scaffolds.

In certain example embodiments, the method comprises a set of iterative steps whose goal is to eliminate misjoins in the input scaffolds. Each step begins with a scaffold pool. Initially, this pool is the set of input scaffolds themselves. The embodiment disclosed herein then order and orient these scaffolds. A misjoin correction module is applied to detect errors in the scaffold pool. The edited scaffold pool is used as an input for the next iteration of the application of the misjoin correction module. The ultimate effect of these iterations is to reliably detect misjoins in the input scaffolds without removing correctly assembled sequence. After the iterations are complete, a scaffolding module is applied to the revised scaffolding inputs, and the output—a single megascaffold which concatenates all chromosomes—is retained for further processing. Further processing may comprise four additional steps; (i) application of a polishing module, which is required for genomes in the Rabl configuration; (ii) application of a chromosome splitting module, which is used to extract the chromosome-length scaffolds from the megascaffold; (iii) a sealing module, which detects false positives in the misjoin correction process and restores the erroneously removed sequences from the original scaffold; and (iv) a merge module, which corrects misassembly errors due to undercollapsed heterozygosity in the input scaffold. Step (ii) may be omitted for genomes that are not in the Rable configuration and step (iv) may be omitted if the original scaffolds lack substantial undercollapsed heterozygosity. In certain example embodiments, the computer-implemented method may be written in the AWK programming language in combination with bash scripting, or other program language that facilitates higher i/o rates. It may be further optimized for speed, for example, by using GNU Parallel shell tool (27), but can also be run without parallelization.

Example System Architectures

FIG. 1 is a block diagram depicting a system for sequencing assemblies from of sequencing reads obtained from DNA proximity ligation assays and/or other sequencing technologies. As depicted in the FIG. 1, the system 100 includes devices 105 and 110 that may be configured to communicate with one another via one or more networks 105.

The sequencing device 105 may be any standard sequencing device capable of creating data files from sequencing reads of a sample. The sequencing device 105 may comprise a sequence database 106 or other storage structure for maintaining such data files.

The genome assembly system 115 comprises a misjoin correction module 116, a scaffolding module 117, a polish module 118, a split module 119, sealing module 120, and a merge module 121. These modules work together to process input sequencing files to obtain a final genome assembly. Such final genome assemblies may be stored in an assembled genome database 122 or other storage media.

Each network 105 may include a wired or wireless telecommunication means by which network devices (including devices 105 and 110) can exchange data. For example, each network 105 can include a local area network ("LAN"), a wide area network ("WAN"), an intranet, an Internet, a mobile telephone network, or any combination thereof. Throughout the discussion of example embodiments, it should be understood that the terms "data" and "information" are used interchangeably herein to refer to text, images, audio, video, or any other form of information that can exist in a computer-based environment.

Each network device 110 and 115 includes a device having a communication module capable of transmitting and receiving data over the network 105. For example, each network device 110, and 115 can include a server, desktop computer, laptop computer, tablet computer, a television with one or more processors embedded therein and/or coupled thereto, smart phone, handheld computer, personal digital assistant ("PDA"), or any other wired or wireless, processor-driven device. In the example embodiment depicted in FIG. 1, the network devices (including systems 110 and 115).

It will be appreciated that the network connections shown are example and other means of establishing a communications link between the computers and devices can be used. Moreover, those having ordinary skill in the art having the benefit of the present disclosure will appreciate that the sequencing device 110 and genome assembly device 115 illustrated in FIG. 1 can have any of several other suitable computer system configurations. For example, a genome assembly device 110 embodied as a mobile phone or handheld computer may not include all the components described above.

Example Processes

Figure 2:
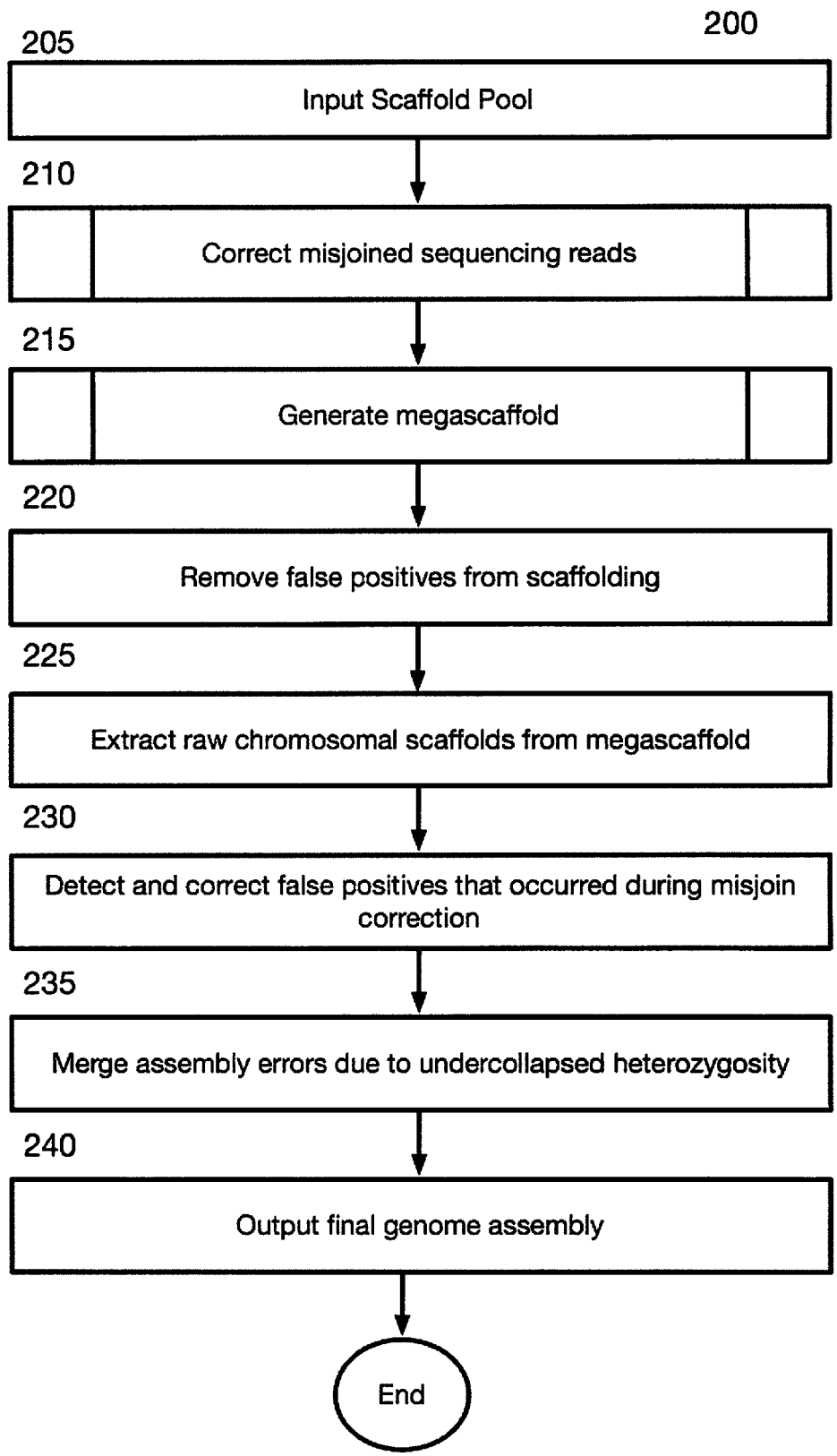
FIG. 2—Shows a block flow diagram depicting a method of generating genome assemblies from contact density data, in accordance with certain example embodiments.
Figure 4:
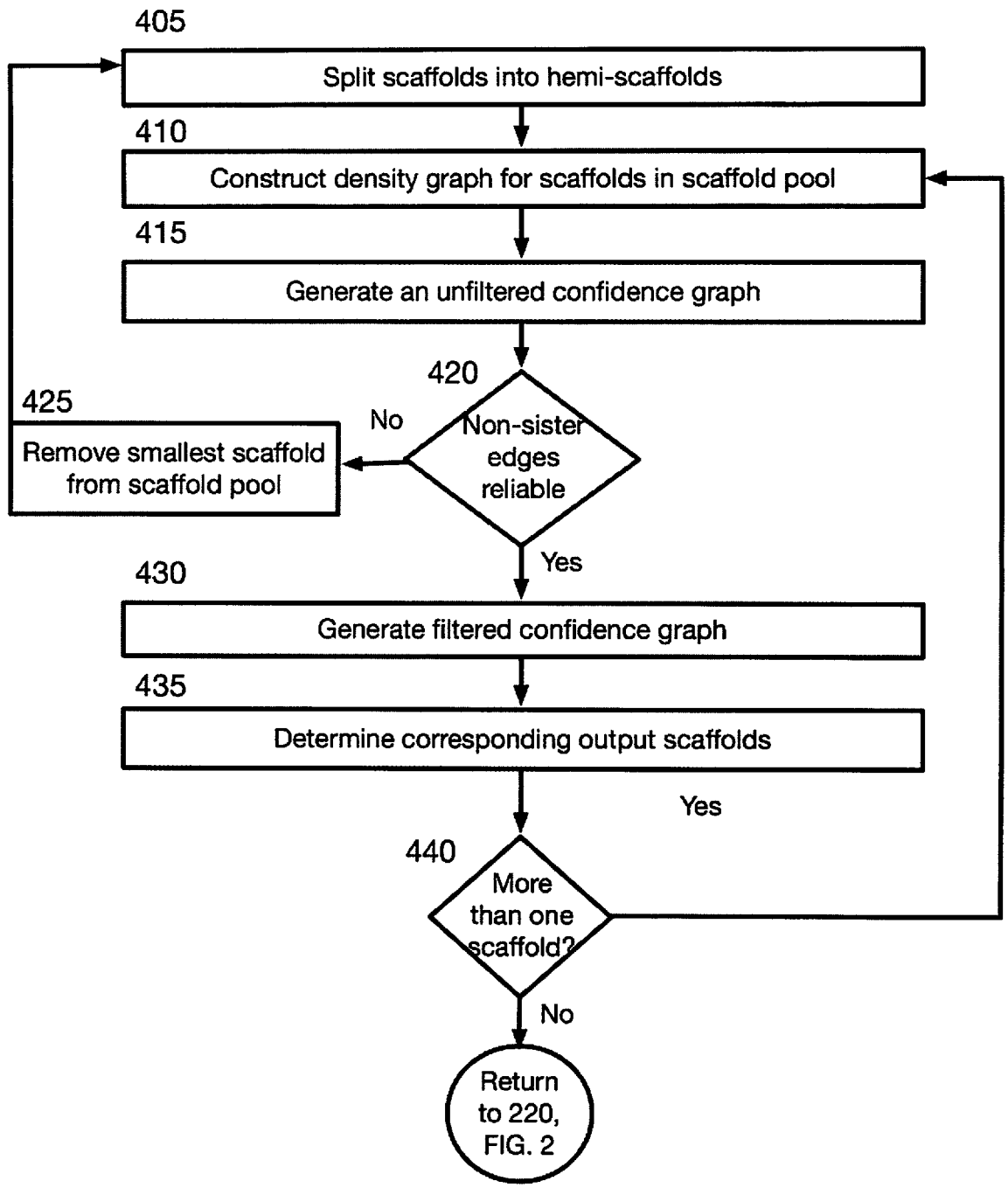
FIG. 4—Shows a block flow diagram depicting a method for generating a concatenated version of all scaffolds (megascaffold), in accordance with certain example embodiments FIG. 5—Shows a representative 3D contact map and the delineation of contact domains within the 3D contact map.
Figure 5:
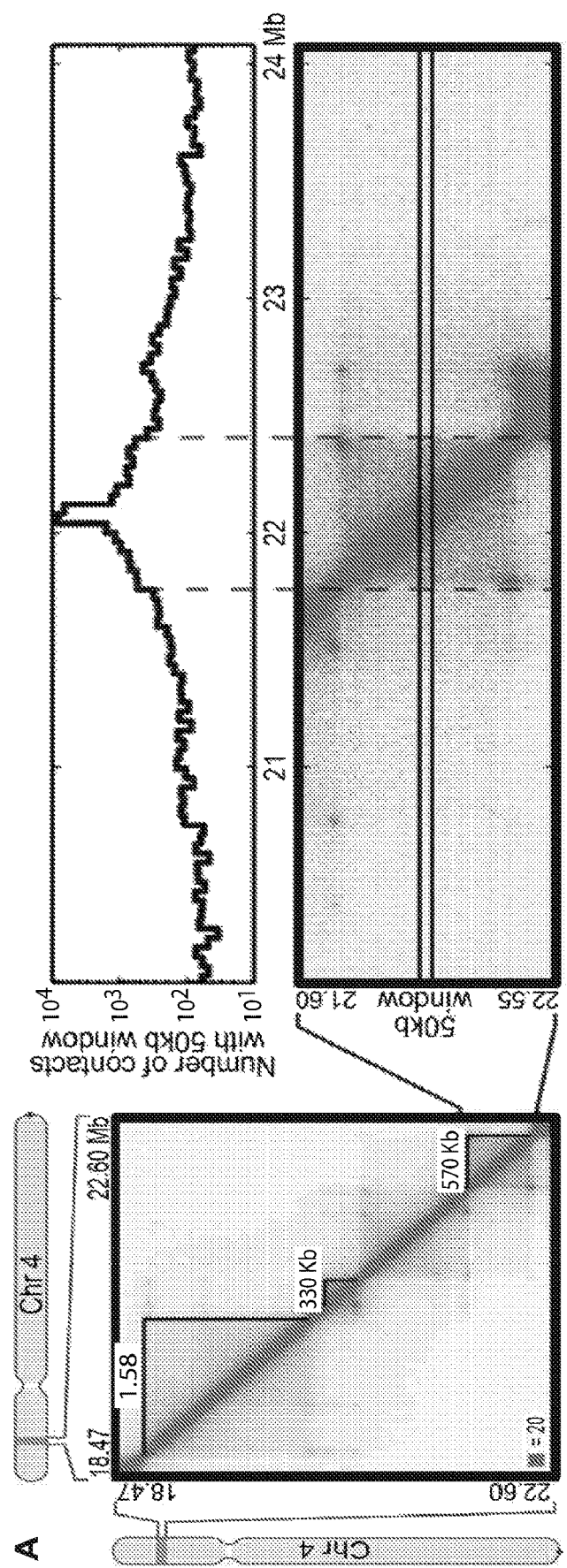

The methods illustrated in FIGS. 2-4 are described hereinafter with respect to the components of the example operating environment 100. The example method of FIGS. 2-4 may also be performed with other systems and in other environments.

FIG. 2 is a block flow diagram depicting a method 200 for sequence assembly from three-dimensional contact maps of sequencing reads obtained, at least in part, from DNA proximity ligation assays. Method 200 begins at block 205, where the misjoin correction module 116 receives input scaffolds. For the sake of generality, the inputs are referred to as scaffolds. The input may be a scaffold, that is sequence that are permitted to contain gaps, or the input may be contigs which comprise gap-free sequences. Input scaffolds may come from a variety of sources and technologies. In certain example embodiments the scaffolds are generated from Hi-C reads (5). In certain example embodiments, the input scaffold may be formatted as a fasta file. In certain example embodiment the input fasta file may comprise a duplicate-free list of paired alignments of Hi-C reads. In certain example embodiments, the pair-alignments of Hi-C reads may be generated by the Juicer pipeline (22).

In certain example embodiments, an optional preliminary filtration step may be used to remove scaffolds that due to their small size have relatively few Hi-C contacts, making them more difficult to reliably analyze. These are not processed further or included in the subsequent analysis. In certain example embodiments, scaffolds less than 15 kb and/or a N50 length of less than 6.1 kb are removed.

At block 110, the misjoin correction module 116, corrects misjoined sequencing reads in the input scaffolds. In certain example embodiments, the input scaffolds are examined for a signal consistent with a misjoin. Scaffolds with no evidence of a misjoin are labeled as 'consistent.' Scaffolds with evidence of a misjoin are partitioned into segments; each segment is classified as either a 'consistent' scaffold or an 'inconsistent' scaffold on the basis of the signal. Inconsistent scaffolds are not processed further. This portioning makes it possible to remove errors while retaining the portions of a scaffold that are correctly assembled for subsequent steps. Note that the terms above specifically refer to the results of the last round of misjoin correction, not the intermediate rounds. Block 210 is described in further detail hereinafter with reference to FIG. 3.

Methods 210 begins at block 305, where the misjoin correction module 116 initializes a scaffold pool using the set of input scaffolds received from block 205.

At block 310 the misjoin correction 116 module determines if there is at least one scaffold in the scaffold pool. If yes, the method proceeds to block 315. If there is not at least one scaffold in the scaffold pool, the method returns to block 215 of FIG. 2.

At block 315, the misjoin correction module 116 calculates an expected mode for contact frequency. When using DNA-DNA proximity reads, the method detects misjoins by relying on the fact that sequences that have been erroneously concatenated in a scaffold form fewer contacts with one another than correctly joined sequences. This is because correctly joined sequences lie adjacent to one another in 1D, and are therefore proximate to one another in 3D, facilitating the formation of DNA-DNA contacts. Because they do not actually lie in close proximity in the one-dimensional sequence of the chromosome, misjoined sequences usually do not exhibit similar 3D proximity or similar contact frequency.

To detect this depletion in contact frequency, one must compare the observed contact frequency between adjacent genomic loci with an expected model that describes the contact frequency typically observed for correctly joined sequences. Given a genome assembly with chromosome-length scaffolds, calculating the expected frequency of contact for a typical pair of sequences at a particular distance during a given experiment is straightforward. (4).

However, the results of such contact probability calculations are influenced by disparate factors, ranging from the organism of interest, the cell population interrogated, the details of the experimental approach, the particular computational methods used to analyze the data, and seemingly random inter-experimental variability. For this reason, expected models derived from a particular experiment in a particular cell population in a particular organism cannot be reliably applied to all experiments in all cell populations in all species. Thus, in the absence of a genome assembly with chromosome-length scaffolds, it is unclear how to determine the relationship between contact probability and distance even if Hi-C data is available.

A second challenge is that the contact probability between a pair of loci varies greatly, with frequent "jackpot" effects where the number of contacts is markedly enhanced with respect to the background model. This variability makes raw contact probability a very noisy indicator of the presence of a misjoin.

To overcome these challenges, the methods disclosed herein estimate a contact probability, as a function of genomic distance, using data from a Hi-C experiment without utilizing a high quality genome. Instead, the embodiments disclosed herein only assumes the availability of a collection of scaffolds that may be short and contain numerous errors. Specifically, it is shown that, even in this scenario, it is possible to calculate a lower bound for the expected number of contacts between a pair of loci at a given distance. The estimation scheme relies on the fact that the frequency of contact between a pair of loci tends to decrease as the 1D distance between the loci increases. For this reason, pixels closer to the diagonal of a Hi-C matrix (which reflect contact frequency between loci that are nearby in 1D) tend to have higher contact counts than pixels further away from the diagonal.

Figure 37:
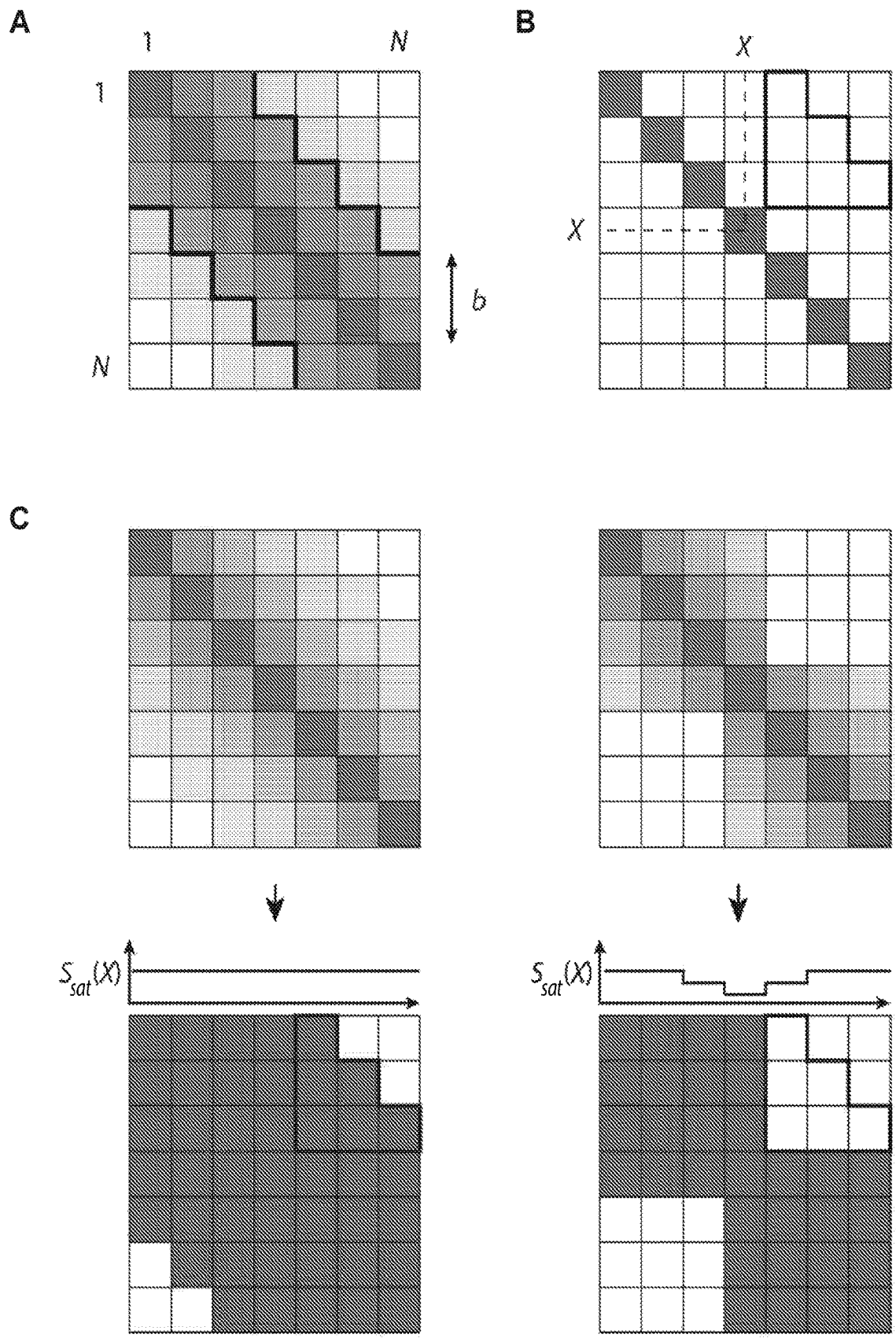
FIG. 37—Shows misassembly detection and algorithm. (A) Calculating the number of bins in between the diagonals from $c_{1+b,1}$ to $C_{N,N-b}$ and from $c_{1,1+b}$ to $c_{N-b,N}$. (B) Triangular shape used to calculate the scores S(X) and $S_{sat}(X, r)$ along the assembly. (C) Schematic representation of matrix saturation and the distribution of the score $S_{sat}(X, r)$, along the genome. Bright red signifies the highest scoring bin in a given matrix.

Consider a N×N Hi-C contact matrix M generated using a known, correct reference genome (FIG. 37). To do so, the genome has been partitioned into N loci of fixed length that is matrix resolution r (measured in base pairs). Each pixel $M_{ij}$ corresponds to all contacts between a pair of loci (in this case, the $i^{th}$ locus and the $j^{th}$ locus). N is simply the genome length divided by the matrix resolution, r. Note that, in such a setting, it is often convenient to measure 1D distance in terms of loci (which are all of fixed size r), which correspond to rows and columns of the matrix, rather than in terms of base pairs.

In such a matrix, the set of pixels that derive from pairs of loci that are within b loci of one another may be considered, i.e. the pixels $M_{ij}$ such that (i−b≤j≤i+b). A principal goal is to estimate the function Q(b), which is the minimum value of all these pixels: $Q(b)=\min M_{ij}$, i−b≤j≤i+b. This function provides a lower bound for the values $M_{ij}$ for pixels within b of the diagonal. Q(b) is useful in identifying misjoins, for the following reason: if the Hi-C data is aligned against an incorrect reference genome, containing numerous misjoins, the presence of a value lower than Q(b) within b pixels of the diagonal would indicate the presence of a misjoin at that position with complete certainty.

Before addressing the estimation of Q(b) in the general case, it is worth considering an idealized example. In FIG. 37 (A) an idealized Hi-C matrix M' is shown where contact probability decreases monotonically as the distance between a pair of loci increases, and the shape of this decay does not vary across the genome.

Notably, in such a matrix, the fraction of pixels $M_{ij}$ that derive from pairs of loci that are within b loci of one another (i−b≤j≤i+b) can be calculated by simply summing the lengths of the principal diagonal and 2×b non-principal diagonals, and dividing by the size of the matrix as a whole (N^2). This yields:

$$F(b)=N+b*(2N-b-1)N^2$$

Thus, if a pixel is selected from the matrix M at random, the probability that the pixel lies within b loci of the diagonal is exactly F.

Similarly, it is possible to determine the probability that a random pixel in the matrix contains a value larger than any arbitrary threshold C, denoted F'(C), by simply counting the number of pixels that contain more than C contacts and again dividing by the size of the matrix (N^2).

It is therefore possible to define a function C(b) so that F'(C(b))=F(b). In other words, C(b) is the number of contacts such that the fraction of pixels in M that is larger than C(b) is the same as the fraction of pixels in M that are within b of the diagonal. Furthermore, in an idealized Hi-C matrix such as the one shown in FIG. 37 (A), the pixels that lie within b of the diagonal will be exactly the pixels whose contact count is larger than C(b).

It follows from the above that—for an idealized, perfectly monotonic Hi-C matrix—Q (b) and C(b) are exactly the same function.

In practice, this is relevant because, like the contact probability scaling, Q(b) can be challenging to reliably estimate without an accurate genome assembly including chromosome length scaffolds. By contrast, F(b) can be calculated analytically using the formula above, without any experimental data at all.

Moreover, F(C) can be estimated for a given Hi-C experiment even assuming that a genome assembly with chromosome-length scaffolds is not available. In fact, F(C) can be accurately estimated using almost any reference genome assembly, so long as the effective scaffold N50 is much larger than the matrix resolution r.

A simple way to see why is that one can generate a proxy for the actual reference genome by concatenating all of the available scaffolds in an arbitrary order. In this proxy genome, the relative order and orientation of loci of size r will be entirely wrong. Nevertheless, most individual loci in the proxy genome will have a counterpart, containing the same sequence and having exactly the same size, in the true (albeit unknown) genome. For this reason, the vast majority of pairs of loci in the proxy genome will correspond to a pair of loci in the true (albeit unknown) genome. Thus, a Hi-C matrix generated with the proxy genome can be thought of as a permutation of the pixels of the Hi-C matrix that would be generated with the true genome. Consequently, the distribution of pixel values F(C) is unaffected by the use of a scrambled proxy genome. (Note that in practice F(C) can also be calculated from a raw scaffold set, without concatenation.)

Given estimates for F(C) and F(b), estimating C(b) is straightforward. Thus, it is possible to estimate C(b) even with a relatively poor, and error-prone, input genome. Although C(b) is not identical to Q(b) for a real Hi-C matrix, it nevertheless provides a serviceable estimate for Q (b). For this reason, C(b) is useful in detecting misjoins.

At block 310, the misjoin calculation module 116 detects misjoins using the expected model derived at block 305. In certain example embodiment, misjoins are detected as follows. Consider a fragment of the Hi-C map shown in FIG. 37(B). One possible misjoin score would be to place a triangular motif along the diagonal, summing the values of the pixels it contains to create a score associated with the particular genomic position:

$$S(X)=\Sigma_{i=X-d}^{X-1}\Sigma_{j=X+1}^{i+d+1}c_{ij}$$

This score reflects the average contact frequency between a particular index locus being examined (X), and all other loci within d of the index locus. If the value of the misjoin score S is anomalously low, it suggests that the corresponding index locus spans a misjoin. Unfortunately, there is not simple and reliable way to calculate an expected value for this particular score. Thus, it is impossible to known whether the score is indeed anomalously low. Moreover, this score is extremely sensitive to "jackpot" effects, when a pixel with an anomalously high value (such as a loop or an alignment error) falls within the triangular motif.

By contrast, consider a slightly modified misjoin score. The score is calculated exactly as before, but with one change. Before calculating this score, we will apply a threshold C* to the Hi-C heatmap, such that, whenever the value of a pixel is larger than C*, the method will change that value to exactly match C. Furthermore, the ability to calculate C(b) may be exploited as a proxy genome in order to select C* to be much less than C(d), such that nearly all pixels in the triangle motif shown will have a value equal to C* in the saturated matrix—except in the case of a misjoin. When combined with an ability to calculate C(b) for a low quality genome, this saturation step makes it simple to calculate an expected value for the misjoin score. Now the following for the saturated score $S_{sat}(X)$ and the expected value can be obtained (see FIG. 37(C))

$$S_{sat}(X)=\Sigma_{i=X-d}^{X-1}\Sigma_{j=X+1}^{i+d+1}\min(c_{ij},C^*);$$

$$S_{sat}^{ex}=\Sigma_{i=X-d}^{X-1}\Sigma_{j=X+1}^{i+d+1}C^*=d^*(d+1)^*C^*/2.$$

On this basis, a locus is annotated as a putative misjoin whenever the misjoin score for that locus satisfies $S_{sat}(X)<k^*S_{sat}^{ex}$, where k is an arbitrary stringency parameter such that 0≤k<1. The availability of a reliable expected model greatly improves the sensitivity and specificity of such an approach. The approach is also much less susceptible to errors due to "jackpot" effects, since the impact of a single pixel is greatly dampened by the saturation step.

Note that, so long as C*<C(d), there is considerable latitude in selecting C*. In practice, since the function C(b), can only be estimated, rather than exactly calculated, it is useful to use C(d) as an upper bound for C*, but to choose values that are smaller, such as C(2*d). In the assemblies performed here, C* is set to equal the 95th percentile of all nonzero pixels in the contact matrix.

At block 315, the misjoin correction module 116 localizes the detected misjoins. In certain example embodiment misassembly detection is performed using two different values of the matrix resolution r. First, misassemblies are annotated at coarse resolution (r=25 kb), to eliminate noise. In areas flagged by the coarse resolution detection, the exact position of the misassembly is localized by repeating the procedure of block 310 at a higher matrix resolution (r=1 kb). This approach achieves high positional accuracy in misjoin identification.

The misjoin detection step is not performed directly on individual input scaffolds. Both misjoin detection and C(b) estimate are more accurate the longer the effective N50 of the input scaffolds. Moreover, misjoin detection is significantly less sensitive if the effective N50 is less than d×r. For this reason, the effective N50 of the scaffold set is maximized by running the scaffolding module 117 described further below on the input scaffolds prior to misjoin detection. The input scaffolds are embedded in the resulting output scaffold, and thus misjoins detected in this output scaffold can be associated with misjoins in the input scaffolds. At block 320, the misjoin correction module 116, classifies the detected misjoins based on whether the misjoin lies inside one of the input scaffolds—implying that there is an error in the input scaffold, which needs to be corrected—or whether the misjoin lies at the junction between the two scaffolds, suggesting that the misjoin is a consequence of an error in the input sequence located at a different position.

Figure 38:
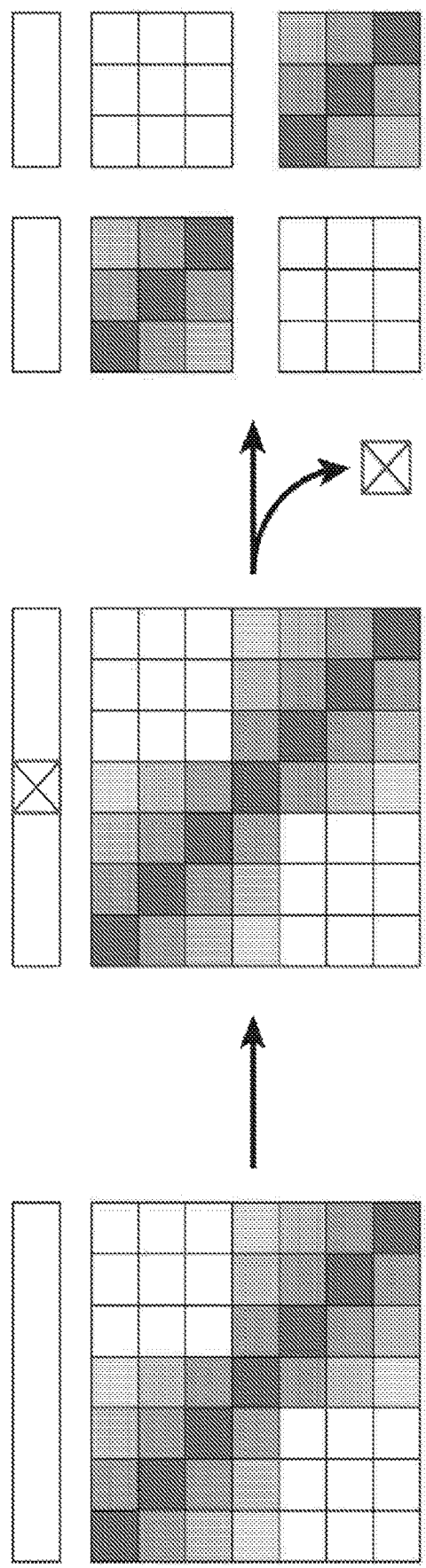
FIG. 38—Shows misassembly correction. Once a problematic region is identified that lies outside an input scaffold (a bin marked with an X), the region gets excised resulting in two internally consistent fragments of the original input scaffold. The third fragment that spans a misassembled region is labeled as inconsistent. Inconsistent fragments do not participate in the next round of scaffolding.

If a misjoin lies inside a scaffold, the scaffold is edited by excising sequence intervals flagged by the misjoin detection module 116 (see FIG. 38). The excised fragment is labeled as an additional, 'inconsistent' scaffold and excluded from subsequent assembly iterations, since its continued presence during the scaffolding process could lead to further misjoins. If the misjoin is sufficiently far from both ends of the scaffold, this results in splitting the affected scaffold into two scaffolds at the site of the misjoin (in addition to the formation of an inconsistent scaffold). Note that multiple misjoins can be identified in a single scaffold during a single round of misjoin detection, which could lead to repeatedly splitting one scaffold into multiple smaller scaffolds.

The Method 210 can be described using the following pseudocode:

---

Misassembly correction:

1) Calculate C(b) for the contact matrix at a coarse resolution $r_1$
2) Computer the saturated score functions $S_{sat}(X, r_1)$ at the course resolution
3) Calculate C(b) for the contact matrix at fine resolution $r_2$
4) Compute the saturated score function $S_{sat}(X, r_1) < k * S_{sat}^{ex}$
5) For each misjoined locus identified:
    a) Localize the misjoin at resolution $r_2$ by finding the minimum of $S_{sat}(X, r_2)$ in the locus
    b) Compare the localized misjoins with scaffold boundaries to distinguish scaffolds containing misjoins from misjoins that lie between scaffolds
    c) Correct the input scaffolds by excising misjoins inside scaffolds and labeling the excised fragment as inconsistent; in addition, if the misjoin is far from the ends of the scaffold, divide the input scaffold into two scaffolds by splitting at the misjoin site

---

Figure 39:
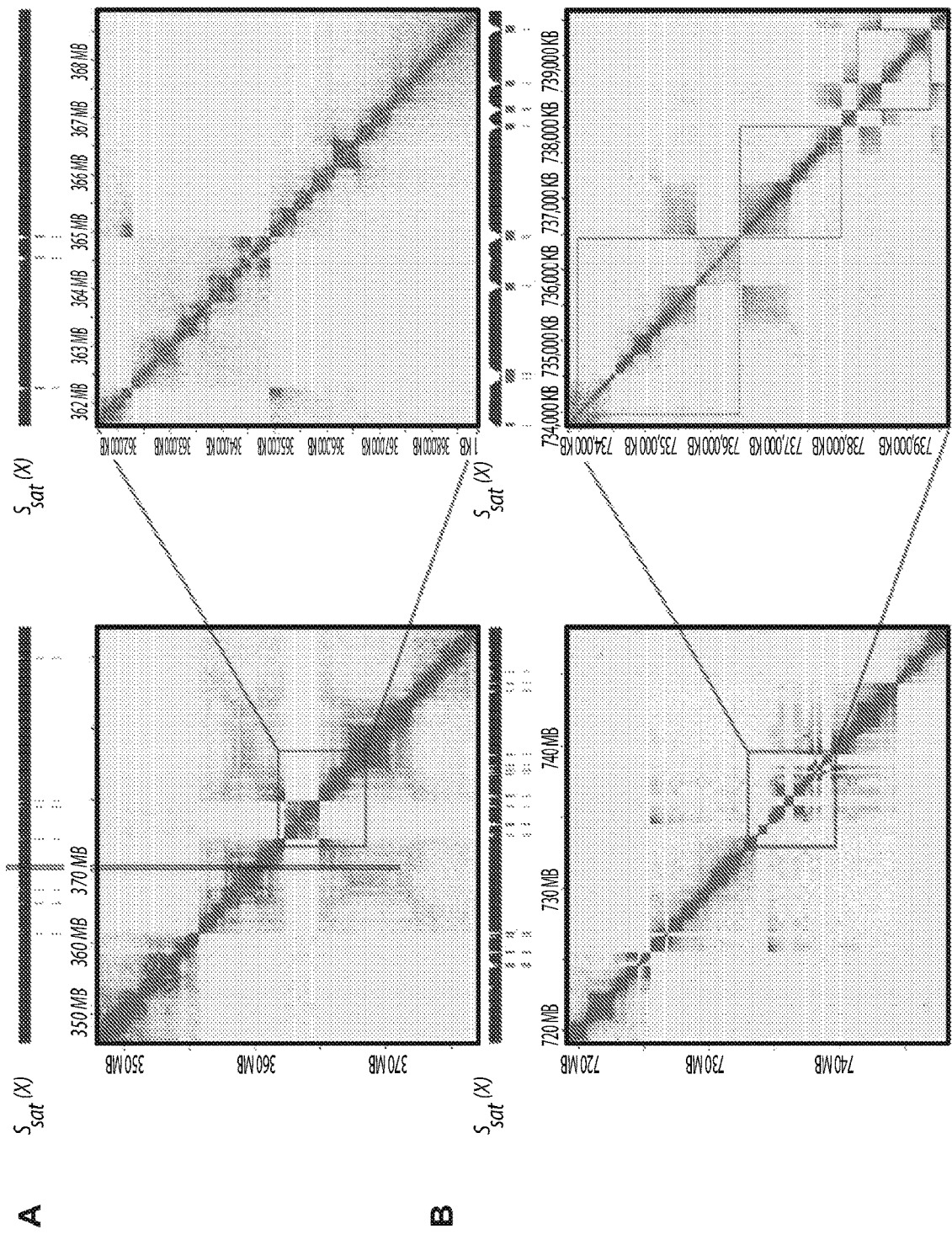
FIG. 39—Shows misassembly detection algorithm performance on Hs1 (A) and AaegL2 (B) input. Left panel shows a fragment of the Hi-C map for the assembly obtained by scaffolding the original input scaffolds, without any editing. The tracks on top of the map show the distribution of S!"# X, r])) along the assembly (blue) as well as coarse (top green track) and fine (bottom green track) positioning of misassembled sequences as identified by the misassembly detector. Right panel shows a zoom-in on a fragment of the map with input scaffold boundaries superimposed to assist in classifying the detected misassemblies. Intrascaffold misassemblies constitute a list of edits to be applied to the original scaffold set; misassemblies that overlap with scaffold boundaries are ignored. There is one intrascaffold misassembly in Hs1 and 5 intrascaffold misassemblies in AaegL2 in the corresponding fields of view.

Overall, the misjoin detection method 210 is characterized by low false positive error rates and accurate localization. It is especially sensitive to large misassemblies that give rise to large-scale errors in the genome. Several examples of automatic misassembly detection are given in FIG. 39.

Returning to FIG. 2 at block 215, where the scaffolding module 117 generates a megascaffold. Block 215 is described in greater detail with reference to FIG. 4

To transform a set of input scaffolds into chromosome-length scaffolds, three problems must be solved. "Anchoring" assigns each scaffold to a chromosome, thus partitioning the set of scaffolds into multiple subsets. "Ordering" assigns a relative position to each scaffold on each chromosome with respect to the other scaffolds assigned to the same chromosome. "Orienting" determines which of the two ends of each scaffold is adjacent to the preceding scaffold in the ordering, and which end is adjacent to the next scaffold in the ordering. (This step is equivalent to assigning each scaffold to one of the two complementary strands that comprise a chromosome.) The algorithm for constructing chromosome-length scaffolds begins with a set of input scaffolds, and simultaneously anchors, orders, and orients them.

Method 215 is iterative; the same steps are performed over and over, often thousands of times. In each step, subsets of the input scaffolds are ordered and oriented with respect to one another to create a new, longer set of scaffolds, which are then used as inputs for the next step. For the remainder of this section, we the term "input scaffolds" is used to refer to the scaffolds which are the inputs to each step; when needed, the term "initial input scaffolds" will be used to refer to the scaffolds which are the inputs to the iterative algorithm as a whole Method 215 begins at block 405, where the scaffold module 117 initializes the scaffold pool with a set of input scaffolds. The scaffold module 117 splits each input scaffold into two "hemi-scaffolds" by bisecting the scaffold sequence at the midpoint. The pair of semi-scaffolds that derive from a single hemi-scaffold are dubbed "sister hemi-scaffolds."

Figure 40:
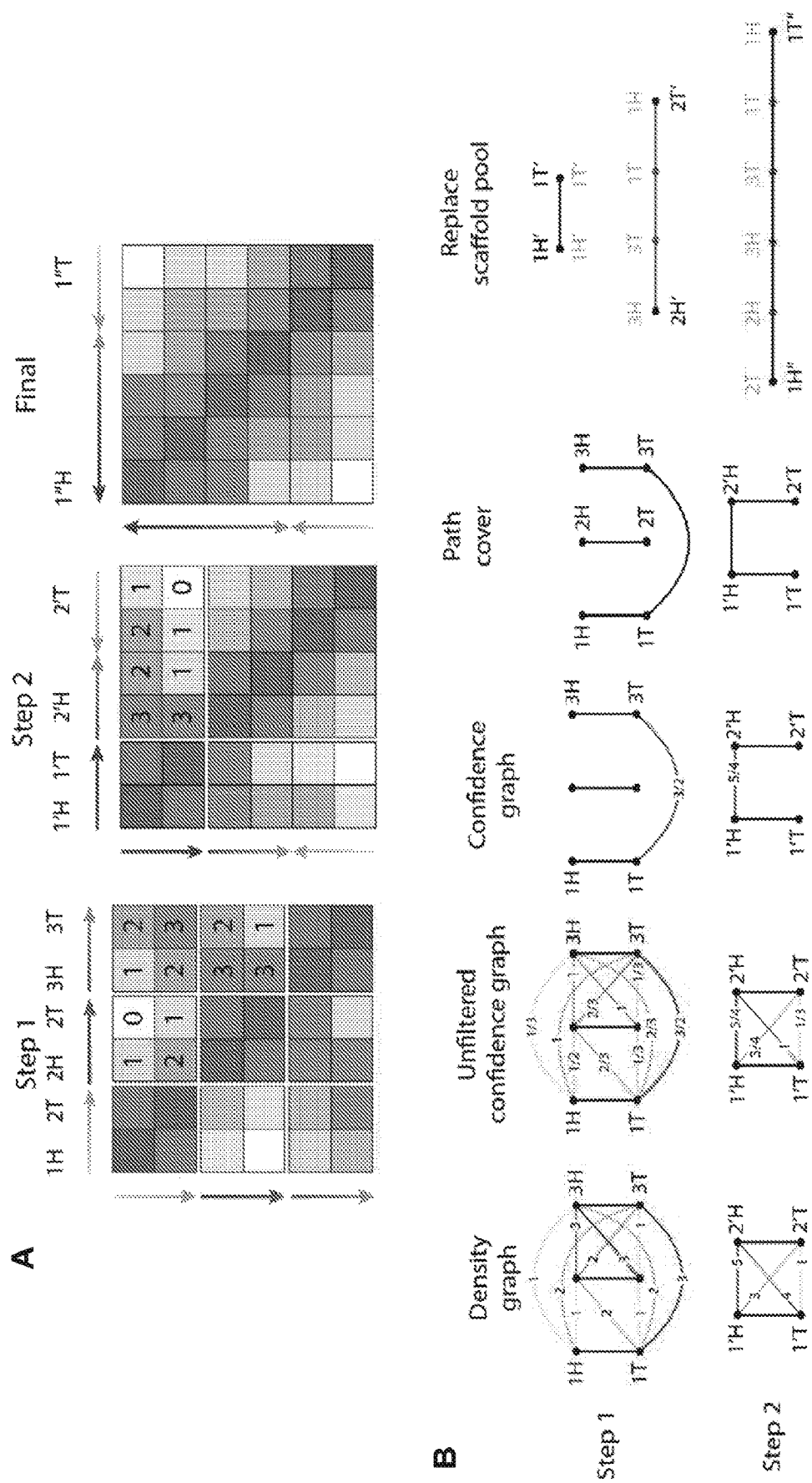
FIG. 40—Shows an example of applying an iterative scaffolding algorithm to a mock Hi-C dataset. The input scaffold pool consists of three scaffolds: 1, 2 and 3. The scaffolds are split into hemi-scaffolds. (To be able to distinguish between the hemi-scaffolds one is annotated as H for head and T for tail. The choice in each case is arbitrary.) The number of pairwise Hi-C contacts observed between all loci in all scaffolds is given as a Hi-C contact map. The assembly finishes in two steps. We show the intermediate results for both steps: density graph, unfiltered confidence graph, confidence graph, path cover and redefinition of scaffold pool. Note that to reduce cluttering the weights on the density graph are given without normalization. For the same reason the weights of sister edges are not shown in the density and confidence graphs; instead the sister edges are marked with black color.

At block 410, the scaffolding module 117 constructs a density graph for the scaffolds in the scaffold pool. For the density graph S, each hemi-scaffold is represented as a single vertex. The edges to the density graph are appended as follows. See FIG. 40.

First, edges between all pairs of vertices are appended that do not correspond to sister hemi-scaffolds. Theses edges are referred to as "non-sister" edges. The weight of each non-sister edge corresponds to the density of the DNA-DNA contacts between the corresponding hemi-scaffolds. To calculate this density (i.e. edge-weight), the count number of contacts where one read is incident on one of the hemi-scaffolds, and the other read is incident on the other hemi-scaffold may be used. The resulting value is then divided by the product of the sequence length of the two hemi-scaffolds to arrive at the density. Not that, all else being equal, having an edge of greater weight between two hemi-scaffolds indicates that the two hemi-scaffolds tend to be more proximate in 3D, and thus are more likely to be nearby along the one-dimensional chromosome sequence as well. The edges may then be appended between all pairs of vertices that correspond to sister hemi-scaffolds. All of these edges are assigned a weight of 2*MAXS, where MAXS is the maximum weight of all of the non-sister edges. This is done in order to encode the fact that sister hemi-scaffolds are adjacent to one another according to the input scaffold set, and that this evidence is—during each scaffolding iteration—regarded as more reliable than any evidence derived from DNA-DNA contacts. Of course, method 210 describes strategies for correcting scaffolds using DNA-DNA contact data. The results of these strategies influence the input scaffold set for any given step of the method 215. However, within the individual iterations, the accuracy of the input scaffold set is regarded as a constraint that takes precedence of the DNA-DNA contact data.

Prior approaches for scaffolding using DNA-DNA contact data relied directly on measures of contact density. This approach is error-prone. For instance, high-coverage scaffolds, scaffolds containing loci engaged in strong long-range interactions, scaffolds containing repeat sequences, etc. might all display frequent contacts with scaffolds that are far away from them along the 1D chromosome sequence. Conversely, input scaffolds from low-coverage regions of the genome might exhibit a relatively low contact density, even with scaffold that are adjacent to them in 1D.

In order to reliably determine the relative positioning and orientation of scaffolds given these potential pitfalls, the embodiments disclosed herein utilize a process for identifying adjacent scaffolds that is not directly based on absolute read density. A pair of input scaffolds are considered "adjacent" if they are on the same DNA molecule, and no other input scaffold has a true sequence position that lies on that same chromosome in between them.

To accomplish this, at block 415, the scaffolding module 117 uses the density graph to define an unfiltered confidence graph C'. The vertices of the unfiltered confidence graph again correspond to the hemi-scaffolds. The edges of the unfiltered confidence graph are defined as follows. See FIG. 40. If A and B are not sister homologs, then an edge is appended between them whose weight is the ratio of the weight of the edge connecting them in the density graph ($s_{AB}$), and the weight of the second-largest non-sister edge incident on either A or B in the density graph. Note that $c_{AB} > 1$ if an only if there is no hemi-scaffold whose contact density with either A or B exceeds the contact density between A and B. Informally, this means that, based on the contact density data, A is the best partner for B, and B is also the best partner for A. Edges whose weight is greater than 1 are considered "reliable." Edges whose weight is 1 or smaller are called "unreliable."

Next, edges are appended between all pairs of vertices that correspond to sister hemi-scaffolds. All of these edges are assigned a weight of 2*MAXC, where MAXC is the maximum weight of all of the non-sister edges in the unfiltered confidence graph. This is done in order to encode the fact that sister hemi-scaffolds are adjacent to one another according to the input scaffold set, and that this evidence is—during each scaffolding iteration—regarded as more reliable than any evidence derived from Hi-C.

At block 420, the scaffolding module 117 determines if the confidence graph does not contain edges linking hemi-scaffolds from distinct scaffolds in the pool ("non-sister edges"). If non-sister edges are present, the method proceeds to block 430. If non-sister edges are not present, the method proceeds to block 435.

If all non-sister edges are unreliable, then the iteration has failed in the sense that no reliable adjacency information could be extract from the contact density data. Therefore, if all the non-sister edges are unreliable, at block 425, the scaffolding module 117 removes the smallest scaffold in the scaffold pool, and the method 215 reiterates through steps 410-420 again. In certain example embodiments, step 405 is also repeated. Note that removing the smallest input scaffold and repeating the step might still not yield a reliable edge, in which case another scaffold is removed, and so on. Eventually, either a reliable edge will be found or there will only be one scaffold left (at which point the method halts and outputs the remaining scaffold).

Assuming there is a reliable non-sister edge in the unfiltered confidence graph, at block 420, the scaffolding module 117 filters the unfiltered confidence graph by removing all edges whose weight is less than or equal to 1. The resulting graph is called the confidence graph. Note that every vertex is adjacent to one sister edge in the confidence graph, and to at most 1 non-sister edge. Thus, all vertices in the confidence graph have either degree 1 or degree 2. Hence, the confidence graph is a collection of disjoint paths and cycles. Vertices that are adjacent in the confidence graph are very likely to correspond to hemi-scaffolds that are adjacent in 1D. Therefore, each path in the confidence graph corresponds to a high-confidence scaffold. Furthermore, each path in the confidence graph whose length is greater than 2 corresponds to a new scaffold comprised of multiple input scaffolds whose relative order and orientation have been determined using DNA proximity ligation assays.

Cycles in the confidence graph contain multiple possible paths (i.e. new scaffolds) spanning all the vertices (hemi-scaffolds) in the cycle. Here the key is to identify the maximal path contained in the cycle, which corresponds to the new scaffold in which the highest confidence is available given the contact density data. The can be accomplished by removing the edge in each cycle whose weight is the smallest. Because of how the confidence graph is constructed, this edge will always be a non-sister edge. In graph theoretic terms, this procedure can be thought of as a way to construct the maximal—in terms of total edge weight—vertex-disjoint path cover of the confidence graph.

A complementary way of formulating this procedure (which is mathematically guaranteed to produce exactly the same output) is to greedily select the highest weight edges from the confidence graph, ensuring that no vertex in the graph will be incident on two or more edges. (This constraint is equivalent to the rule that, after selecting non-sister edge AB, we must remove all other non-sister edges incident on either A or B.) Following this procedure, a maximum weight vertex-disjoint path cover is eventually obtained. Notably, for the special case of confidence graphs, this complementary formulation is equivalent to Kruskal's algorithm for constructing a maximal spanning forest (29). Because a confidence graph consists of disjoint paths and cycles, its maximal spanning forest is always a vertex-disjoint path cover.

Since vertices that are adjacent in the confidence graph are very likely to correspond to hemi-scaffolds that are adjacent in 1D, and since each path in the confidence graph corresponds to a high-confidence scaffold, the maximum weight vertex-disjoint path cover in the confidence graph corresponds to a new set of scaffolds that is optimal with respect to the input scaffolds and the contact density data. Thus, at block 435, the scaffolding module 117 defines one or more output scaffolds based on the confidence graph.

Once the output scaffolds are obtained, the iteration ends. Thus, at block 440, the scaffolding module 117 determines if more than one output scaffold in the scaffold pool. If there is more than one scaffold in the scaffold pool, steps 405-440 are repeated. The output scaffolds from the previous iteration can be used as input scaffolds for the new iteration and the density and confidence graphs are constructed for the new inputs. Note that reconstructing the graph from scratch allows more contact density data spanning larger scales to be incorporated into the analysis. In certain example embodiments, an alternative to recalculating the density graph is to use a more permissive threshold for including edges in the confidence graph i.e. require $c_{AB}>k$, wherein k<1. This would allow more scaffolding information to be extracted at each step, and thus fewer steps would be required to complete the scaffolding procedure.

To summarize the above process may be executed the following example pseudocode:

---

Scaffolding

---

Initialize the scaffold pool using a set of input scaffolds
While there is more than one scaffold in the scaffold pool:
    a) Construct the density graph for the scaffolds in the scaffold pool
    b) Transform the density graph into a confidence graph
    c) If the confidence graph does not contain edges linking hemi-scaffolds form distinct scaffolds in the pool ("non-sister edges"):
        i. remove the smallest scaffold from the scaffold pool
    d) Else:
        i. Find maximum weight of vertex-disjoint path cover of the confidence graph
        ii. Determine the corresponding output scaffolds
        iii. Replace the scaffold pool with the output scaffolds

---

If the scaffolding module 117 determines there is only scaffold left, then the method returns to block 215 of FIG. 2

Note that the embodiments disclosed herein do not rely on a preliminary contact density clustering step to identify chromosomes. Compare to (10). This is particularly useful for species like mosquito, where loci that lie far apart on the same chromosome may not exhibit enhanced contact frequency relative to loci on different chromosomes. See FIG. 34 and FIG. 49.

Returning to FIG. 2, the method 200 proceeds to block 220, where the polishing module 118, removes false positives. The polishing step is an optional step designed to address challenges associated with unusual 3D features that arise from organisms exhibiting strong telomere and centromere clustering. This can create false positive during scaffolding, since extremely strong off-diagonal 3D signals associated with telomere and centromere clustering can sometimes be strong enough to rival the contact frequencies observed for loci that are adjacent in 1D.

Figure 41:
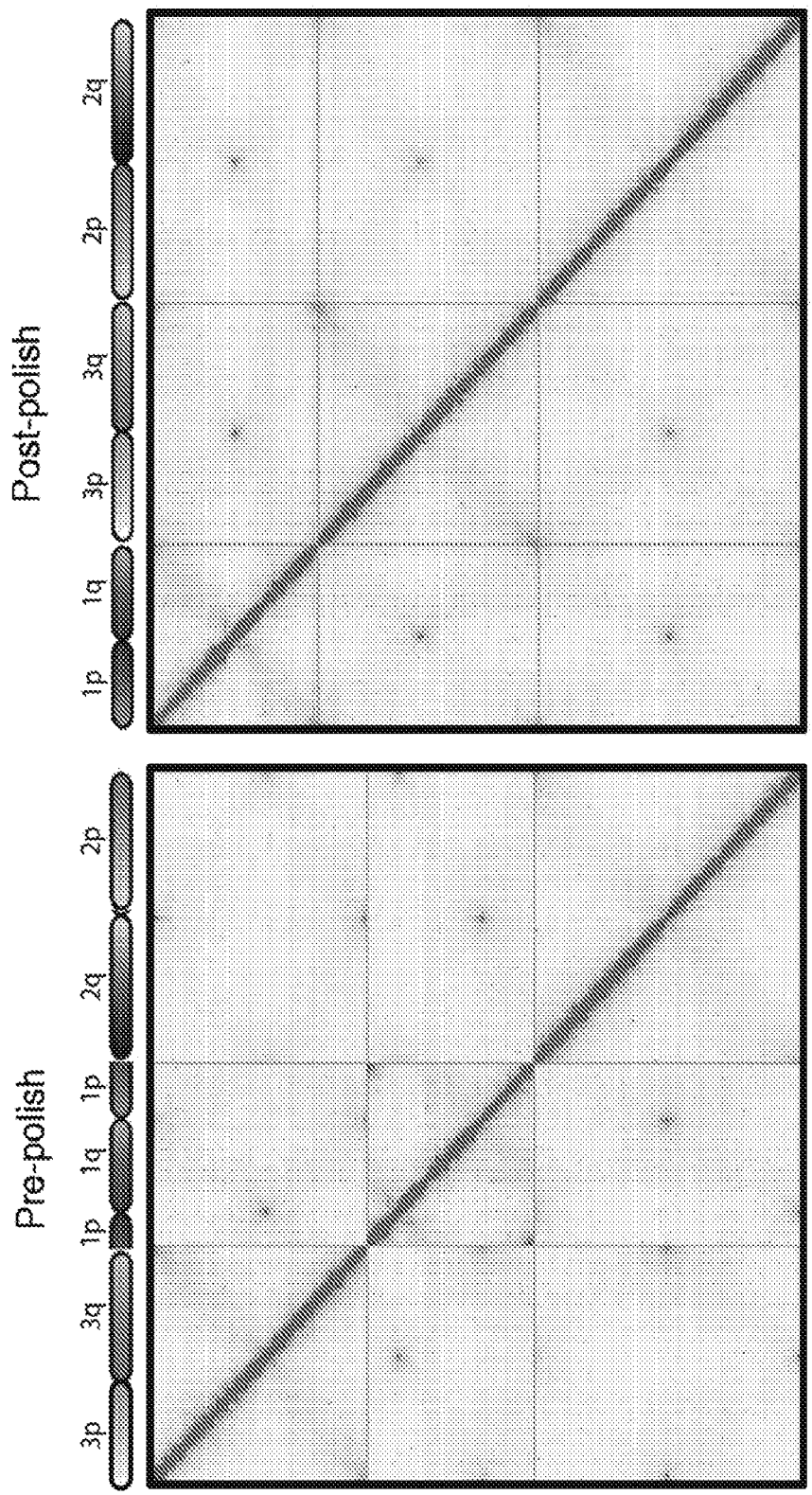
FIG. 41—Shows polishing the assembly during the construction of AaegL4 genome. Clustering of telomeres and centromeres can create false positives during scaffolding, since extremely strong off-diagonal 3D signals associated with telomere and centromere clustering can sometimes be strong enough to rival the contact frequencies observed for loci that are adjacent in 1D. Such errors are corrected by low-resolution misassembly detection and reassembly of the resulting multimegabase fragments.

FIG. 41 shows a Hi-C contact map built with respect to the *Ae. aegypti* genome assembly before and after the polishing step. The map suggests that chromosome 3 is very accurately assembled, but chromosomes 1 and 2 contain a type of error that is characteristic of assembly in genomes that exhibit strong telomere-to-telomere clustering. In this error, the enhanced proximity between the two telomeres is mistaken for 1D proximity. As a result, the raw chromosomal scaffolds corresponding to chromosomes 1 and 2 exhibit a cyclic permutation with respect to the true chromosome.

As an example, if the sequence of the true chromosome was ABCDEFG, where locus A and G are telomeres, then the erroneous sequence might be DEFGABC. This sort of error is called a "cycle break." Note that, when a cycle break occurs, an off-diagonal peak linking the two putative ends of the chromosome (in the example, D and C) is still seen in the Hi-C map. However, this signal is actually due to the true 1D proximity between the two ends of the putative chromosome, rather than at true 3D signal. Conversely, the on-diagonal signal between A and G, which appears to reflect 1D proximity, is in fact due to the telomere clustering. (Similar errors may arise due to strong interaction between telomeres of two different chromosomes. They are addressed in the same way. See FIG. 41, chromosomes 2 and 3.)

The polishing module 118 can correct such errors by a single additional round of misjoin correction, performed at extremely low resolution (r~1 Mb). The low-resolution misassembly detection identifies reliable "superscaffolds", each of which is many megabases in length. These superscaffolds are then ordered and oriented using a version of the scaffolder that exploits the large size of the superscaffolds to more reliably distinguish 1D and 3D signal by utilizing Hi-C contacts incident only on the superscaffold ends, rather than on the whole superscaffold.

At block 225, the split module 119, extracts raw chromosomal scaffolds from the megascaffold (i.e. concatenation of all chromosomes) output generated by block 215. For genomes that do not exhibit pronounced telomere clustering in the Hi-C map (such as human), the megascaffold is split into chromosomes by running a variant of the misassembly detector to identify the chromosome boundaries. This algorithm relies on the fact that the contact frequency between scaffolds that are adjacent on the megascaffold but which lie on different chromosomes is relatively low, since they are not actually in 1D proximity. Thus, the boundaries between chromosomes generate a signal that is similar to a typical misjoin. Moreover, this effect is enhanced by the tendency of loci on the same chromosome to exhibit elevated contact frequency.

If the spatial clustering of telomeres is evident in the contact density data, the phenomenon can be exploited in the effort to partition the genomes into chromosomes. In particular, the first scaffold in the megascaffold must come from the end of a chromosome, and therefore derives from a telomere. Identifying positions in the contact frequency data (such as a Hi-C matrix) that have an enriched number of contacts with the megascaffold edge thus enables the detection of chromosome boundaries.

At block 230, the sealing module 120 detects and corrects false positive that occurred during the misjoin correction. During this step, sequences that were erroneously excised during misjoin correction may be re-introduced. In particular, if the two parts of a corrected scaffold remain adjacent to one another in the raw chromosomal scaffold, it suggests that the original scaffold was correct, since the independent contact patters from both parts are consistent with the original scaffold. in this case, the misjoin that led to the correction is judged to be a false positive and the intervening sequence is restored.

At block 235, the merge module 121 merges assembly errors due to undercollapsed heterozygosity. A frequent error modality found in draft haploid genome assemblies is undercollapsed heterozygosity. This is when there exists a subset of the scaffolds such that each scaffold accurately corresponds to a single locus in the genome, but these loci overlap one another. Consequently, there are individual loci in the genome that are covered multiple times by different scaffolds. This error is typically caused by the presence of multiple haplotypes in the input sample material, which are sufficiently different from one another that the contig and scaffold generation algorithms do not recognize them as emerging from a single locus. This class of error is frequent in AaegL2; the step can be omitted when assembling genomes of organisms with low heterozygosity such as Hs1.

Undercollapsed heterozygosity error leads to highly fragmented draft assemblies with a larger-than-expected total size (30, 31). This, in turn, causes numerous problems in downstream analyses such as erroneous gene copy number estimates, fragmented gene models etc. The challenge remains significant even when special effort is taken to reduce the levels of heterozygosity in genomic data by inbreeding as has been done with the draft AaegL2 assembly (18). It is therefore important to ensure that the final genome reported by our assembler minimizes the number of assembly errors due to undercollapsed heterozygosity.

To specifically address this class of misassembly error, the goal of merging module 121 is to merge these overlapping scaffolds into a single scaffold accurately incorporating the sequence from the individual scaffolds. The result of this is a merged haploid reference scaffold.

One assumption of the merging module 121 is that, when multiple scaffolds correspond to multiple haplotypes, these scaffolds will exhibit extremely similar contact patterns, genome-wide. (Note that although some interesting examples of homolog-specific folding have been documented (5, 32), the relative input from the differential signal is very small as compared to that coming from the 'diagonal', i.e. from 3D interaction associated with proximity in 1D, so the assumption seems to hold true for the vast majority of candidate loci.) Because they exhibit similar long-range contact patterns, the scaffolding module 117 tends to assign such scaffolds to nearby positions in the genome. Thus, the merge module 121 seeks to identify pairs of resolved scaffolds that (i) lie near one another in the raw chromosomal scaffolds, and (ii) exhibit long stretches of extremely high sequence identity.

Figure 42:
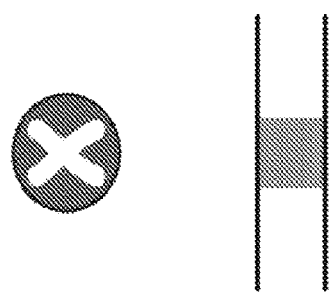
FIG. 42—Shows the location of the overlap relative to input scaffold boundaries is taken into account in determining whether the scaffolds can be correctly merged FIG. 43—Shows dotplots showing alignment of Hs2-HiC chromosome-length scaffolds vs hg38 chromosome-length scaffolds. The hg38 reference (NCBI accession number GCA 000001405.23) is shown on the X axis. The Y axis shows the 23 largest scaffolds of the Hs2-HiC assembly; they have been ordered and oriented to match the chromosomes as defined in hg38 in order to facilitate comparison. (For the same reason, all gaps are removed in both assemblies.) Each dot represents the position of an individual resolved scaffold aligned to hg38. The color of the dots reflects the orientation of individual alignments with respect to hg38 (red indicates a match, whereas blue indicates disagreement). The track on top illustrates the scaffold N50 of the draft DISCOVAR de novo assembly Hs1 as a function of position (calculated in windows of 1 Mb for individual chromosomes and 10 Mb for the whole-genome graph). Alignment was performed using BWA (34). The dotplots illustrate excellent correspondence between hg38 and Hs2-HiC, with the exception of a few low-complexity regions of the human genome.
Figure 42:
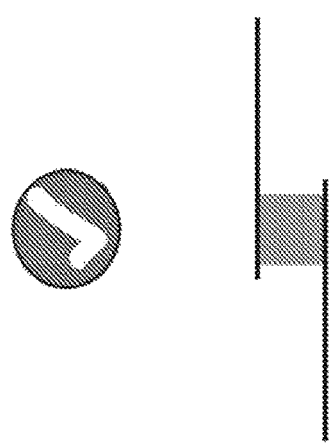
Figure 42:
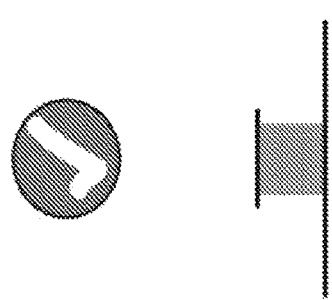
Figure 42:

Briefly, undercollapsed loci is searched by running a sliding window of fixed width along the raw chromosomal scaffolds. LASTZ is then used to do pairwise alignment of all pairs of resolved scaffolds that fall in the sliding window (28). The total score of all collinear alignment blocks (stanzas), normalized by the length of the overlap, is used as a primary filtering criterion to distinguish between alternative haplotypes and false positive sequence similarity. The location of the overlap relative to input scaffold boundaries is also taken into account in determining whether the scaffolds can be correctly merged (see FIG. 42).

Next a graph is constructed whose nodes are resolved scaffolds, and where edges reflect significant sequence overlap between resolved scaffolds that are proximate on the raw chromosomal scaffold. The resulting graph contains a series of connected components. Cycles in the graph are analyzed in order to filter out components with overlaps on conflicting strands.

Finally, a tiling path is constructed through the scaffolds of each individual connected component, recursively aligning scaffolds to an already collapsed portion of the group, finding the highest scoring alignment block and switching from one haploid sequence to the other at the endpoints of the alignment.

Ideally the resolved scaffolds in each connected component are consecutive on the raw chromosomal scaffold, and with relative orientations that match those suggested by the pairwise alignments. In practice, however, this is not always the case. This can be due to differences in haplotype representation between the genomic data used to produce the draft assembly and that of the Hi-C experiment. For example, sequences belonging to different clusters may be intertwined. Similarly, the orientation of contigs/scaffolds within the cluster as suggested by pairwise alignment may not match those suggested by the scaffolding step. In such cases the relative position and orientation of the connected components with respect to the rest of the assembly is decided by majority vote with each input scaffold's contribution weighed by its length. Alternatively, assembly can be rerun using the merged components as input.

Note that although it is possible to add additional constraints when appropriate, such as the exact number of haplotypes present in the data, we do not rely on such knowledge in general, or in any of the assemblies we performed in this paper. This allows us to work with polymorphic assemblies, such as when multiple individuals were used to produce the draft assembly. In particular it allows us to handle cases where the degree of polymorphism is unknown.

At block 240, the merge module 121 outputs the final genome assembly. In certain example embodiments, the genome assembly may be output as a fasta file. Various existing visualization software and/or modules may be used to further visualize and analyze the genome assembly.

Additional Applications

The genome assembly methods described above may also be used for additional applications as discussed in further detail below.

In one embodiment, the sequencing method provides de novo genome assembly by combining reads from a test sample DNA proximity ligation dataset, such as a Hi-C dataset described herein, with reads from a reference sample DNA proximity ligation dataset. The DNA proximity ligation reads of the test and reference sample are aligned to generate a combined contact map. The test and reference samples may be from a same species or from two closely related species (e.g. zebra and horse). Chromosomal breakpoints and fusions between the first and second sample are determined from the contact map. For example, breakpoints manifest as strong off-diagonal bocks and fusions manifest as depleted off-diagonal blocks. The test sample reads are then realigned according to the identified breakpoints and fusions. This alignment may contain one or more nucleotide variants. Thus, SNP or variant calling methods known in the art may be used to complete the genome assembly. For example, if multiple reads from the test sample aligning to the realigned contact map differ in sequence from the reference sample at one or more specific loci, then the nucleotide sequence from the test sample will be incorporated into the final genome assembly of the test sample. In addition, allowing for de novo gene assemblies, the method may also be used to identify karyotypic differences between two samples. For example, the method may be used to determine karyotypic differences between a clinical sample and a reference sample, where the reference sample may represent the chromosomal arrangement of a healthy or diseased tissue depending on the intended use.

Figure 11:
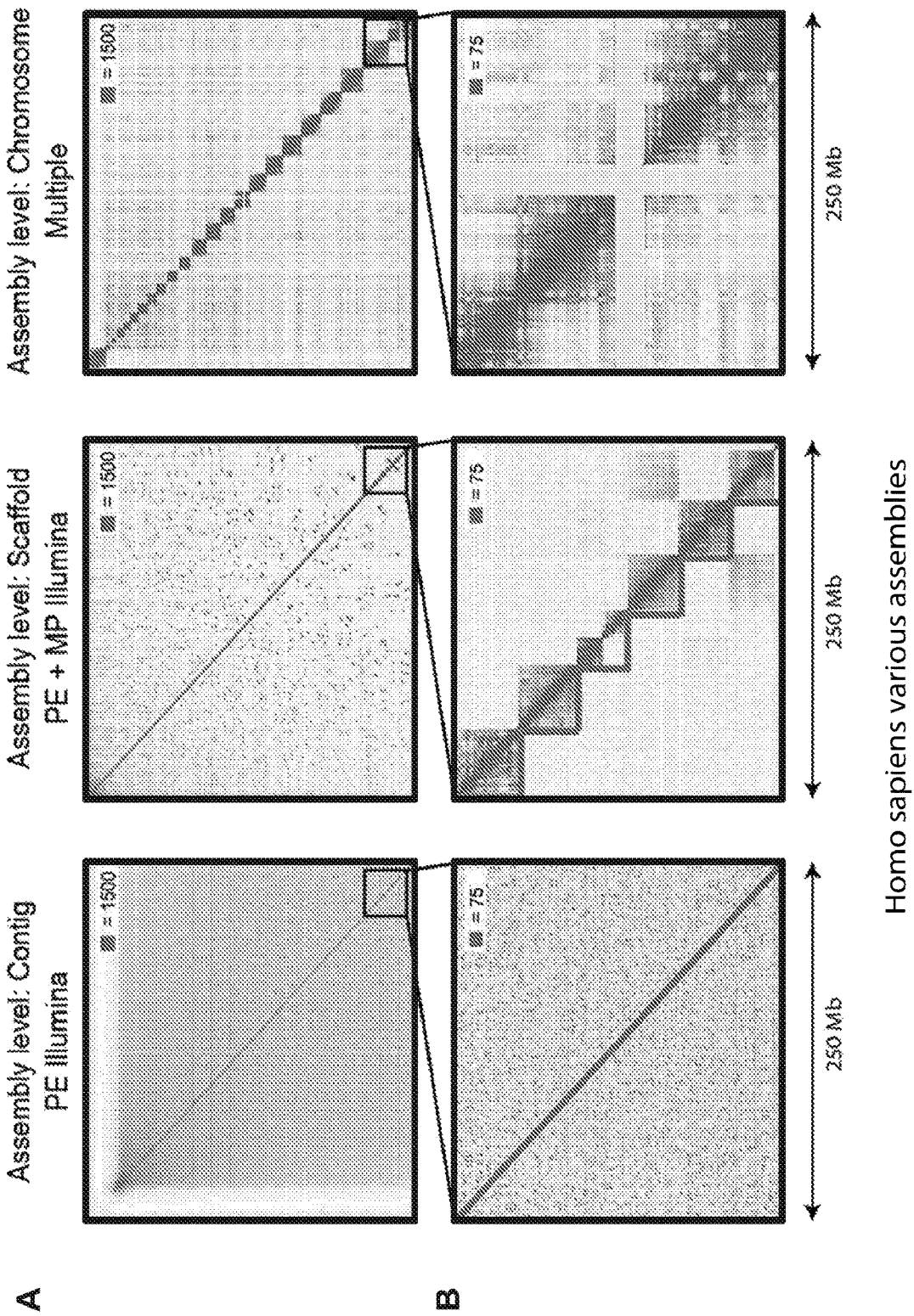
FIG. 11—Shows a set of 3D contact maps demonstrating the ability to assess the quality of genome assemblies at the contig, scaffold, and chromosome level. Both contiguity and accuracy (the rate of contigs and scaffold misjoins as well as misassignment to chromosomes) are well-reflected by the 3D contact pattern.
Figure 12:
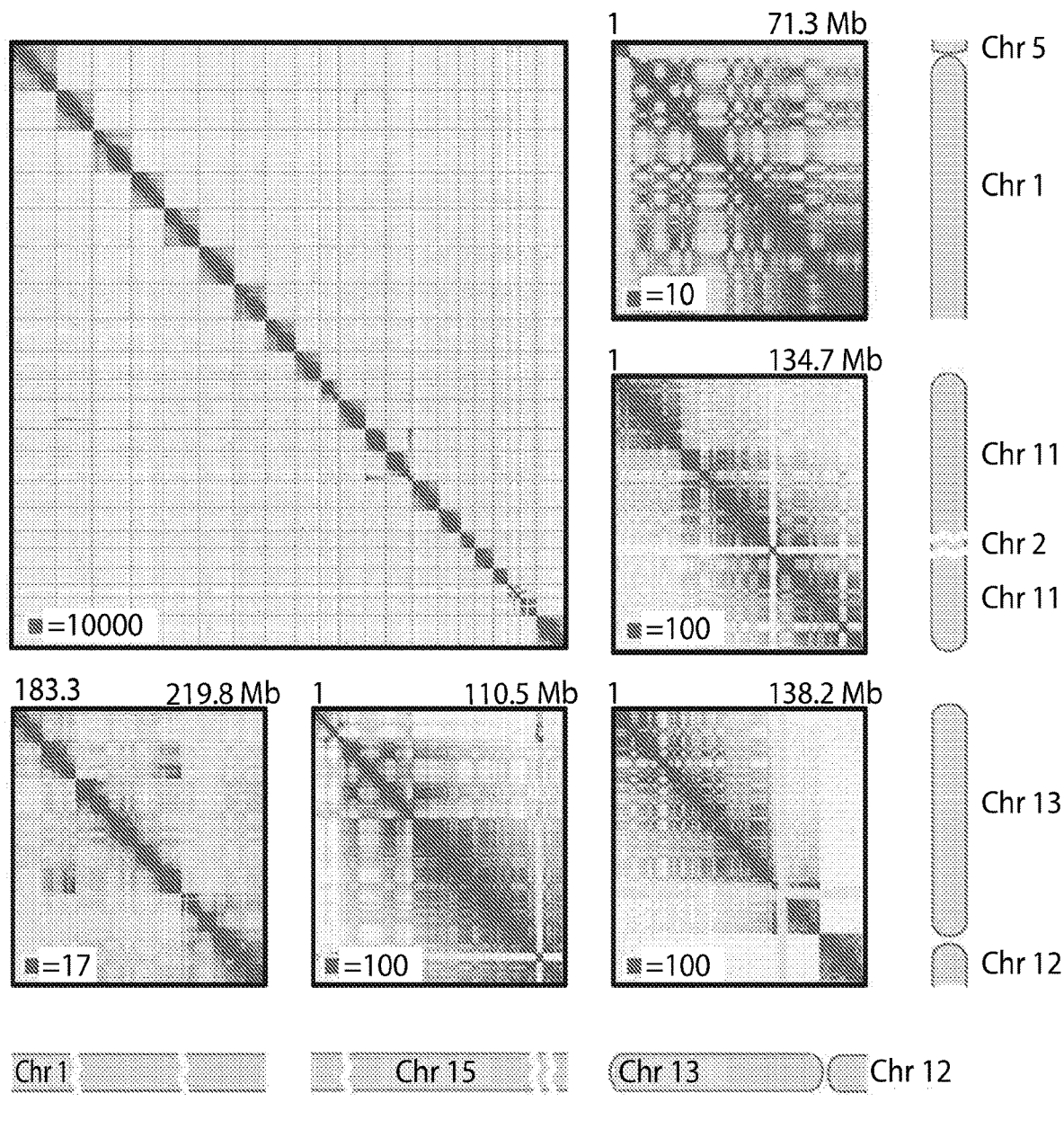
FIG. 12—Shows a set of 3D contact maps demonstrating the ability to use such maps to identify errors in chromosome-scale assemblies.
Figure 13:
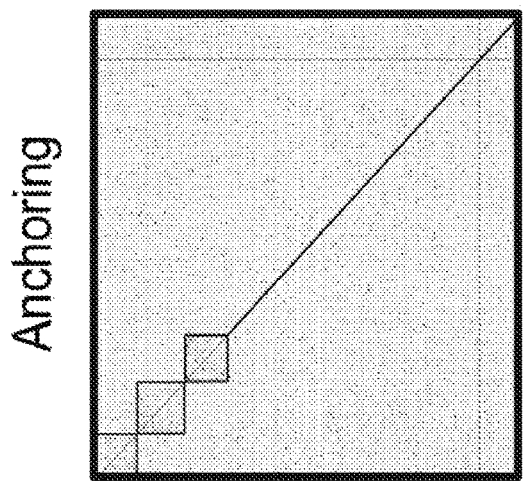
FIG. 13—Shows a set of 3D contact maps demonstrating the ability to identify errors in draft assemblies.
Figure 13:
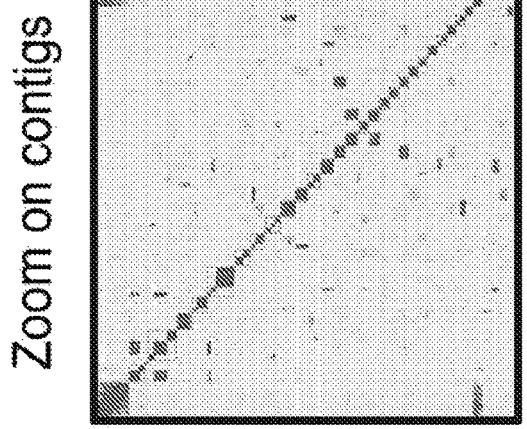
Figure 13:
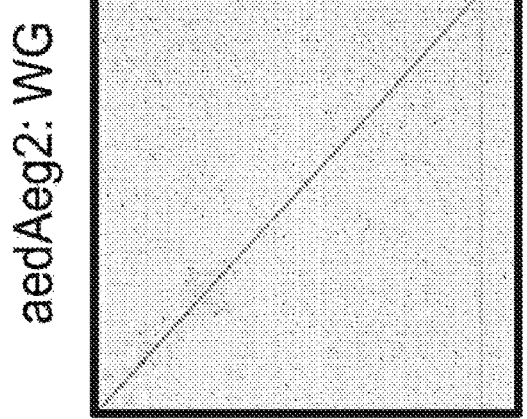
Figure 14:
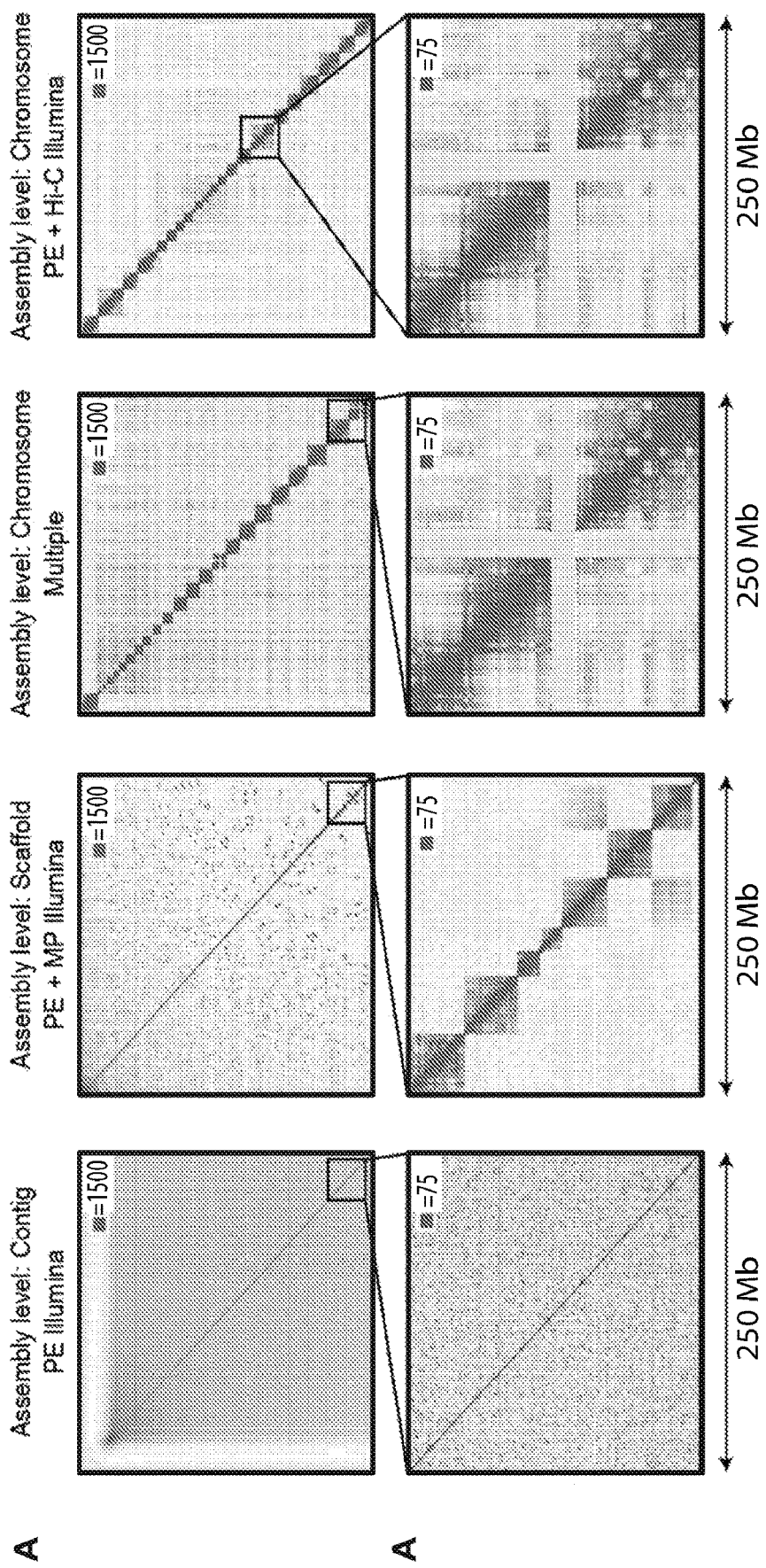
FIG. 14—Shows a set of 3D contact maps demonstrating the ability to use such maps for end-to-end assembly of large genomes from short sequencing reads.
Figure 15:
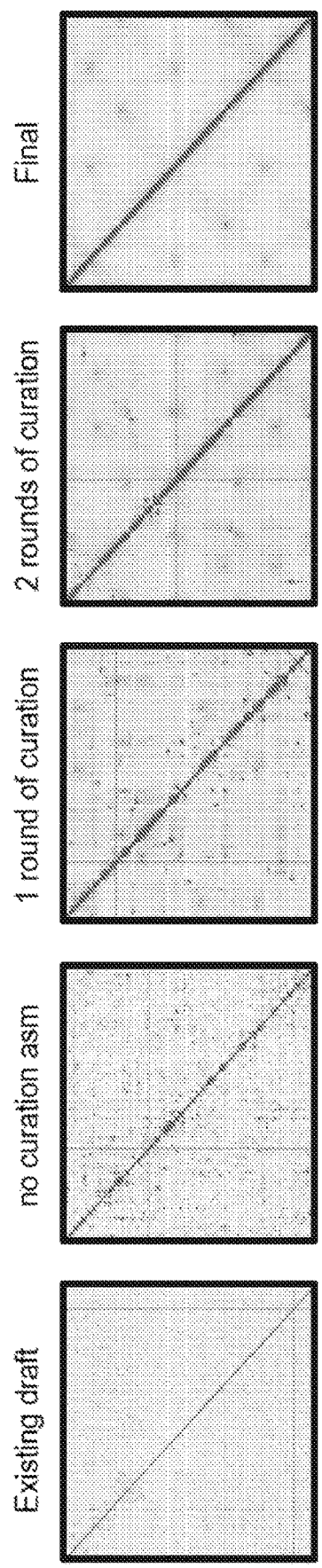
FIG. 15—Shows a set of 3D contact maps and use of such maps in editing and reassembling draft genomes.

The methods disclosed herein may be used to not only assemble genomes but to assess the quality of genome assemblies at the contig, scaffold and chromosome levels for both contiguity and accuracy, i.e. the rate of contigs and scaffold misjoins as well as misassignment to chromosomes) are well-reflected in the 3D contact pattern. See FIGS. 11-13.

The methods herein may be used to generate high-quality end-to-end (whole chromosomes) assembly of large genomes, including de novo assembly from short-read data as well as the ability to edit and reassemble published assemblies. See FIGS. 10 and 11, 12, and 15.

The methods disclosed herein may also be used to create reference-assisted assembly using a genome assembly of a closely related organism or a group of organisms. This is done by identifying synteny blocks between the species and reassembling them into a new genome using the proximity ligation data. See Example 2 and FIGS. 16 and 17.

Figure 18:
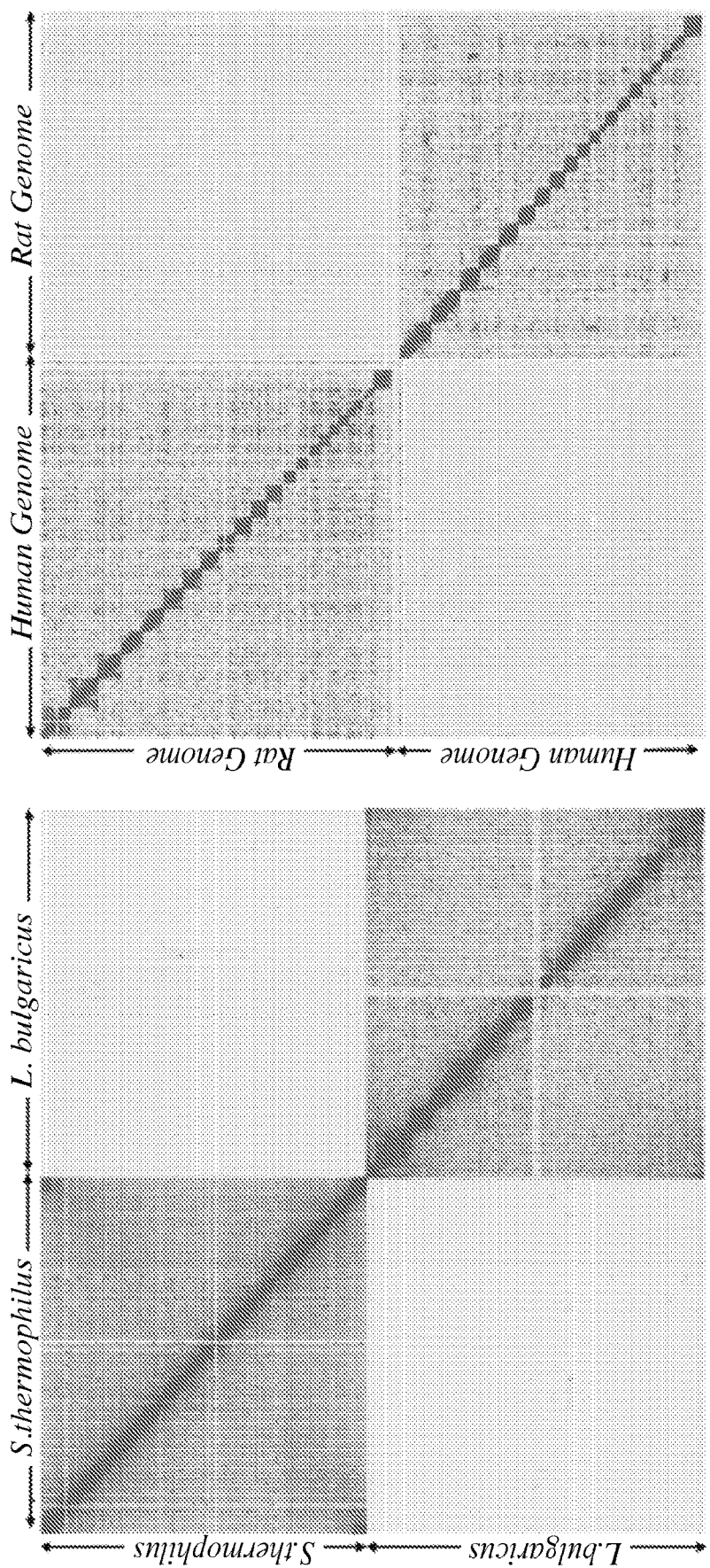
FIG. 18—Shows a set of meta 3D contact map of a 2-component prokaryotic and eukaryotic communities determined at the same time.
Figure 19:
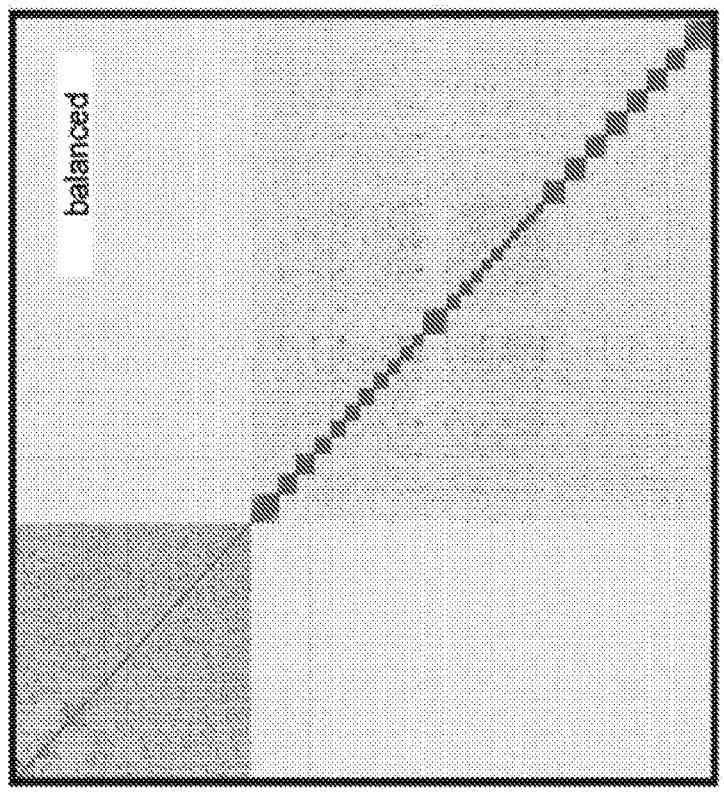
FIG. 19—Shows a meta 3D contact map of mosquito and cow genomes derived from a mosquito fed cow blood prior to sequencing and a cow genome assembly from genomic material isolated from cow milk.
Figure 19:
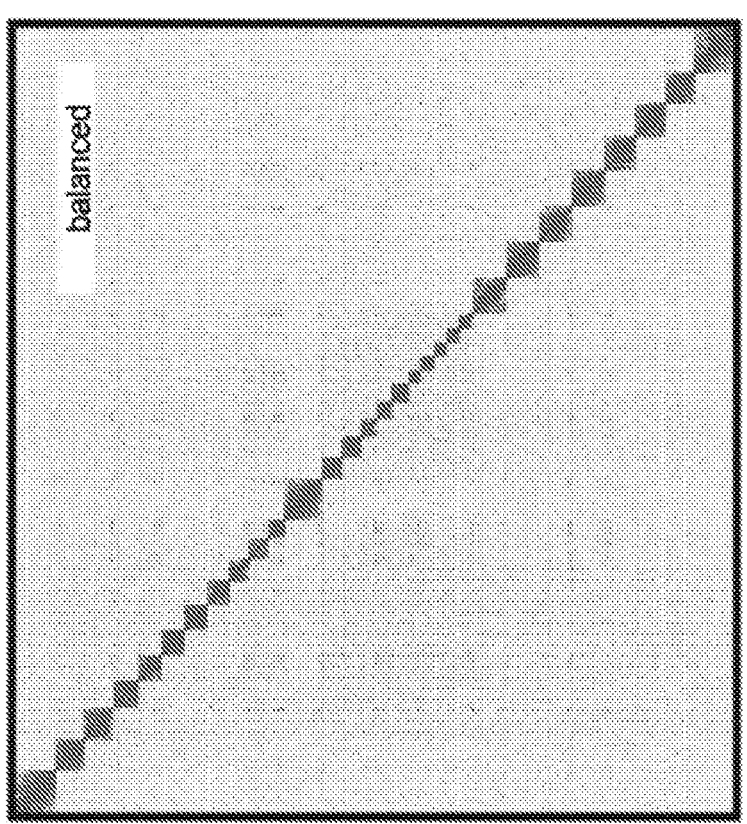

The methods disclosed herein may also be used to assemble/identify genomes in a metagenomic context. The applications include, but are not limited to, sequencing prokaryotic, eukaryotic and mixed communities from the same samples. For example, the methods may be used, among other metagenomic applications, to sequence the metagenome with the host genome, disease vectors and pathogens, and disease vectors and host etc. See FIGS. 18 and 19.

Figure 20:
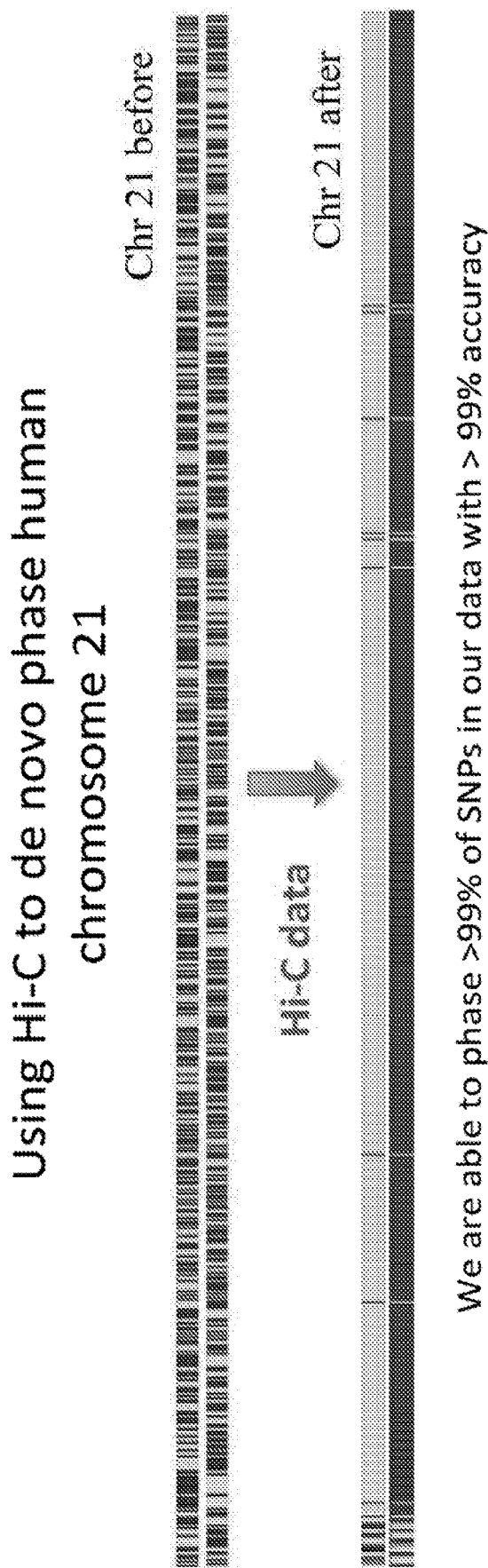
FIG. 20—Shows a 3D contact map to de novo phase human chromosome 21.
Figure 21:
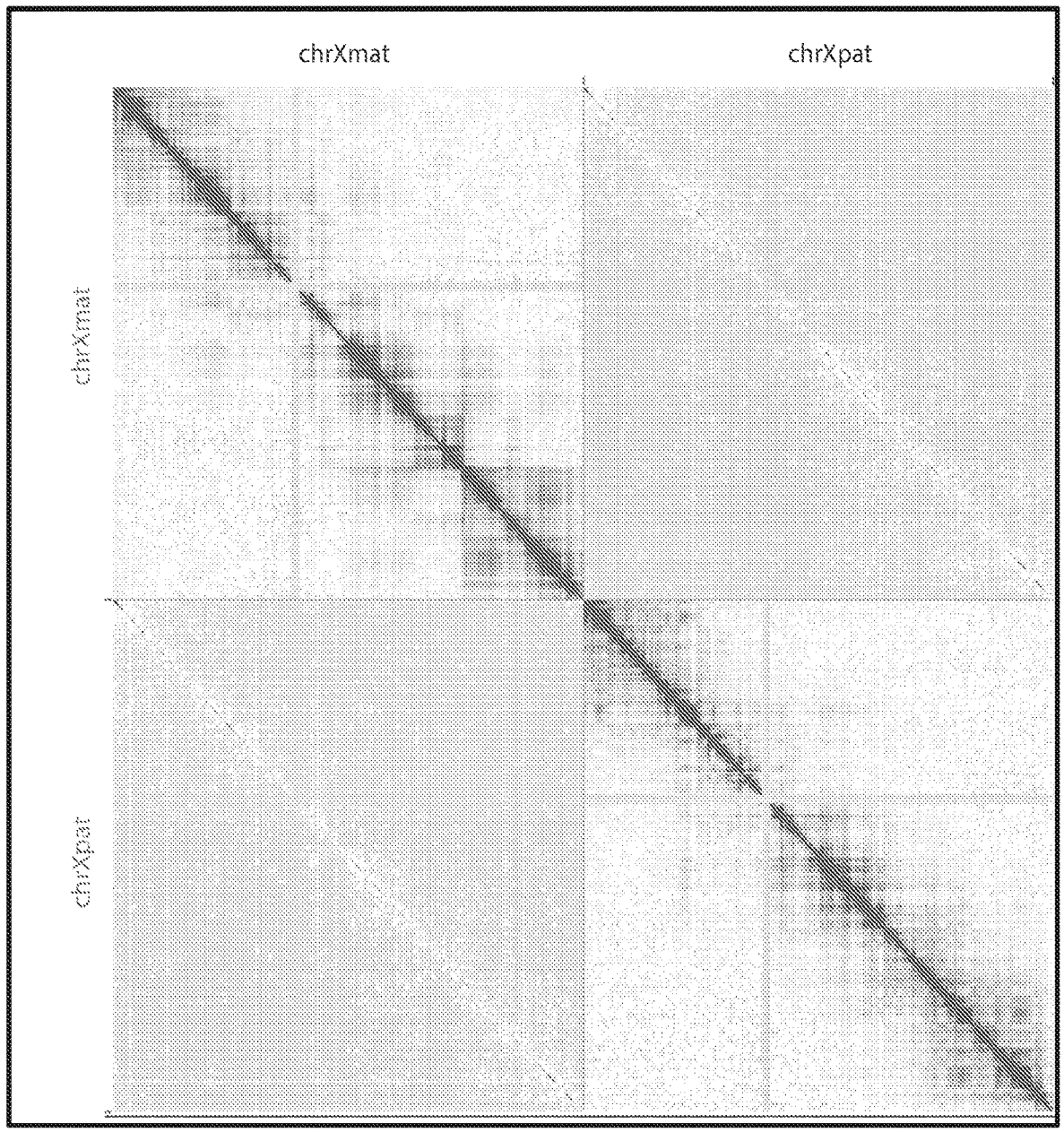
FIG. 21—Shows a 3D contact map and use in phasing and quality assessment of the human chromosome X.

The methods disclosed herein may also be used to assist in phasing of the human genome. Phasing can be performed de novo and using population data. The 3D contact maps can be used to assess the accuracy of phasing results. See FIGS. 20 and 21.

Figure 22:
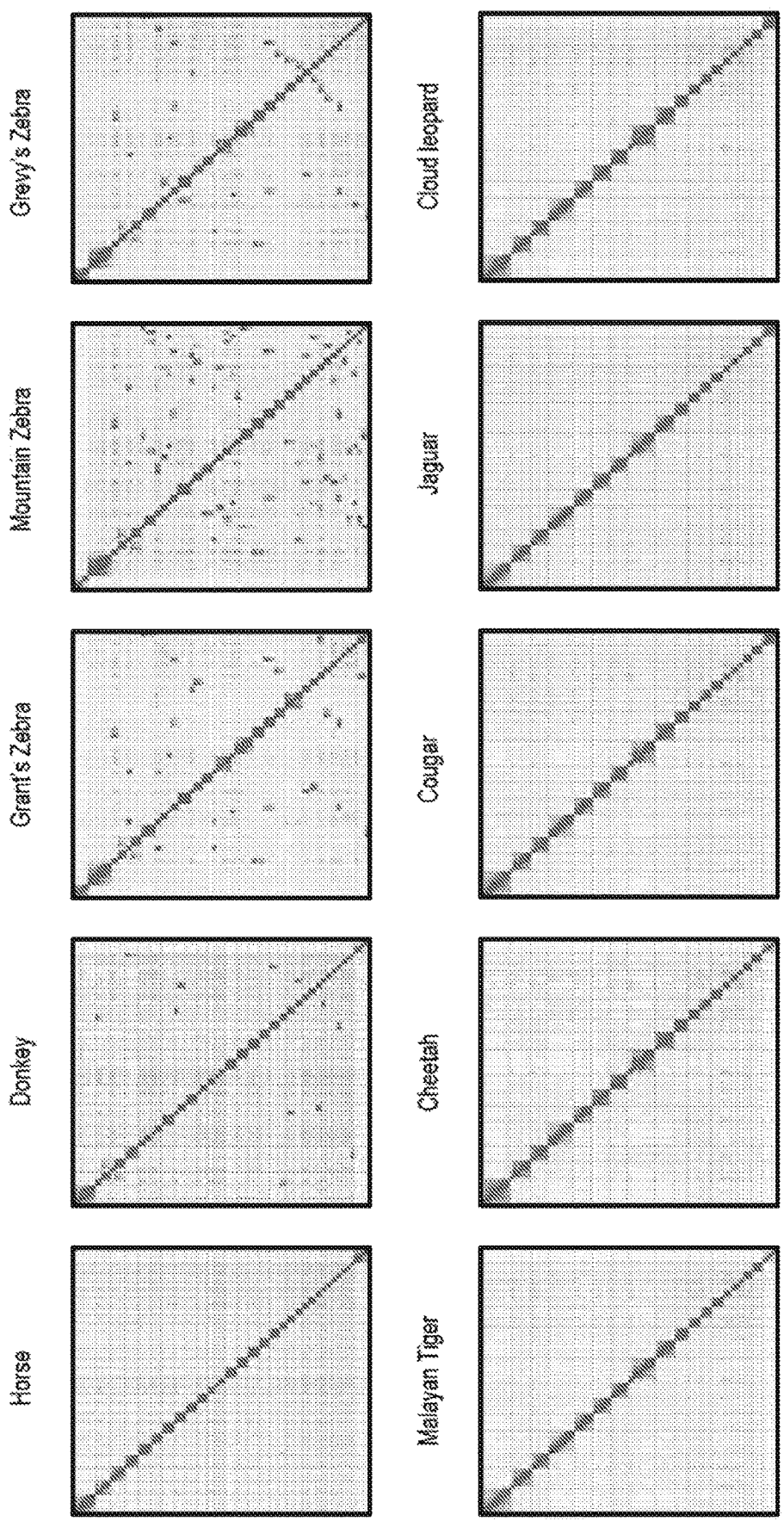
FIG. 22—Shows a set of 3D contact maps and use of such maps for visualizing karyotype evolution.
Figure 23:
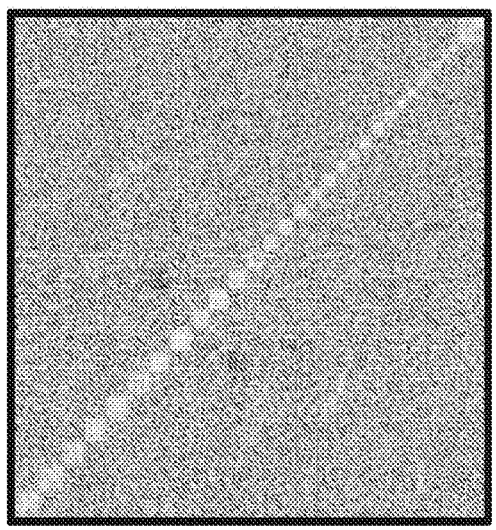
FIG. 23—Shows a set of 3D contact maps and use of such maps for identification of centric fusion polymorphism in a species.
Figure 23:
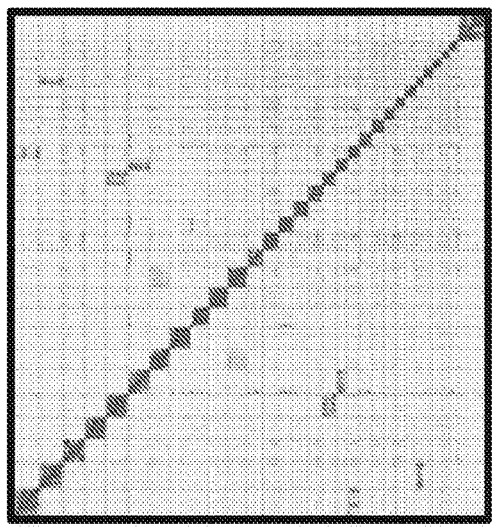
Figure 23:
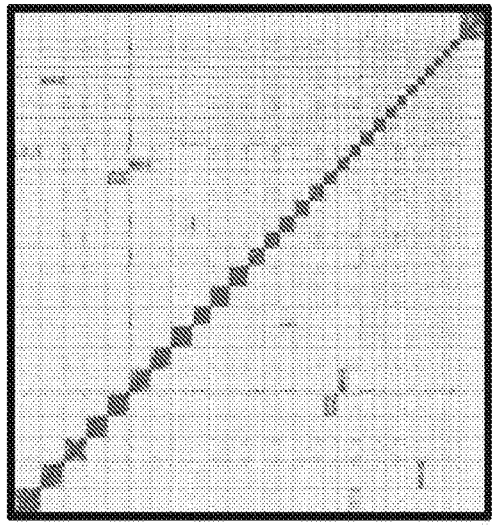
Figure 24:
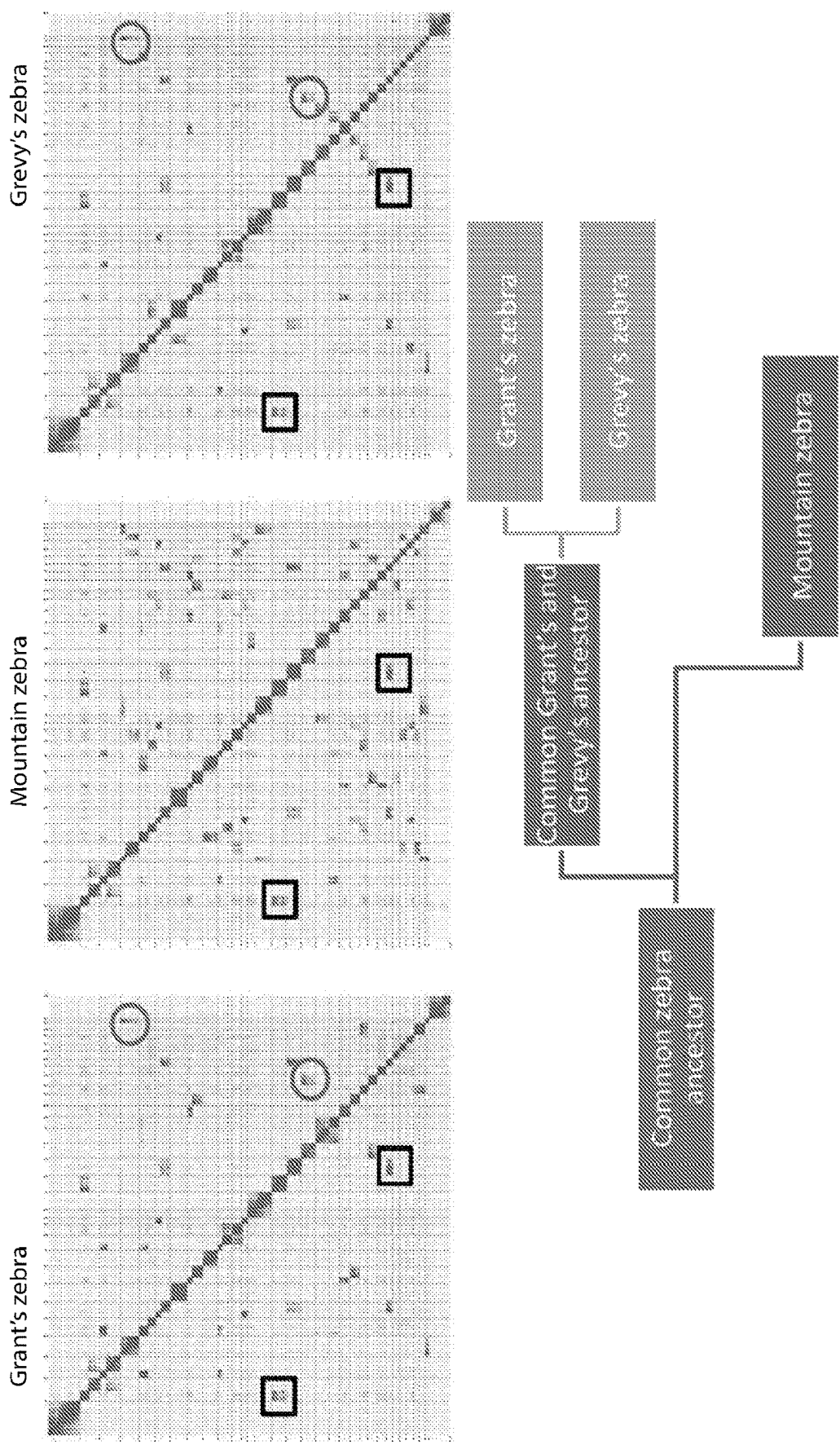
FIG. 24—Shows a set of 3D contact maps and use of such maps to build a phylogenetic tree with karyotype-level 3D contact map data.

The methods disclosed herein may also be used to analyze karyotype evolution in given group of species as well as to detect karyotype polymorphisms, even at low-coverage. The karyotype data can be used to identify phylogenetic relationships, either by itself or with sequence level data. See FIGS. 22-24.

Figure 25:
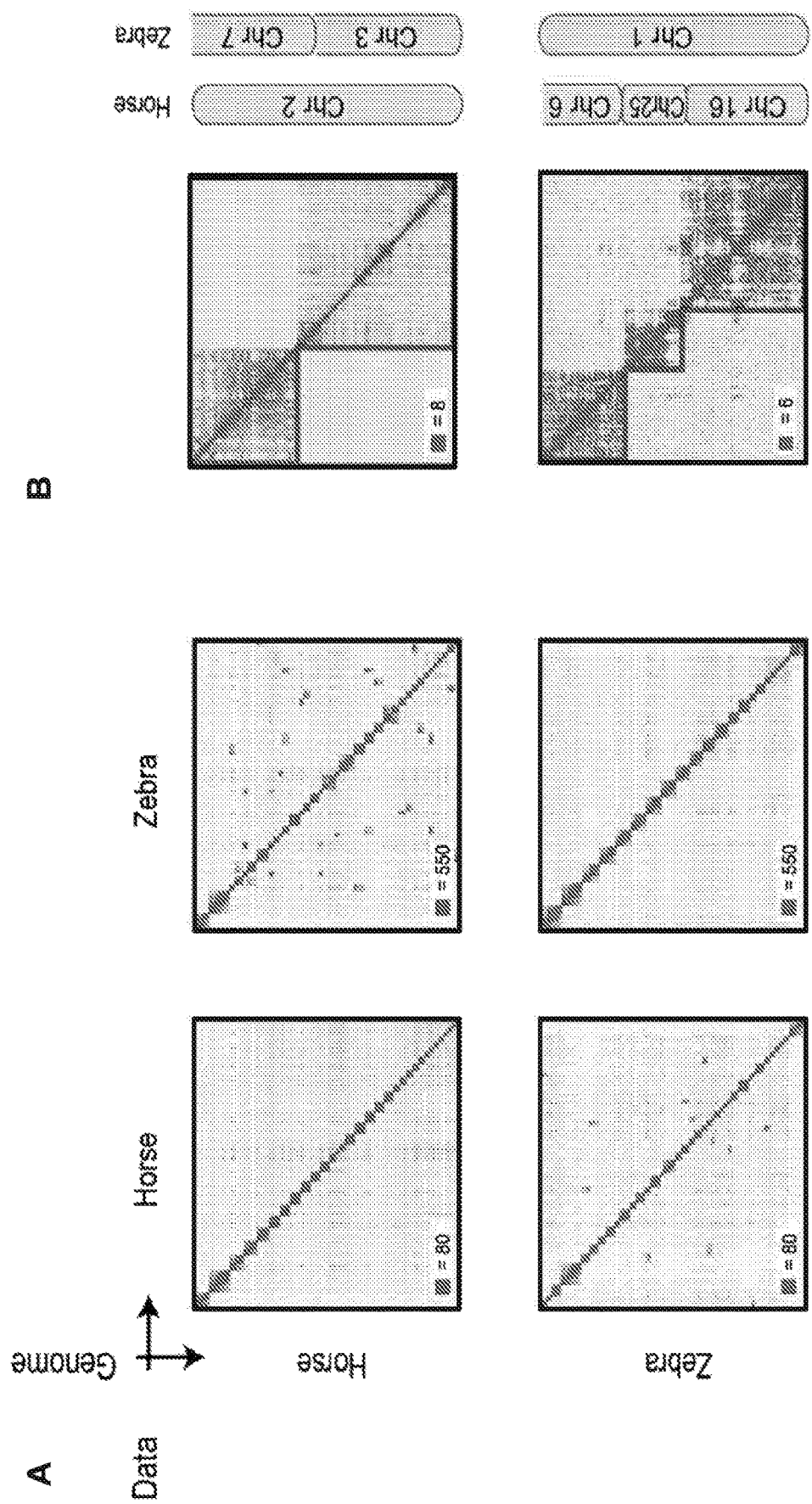
FIG. 25—Shows a set of 3D contact maps and use of such maps to alleviate need for inter-species chromosome painting.

The methods disclosed herein may also be used to substitute for inter-species chromosome painting, including at low coverage. See FIG. 25.

Figure 26:
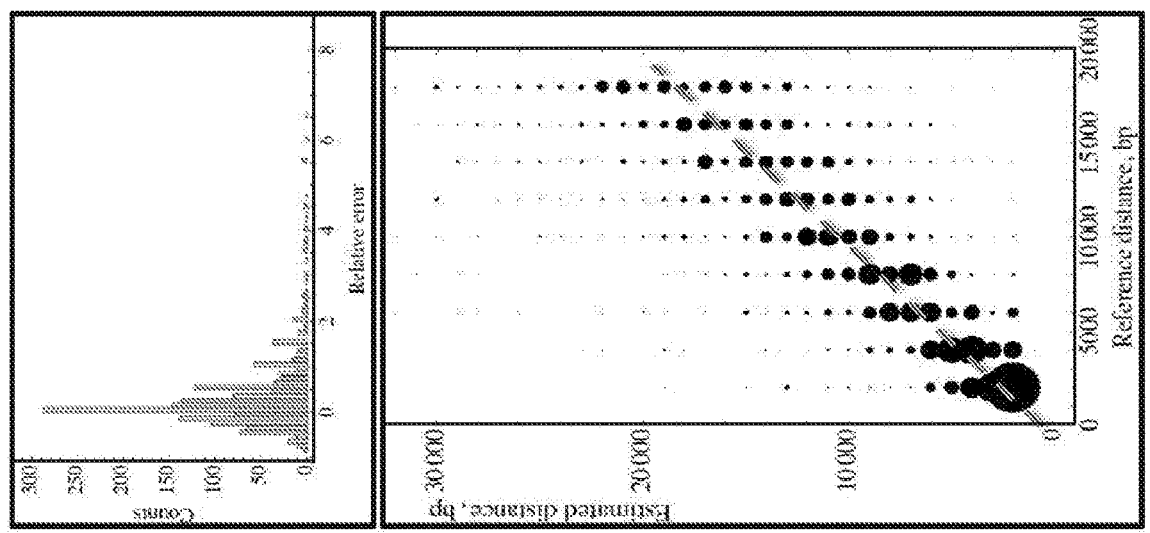
FIG. 26—Shows a set of graphs demonstrating how 3D contact data can be used to estimate gaps between a pair of genomic loci.
Figure 26:
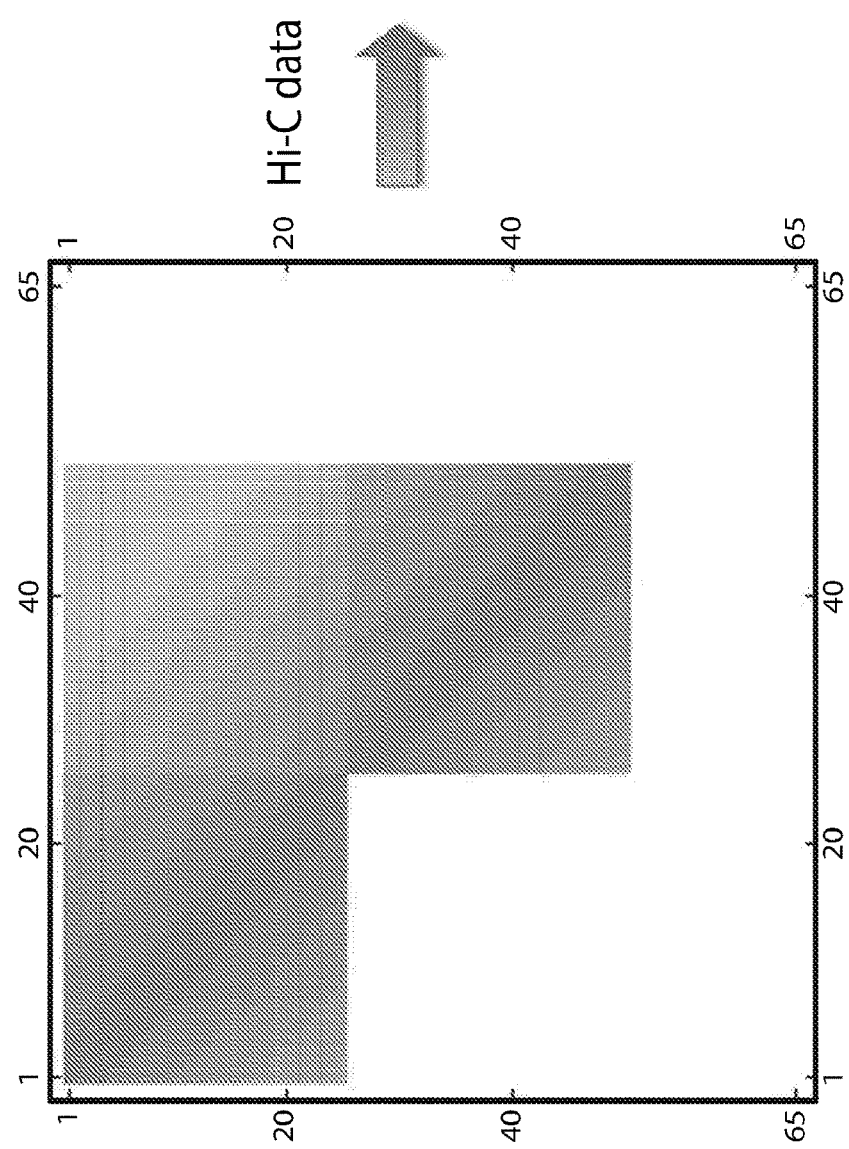

The methods disclosed herein may also be used to estimate the distance along the 1D sequence between any two given genomic sequences. See FIG. 26.

The methods disclosed herein may use the features of 3D contact maps. For example, identification of chromatin motifs in their proper convergent orientation can be use to properly orient other contigs in the assembly. See FIG. 27.

The invention is further described in the following examples, which do not limit the scope of the invention described in the claims.

EXAMPLES

Example 1—De Novo End-to-End Scaffolding of Short Contigs Using Hi-C Data

Disclosed herein is a computer-implemented method called LIGER which takes two inputs: (1) a Hi-C map for a species, and (2) a set of short contigs for the species. LIGER uses a greedy algorithm to join contigs that form frequent contacts with one another. It is able to orient the contigs by checking which contig-ends form contacts with one another more frequently. Because in situ Hi-C data is able to achieve such high-resolution, the rate of misjoins present after using the LIGER algorithm is extremely low: <0.03%.

Three mammalian assemblies using LIGER have been completed: *Homo sapiens* (human, NA12878), *Saimiri boliviensis* (squirrel monkey), and *Canis lupus familiaris* (dog, golden retriever).

Figure 6:
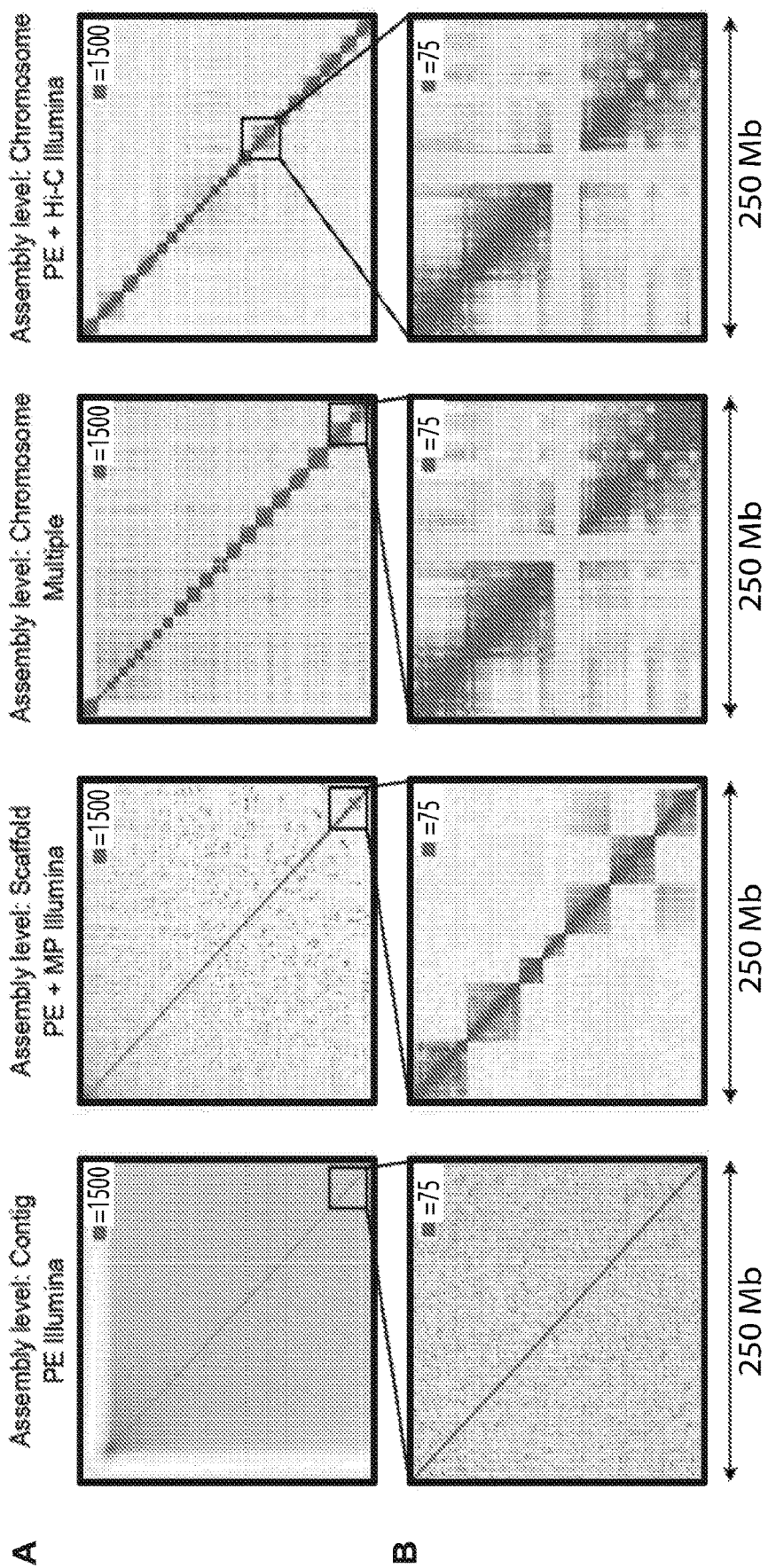
FIG. 6—Shows that a Hi-C data enables end-to-end assembly of entire chromosomes from short contigs. A Hi-C map also provides a simple way to assess the quality of an assembly. A: Human genome assemblies created by different technologies as visualized by in situ Hi-C data. Presented are short read paired-end lllumina {DISCOVAR de novo assembly produced as part of the preliminary dataset}; paired-end+mate pair and Fosmid data {Gnerre et al. 2011}; hg19; and a de novo Hi-C assembly created by applying the methods disclose herein to DISCOVAR contigs. Contigs, correct scaffolds, and chromosomes manifest themselves in Hi-C maps as bright, relatively uniform squares along the diagonal. Off-diagonal squares indicate nearby pieces of the genome that were not correctly scaffolded. The methods disclosed herein analyze these strong off-diagonal signals to order and orient contigs into chromosome-sized scaffolds. In an assembly featuring end-to-end chromosomal scaffolds, the number of squares along the diagonal equals the number of chromosomes; so long as there are no errors, bright blocks are not seen off the diagonal. No mis-assembly errors are seen in generated de novo human assembly. B: Zoomed in portions of the map {250 Mb×250 Mb}. Note that the centromere gap in the Hi-C assembly has been added for ease of visual comparison. Further, Hi-C data make it possible to calculate gap sizes in an automated fashion.
Figure 7:
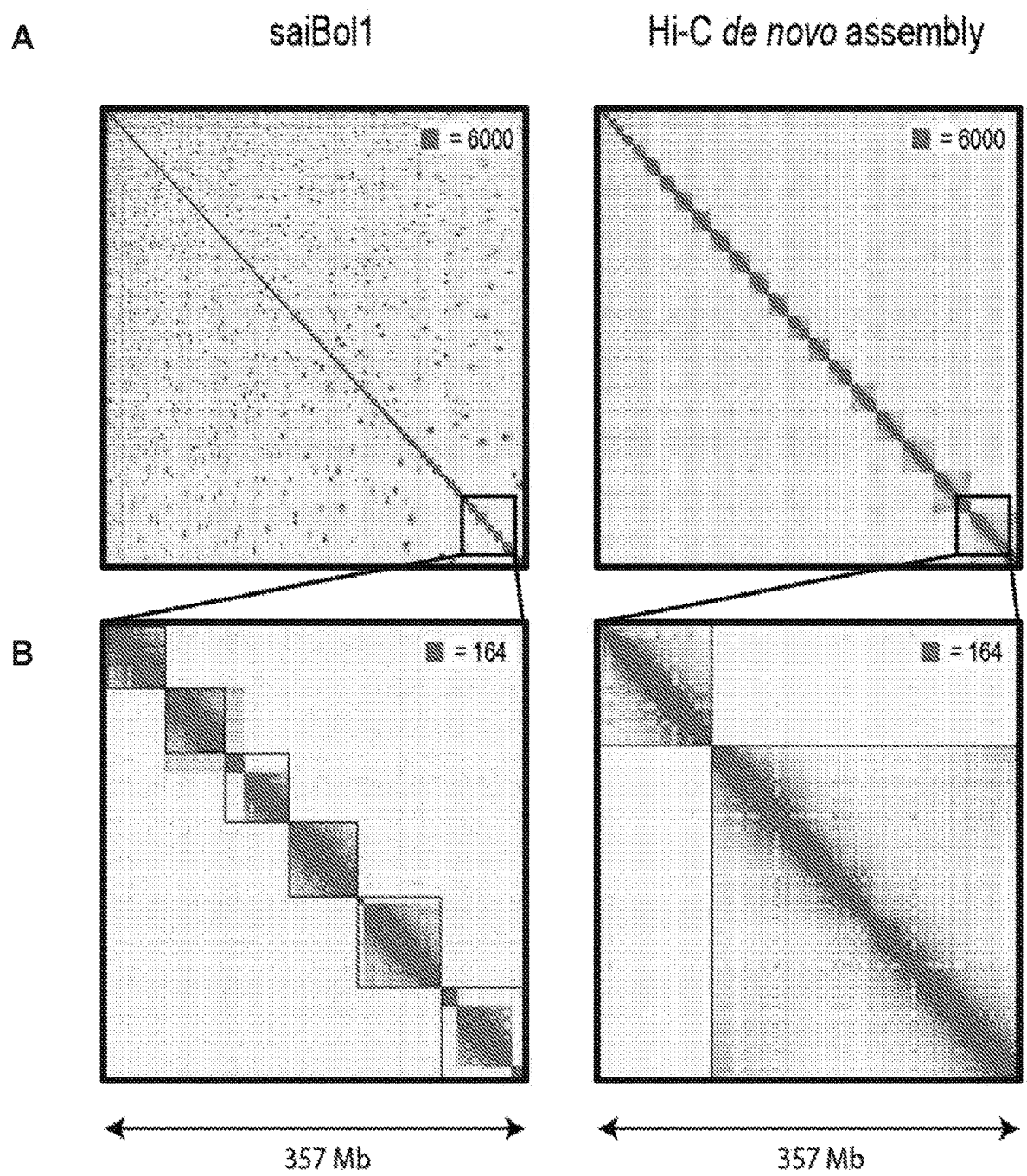
FIG. 7—Shows Hi-C de novo assembly of *Saimiri boliviensis* (squirrel monkey) as compared to saiBol1, the currently available assembly for the species. A: Genome-wide view, with scaffolds in both assemblies sorted by size. The number of blocks in the Hi-C assembly is 22, the number of squirrel monkey chromosomes. This indicates that the Hi-C assembly has successfully generated an end-to-end scaffold for each chromosome. B: Zooming in on the largest scaffolds.
Figure 8:
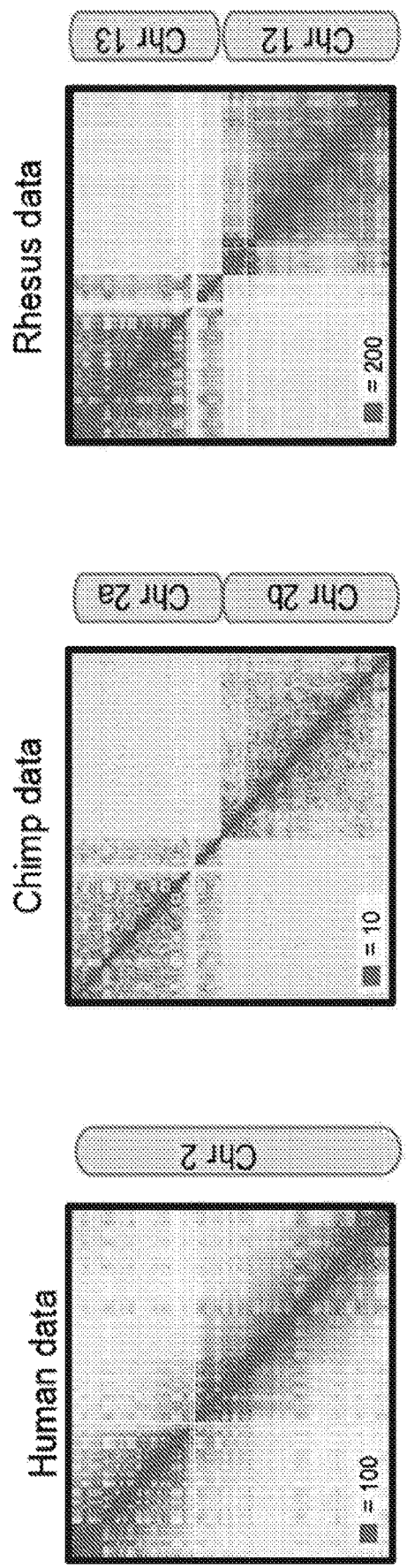
FIG. 8—Shows in one example embodiment, maps of human chromosome 2 generated using methods disclosed herein indicate that chromosome 2 is a result of fusion of two ancestral chromosomes: when chimp or rhesus Hi-C data are aligned to the human genome, the formation of depleted anti-diagonal blocks indicates the breakpoint.
Figure 9:
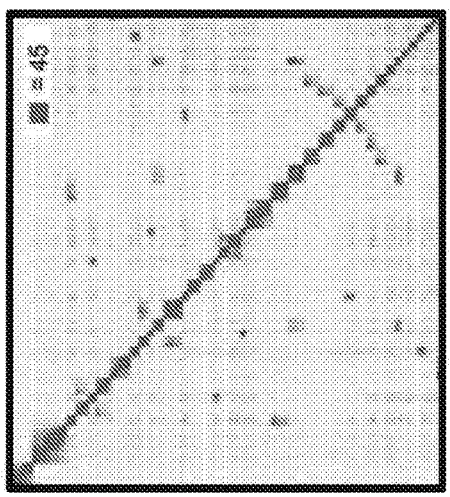
FIG. 9—Shows assisted assembly of three zebra species: Grant's Zebra, Mountain Zebra, and Grevy's Zebra. In panel A, the data for each species are aligned to the horse genome. Each off-diagonal block corresponds to a breakpoint (note that the matrix is symmetric, so a breakpoint yields two corresponding off-diagonal blocks., B: Shows the data aligned to an assembly generated using these data. The choice of chromosome order and orientation is arbitrary. These assemblies allowed exact recapitulation of karyotypic analyses performed using microscopy to determine syntenic blocks between horse and zebra.
Figure 9:
Figure 9:
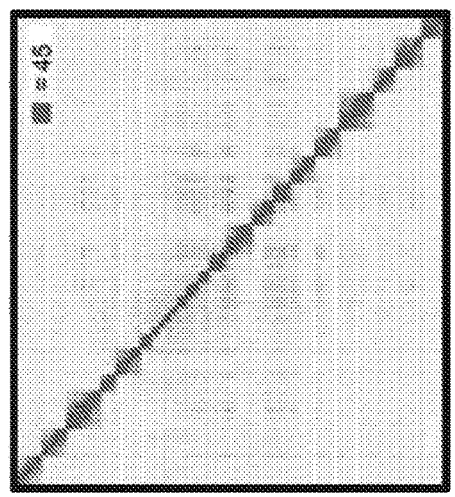
Figure 9:
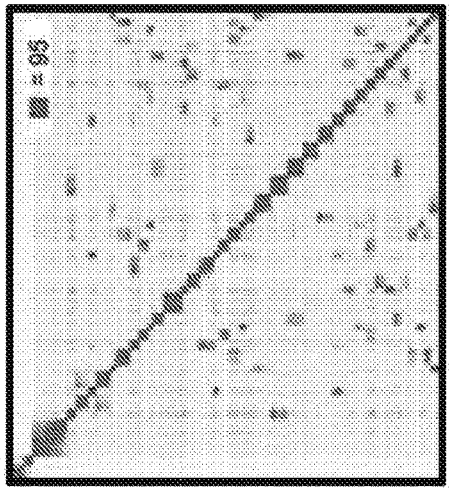
Figure 9:
Figure 9:
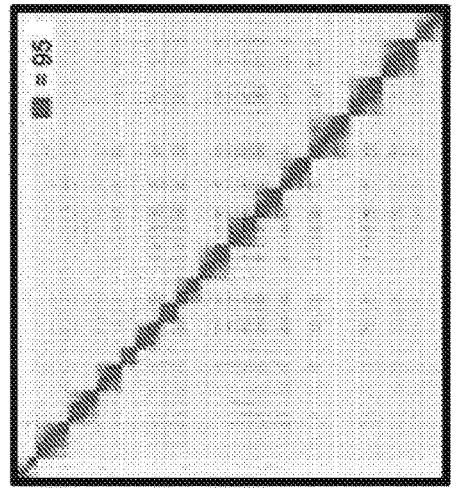
Figure 9:
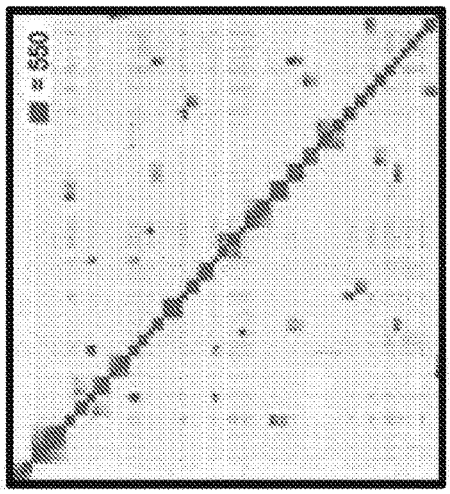
Figure 9:
Figure 9:
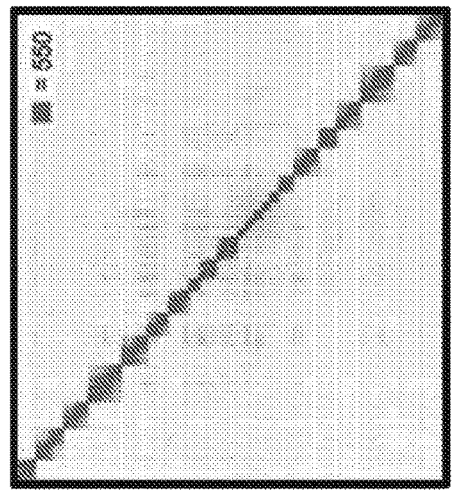
Figure 10:
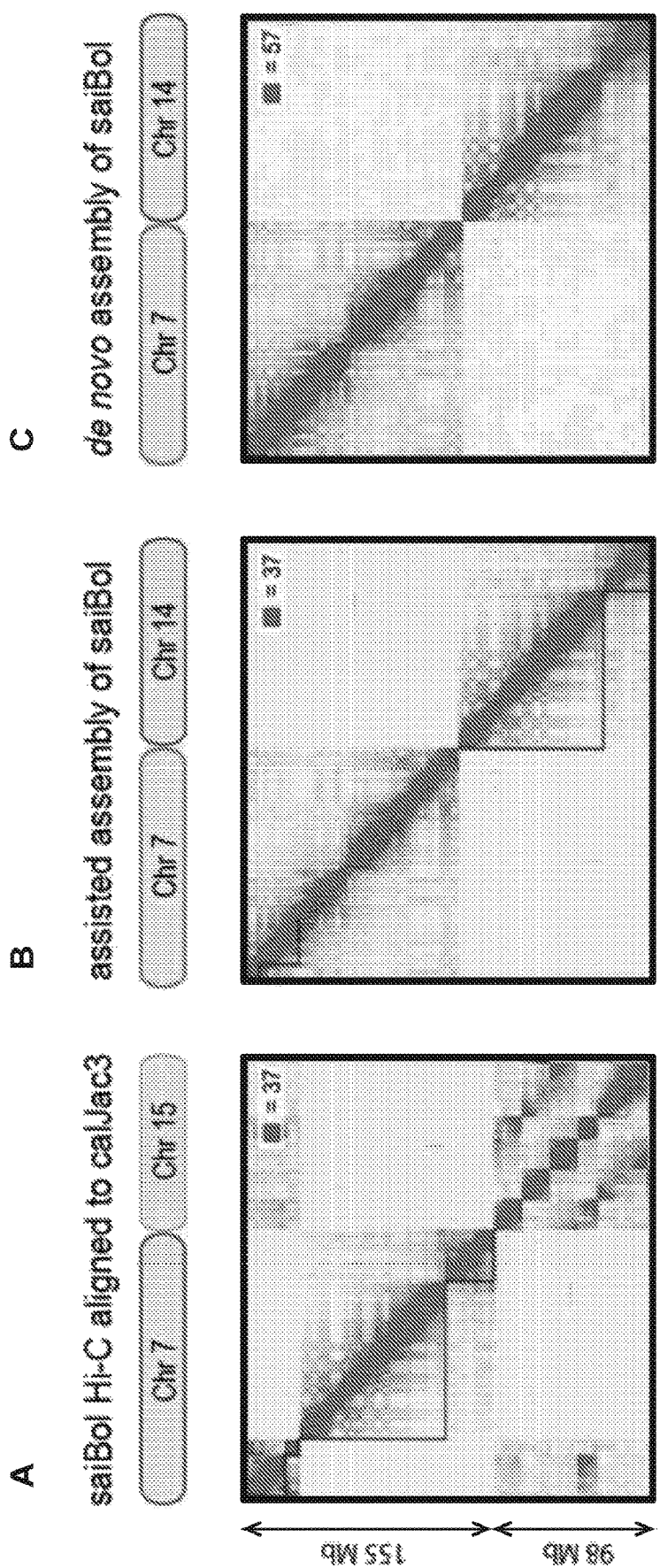
FIG. 10—Shows assisted Hi-C assemblies correspond perfectly to de novo assemblies. A: *S. boliviensis* data aligned to the common marmoset assembly {fragment}. Note the outlined breakpoints in the map suggesting karyotypic differences between the two species. B: Assisted assembly of *S. boliviensis* based on marmoset; syntenic blocks are outlined, illustrating how the algorithm shuffles one genome to determine another. C: De novo assembly of the same pair of chromosomes. *S. boliviensis* chromosomes are numbered according to size, from larger to smaller. B and C are indistinguishable.

By combining Hi-C and DNA-Seq as described above, de novo assemblies of all three species containing individual scaffolds spanning every single chromosome from end-to-end were generated. These assemblies demonstrate the feasibility of assembling short reads using in situ Hi-C data. For instance, in squirrel monkey, the scaffold N50 is now 109 mb which is more than a 1000-fold improvement over previous results using an existing method called DISCOVAR. The results in other species are comparable. See FIGS. 6 and 7.

visualizing and exploring karyotypic relationships at arbitrary resolution. Thus, the method may also be used to determine karyotypic relationships between the same species. For example, the method may be used to assess karyotypic relationships between clinical human samples and a reference contact map representing healthy tissue or a particular disease state.

In addition, the method may be used to complete an assembly of a test genome "A." For example, using a simple block detection algorithm, the method enables accurate reconstruction of a test genome "A" using only Hi-C data and a reference genome "B." This is accomplished by "shuffling" the genome of test genome A to recapitulate the effects of breakpoints, then using the Hi-C reads to correct the "shuffled" genome. The assembly may then be completed by variant calling to identify single nucleotide differences between the "shuffled" test genome "A" and the reference genome "B."

To date, twelve assisted assemblies have been completed using this methodology: *S. boliviensis* (Squirrel monkey), *E. quagga boehmi* (Grant's zebra), *E. zebra* (Mountain zebra),

TABLE 1

Assembly statistics for current de novo Hi-C assemblies in human and dog as compared to existing assemblies

| Assembly | Total Bases in all Contigs (excluding N) | Scaffold N50 (Mb) | Largest Scaffold Length (Mb) | # of bases in chromosome scaffolds | % observed bases in chromosome scaffolds |
|---|---|---|---|---|---|
| Human (hq19) | 2,661,327,131 | 155.3 | 249.2 | 2,861,327,131 | 93.60% |
| Human (hq38) | 3,049,315,783 | 145.1 | 246.9 | 3,049,315,783 | 99.75% |
| Human: DISCOVAR | 3,057,108,282 | 0.2 | 1.3 | n/a | n/a |
| Human: DISCOVAR + Hi-C | 3,057,108,282 | 136.3 | 220.7 | 2,632,621,009 | 86.11% |
| Dog (canFam3) | 2,392,715,236 | 63.2 | 123.9 | 2,327,633,984 | 93.18% |
| Dog: DISCOVAR | 2,497,953,281 | 0.2 | 2.1 | n/a | n/a |
| Dog: DISCOVAR + Hi-C | 2,497,963,281 | 61.1 | 116.9 | 2,238,511,747 | 89.61% |
| Rhesus (rheMac3) | 2,639,129,266 | 150.1 | 206.5 | 2,562,947,788 | 86.30% |
| Chimp (canTro4) | 2,902,322,413 | 144.0 | 216.5 | 2,756,176,116 | 83.28% |
| Squirrel monkey (saiBol1) | 2,477,131,095 | 18.7 | 65.9 | n/a | n/a |
| Tarsfer (tarSyr2) | 3,405,738,560 | 0.4 | 4.0 | n/a | n/a |

Figure 16:
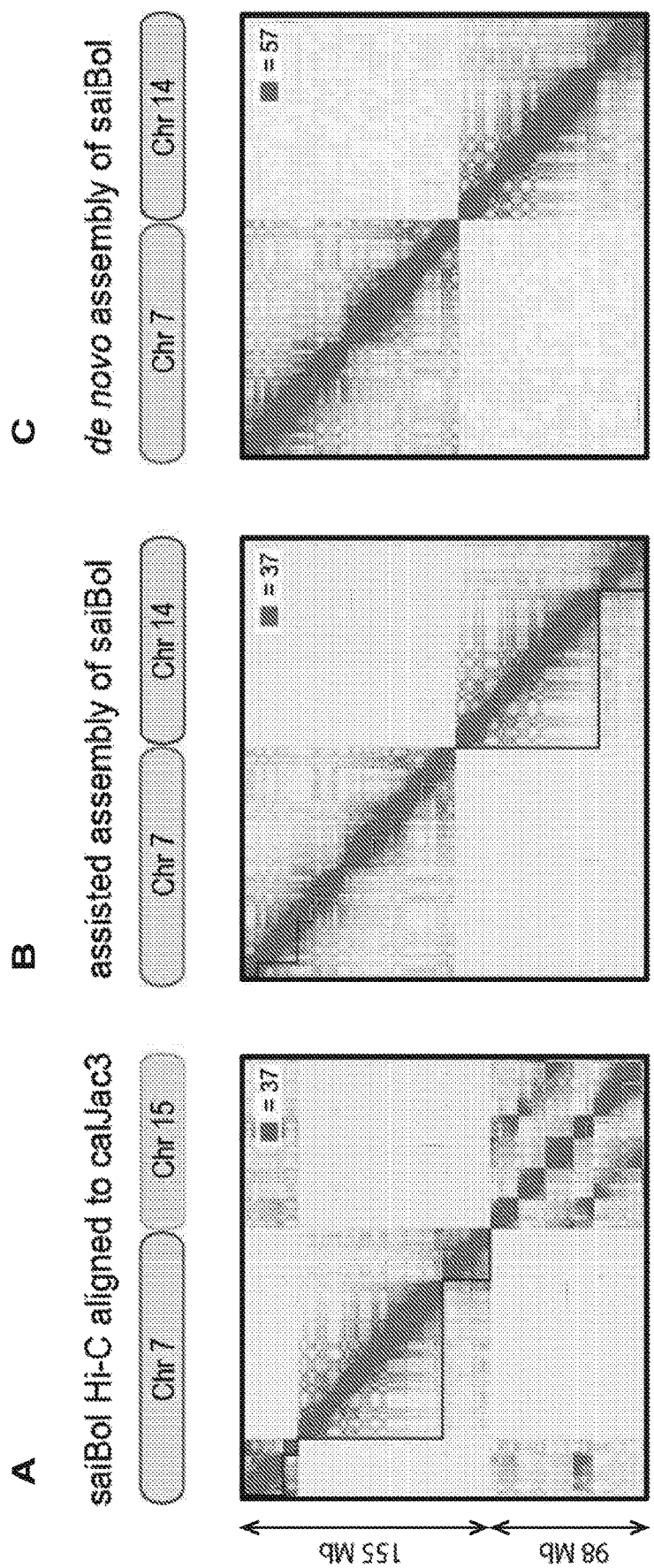
FIG. 16—Shows a set of 3D contact maps showing assisted assembly of the squirrel monkey genome from the common marmoset genome and comparison to a de novo assembly of the same species.
Figure 17:
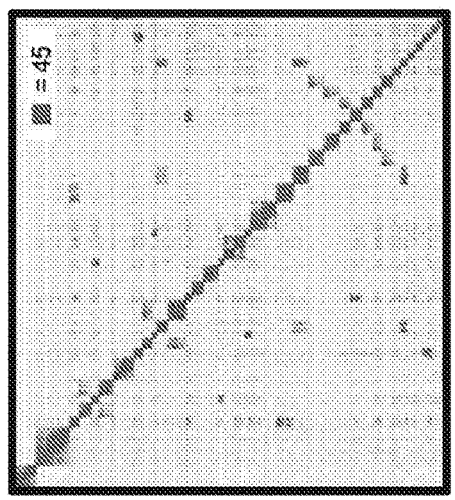
FIG. 17—Shows a set of 3D contacts maps showing reference-assisted assembly of 3 zebra genomes from a horse genome.
Figure 17:
Figure 17:
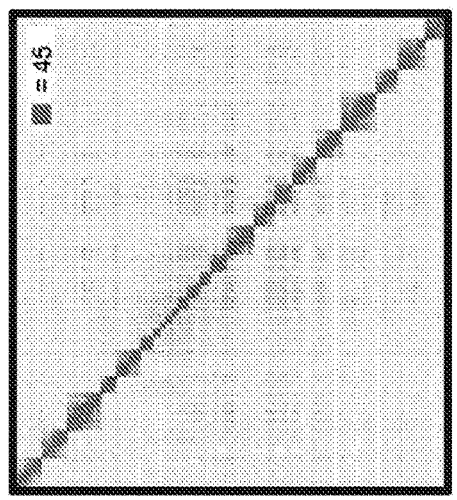
Figure 17:
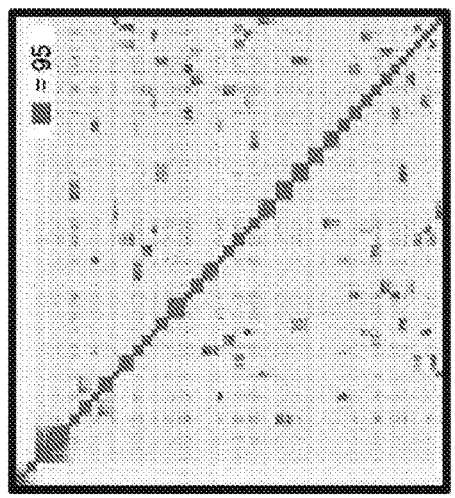
Figure 17:
Figure 17:
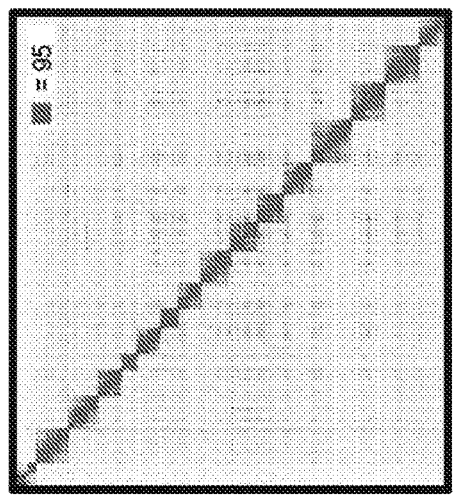
Figure 17:
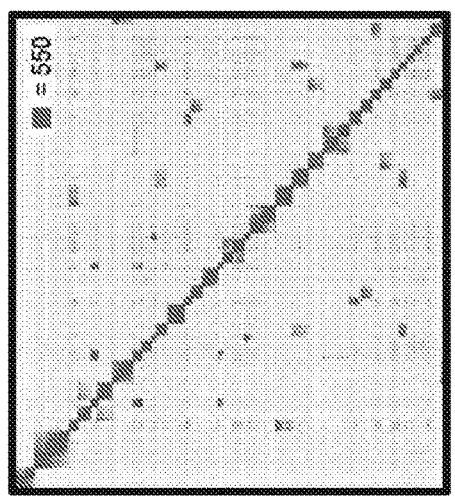
Figure 17:
Figure 17:
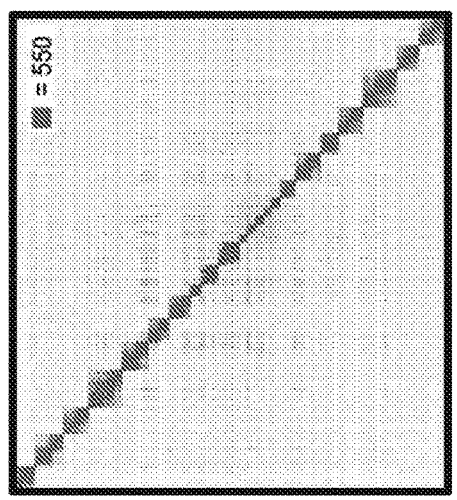

Example 2—Use of Hi-C Data to Derive, Order, Orient, and Modify Syntenic Contigs from a Closely Related Genome The synteny relationships between species A and species B manifest very clearly in "cross-species" contact maps. Cross-species contact maps are generated as follows: to create an AB contact map, a Hi-C dataset for species A is aligned to closely related species B. From said alignment, breakpoints are very clearly observed in cross-species contact maps. They manifest as follows: suppose a single ancestral chromosome remained intact in zebra but has broken into two chromosomes in horse. Then a zebra/horse contact map will show intense interactions between the two chromosomes, manifesting as two bright off-diagonal blocks. Conversely, suppose the two ancestral chromosomes are joined in horse, but not in zebra. Then a zebra/horse contact map will show strongly depleted off-diagonal blocks in the intra-chromosomal square corresponding to the single horse chromosome (FIG. 17). Smaller-scale rearrangements can be identified in a similar manner (FIG. 16). In this fashion, the contact map encodes all breakpoints that distinguish between a pair of species. Such maps can thus be viewed as a high-throughput, high-resolution method for and *E. grevyi* (Grevy's zebra), *E. africanus asinus* (Domestic donkey), *Macaca mulatta* (Rhesus monkey), *Homo sapiens* (Human, Coriell sample NA12878), *Panthera tigris jacksoni* (Malayan tiger), *Acinonyx jubatus* (Cheetah), *Panthera onca* (Jaguar), *Puma concolor* (Cougar), and *Neofelis nebulosa* (Clouded leopard). These assemblies yielded end-to-end scaffolds for every chromosome.

Assisted assemblies correspond to de novo assemblies discussed in Example 2. See FIG. 16.

Example 3

Three end-to-end genome assemblies of mosquito species were generated. Two are end-to-end genome assemblies of *Aedes aegypti*, which spreads viral diseases such as yellow fever, dengue, chikungunya, and Zika to humans (Assembly #1: contig N50, 81 kb; scaffold N50, 419 Mb. Assembly #2: contig N50, 4.05 Mb; scaffold N50, 430 Mb.) The third is an end-to-end assembly of *Culex quinquefasciatus*, which spreads West Nile virus and St. Louis encephalitis virus (contig N50, 26 kb; scaffold N50, 200 Mb). All three were generated by combining prior assemblies with in situ Hi-C data, demonstrating that Hi-C enables reliable, end-to-end genome assembly from a variety of contig types.

These assemblies were used, along with a published genome for the malaria vector *Anopheles gambiae*, in order to examine the evolutionary relationships among mosquitoes. An almost perfect one-to-one correspondence exists between the chromosome arms of *Ae. aegypti, Cx. quinquefasciatus*, and *An. gambiae*, suggesting that the chromosome arms in all three species descend from chromosome arms that were present in their most recent common ancestor, which lived approximately 150-200 million years ago. Although the order of conserved DNA sequences is extensively rearranged within each chromosome arm, DNA sequences rarely move from one chromosome arm to another. Similarly, breakage and fusion events affecting mosquito chromosomes almost never alter the content of individual arms.

Furthermore, the chromosome arm identity can be traced back to *Drosophila melanogaster*, suggesting that many chromosome arms in extant Dipterans (true flies) descend from ancestral structures more than 250 million years old.

Due to its role in the spread of the Zika virus in the Americas, *Ae. aegypti*—an important mosquito vector of many human diseases—is causing a new wave of widespread concern. The lack of an end-to-end genome assembly limits our understanding of the biology of this major arbovirus vector and hinders efforts at disease control.

To aid in the response to Zika virus, two end-to-end assemblies of the *Aedes aegypti* genome were generated. An end-to-end assembly of the *Culex quinquefasciatus* genome was also generated because it is an important disease vector and would facilitate comparative analyses of the mosquito family.

Results

Two End-to-End Assemblies of *Aedes aegypti* were Created by Combining Publicly Available Data with Hi-C Contact Maps Two assemblies of the *Ae. aegypti* genome were created. Both were created by combining publicly available *Ae. aegypti* genomes with in situ Hi-C data derived from two female *Ae. aegypti* mosquitoes of the Orlando strain. (In situ Hi-C is a method for determining how often pairs of DNA sequences are in physical proximity, in 3D, in cell nuclei Rao et al. Cell 2014, 159(7):1665-80). In both cases, the result is an end-to-end assembly of the *Ae. aegypti* genome. On account of the fact that the assemblies were generated using different input genomes, they are not identical. However, they are highly consistent with one another, supporting the validity of the methods disclosed herein and the suitability of both assemblies for downstream applications.

Briefly, for each publicly available genome, an assembly was performed by using in situ Hi-C data to: (1) split contigs and scaffolds that were erroneously joined in the original genome; (2) determine the order and orientation of the resulting contigs and scaffolds; and (3) merge contigs that correspond to overlapping portions of the genome. We note that the methods we use for (3) are particularly relevant for highly heterozygous genomes, when the contig assemblers fail to correctly collapse homologous sequences, leading to multiple contigs that correspond to the same genomic interval.

The first assembly of *Ae. aegypti* is based on the AaegL2 genome (Nene et al. Science 2007, 316:1718-23), which was generated using Sanger reads (8× coverage) assembled using ARACHNE (Jaffe et al. Genome Research 2003, 13(1):91-96). AaegL2 consists of 4,756 scaffolds spanning 1.3 Gb of sequence, with a contig N50 of 83 Kb and a scaffold N50 of 1.5 Mb.

In situ Hi-C data was used to improve this assembly, resulting in an end-to-end genome of *Ae. aegypti*. This genome, dubbed AaegL4, has a contig N50 of 81 kb and a scaffold N50 of 419 Mb (see Table 2). The AaegL4 assembly is included and labeled SEQ ID NO: 1.

TABLE 2

Assembly statistics for AaegL2 and AaegL4.

|  | AaegL2 | AaegL4 |
| --- | --- | --- |
| Base Pairs | 1,310,076,332 | 1,310,076,332 |
| Number of contigs | 36,204 | 37,966 |
| Contig N50 | 82,618 | 80,812 |
| Number of scaffolds | 4,756* | 3,919 |
| Scaffold N50 | 1,547,048* | 419,154,428** |
| Anchored sequence length | 31.6%* | 96.9% |

*Note that these numbers may be inaccurate due to scaffolding errors in AaegL2.
**This is the length of chromosome 3 in AaegL4, without including gaps. Incorporating inter-contig gap estimates reported by (Nene et al. 2007), which was not validated, would increase the scaffold N50 estimate for AaegL4 to ~430 Mb.

The second assembly of *Ae. aegypti* is based on the work of Kunitomi and colleagues working in the laboratory of Raul Andino and in collaboration with Pacific Biosciences. They generated an assembly of the *Ae. aegypti* cell line Aag2 using Pacific Biosciences long reads (58× coverage) assembled using the Falcon software package ("PacificBiosciences/FALCON" 2016). Their assembly, called Aag2, consists of contigs spanning 1.7 Gb of sequence, with a contig N50 of 1.42 Mb.

It is noted that the length of Aag2 (1.7 Gb) was much greater than that of AaegL2 (1.3 Gb). When Aag2 was examined more closely, many cases in which nearly identical sequences, up to several megabases in length, appeared in exactly two Aag2 contigs were found. These sequences were typically located at or near the end of a contig. There homologies are likely due to undercollapsed heterozygosity in the creation of the Aag2 assembly, and that many of these pairs actually arose from overlapping regions of the *Ae. aegypti* genome. This is consistent with the larger size of the Aag2 assembly, and is an error mechanism that has been reported in some Pacific Biosciences assemblies.

In situ Hi-C data was used to improve this assembly. To eliminate undercollapsed heterozygosity, a step was added to merge contigs when such a merge was supported both by overlapping sequences and Hi-C data. This resulted in a second end-to-end genome assembly of *Ae. aegypti*. This assembly, dubbed AaegCL1 ("*Ae. aegypti* Cell Line 1"), is much shorter than the Aag2 assembly from which it was derived, spanning 1.25 Gb, and is comparable in length to AaegL4. AaegCL1 has a contig N50 of 2.86 Mb and a scaffold N50 of 430 Mb (see Table 3). The improved contiguity of AaegCL1 is due both to the improved contigs and to the efficacy of the overlap recognition step. The AaegCL1 assembly is shared at tinyurl.com/AaegCL1.

TABLE 3

Assembly statistics for Aag2 and AaegCL1. The Aag2 assembly was downloaded from VectorBase Release VB-2016-06.

|  | Aag2 | AaegCL1 |
| --- | --- | --- |
| Base Pairs | 1,723,952,533 | 1,254,343,979 |
| Number of contigs | 3,753 | 2310 |
| Contig N50 | 1,420,115* | 4,014,017 |

TABLE 3-continued

Assembly statistics for Aag2 and AaegCL1. The Aag2 assembly was downloaded from VectorBase Release VB-2016-06.

|  | Aag2 | AaegCL1 |
|---|---|---|
| Number of scaffolds | n/a | 1,715 |
| Scaffold N50 | n/a | 429,750,045** |
| Anchored sequence length | n/a | 96.0%*** |

*This number might be an overestimate as some of the contigs displayed evidence of misassemblies. The contig N50 after the correction step was 1.27 Mb.
**This is the length of chromosome 3 in AaegCL1, without including the gaps.
***This number might be an underestimate as overlapping contigs were merged only in the anchored portion of the genome, making the unanchored set more likely to be enriched in undercollapsed sequences.

In both cases the Hi-C data was used to identify centromeric and telomeric sequences.

Comparison of Hi-C based scaffolds to long contigs and linkage maps confirms the accuracy of this assembly approach.

AaegL4 was publicly shared prior to the availability of the long contigs released by Kunitomi and colleagues Likewise, the long contigs were generated prior to release of AaegL4. As such, the two datasets are independent of one another.

Figure 28:
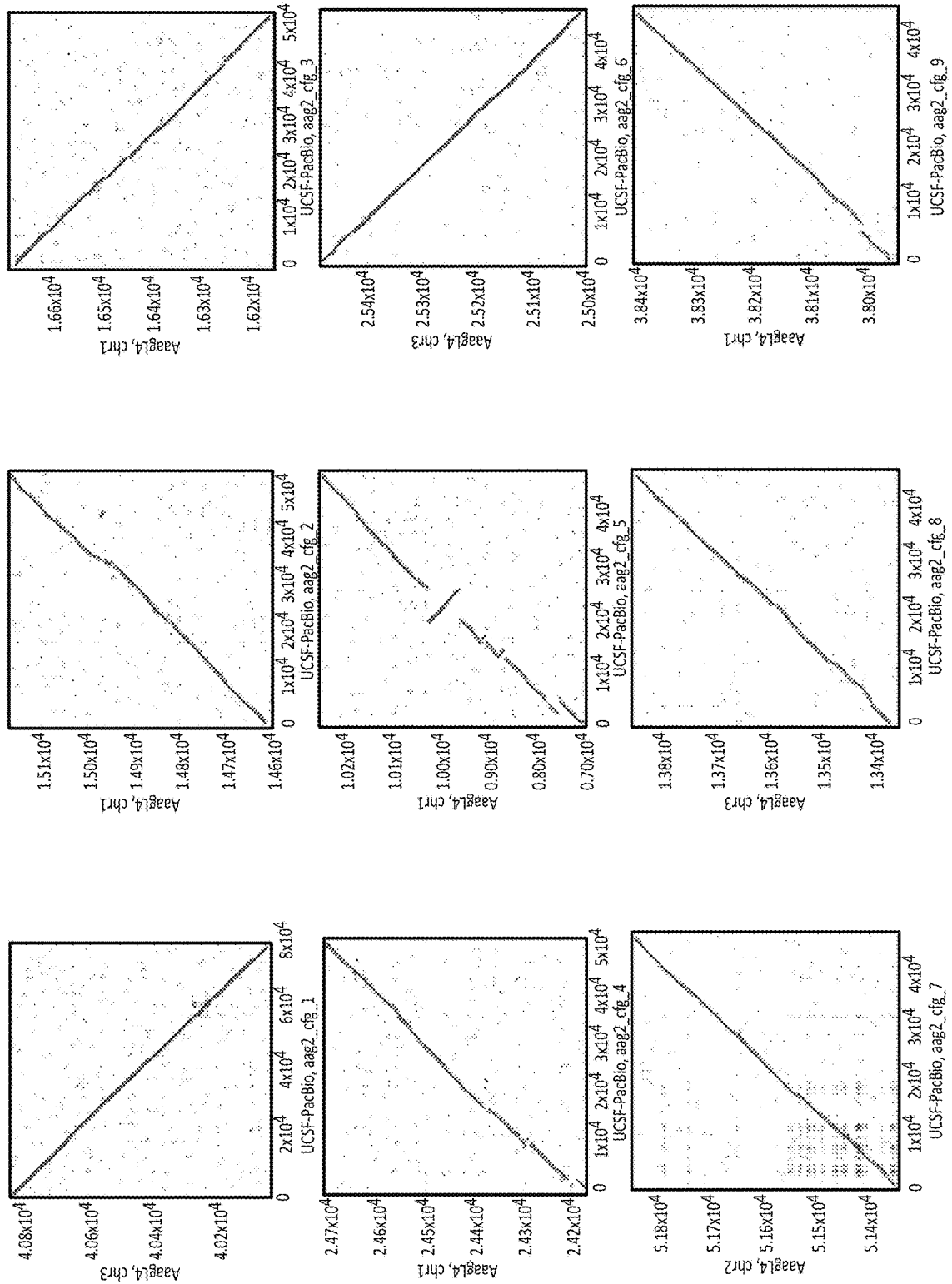
FIG. 28—Shows the AaegL4 genome, generated by ordering and orienting short contigs derived from the work of Nene et al. was aligned to the 9 largest contigs generated by Kunitomi et al. (average length 5.2 Mb) using the LastZ alignment algorithm (Robert S. Harris 2007). The resulting dot plots exhibit a strong correspondence between the two datasets for all contigs except contig #5, which reveals an inversion in the AaegL4 assembly. This inversion was confirmed upon examination of our in situ Hi-C data.

Therefore, in order to validate the overall assembly strategy, AaegL4 was aligned to the nine longest contigs from Kunitomi et al. These nine contigs do not overlap one another; they range in length from 4.5 Mb to 7.9 Mb and, together, span 46.8 Mb. The results are shown in FIG. 28.

We found that these nine contigs spanned hundreds of AaegL4 contigs. (The number of AaegL4 contigs spanned by each of the nine largest Kunitomi et al. contigs ranges from 57 to 133, with a mean of 99.)

Crucially, the observed correspondence between the AaegL4 end-to-end chromosome scaffolds and the Aag2 contigs is extremely strong. The only exception is a large inversion we observed on contig 5. Upon re-examining the data underlying the AaegL4 assembly, we confirmed that this inversion was an error in AaegL4, reflecting a limitation of our current scaffolding algorithms.

To further assess the anchoring accuracy of AaegL4, we analyzed the positions of 106 *Ae. aegypti* genetic markers that had been characterized in prior work (Jiménez et al. Insect Molecular Biology 2004, 13(1):37-44). Each of these markers had been associated with a pair of primers separated by a known genomic distance, and had been assigned to a specific *Ae. aegypti* chromosome on the basis of linkage mapping. When the primer sequences to AaegL4 were aligned, it was determined that, in 92 out of 106 cases, both primers aligned to the anchored portion of AaegL4 and were separated from one another by the expected distance. For 86 of these 92 primer pairs, both primers aligned to the same chromosome in AaegL4 as had been expected based on linkage mapping. In the remaining 6 cases, the chromosomal assignment of the primer pair in AaegL4 disagreed with the assignment that had been determined using linkage mapping. Possible causes of these differences are addressed below, in the Discussion.

Taken together, these results demonstrate the reliability of the AaegL4 scaffolds and thereby confirm the accuracy of the methods disclosed herein.

An End-to-End Assembly of *Culex quinquefasciatus* was Created by Combining Publicly Available Data with Hi-C Contact Maps An assembly of the *Cx. quinquefasciatus* genome was generated based on the CpipJ2 genome (Arensburger et al. Science 2010, 330:86-88), which was generated using Sanger reads (8× coverage) assembled using ARACHNE (Jaffe et al. 2003). CpipJ2 consists of 3172 scaffolds spanning 580 Mb of sequence, with a contig N50 of 28.5 kb and a scaffold N50 of 487 kb.

In situ Hi-C data was used to improve this assembly, resulting in an end-to-end genome of *Cx. quinquefasciatus*. This genome, dubbed CpipJ3, has a contig N50 of 26 kb and a scaffold N50 of 200 Mb (see Table 4). The CpipJ3 assembly is attached and labeled SEQ ID NO: 2 at tinyurl.com/CpipJ3.

TABLE 4

Assembly statistics for CpipJ2 and CpipJ3.

|  | CpipJ2 | CpipJ3 |
|---|---|---|
| Base Pairs | 539,974,961 | 539,974,961 |
| Number of contigs | 48,486 | 48,510 |
| Contig N50 | 28,546* | 26,116 |
| Number of scaffolds | 3,172 | 1,715 |
| Scaffold N50 | 486,756* | 199,942,179** |
| Anchored sequence length | 5% | 97.0% |

*Note that these numbers may be inaccurate due to assembly errors in CpipJ2.
**This is the length of chromosome 3 in CpipJ3, without including gaps.

Despite internal rearrangements, the contents of ancestral chromosome arms are preserved during mosquito evolution The new assemblies allowed for the study of the evolution of the *Ae. aegypti* and *Cx. quinquefasciatus* genomes by comparing them to the genome of *An. gambiae*, a more distantly related mosquito species.

Whole genome alignment between the *An. gambiae* genome, which is 265 Mb long, and the *Ae. aegypti* genome, which is ~1.25 Gb long (AaegL4: 1.3 Gb; AaegCL1: 1.2 Gb). (For AaegL4 and CpipJ3 the liftover of alignments shared via VectorBase were used.) As expected, this analysis identified numerous conserved DNA sequences that were present in both species, comprising a large number of synteny blocks. The typical synteny block size was short relative to the size of the chromosomes in either species.

Figure 29:
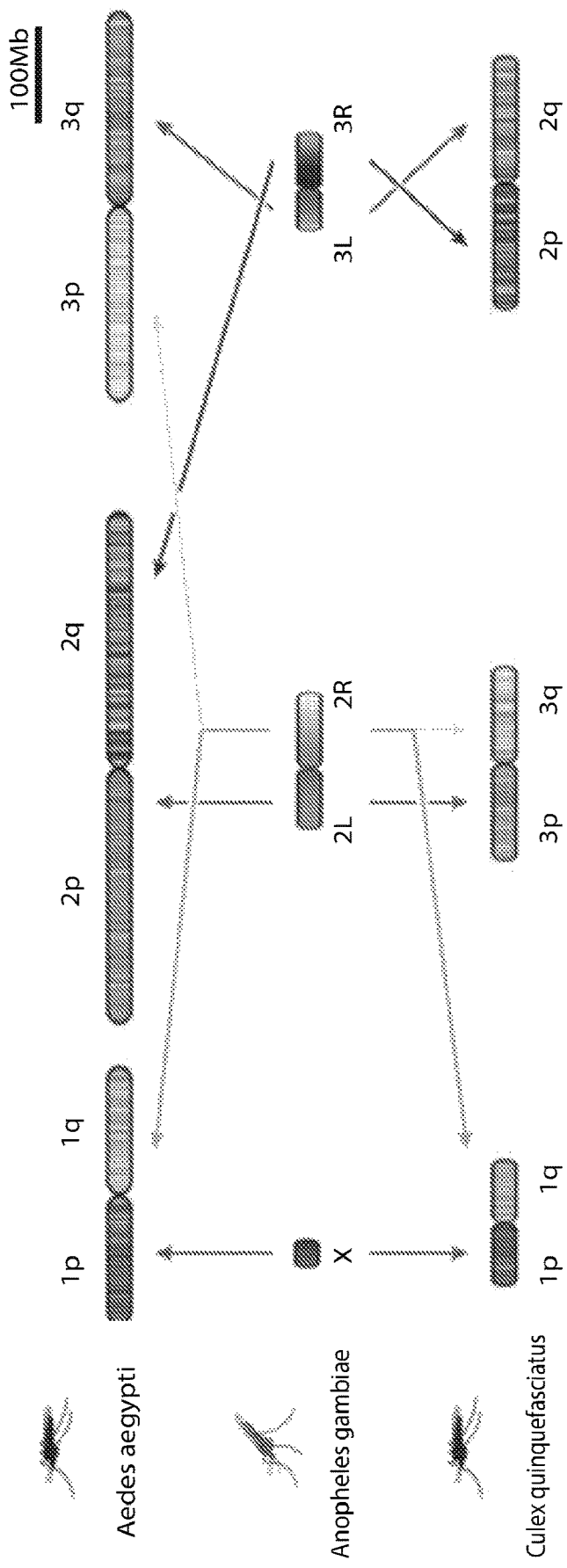
FIG. 29—Shows syntenic relationships between the *Aedes aegypti, Anopheles gambiae* and *Culex quinquefasciatus* mosquito genomes reveal conservation of the contents of ancestral chromosome arms. The *An. gambiae* mosquito is used as a reference. The chromosome arms of *Ae. aegypti* and *Cx. quinquefasciatus* are shown at 500 kb resolution. Each 500 kb pixel is a colored with a blend of colors corresponding to individual synteny blocks in *An. gambiae* weighted by block lengths. Chromosome arms deriving from the same ancestral arm exhibit similar colors. In one case, a single chromosome arm (*An. gambiae* 2R) corresponds to two arms in the other species. Chromosome arms are paired differently in each species.

Strikingly, an almost perfect one-to-one correspondence between *An. gambiae*, *Cx. quinquefasciatus* and *Ae. aegypti* chromosome arms was observed, such that the vast majority of conserved DNA sequences found on a particular chromosome arm in one of the three species were also found on a single chromosome arm in the other two species (see FIG. 29). For instance, 70% of DNA sequences located on *An. gambiae* chromosome 2L that were conserved in *Ae. aegypti* were located on chromosome 2p; similarly, 75% of DNA sequences located on *An. gambiae* chromosome 2L that were conserved in *Cx. quinquefasciatus* were located on chromosome 3p.

The only exception to this one-to-one correspondence between chromosome arms is the observation that a single arm in *An. gambiae* (2R) corresponds to two arms in both *Ae. aegypti* (1q and 3p) and *Cx. quinquefasciatus* (1q and 3q). This suggests that, although chromosome arms in the mosquito lineage can break and fuse to form new arms, such events are extraordinarily rare, since there is evidence for only one such example during the last 150 million years.

Ancestral Chromosome Arms are Paired Differently in Each Mosquito Species

Despite the strong conservation of individual arms, the pairing of chromosome arms to form entire chromosomes is not preserved between *Ae. aegypti*, *Cx. quinquefasciatus* and *An. gambiae*. For instance, the arms of chromosome 2 in *Ae. aegypti* lie on different chromosomes in *An. gambiae* (where they correspond to arms 2L and 3R) and *Cx. quinquefasciatus* (3p and 2p).

This implies that chromosome breakage and fusion events have occurred on multiple occasions during mosquito evolution, but that such events almost always preserve the content of the individual arms.

Figure 30:
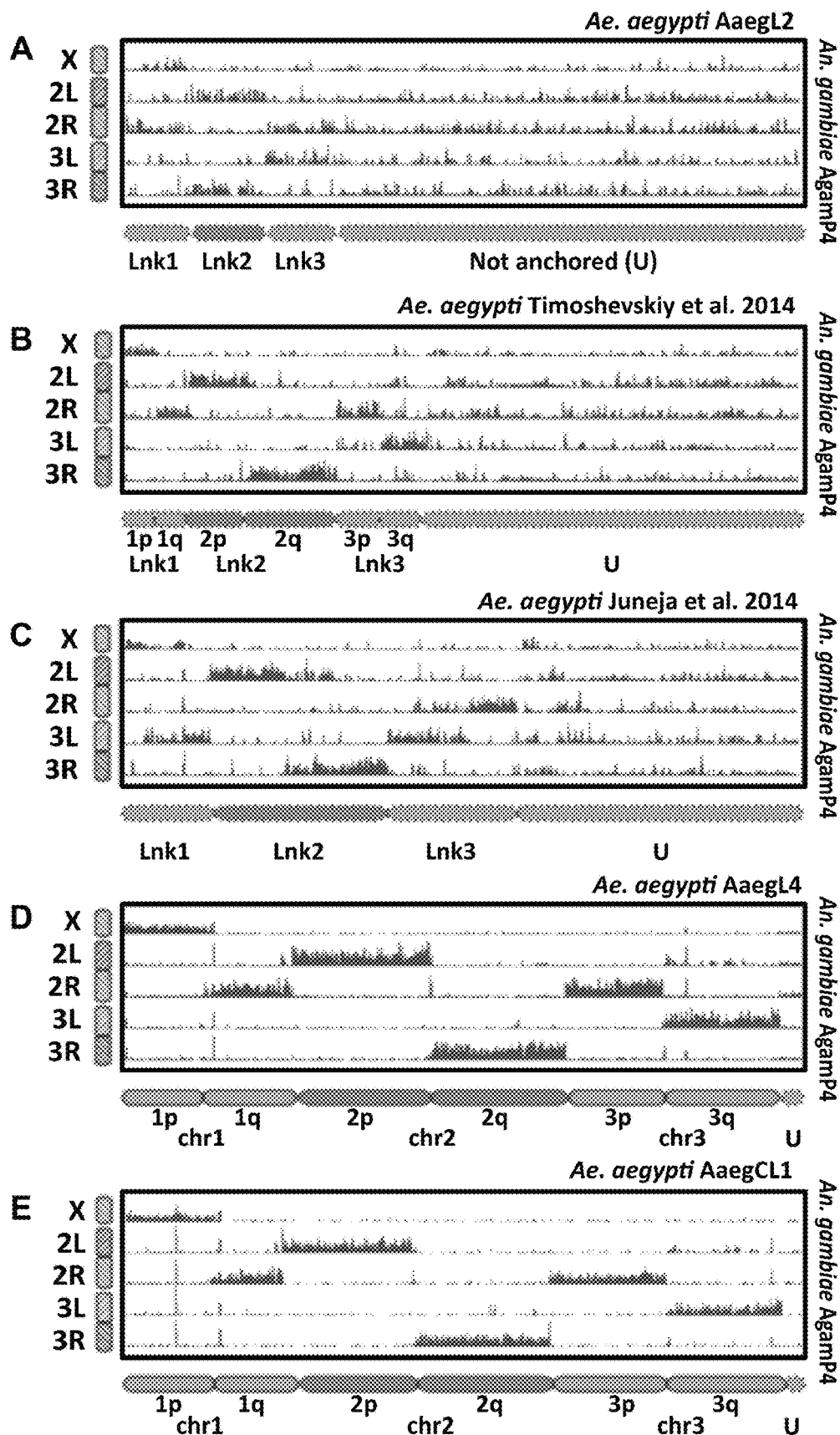
FIG. 30—Shows the AaegL4 and AaegCL1 assemblies enable genome-wide synteny analysis between *Ae. aegypti* and *An. gambiae* A) Conservation of synteny between chromosomes of *Ae. aegypti* and *An. gambiae* as suggested by the AaegL2 assembly. To perform this analysis, whole-genome alignment data was downloaded from VectorBase (Robert S. Harris 2007; Giraldo-Calderón et al. 2015) comprising pairs of orthologous positions in AaegL2 and Agam4. Orthologous pairs associated with a particular arm in *An. gambiae* (indicated at left) were grouped together, and the corresponding positions on AaegL2 are shown using a histogram at 1 Mb resolution. (The y-axes in this panel and throughout the figure correspond to raw counts, from 1 to 100.) Below the histogram tracks, we show the linkage groups reported in AaegL2 (Nene et al. 2007). The unanchored portion of the assembly is shown in grey. B) The synteny analysis from panel A is repeated using improved linkage groups generated via physical mapping (Timoshevskiy et al. 2014), which are indicated below the plot. C) The synteny analysis from panel A is repeated using improved linkage groups generated via genetic linkage mapping (Juneja et al. 2014), which are indicated below the plot. D) Synteny analysis for the AaegL4 assembly. A one-to-one correspondence between the chromosome arms of *Ae. aegypti* and *An. gambiae* is apparent. E) Synteny analysis for the AaegCL1 assembly. To generate this plot, we performed whole-genome alignment of the Aag2 contigs and the AgamP4 genome using the LastZ alignment algorithm with *An. gambiae* as a reference species. After running LastZ the raw alignment blocks were chained and netted according to their location in the AgamP4 genome.
Figure 31:
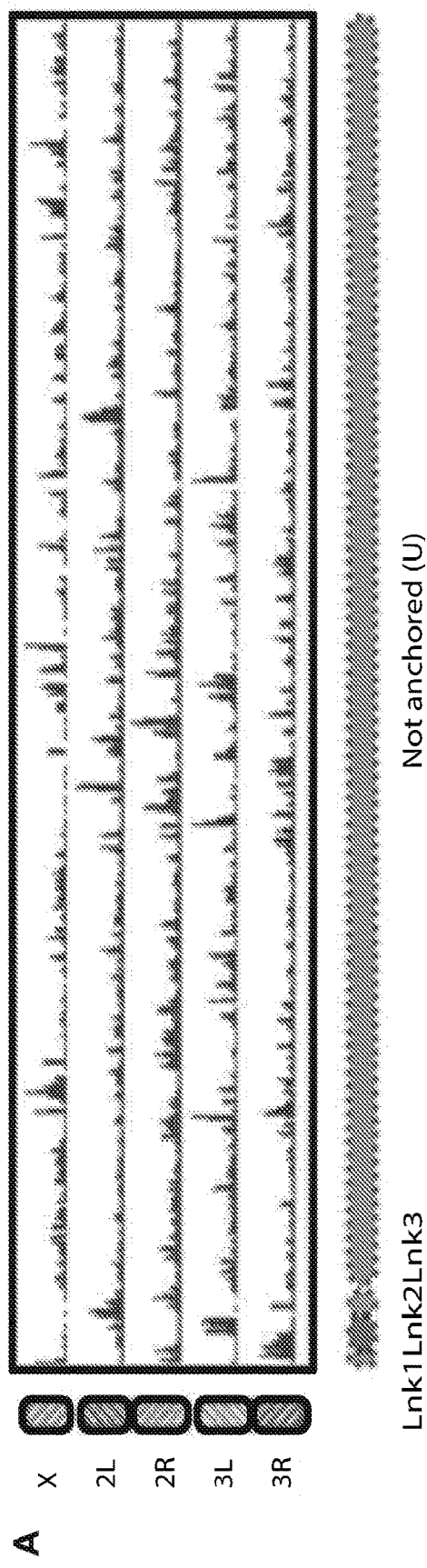
FIG. 31—Shows the CpipJ3 assembly reveals strong conservation of the contents of chromosome arms between *Cx. quinquefasciatus* and *An. gambiae*. A) Conservation of synteny between chromosomes of *Cx. quinquefasciatus* and *An. gambiae* as suggested by the CpipJ2 assembly. B) Conservation of synteny as represented by the CpipJ3 assembly. To perform this analysis, LASTZ_Net whole-genome alignment data from VectorBase was used (Robert S. Harris 2007; Giraldo-Calderón et al. 2015).
Figure 31:
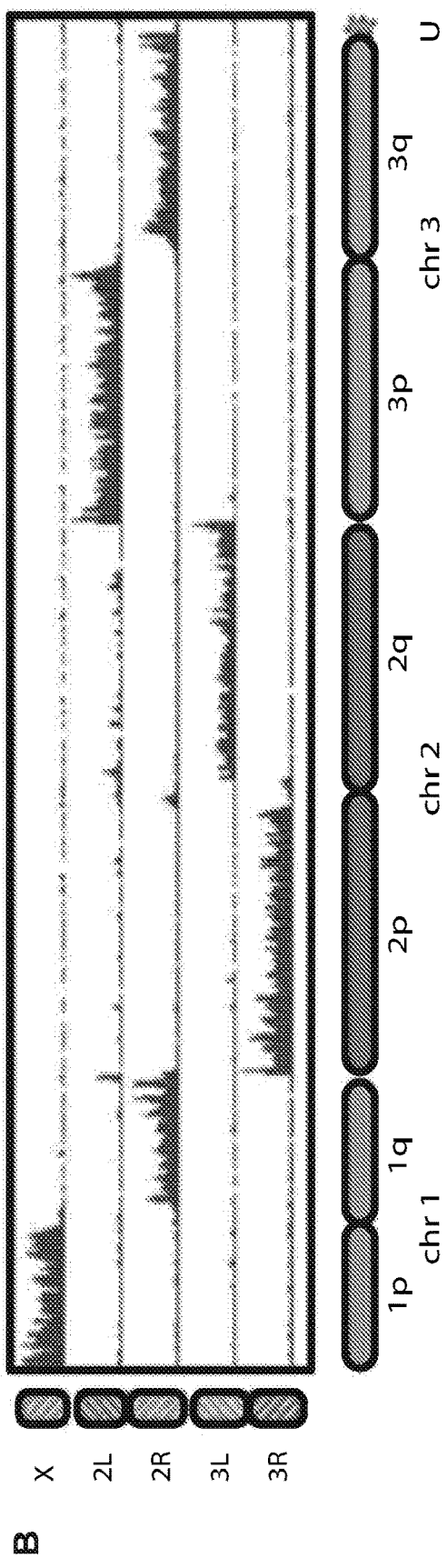

The observed correspondences are consistent with several cytogenetic studies (Nene et al. 2007; Arensburger et al. 2010; Juneja et al. 2014) which sought to determine synteny relationships between chromosome arms in *Ae. aegypti* and *An. gambiae* via FISH and linkage mapping. However, many of these correspondences were not apparent from earlier genome assemblies (FIGS. 30 and 31). The improved consistency between our results and cytogenetic methods highlights the reliability of our end-to-end scaffolding.

At least one chromosome arm has been strongly preserved throughout the evolution of Dipterans (true flies)

Figure 32:
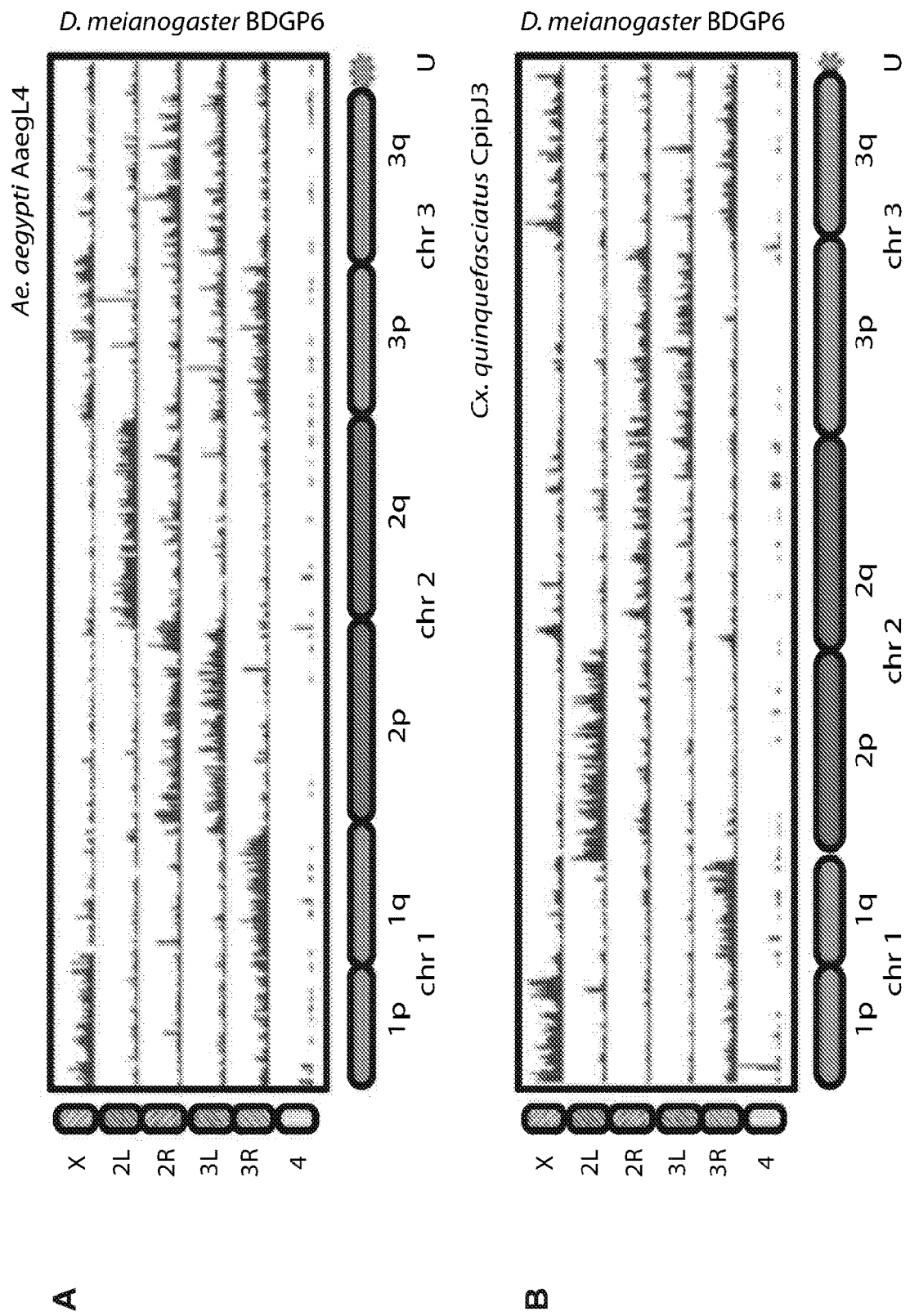
FIG. 32—Shows conservation of synteny across dipterans. Several chromosome arms, such as *Ae. aegypti* 2q (AaegL4), *Cx. quinquefasciatus* 2p and *D. melanogaster* 2L (BDGP6), show strong conservation of content. The whole-genome alignments for this analysis has been downloaded from Ensembl (Yates et al. 2016).

The correspondence between mosquito genomes and the genome of the fruit fly *D. melanogaster*. These species diverged roughly 250 million years ago. The resulting homologies are shown in FIG. 32. The left arm of chromosome 2 in *D. melanogaster* 2L is highly conserved across dipterans, corresponding to 3R in *An. gambiae*, 2q in *Ae. aegypti*, and 2p in *Cx. quinquefasciatus*. As before, the contents of chromosome arm 2L rearrange extensively, but rarely move to another chromosome arm. (This is particularly notable given the significant differences between the genomes of the three species; for instance, as reflected in the best present estimates of their genome sizes: 144 Mb for *D. melanogaster*, 265 Mb for *An. gambiae*, 540 Mb for *Cx. quinquefasciatus*, and ~1250 Mb for *Ae. aegypti*.)

Other chromosome arms were also preserved, but to a lesser degree. Notably, chromosome arms 1q and 3p in *Ae. aegypti* and arms 1q and 3q in *Cx. quinquefasciatus* correspond to a single arm, 3R, in *D. melanogaster*. As noted above, these pairs of chromosome arms also correspond to a single arm in *An. gambiae*. This is consistent with the hypothesis that these two arms were a single arm in the most recent common ancestor of all mosquitoes, and that the breakage of this ancestral chromosome arm in a shared ancestor of *Ae. aegypti*, and arms 1q/3q in *Cx. quinquefasciatus* caused the anomalous, one-to-two relationship.

All of the analyses in the preceding 3 sections yield similar results for both the AaegL4 and AaegCL1 assemblies.

Methods

In situ Hi-C was performed as described previously (Rao et al. 2014) using two adult female *Ae. aegypti* mosquitoes of the Orlando strain: "Daisy E. Pagete" and "Pieta E. Deygas." The resulting libraries were sequenced to yield approximately 40× coverage of the *Ae. aegypti* genome. In situ Hi-C was also performed on a female *Cx. quinquefasciatus* mosquito of the Johannesburg strain ("Tequila Fauxcuss Quince"), and sequenced to yield approximately 80× coverage of the *Cx. quinquefasciatus* genome.

The resulting data were used to improve existing genome assemblies of *Ae. aegypti* and *Cx. quinquefasciatus*. Briefly, to split contigs (or scaffolds), positions where long-range contact pattern changed abruptly were identified, which would be extremely unlikely for a correctly assembled contig. To merge contigs, pairs of contigs exhibiting strong sequence homology and similarity in long-range contact pattern were identified. To create scaffolds, the contact frequency between a pair of contigs from an input assembly was used as an indicator of their proximity in the 1D genome sequence. These data were provided to an algorithm which determined the correct order and orientation of the input contigs. A thorough description of our methodology is currently in preparation.

Figure 33:
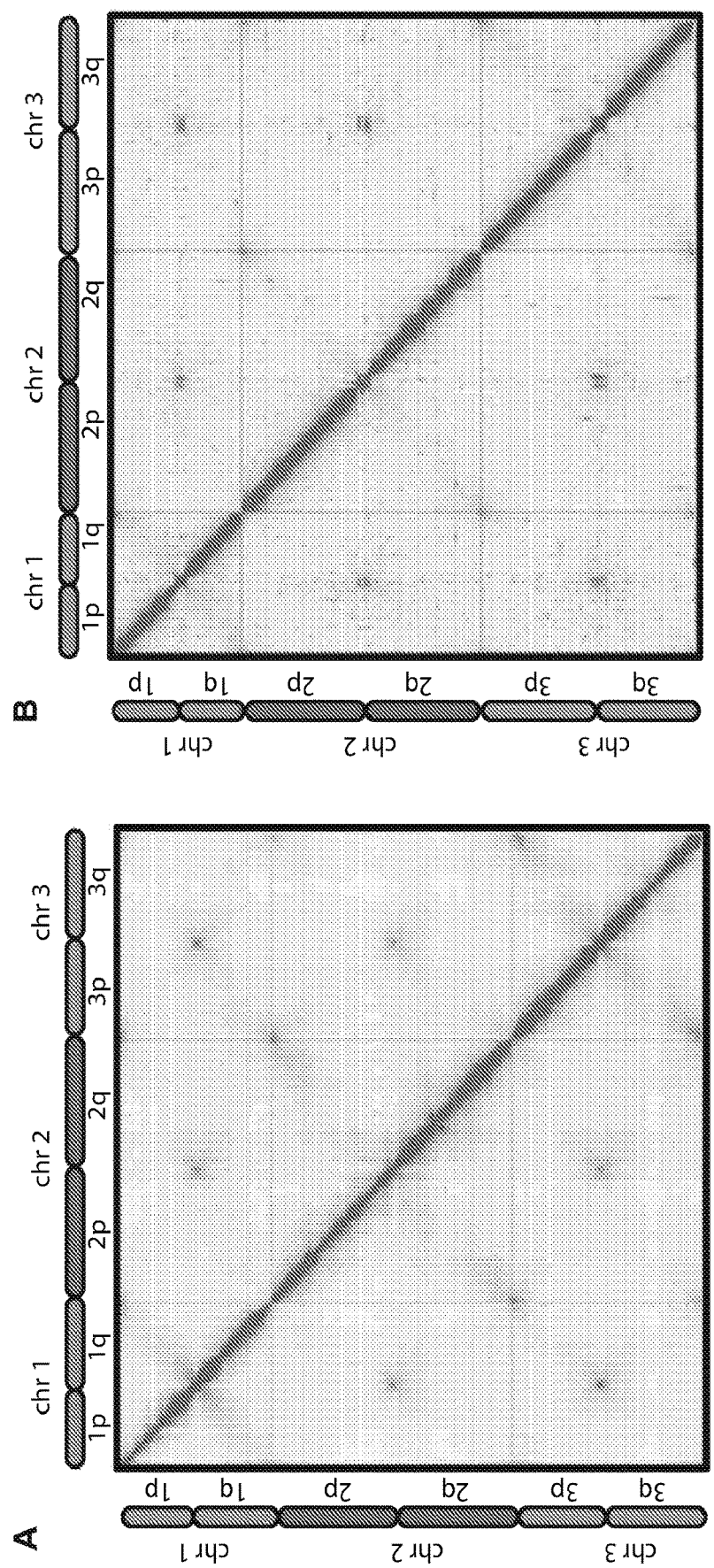
FIG. 33—Shows Hi-C map of the end-to-end assembly AaegL4 (A) and CpipJ3 (B). Bright, off-diagonal peaks indicate the spatial clustering of telomeres and centromeres, an arrangement known as the Rabl configuration. The map of AaegCL1 is similar. The genomes are not to scale.

FIG. 33 shows the Hi-C data corresponding to both assemblies of the *Ae. aegypti* mosquito, as well as for the assembly of *Cx. quinquefasciatus*. Both were visualized using the Juicebox visualization software for Hi-C data (Durand et al. Cell Systems 2016, 3(1):99-101). Spatial clustering of both telomeres and centromeres is visually apparent in both species, an arrangement known as the Rabl configuration (Hubner and Spector. Annual Review of Biophysics 2010, 39:471-89).

Discussion

The above data suggest that the chromosome arms in the *Aedes*, *Culex* and *Anopheles* species descend from arms that were present in their most recent common ancestor, which lived approximately 150-200 million years ago. Since that time, DNA sequences have rearranged extensively within the chromosome arms, but have rarely moved between arms. Similarly, chromosomes have broken and fused on multiple occasions, but only in a single case has such an event (likely the fusion of two chromosome arms in the ancestor of *An. gambiae*) significantly altered the content of a chromosome arm (see FIG. 29).

These facts clearly bear on the mechanisms underlying large-scale genome sequence evolution in mosquitoes. For instance, the findings suggest that the principal drivers of sequence rearrangement in mosquitoes are likely to be mechanisms that facilitate rearrangements within a chromosome arm, such as the repeat-mediated formation of DNA loops.

The above observations also highlight the ways in which end-to-end genome assemblies can illuminate comparative genomic analyses. Yet, although these assemblies are improvements with respect to existing, highly fragmented assemblies of the *Ae. aegypti* and *Cx. quinquefasciatus* genomes, several limitations of the assemblies reported here ought to be borne in mind.

First, these assemblies were not generated de novo. Rather, they are based on genome data that has been publicly shared by other groups. In particular, the contigs that were generously shared by Kunitomi et al. (Kunitomi et al. 2016) are the basis of AaegCL1, and we are grateful to them for making this data publicly available ahead of publication.

Second, the *Ae. aegypti* Hi-C data used in this paper was not generated from the same strain as the data used to assemble the original contigs. In particular, our Hi-C data was generated using the Orlando strain, whereas AaegL2 was generated using the Liverpool strain and Aag2 was generated using a cell line. This concern is mitigated somewhat by the observed correspondence between the Aag2 contigs and the AaegL4 assembly (FIG. 28), which suggests that, at a coarse scale, the genomes of different strains are in good agreement with each other. Ideally, both the contigs and the Hi-C data would be generated using samples with the same genetic background, or even using a single individual.

Third, some errors of the input assembly (AaegL2, Aag2, CpipJ2, respectively) remain in the final genomes (AaegL4, AaegCL1, CpipJ3, respectively). Our analysis suggests that for AaegL4 and CpipJ3 these are primarily cases of erroneously concatenated contigs and scaffolds which are not picked up by our current algorithms. For AaegCL1 these errors appear to be mostly associated with the unexpected level of heterozygosity of the genome, i.e., the limitations of current methods in recognizing the overlapping contigs that result. Conversely, our methods also, on occasion, merge similar sequences too aggressively. These errors could be significantly mitigated with access to the original reads.

Example 4

Hi-C is a sequencing-based approach for determining how a genome is folded by measuring the frequency of contact between pairs of loci (4, 5). Contact frequency depends strongly on the one-dimensional distance, in base pairs, between a pair of loci. For instance, loci separated by 10 kb in the human genome form contacts 8 times more often than those at a distance of 100 kb. In absolute terms, a typical distribution of Hi-C contacts from a given locus is 15% to loci within 10 kb; 15% to loci 10 kb-100 kb away; 18% to loci 100 kb-1 Mb away; 13% to loci 1 Mb-10 Mb away; 16% to loci 10 Mb-100 Mb away; 2% to loci on the same chromosome, but more than 100 Mb away; and 21% to loci on a different chromosome.

Hi-C data can provide links across a variety of length scales, spanning even whole chromosomes. However, unlike paired-end reads from clone libraries, any given Hi-C contact spans an unknown length and may connect loci on different chromosomes. This challenge may be mitigated, in part, by the physical coverage achieved by Hi-C datasets. For the maps reported in (4, 5), summing the span of each individual contact reveals that 1× of sequence coverage of the target genome translates, on average, into 23,000× of physical coverage. This suggests that a statistical approach analyzing the pattern of Hi-C contacts as a whole could generate extremely long scaffolds.

Computational experiments with simulated input data have suggested that Hi-C should be able to produce chromosome-length scaffolds (6-8). Indeed, Hi-C has been used to improve draft genome assemblies (7, 9) and to create chromosome-length scaffolds for large genomes (10). In this process, Hi-C data is used to assign draft scaffolds to chromosomes, and then to order and orient the draft scaffolds within each chromosome. Unfortunately, the resulting predictions contain large errors, including chromosome-scale inversions and misjoins that fuse chromosomes (10). Such misassemblies may be caused by errors in the original draft assembly (10). One approach to avoiding such errors might be additional types of information, such as longer reads or optical mapping data (see e.g., (11, 12)).

Figure 34:
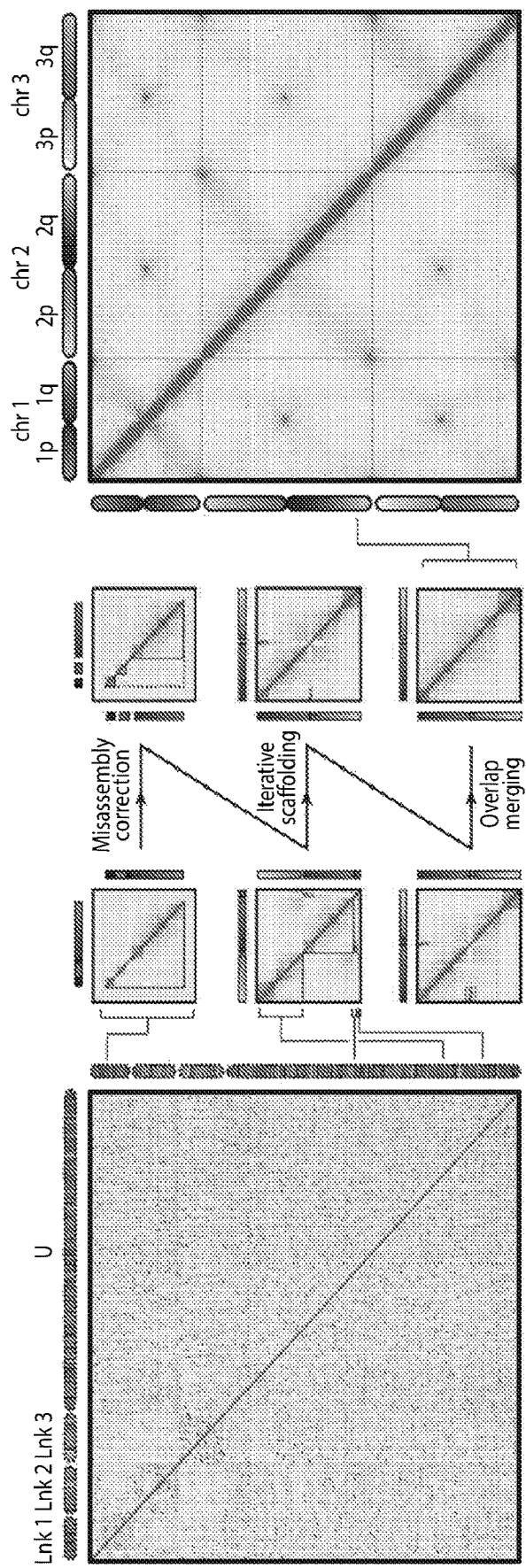
FIG. 34—Shows a draft assembly used to generate a chromosome-length scaffold using Hi-C vis misjoin correction, scaffolding, and merging of overlapping scaffolds. These three steps are illustrated with a scaffold from the AaegL2 assembly ('supercontig 1.12'). The scaffold is examined for misjoins and split into segments, each of which exhibits a continuous Hi-C signal. The segments are treated independently in an example iterative scaffolding step. One is placed on chromosome 1, and the rest on 2q. Segments exhibiting a similar 3D signal are examined for overlapping sequences and merged.

The results disclosed before were obtained using the computer-implement method disclosed and discussed above in reference to FIGS. 2-4. A key aspect of the approach is to first use Hi-C data to identify and correct errors in the scaffolds of the initial assembly. Briefly, misjoins are corrected by identifying positions where a scaffold's long-range contact pattern changes abruptly, which is unlikely for a correctly assembled scaffold. Next, a novel algorithm is used to anchor, order, and orient the resulting sequences, employing the contact frequency between a pair of sequences as an indicator of their proximity in the one-dimensional genome. Finally, contigs are merged and scaffolds that correspond to overlapping regions of the genome by identifying pairs of scaffolds exhibiting both strong sequence homology as well as strong similarity in long-range contact pattern (FIG. 34).

The approach was validated by creating a de novo assembly of a human genome (the GM12878 cell line), comprising 23 chromosome-length scaffolds, using only short Illumina reads (67× coverage). A draft assembly was created from 250 bp paired-end reads (60× coverage, generated by Illumina sequencing with a PCR-free protocol, downloaded from Sequence Read Archive (SRX297987); assembled with DISCOVAR de novo (13)). This assembly, dubbed Hs1, comprises 2.82 Gb of sequence (contig N50 length: 103 kb) partitioned among 73,770 scaffolds (scaffold N50: 126 kb; Table 5).

In situ Hi-C data was then used (6.7× sequence coverage) to improve Hs1. Tiny scaffolds (43,231 scaffolds shorter than 15 kb, whose N50 length is 6.1 kb). Together, these contain 5.4% of sequenced bases in Hs1. Due to their small size, they have relatively few Hi-C contacts, and are more difficult to analyze. Hi-C data was then used to split, anchor, order, and orient the remaining 30,539 scaffolds.

The resulting assembly (Hs2-HiC) consisted of 23 huge scaffolds (lengths from 28.8 Mb to 225.2 Mb) containing 99.5% of the total sequence, together with an additional 811 small scaffolds (N50 length of 30 kb; maximum length of 231 kb) making up the remaining 0.5% of the genome (Table 5). Crucially, the assembly was generated entirely de novo.

TABLE 5

Assembly statistics for the Hs2-HiC, AaegL2, and CpipJ3 assemblies. No further assembly of tiny scaffolds contained in each draft was attempted. The other scaffolds in each draft were assembled using Hi-C to create huge, chromosome-length scaffolds, and additional small scaffolds.

|  | Hs2-HiC | AaegL4 | CpipJ3 |
|---|---|---|---|
| Draft Scaffolds | | | |
| Base Pairs | 2,819,306,710 | 1,310,076,332 | 539,974,961 |
| Number of contigs | 80,223 | 36,204 | 48,672 |
| Contig N50 | 102,922 | 82,618 | 28,546 |
| Number of scaffolds | 73,770 | 4,756 | 3,172 |
| Scaffold N50 | 125,775 | 1,547,048 | 486,756 |
| Chromosome-length scaffolds | | | |
| Base Pairs | 2,654,127,695 | 1,157,961,392 | 492,400,177 |
| Number of contigs | 36,616 | 25,585 | 41,051 |
| Contig N50 | 108,937 | 93,132 | 30,599 |
| Number of scaffolds | 23 | 3 | 3 |
| Scaffold N50* | 141,244,516 | 404,248,146 | 190,989,159 |
| Small scaffolds | | | |
| Base Pairs | 13,416,754 | 82,464,476 | 31,168,201 |
| Number of contigs | 850 | 9,416 | 5,609 |
| Contig N50 | 27,968 | 14,202 | 10,570 |
| Number of scaffolds | 811 | 3,981 | 1224 |
| Scaffold N50 | 30,467 | 65,348 | 45,079 |
| Tiny scaffolds | | | |
| Base Pairs | 151,762,261 | 14,122,292 | 112,343 |
| Number of contigs | 43,259 | 2,223 | 61 |
| Contig N50 | 6,129 | 6,574 | 2110 |
| Number of scaffolds | 43,231 | 2,222 | 25 |
| Scaffold N50 | 6,144 | 6,577 | 9,403 |

Figure 43:
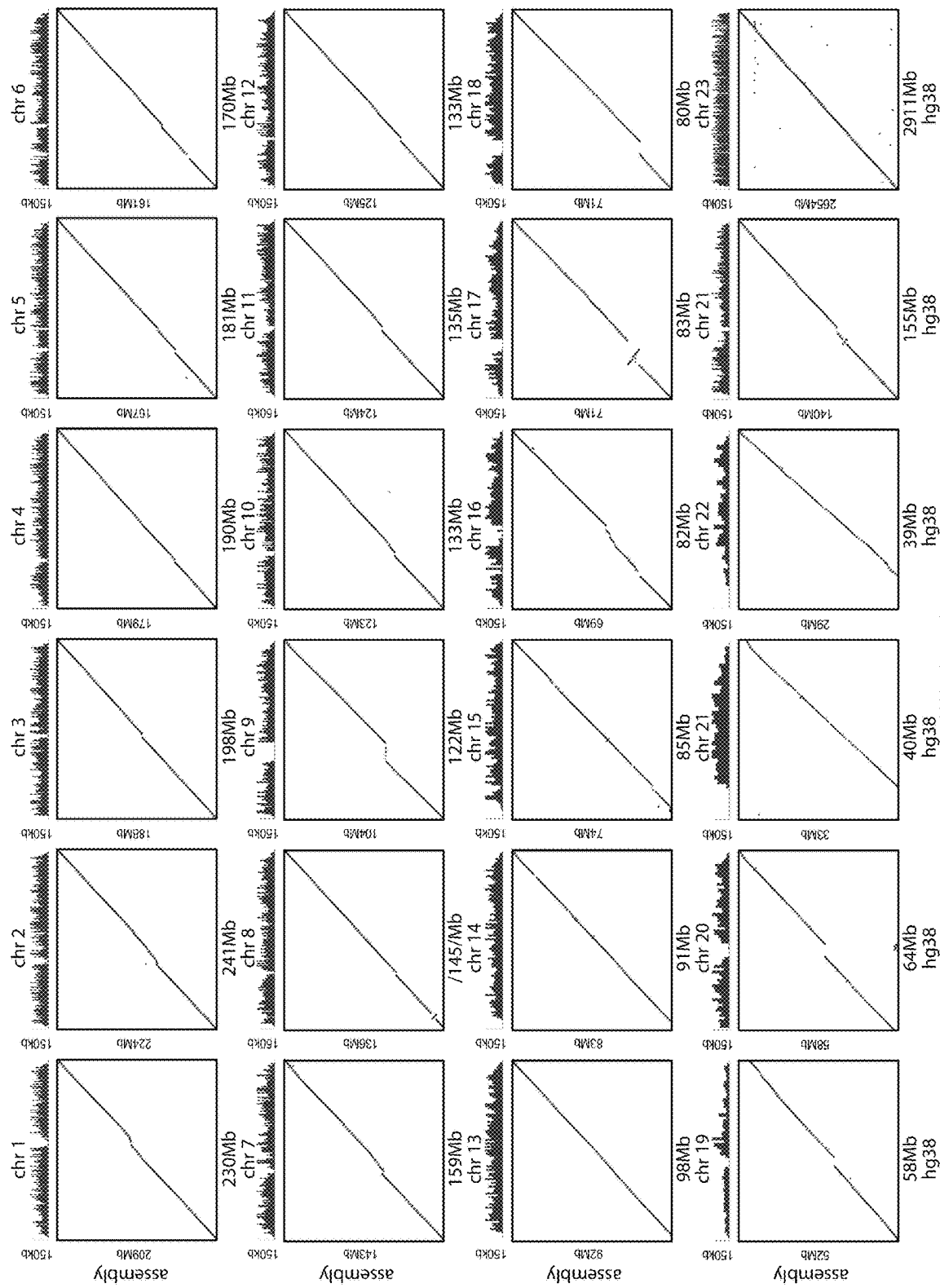
Figure 44:
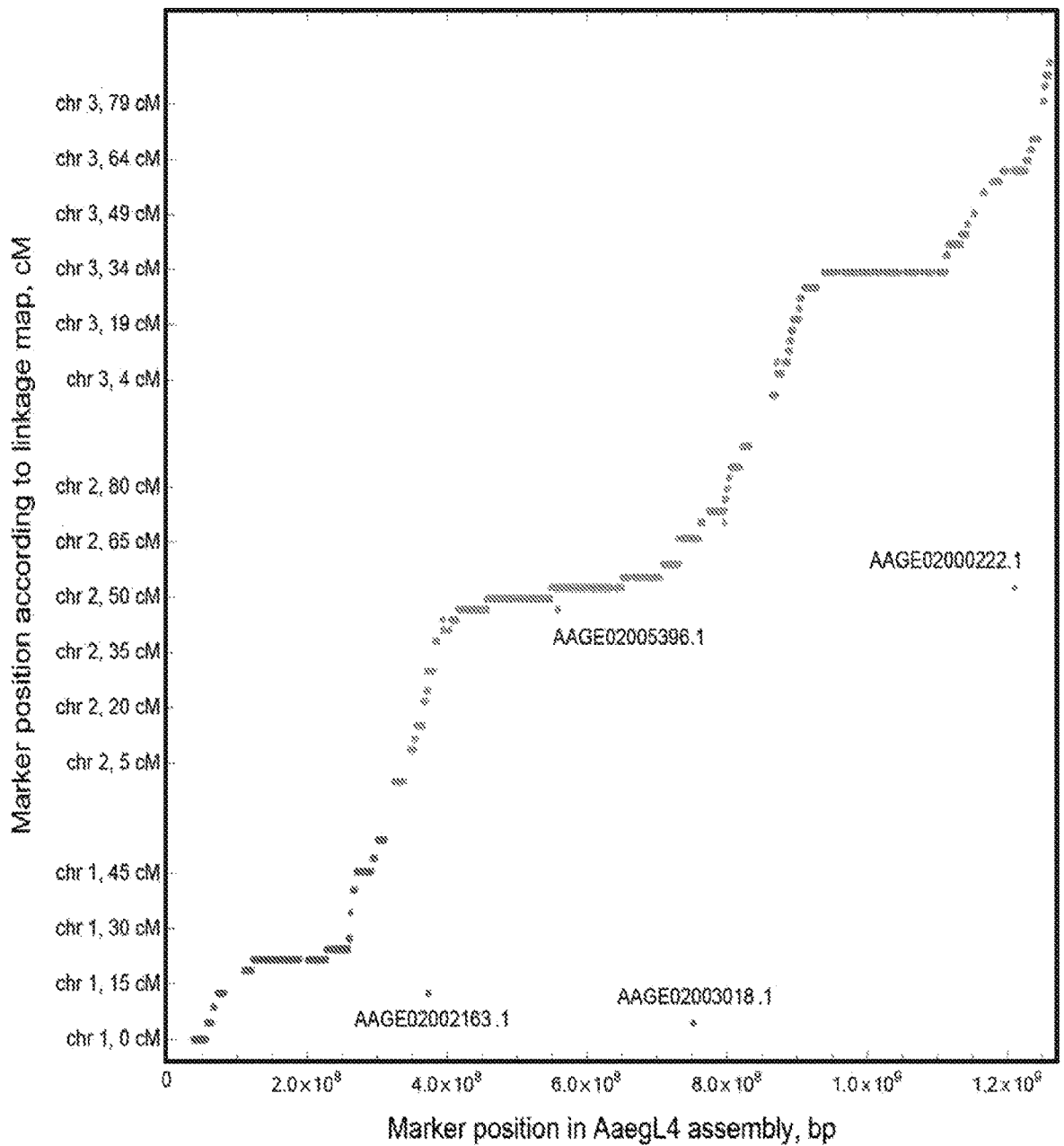
FIG. 44—Shows the correlation between the position of a scaffold on a genetic linkage map in centimorgans (cM) and its position in the AaegL4 assembly. Out of 1826 markers, only four are inconsistent. These inconsistencies are due to errors in the draft assembly (AaegL2) that were not flagged by our approach FIG. 45—Shows misassembly detection using Hi-C: comparison with evidence from linkage mapping. Shown are contact maps for the first four AaegL2 scaffolds that were identified as misassembled in a genetic linkage mapping study (19). The boundaries of consistent fragments as identified via automatic misassembly detector are overlaid over the contact maps (green squares). The upper track shows the location of breakpoints as well as the position of the resulting scaffold fragments (indicated using color) along the *Ae. aegypti* chromosomes according to the linkage map (19). White bars indicate a lack of markers on the fragment, making more precise identification of breakage position on the basis of the genetic map impossible. The lower track illustrates the location of breakpoints as well as the position of the resulting scaffold fragments (indicated using color) according to current study. The overall coloring scheme used is shown; however, note that the individual color gradients along each scaffold fragment were enhanced in order to heighten the contrast between nearby positions on the same chromosome. All 63 scaffolds that were identified as misassembled in (19) through linkage mapping were independently flagged as misassembled based on their Hi-C signal.
Figure 45:
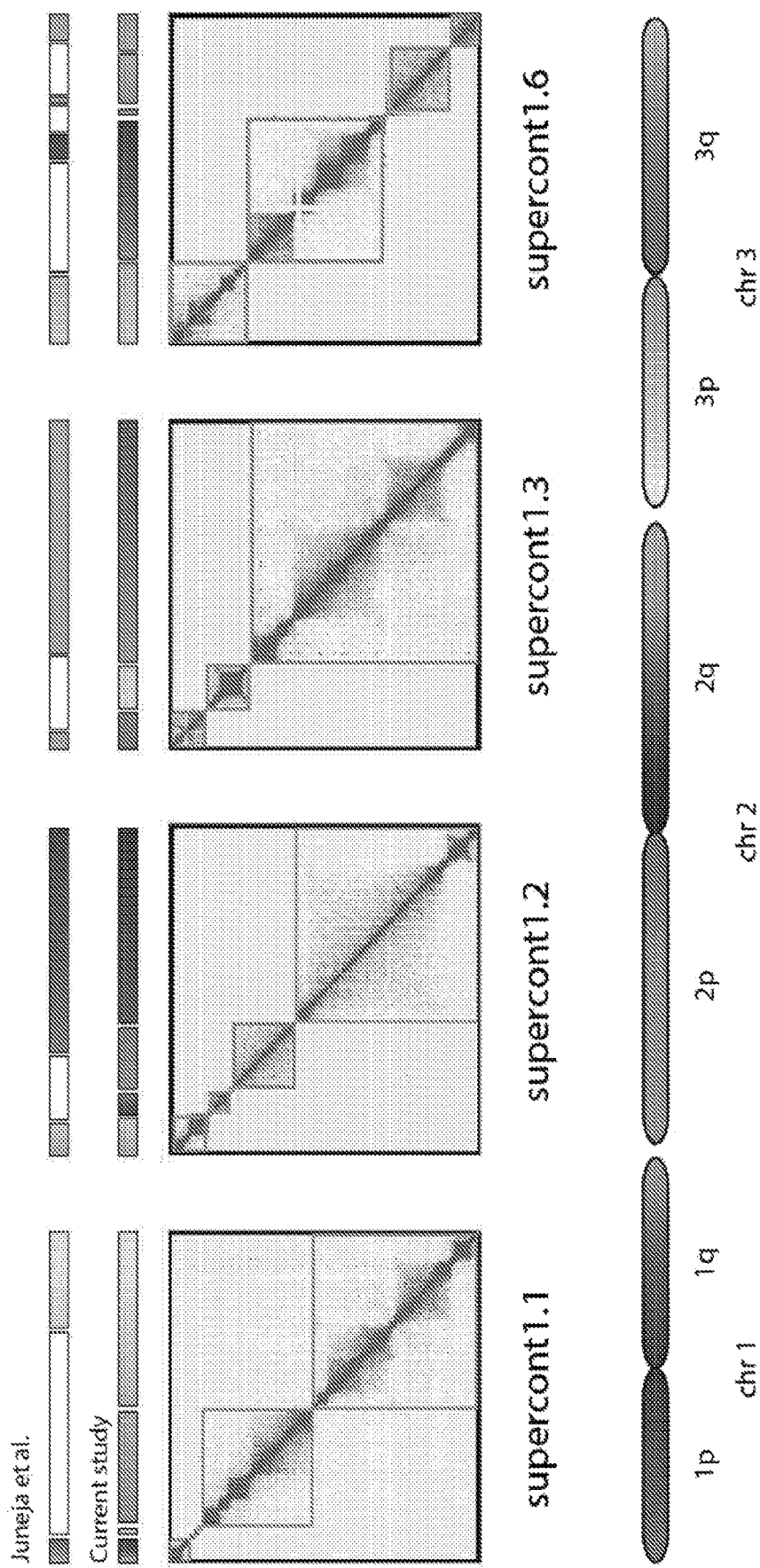

The quality of Hs2-HiC by comparing it to the human genome reference, hg38 (FIG. 43). The 23 scaffolds correspond to the 23 human chromosomes, spanning 99% of the length and containing 91% of the sequence in the chromosome-length scaffolds (table S1). These scaffolds are comparable in length to those reported by the International Human Genome Sequencing Consortium (14), and longer than those reported by (15).

Of the 29,344 scaffolds that were incorporated into chromosome-length scaffolds in Hs2-HiC and that could be uniquely placed in hg38, 99.70% (comprising 99.88% of the sequenced bases) were assigned to the correct chromosome. For randomly selected pairs of scaffolds assigned to the same chromosome-length scaffold in Hs2-HiC, the order in Hs2-HiC agreed with the order in hg38 in 99% of cases. The agreement was 96% for pairs of scaffolds that were adjacent in Hs2-HiC, reflecting the fact that the Hi-C data provides less information to resolve the fine-structure order of short scaffolds. However, the agreement was 99% for scaffolds of length at least 120 kb. Similarly, the orientation was correct for 93% of scaffolds, with errors mostly due to short scaffolds.

Taken together, the chromosome-length, small, and tiny scaffolds accounted for 97.3% of the chromosome-length scaffolds of hg38; the remainder was mostly due to repetitive sequences that could not be adequately assembled from short reads. The method was further validated by obtaining similar results using a draft assembly generated with Pacific Biosciences long reads, which contained longer contigs (16).

Next, the approach was applied to *Ae. aegypti*, which was previously assembled from Sanger reads (8× coverage) (17). This assembly, 'AaegL2', contains 1.3 Gb of sequence (contig N50: 83 kb) partitioned among 4,756 scaffolds (scaffold N50: 1.5 Mb).

To improve AaegL2, in situ Hi-C data (40× sequence coverage) was generated. After setting aside 2,222 scaffolds shorter than 10 kb (spanning 1% of the bases in the initial assembly), Hi-C data was used to split, anchor, order, orient, and merge the remaining 2,534 scaffolds. Notably, our pipeline identified apparent misjoins in 1,422 of these input scaffolds (56%).

The resulting assembly, AaegL4, contained three huge scaffolds (307 Mb, 472 Mb, and 404 Mb in length) comprising 93.6% of the input sequence, together with an additional 3981 small scaffolds (N50 of 65 kb, maximum of 474 kb) comprising the remainder. The three huge scaffolds correspond to chromosomes 1, 2, and 3 of the *Ae. aegypti* genome (18) (Table 1).

Figure 35:
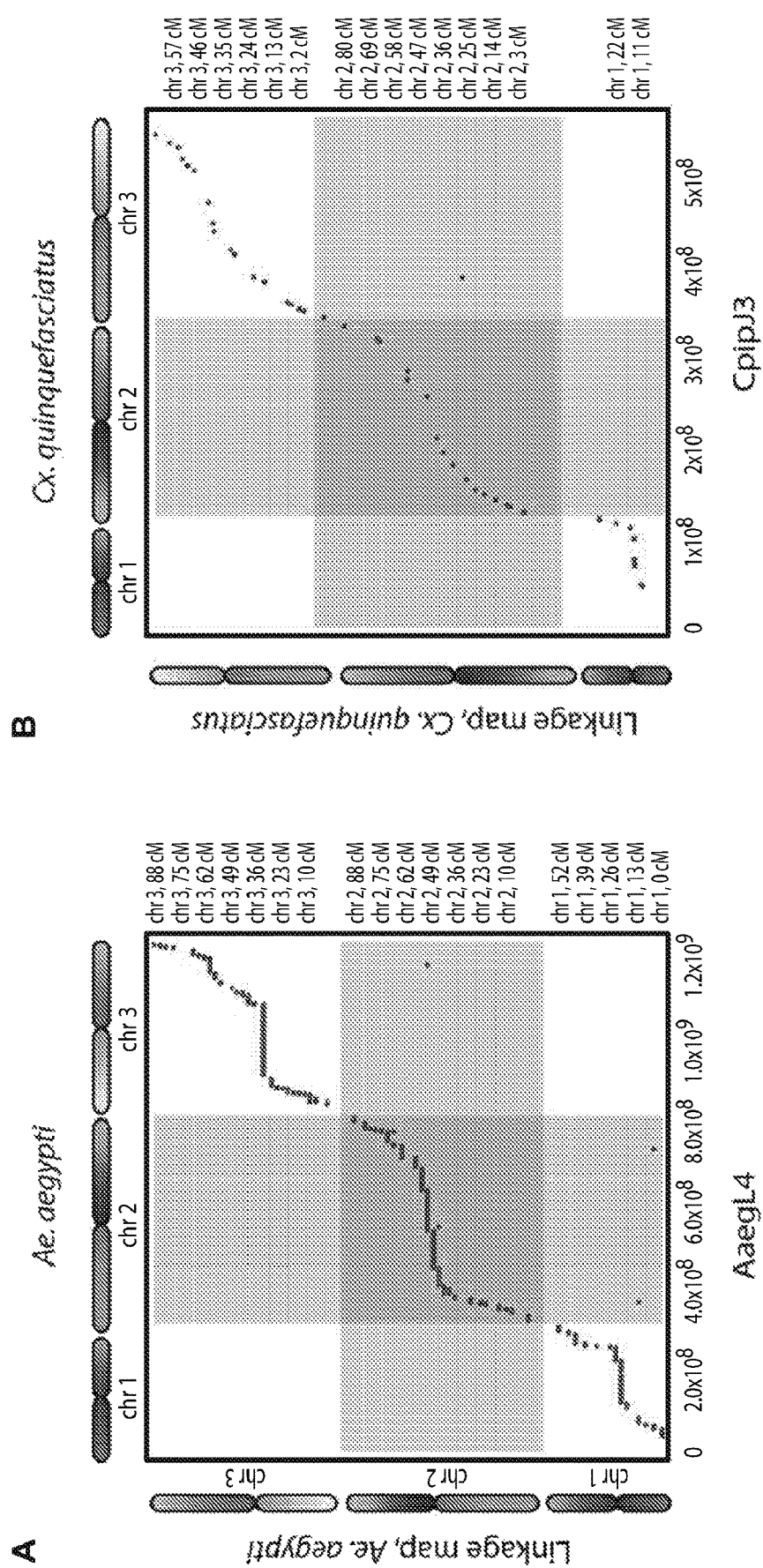
FIG. 35—Shows a comparison of AaegL4 and CpipJ3 with genetic maps. (A) compares AaegL4 with a genetic map of *Ae. aegypti* (19). The assembly agreed with the genetic map on 1822 of the 1826 markers. The exceptions are due to misjoins in AaegL2 that were not corrected in AaegL4. (B) Similarly, CpipJ3 is in agreement with a genetic map of *Cx. quinquefasciatus* (21).
Figure 46:
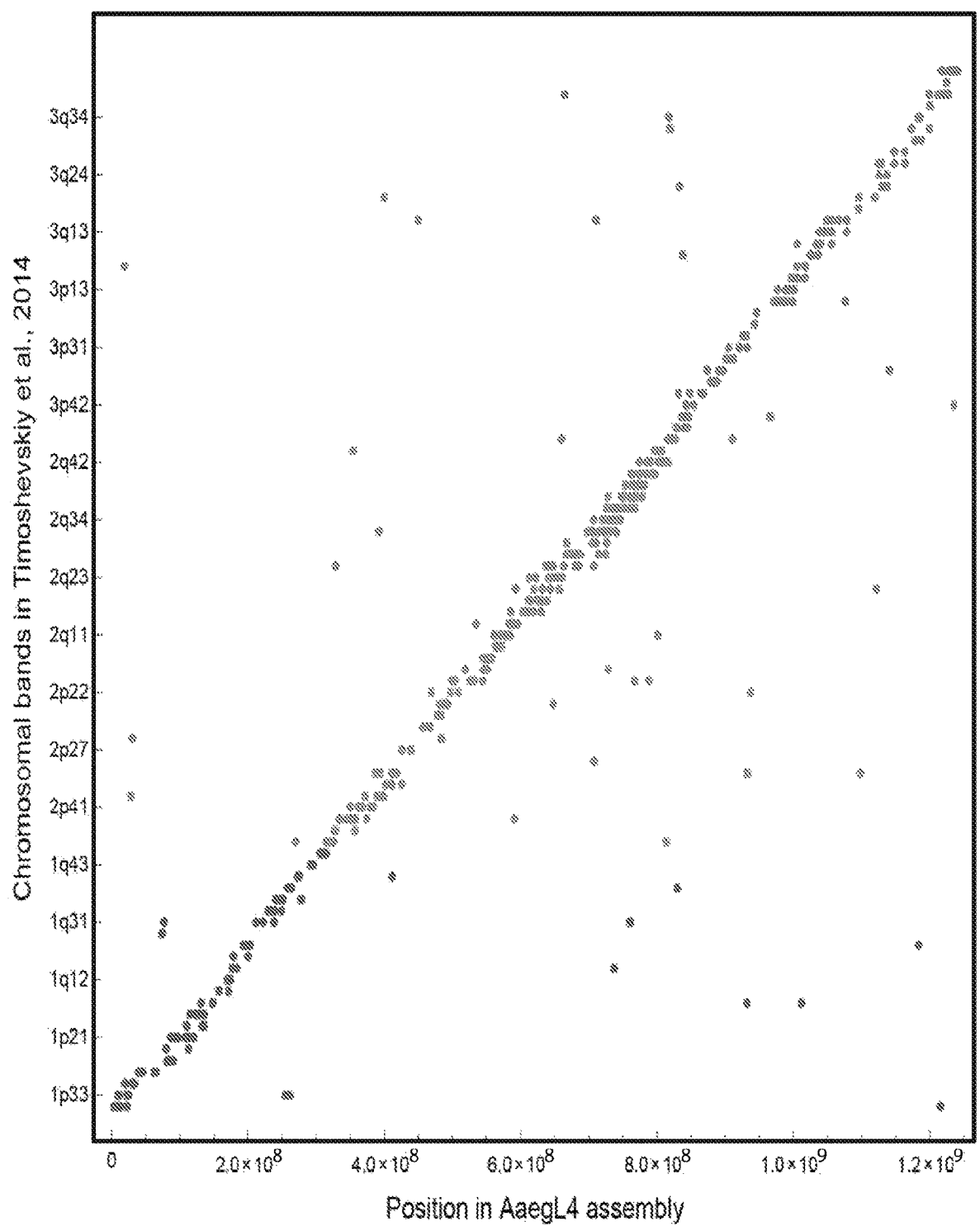
FIG. 46—Shows the correlation between chromosomal band assignment by physical mapping (36) and position in the AaegL4 genome.

The resulting assembly was compared to a genetic map of *Ae. aegypti* (19). Of the 2006 markers in the genetic map, 1826 markers could be unambiguously mapped in AaegL4. Strikingly, our assembly agreed with the genetic map for 1822 of these 1826 markers (FIG. 35). All exceptions were due to misjoins in AaegL2 that had not been detected in AaegL4. We also observed close correspondence with a physical map of the *Ae. aegypti* genome (FIG. 46).

Figure 47:
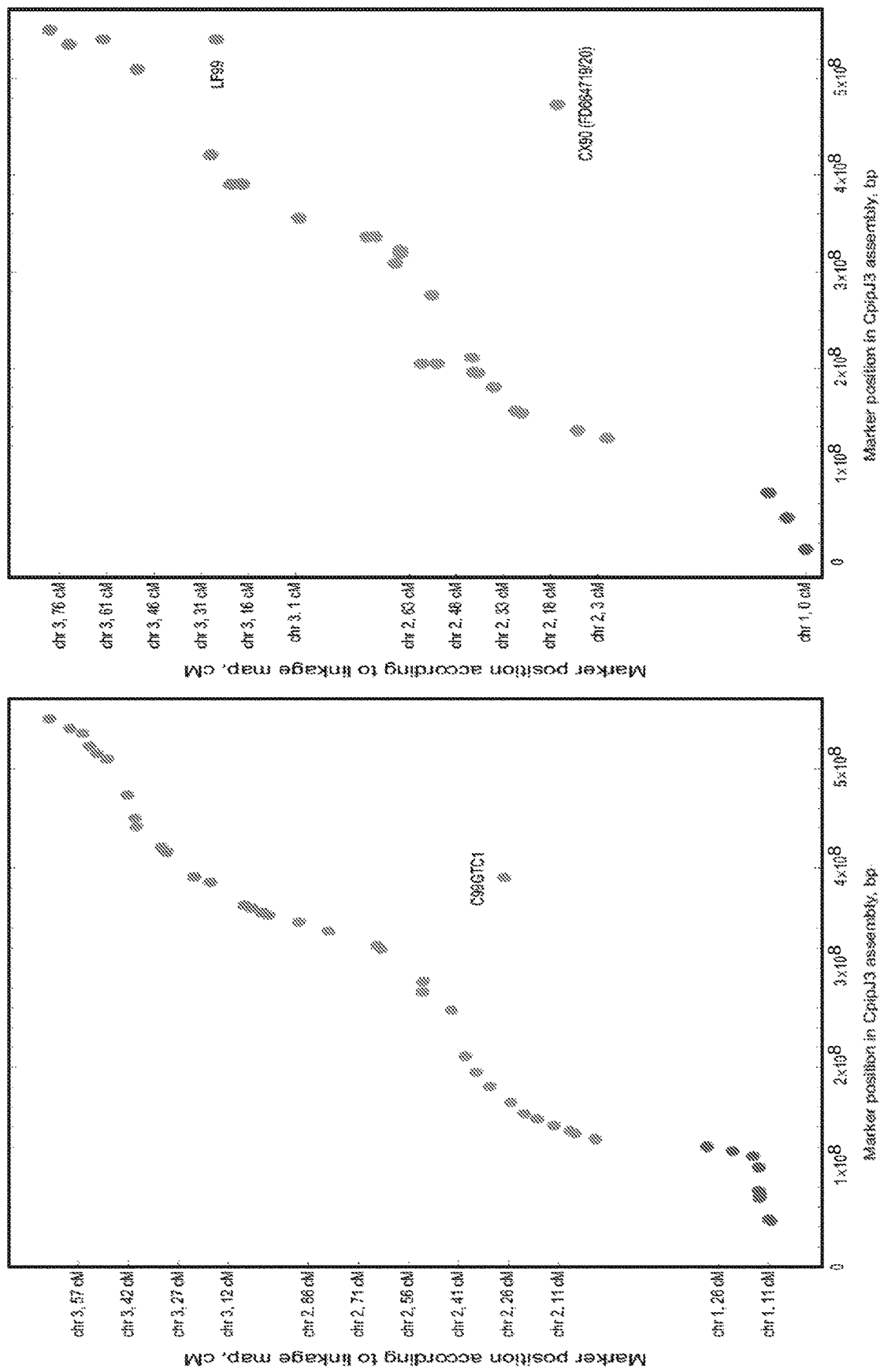
FIG. 47—Shows the correlation between the position of a marker on a genetic linkage map in centimorgans (cM) and its position in the CpipJ3 assembly. (A) Map of microsatellite loci (21); (B) Map of restriction fragment length polymorphism (RFLP) markers (20).
Figure 48:
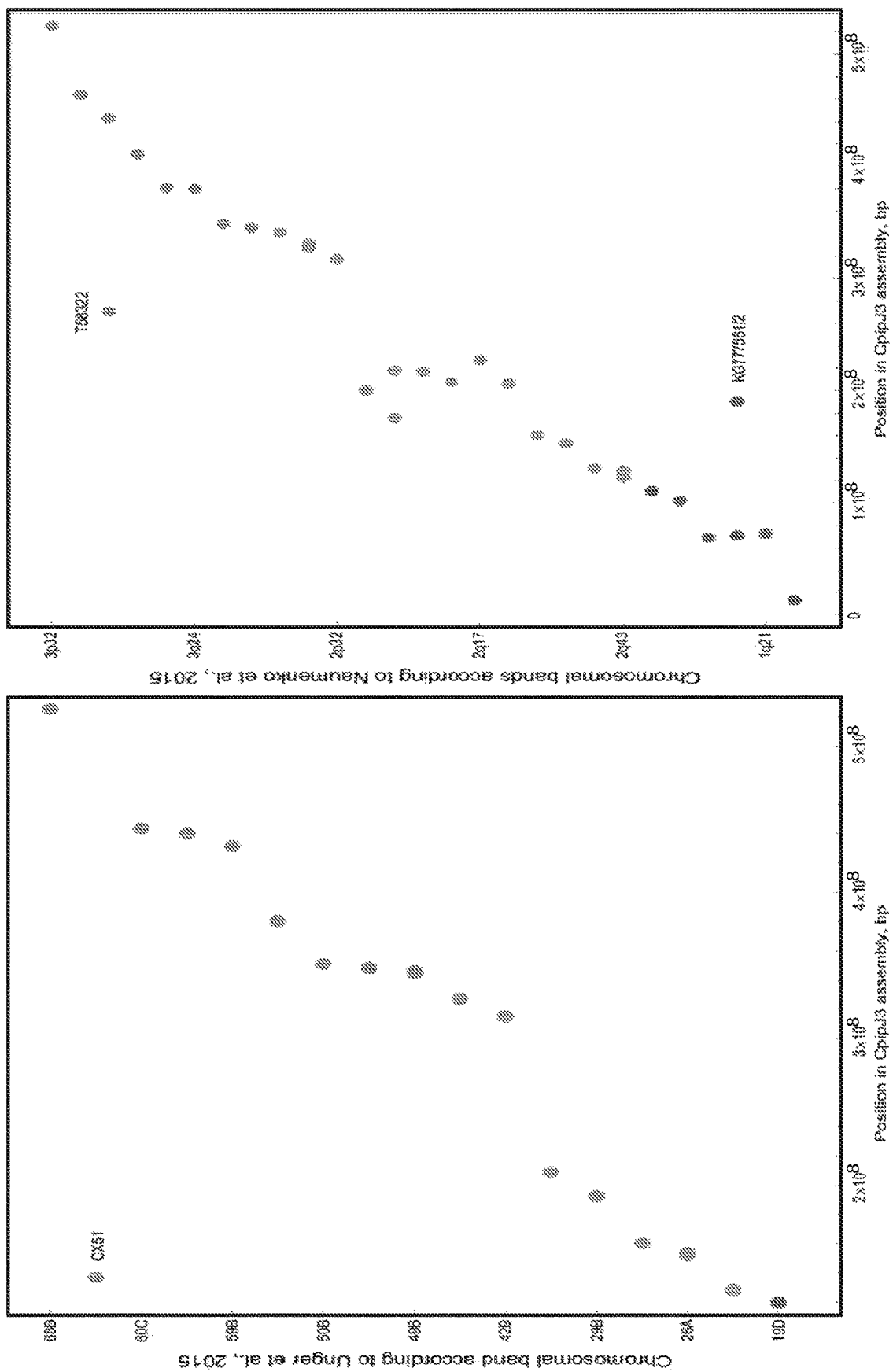
FIG. 48—Shows correlation between chromosomal band assignment by physical mapping and position in CpipJ3 genome. (A) Physical mapping of polytene *Cx. quinquefasciatus* chromosomes (37); (B) Mitotic chromosome-based physical mapping (38)

Next, the approach was used to create a genome assembly of the mosquito *Culex quinquefasciatus*, which, like *Ae. aegypti*, is a disease vector—in this case for West Nile virus, St. Louis encephalitis, and lymphatic filariasis. In situ Hi-C data (100× sequence coverage) was generated and used it to improve the previous assembly, CpipJ2 (20), obtaining a new assembly, CpipJ3, with three chromosome-length scaffolds that together contain 94% of the sequence in the initial assembly (Tables 1, S2-S7). CpipJ3 was validated by comparing it to existing genetic and physical maps of the *Cx. quinquefasciatus* genome (20, 21) (FIGS. 35, 47, 48).

Figure 49:
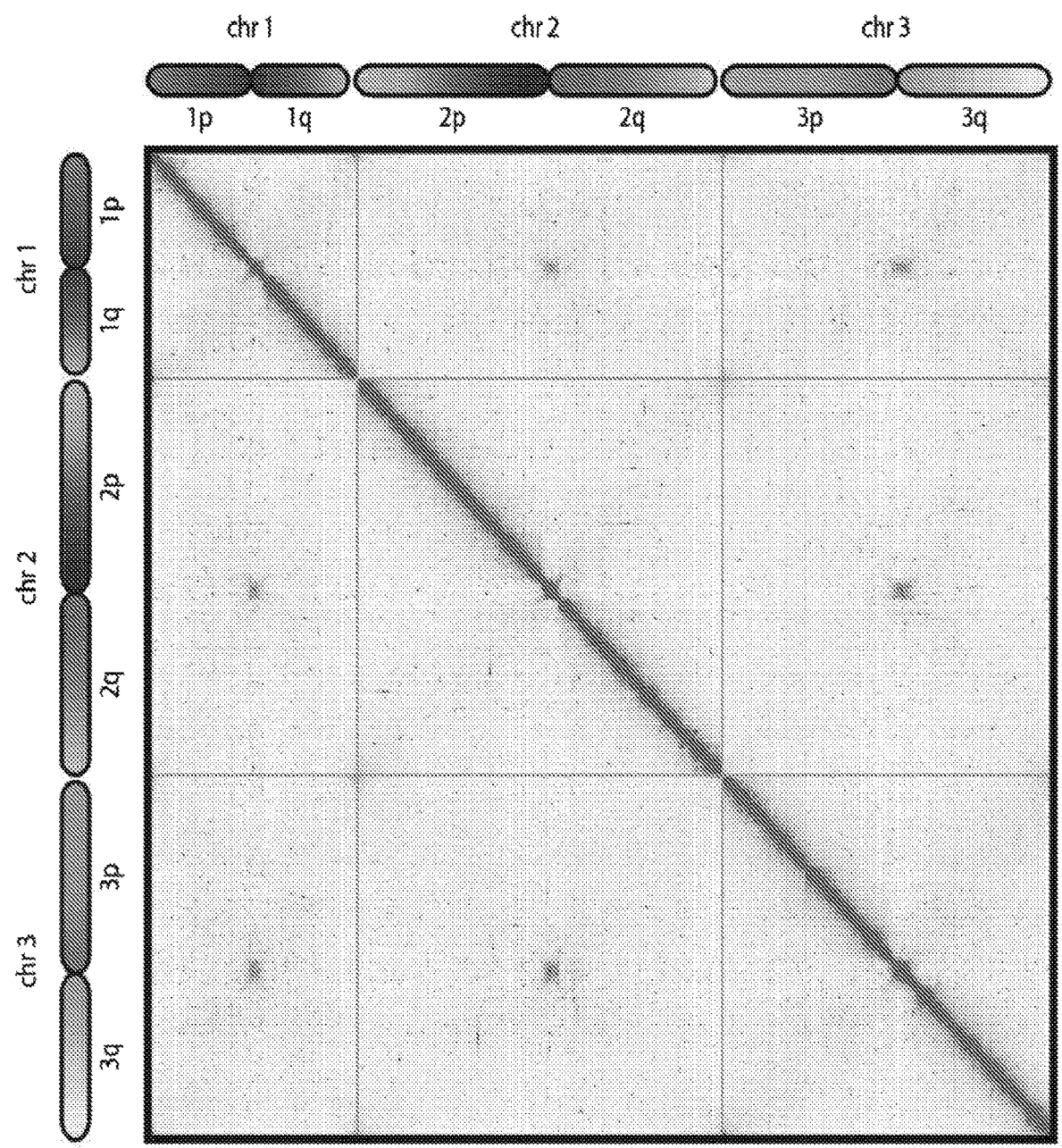
FIG. 49—Shows the 3D map of the *Cx. quinquefasciatus* genome. Both *Ae. aegypti* and *Cx. quinquefasciatus* genomes exhibit bright, off-diagonal peaks, which indicate the spatial clustering of telomeres and centromeres. These peaks facilitate the annotation of centromeric sequences for each chromosome (41).

The creation of chromosome-length scaffolds for *Ae. aegypti* and *Cx. quinquefasciatus* allowed us to use the Hi-C data to create a Hi-C heatmap showing proximity relationships between chromosomal loci throughout both genomes (22, 23) (FIGS. 34, 49). Strikingly, the distal ends of the three chromosomes show spatial clustering in both species. Both species also exhibited a second spatial cluster, comprising three loci: one locus from each chromosome, positioned roughly in the middle. This clustering is consistent with the spatial clustering of centromeres, which is known to be present in many organisms. Taken together, the 3D maps are consistent with a spatial arrangement known as the Rabl configuration (24). Our findings also suggest the position of each chromosome's centromere, and thereby partition each mosquito chromosome into two arms.

Figure 36:
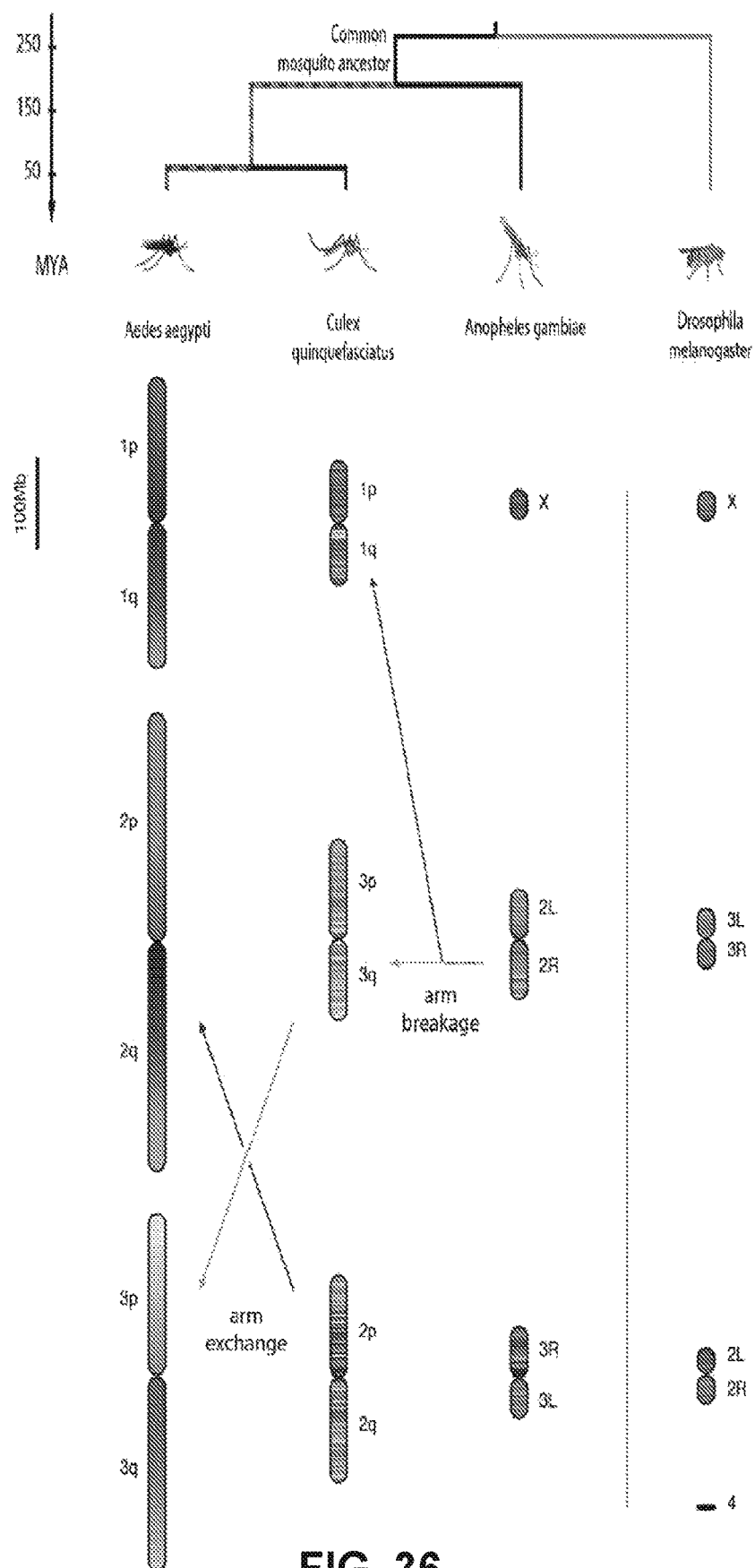
FIG. 36—Shows the content of chromosome arms is strongly conserved across mosquitoes. Here, each 100 kb locus in *Ae. aegypti* is assigned a color. For the other species, each 100 kb locus is assigned a combination of the colors of the corresponding DNA sequences in *Ae. aegypti*, weighted by length.
Figure 50:
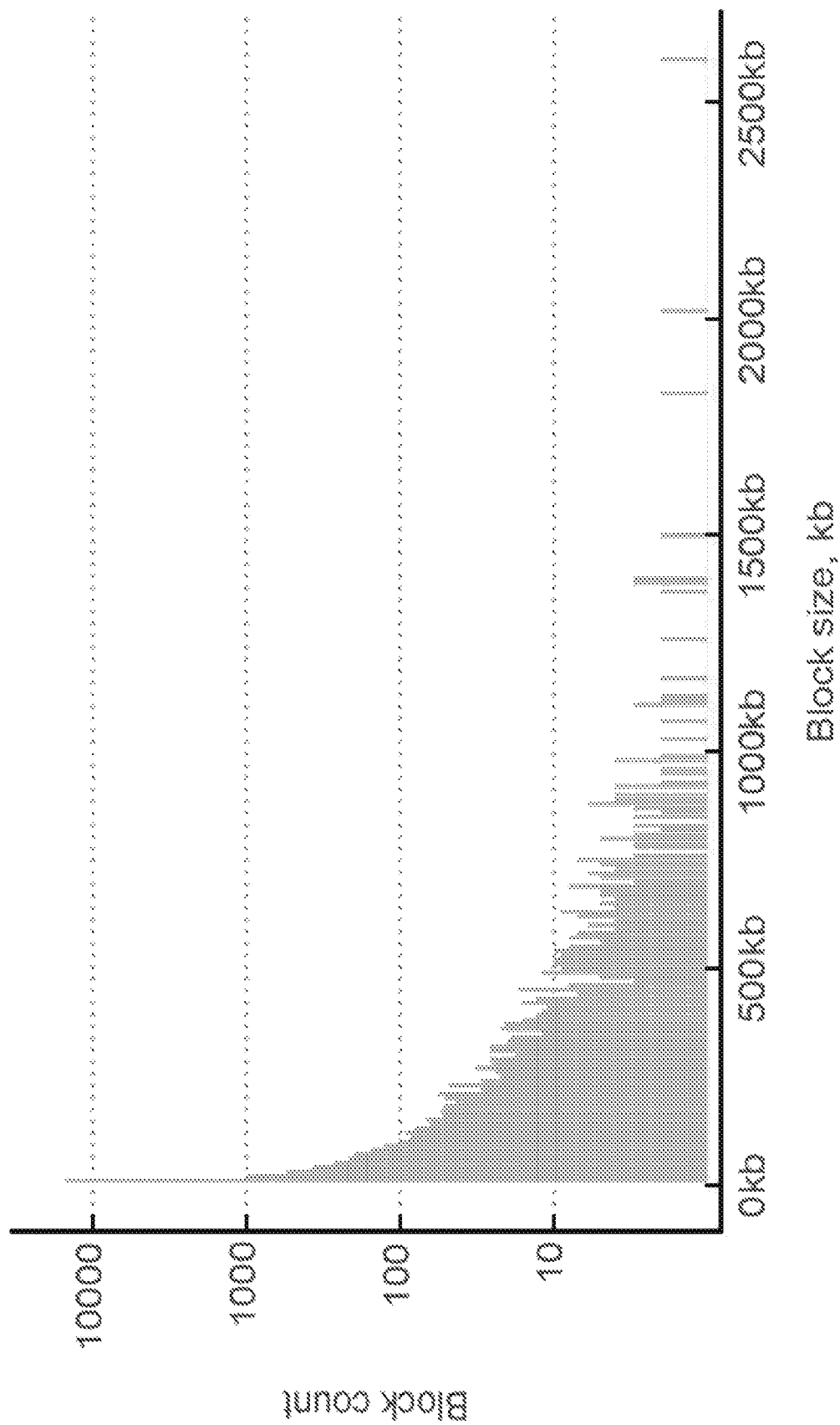
FIG. 50—Shows size distribution for synteny blocks between *Ae. aegypti* and *An. gambiae*. The block sizes are measured with respect to the *Ae. aegypti* genome. The blocks are defined as chains of conserved sequence markers that are both consecutive and collinear in both genomes. The chain ends when two consecutive markers disagree with the rest of the chain; however, one marker in the wrong order and/or the wrong orientation does not break the chain.
Figure 51:
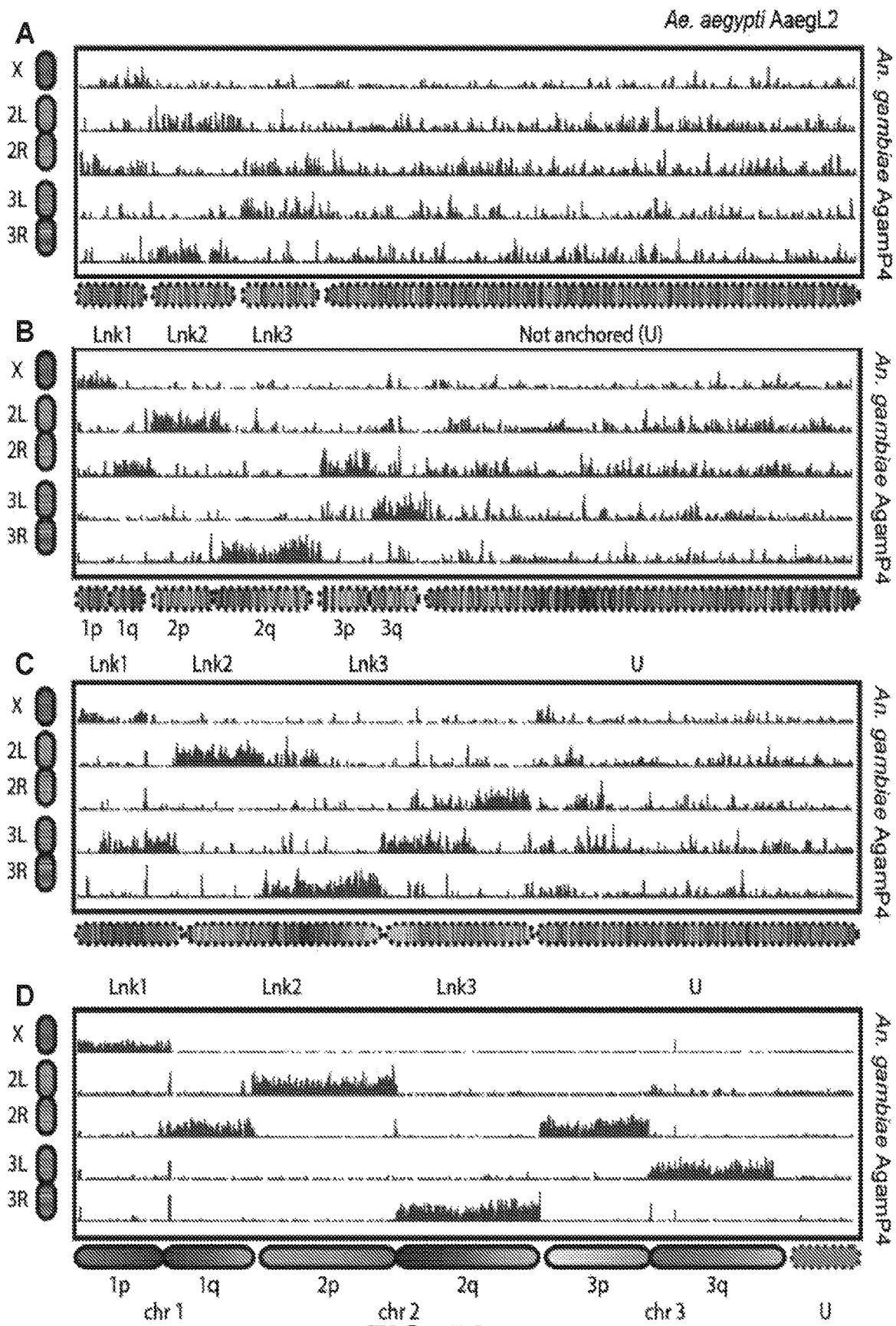
FIG. 51—Shows the AaegL4 genome assembly enables genome-wide analysis of conservation of synteny between *Ae. aegypti* and *An. gambiae*. (A) Density of conserved alignments between chromosomes of *Ae. aegypti* and *An. gambiae* as suggested by the AaegL2 assembly. Below the histogram tracks we show the linkage groups reported in AaegL2 (18). (B) The synteny analysis from panel A is repeated using improved linkage groups generated via physical mapping (36), which are indicated below the plot. (C) The synteny analysis from panel A is repeated using improved linkage groups generated via genetic linkage mapping (19), which are indicated below the plot. (D) Synteny analysis for the AaegL4 assembly. A one-to-one correspondence between the chromosome arms of *Ae. aegypti* and *An. gambiae* is apparent. Chromograms along the x- and y-axes indicate which portions of AaegL4 correspond to which positions in the other genomes and genome assemblies.
Figure 52:
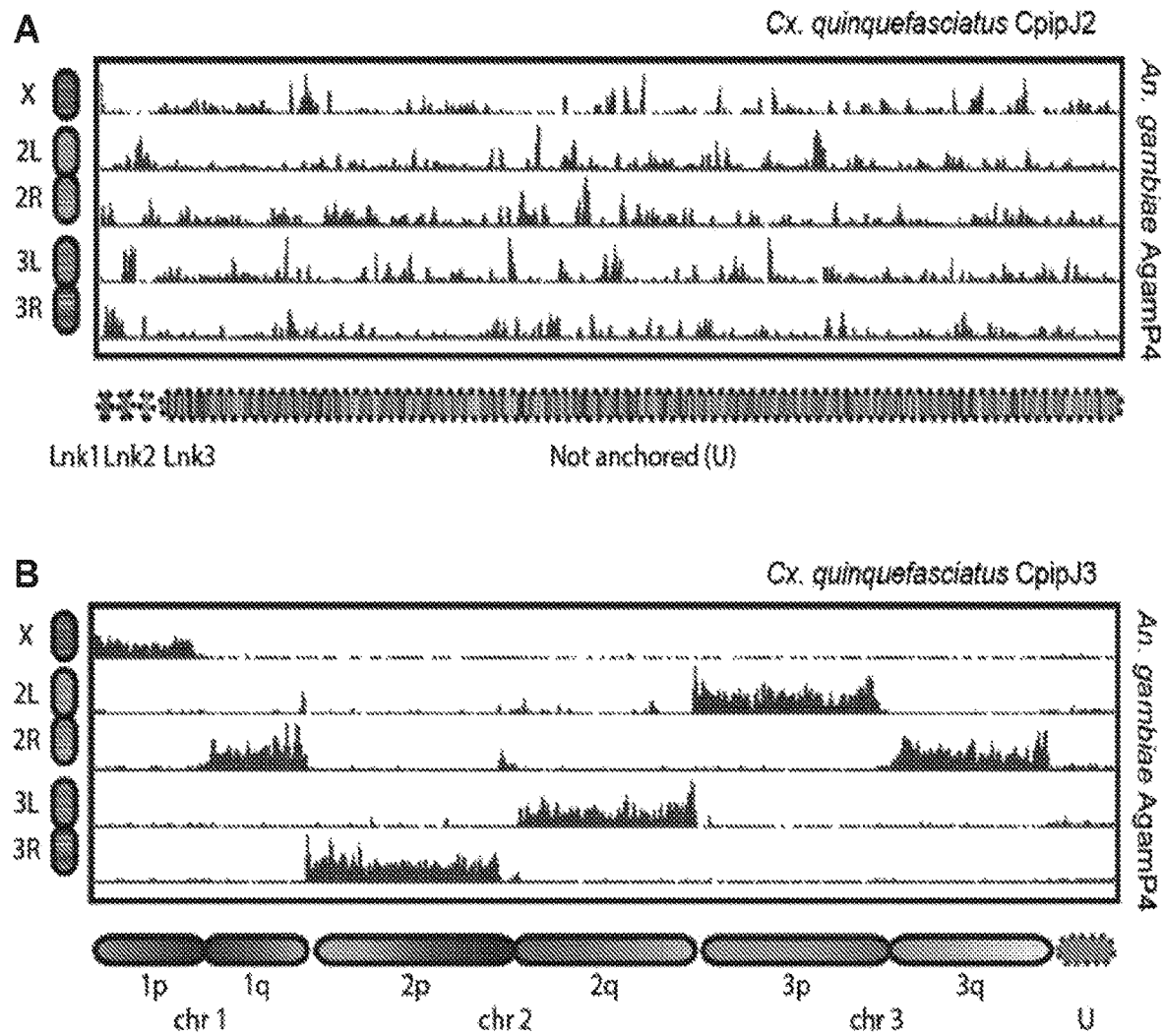
FIG. 52—Shows the CpipJ3 mapping reveals strong conservation of the contents of chromosome arms between *Cx. quinquefasciatus* and *An. gambiae*. A) Conservation of synteny between chromosomes of *Cx. quinquefasciatus* and *An. gambiae* as suggested by the CpipJ2 assembly. B) Conservation of synteny as represented by the CpipJ3 assembly. Chromograms along the x- and y-axes indicate which portions of CpipJ3 correspond to which positions in the other genomes and genome assemblies.
Figure 53:
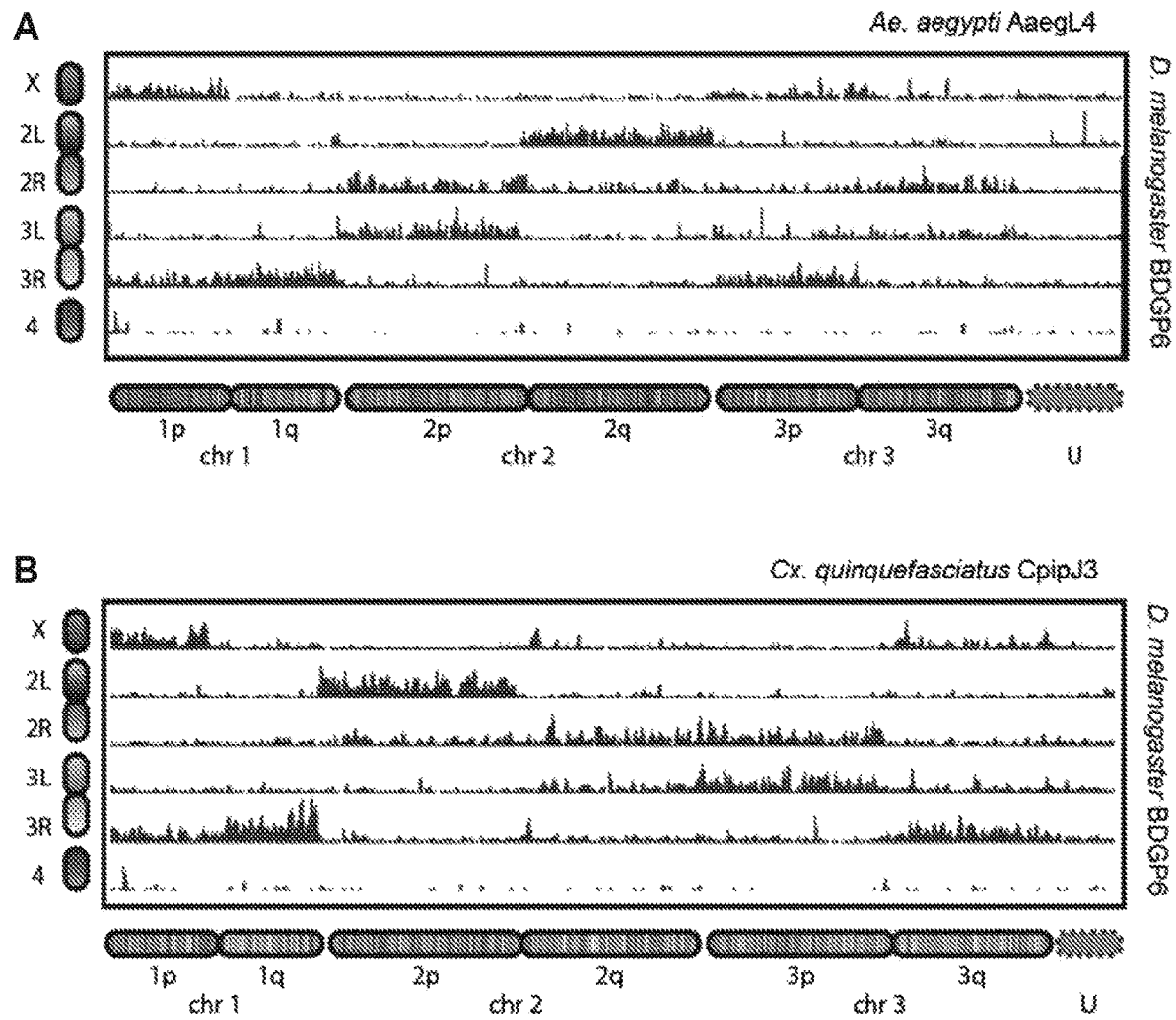
FIG. 53—Shows conservation of synteny across dipterans. Several chromosome arms, such as *D. melanogaster* 2L, *Ae. aegypti* 2q, and *Cx. quinquefasciatus* 2p, show strong conservation of content. Chromograms along the x- and y-axes indicate which portions of BDGP6 correspond to which positions in the other genomes and genome assemblies.
Figure 54:
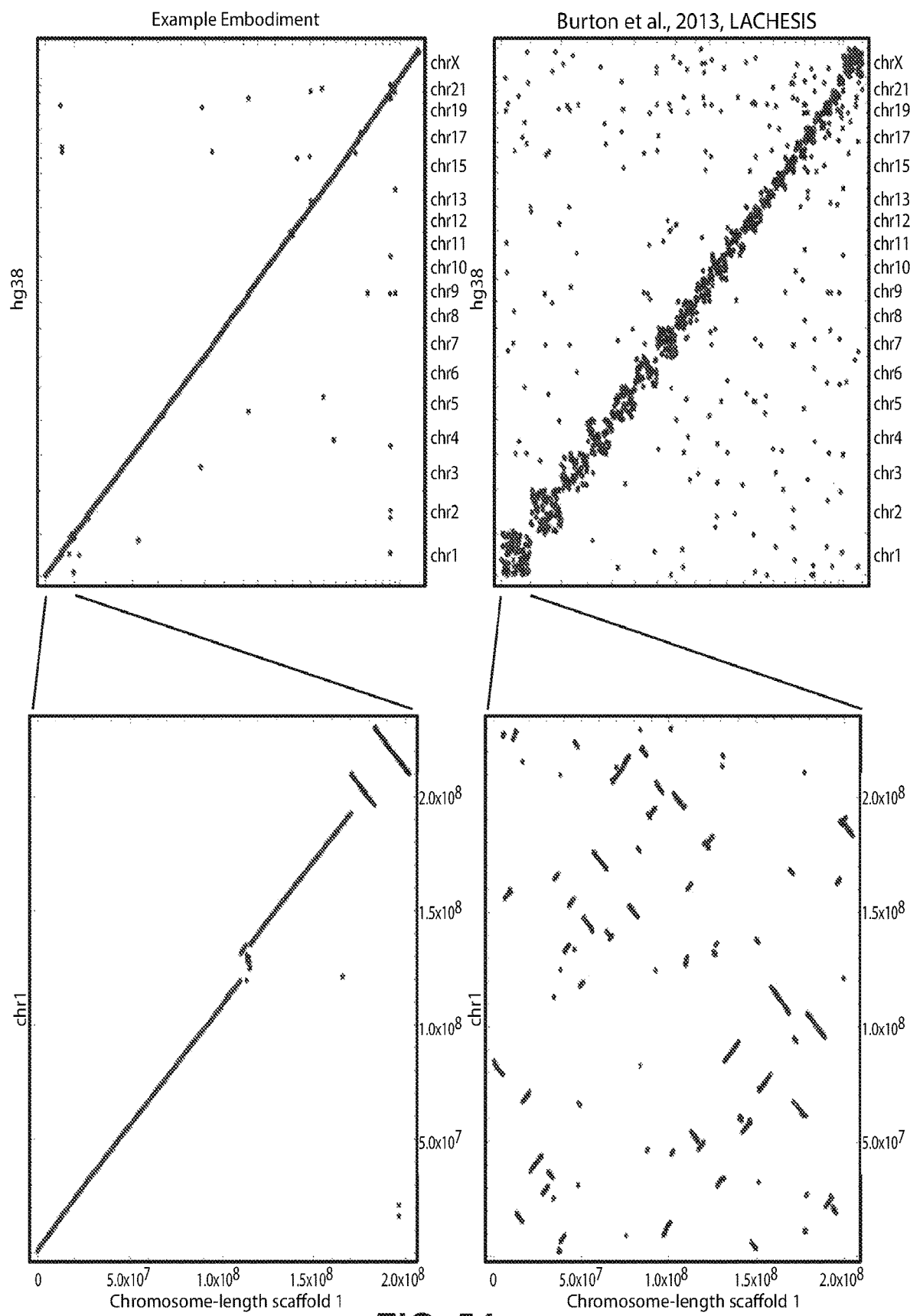
FIG. 54—Shows comparison of scaffolding algorithms presented in (10) and the current paper. Misassembly detection has been disabled in our pipeline to focus the comparison specifically on scaffolding abilities. The algorithms have been given the same data as input: set of DISCOVAR de novo scaffolds from 60× PE250 Illumina short reads and 6.7× of Hi-C data. In both cases only scaffolds longer than 20 kb have been used. Although clustering is clearly visible in the LACHESIS output individual chromosome-length scaffolds were not correctly reconstructed.
Figure 55:
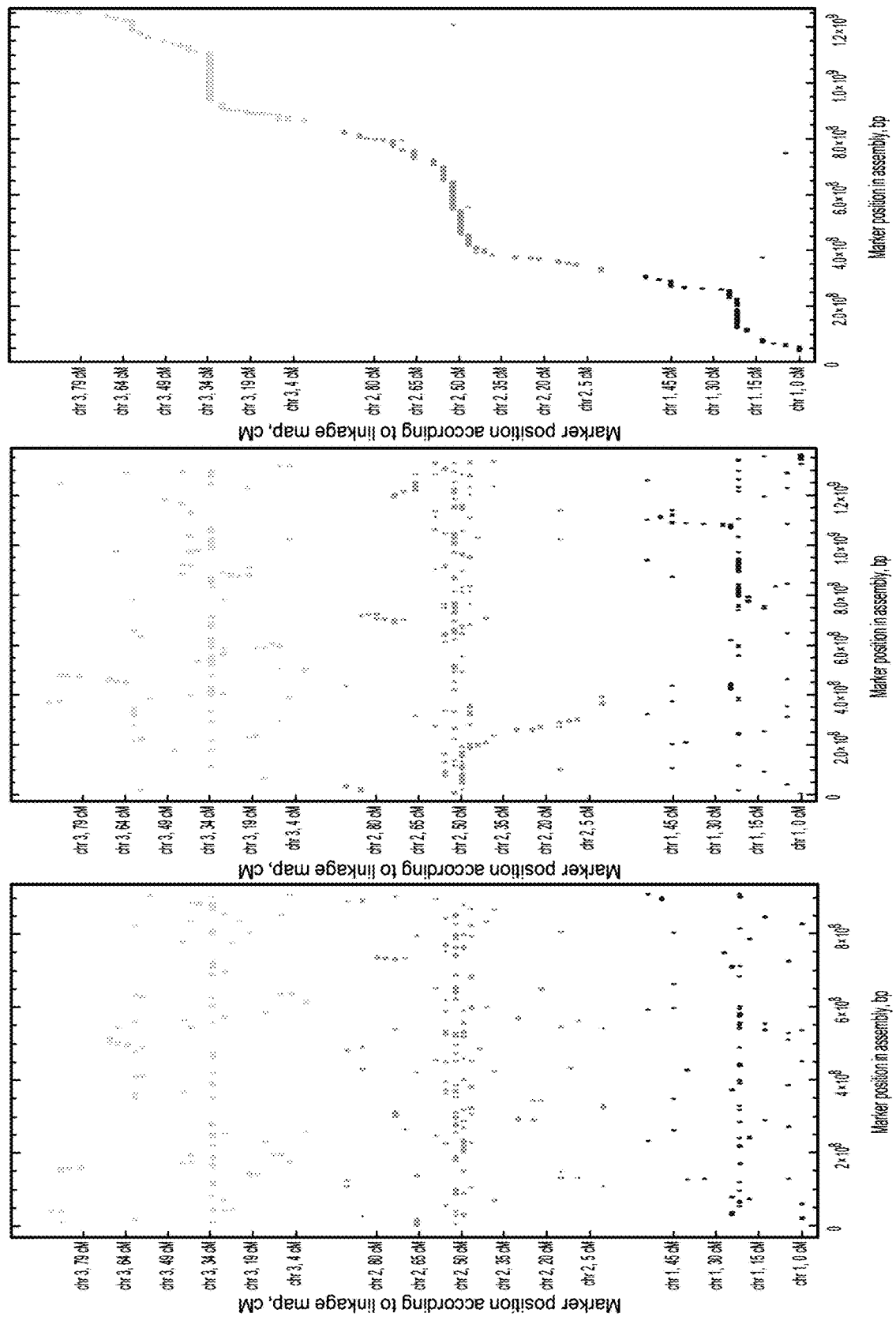
FIG. 55—Shows comparison of the results of running LACHESIS (10), scaffolding algorithm (without misjoin correction) in accordance with an example embodiment, and full pipeline (including misjoin correction) on AaegL2 with the existing linkage map (19).
Figure 56:
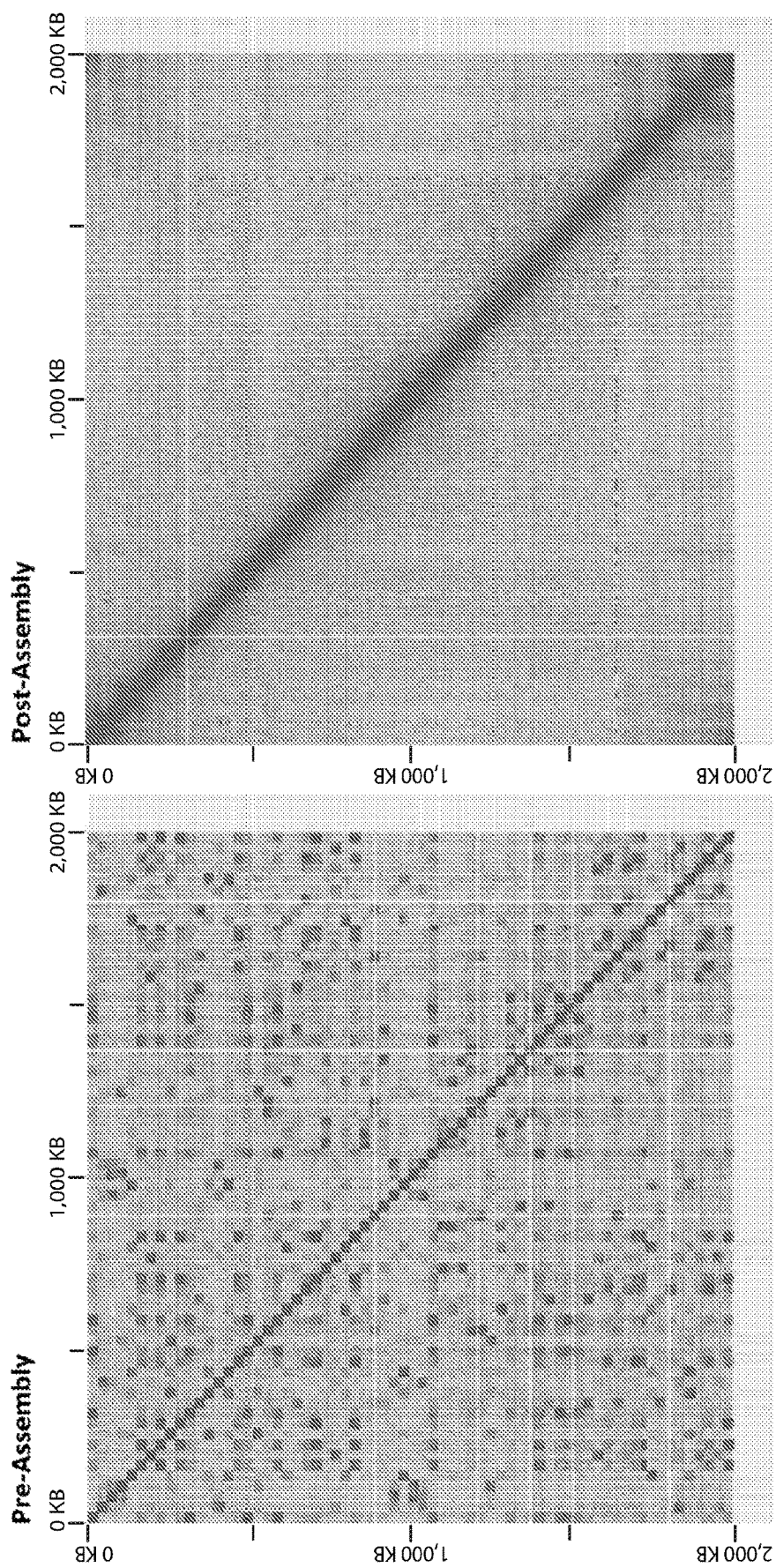
FIG. 56—shows application of H—C methods in accordance with example embodiments to assemble the genome of *L. acidophilus* bacterium from 30 kb input contigs.
Figure 57:
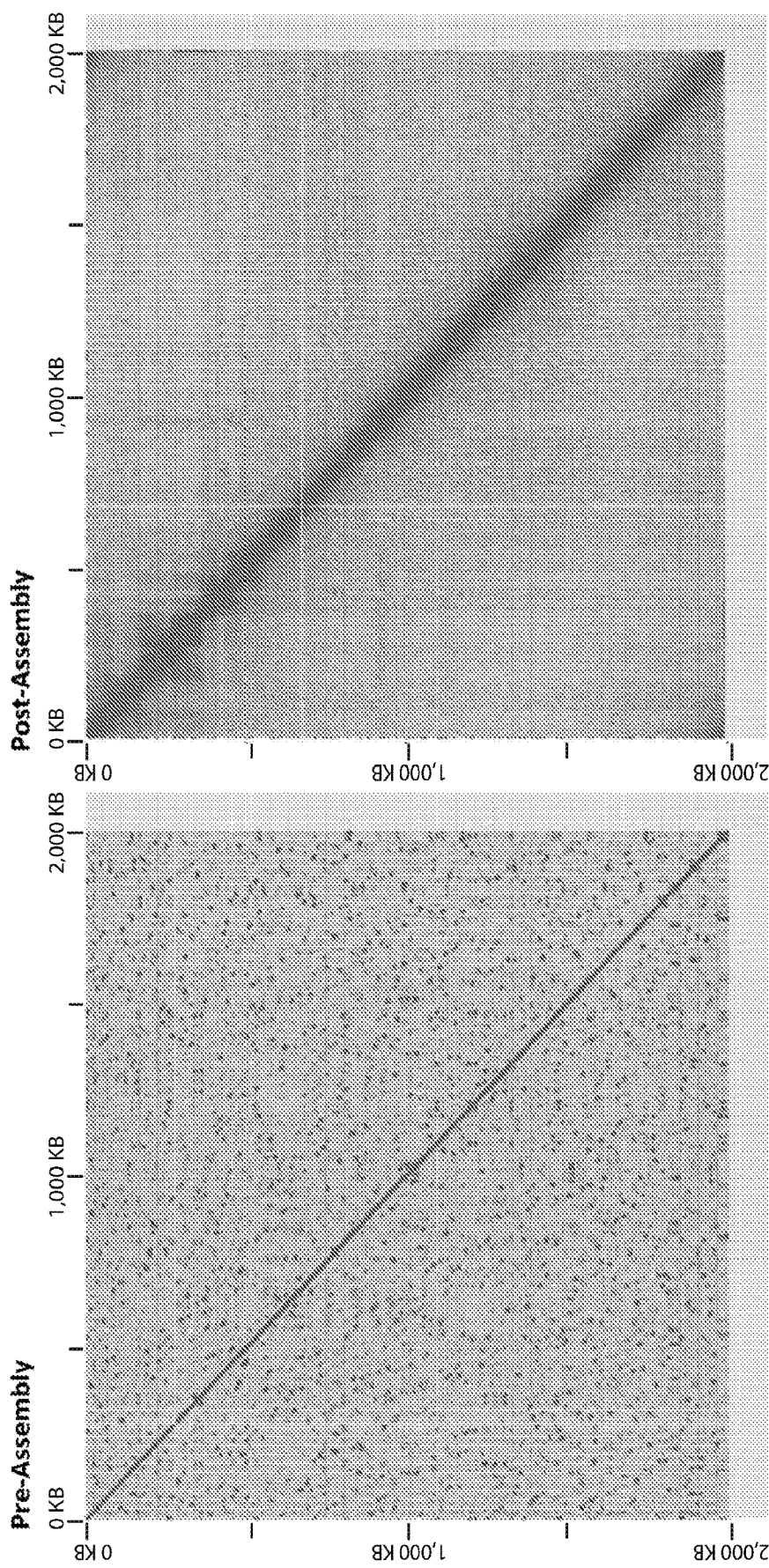
FIG. 57—shows application of Hi-C methods in accordance with example embodiments to assemble the genome of *L. acidophilus* bacterium from 10 kb input contigs.
Figure 58:
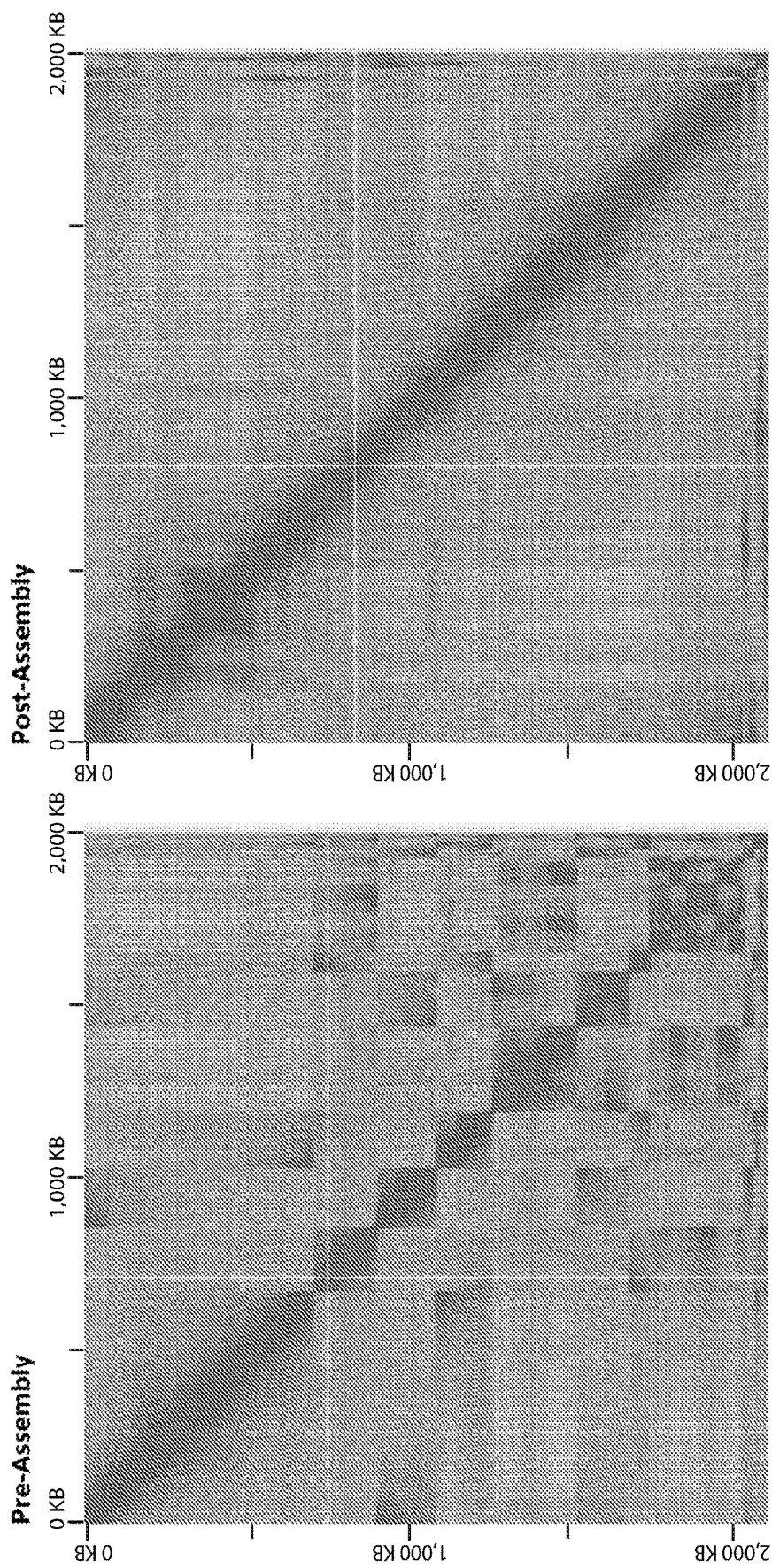
FIG. 58—shows application of Hi-C methods in accordance with example embodiments to assemble the genome of *L. acidophilus* using DNA-seq and Hi-C data as input. The input contigs were produced from DNA-seq using SPAdes genome assembler.
Figure 59:
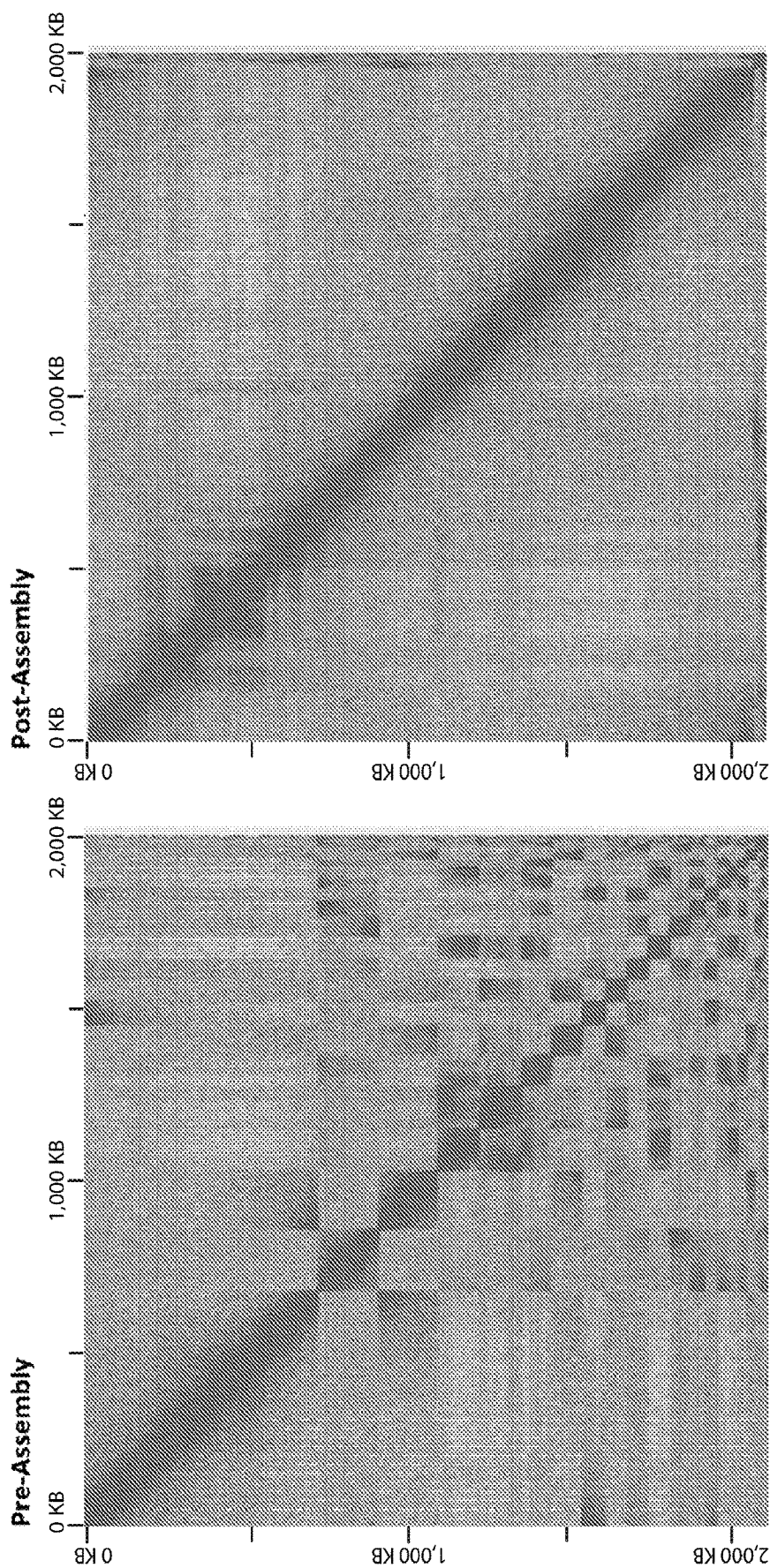
FIG. 59—shows application of Hi-C methods in accordance with example embodiments to assembling the genome of *L. acidophilus* assuming only Hi-C data as input. The input contigs were produced from Hi-C reads using SPAdes genome assembler.
Figure 60:
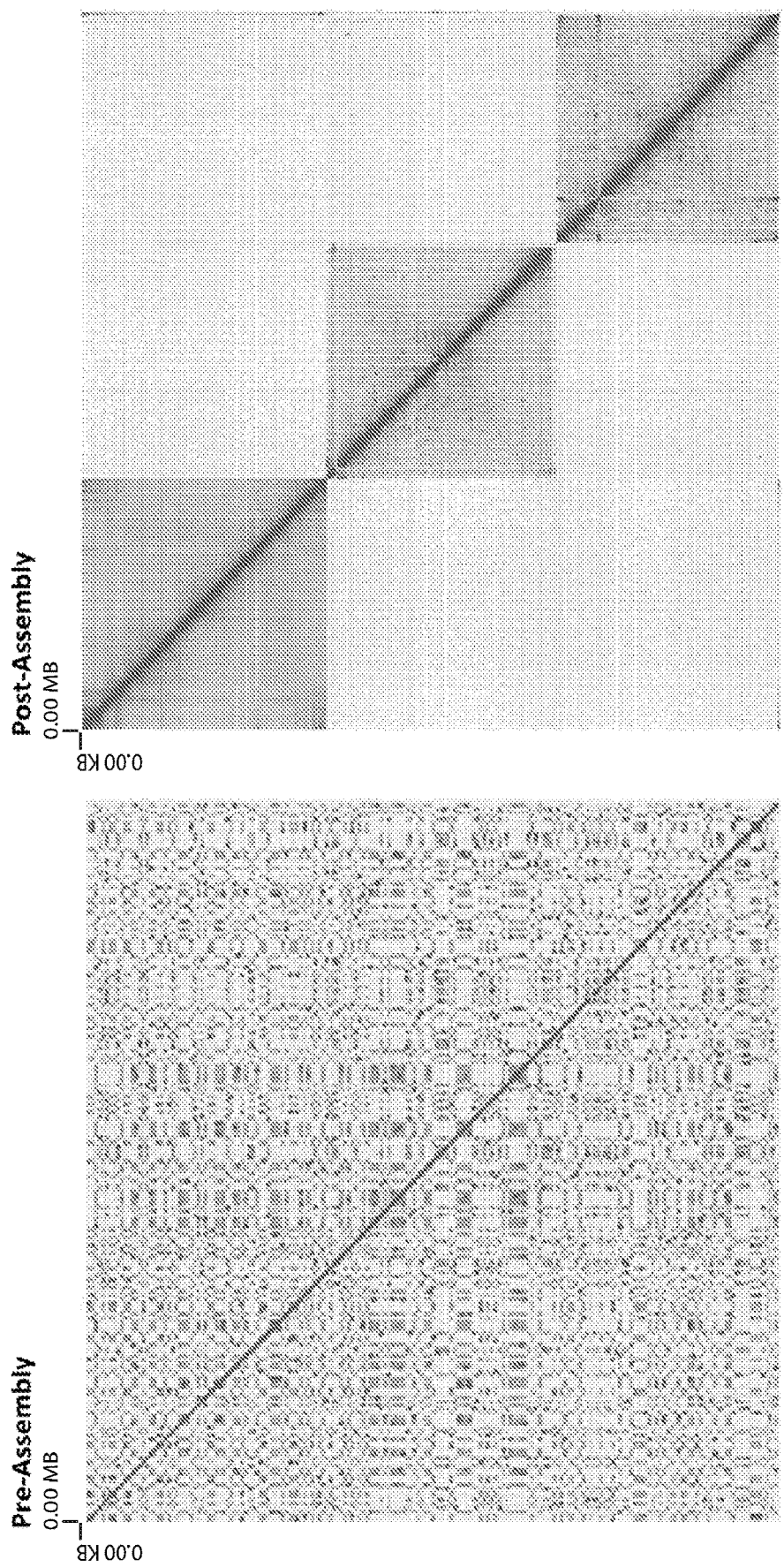
FIG. 60—shows application of Hi-C methods in accordance with certain example embodiments to assembling the genome of *L. acidophilus*, *L. delbueckii* (subspecies *blugaricus*) and *S. thermophiles* simultaneously.

The assemblies of the *Ae. aegypti* and *Cx. quinquefasciatus* genomes provided an opportunity to study genome evolution. First, a whole-genome alignment between the published *Anopheles gambiae* genome, which is 278 Mb long, and *Ae. aegypti*, which is ~1.3 Gb long were examined. This analysis identified 1,389 large blocks of conserved synteny (FIG. 50). Similar results were observed for *Cx. quinquefasciatus*. Despite extensive rearrangements, correspondence of sequence content among chromosome arms in *An. gambiae*, *Cx. quinquefasciatus* and *Ae. aegypti* was observed. Specifically, for the vast majority of DNA sequences on a particular chromosome arm in one of the three species, the homologous sequences were all found on a single chromosome arm in the other two species. The only exception is the observation that a single arm in *An. gambiae* (2R) corresponds to two arms in both *Ae. aegypti* (1q and 3p) and *Cx. quinquefasciatus* (1q and 3q). This is consistent with the breakage of this arm in the lineage leading to the shared ancestor of *Ae. aegypti* and *Cx. quinquefasciatus* (FIG. 36). These observations are consistent with cytogenetic analyses (18-20) (FIGS. 51, 52). Taken together, these results suggest that—with the exception of the breakage event noted above—each chromosome arm in the *Aedes*, *Culex*, and *Anopheles* species descends from a single arm present in their common ancestor approximately 150-200 million years ago. The preference for within-arm rearrangement in mosquitos is stronger than has been observed in mammals (25). Interestingly, the left arm of chromosome 2 in *Drosophila melanogaster* has a clear counterpart in all three mosquito species. Thus, all four arms derive from a single chromosome arm present in their dipteran ancestor a quarter of a billion years ago. (See FIGS. 36, 53.) Overall, the results show that incorporating Hi-C data into genome assembly provides a rapid, inexpensive methodology for generating highly accurate de novo assemblies with chromosome-length scaffolds.

It is important to bear in mind that these assemblies still contain errors. For example, while the Hi-C data provides extensive links covering large distances, the current approach is not perfect for local ordering of small adjacent contigs. This might be circumvented by more sophisticated analysis of Hi-C data. Additional data (such as long or paired-end reads) could also improve the results.

The ability to rapidly and reliably generate genome assemblies with chromosome-length scaffolds should accelerate genomic analysis of many organisms.

Example 5—In Situ Hi-C Protocol on Microbes

Day 0: Crosslinking (1 Hour)
1) Grow bacteria in solid or liquid media under recommended culture conditions and plan to crosslink cells while still in log (exponential) phase. If working with solid media, pick colonies and resuspend in room temperature 1×PBS (phosphate-buffered saline) immediately prior to crosslinking.
2) If possible to determine bacterial culture density, dilute bacterial cultures in order to obtain a final concentration of 1 billion cells per milliliter.
3) In a chemical fume hood, add freshly opened formaldehyde solution to a final concentration of 1%. Incubate at room temperature for exactly 30 minutes with constant mixing.
4) Add glycine solution to a final concentration of 0.2 M to quench the reaction. Incubate at room temperature for 5 minutes with constant mixing.
5) Centrifuge at 3000-5000×G, 4° C. for 5 minutes. Discard the supernatant into an appropriate hazardous waste container.

6) Resuspend the cells in x ml of ice-cold 1×PBS (phosphate-buffered saline), where x=the number of pellets you intend to make.
7) Mix well to disperse clumps of cells and aliquot into labeled 1.5 ml microcentrifuge tubes at 1 ml per tube.
8) Centrifuge at 3000-5000×G, 4° C. for 5 minutes. Immediately discard the supernatant and immediately flash-freeze the cell pellets in a dry ice/ethanol bath or a liquid nitrogen bath.
9) Store the frozen cell pellets at −80° C. or proceed directly to the Hi-C protocol.

Day 1: Permeabilization and Restriction Digest (1 Hour)

10) Allow cross-linked sample to cool on ice for ~30 min.
11) Gently resuspend pellet in 25 µl of 10 mM Tris-HCl [pH 7.5].
12) To permeabilize the cellular membrane and solubilize proteins, add 25 µl of 1.0% sodium dodecyl sulfate (SDS) [final: 0.5%]. Quickly mix by flicking the tube, and incubate at 62° C. for 10 minutes.
13) Add 148 µl of water and 25 µl of 10% Triton X-100 to quench SDS. Mix well by pipetting, avoiding excessive foaming. Incubate at 37° C. for 15 minutes.
14) Add 25 µl of 10× NEBuffer 2 (New England BioLabs [NEB], B7002S). Alternatively, 100 U of BfuCI restriction enzyme (NEB, R0636S) may be used.

Day 2: Fill-in, Proximity Ligation, and Crosslink Reversal (7-8 Hours)

15) To inactivate MboI, incubate at 62° C. for 20 minutes, then cool to room temperature.
16) To fill in the 5' restriction fragment overhangs and mark the DNA ends with biotin, add 50 µl of fill-in master mix:
    22.5 µl of water
    15 µl of 1 mM biotin-11-dUTP (Thermo, R0081)
    1.5 µl of 10 mM dATP
    1.5 µl of 10 mM dCTP
    1.5 µl of 10 mM dGTP
    8 µl of 5 U/µl DNA polymerase I, large (Klenow) fragment (NEB, M0210L)
17) Mix by pipetting and incubate at 37° C. for 1.5 hours with rotation.
18) To catalyze proximity ligation, add 900 µl of ligation master mix:
    669 µl of water
    120 µl of 10× T4 DNA ligase reaction buffer (NEB, B0202S)
    100 µl of 10% Triton X-100
    6 µl of 20 mg/ml bovine serum albumin (BSA) (NEB, B9000S)
    5 µl of 400 U/µl T4 DNA ligase (NEB, M0202L)
19) Mix by inverting and incubate at room temperature for 4 hours with slow rotation.
20) Centrifuge at 2500×G, 25° C. for 5 minutes. Discard the supernatant.
21) Add enough water to bring final volume of sample to 297 µl, then add 33 µl of 10% sodium dodecyl sulfate (SDS) [final: 1.0%]
22) To degrade proteins and reverse crosslinks, add 35 µl of 0.8 U/µl proteinase K (NEB, P8107S) and 45.7 µl of 5 M NaCl. Mix by pipetting and pulse centrifuge. Incubate at 55° C. for 4 hours.
23) Raise the temperature to 68° C. and incubate overnight.

Day 3: DNA Precipitation and Shearing (4-7 Hours)

24) Cool sample to room temperature, not on ice.
25) To precipitate DNA, add 875 µl of pure 100% ethanol (70% final concentration) and 3.13 µl of 20 mg/ml glycogen (50 µg/ml final concentration).
26) Mix well by inverting and incubate at −80° C. for at least 1 hour or at −20° C. overnight.
27) Centrifuge at maximum speed, 2° C. for 15 minutes.
28) Immediately after centrifugation, keeping the sample on ice as much as possible, discard the supernatant by pipetting.
29) Resuspend in 800 µl of freshly prepared 80% ethanol to remove traces of salt. Centrifuge at maximum speed for 5 minutes.
30) Discard the supernatant by pipetting and incubate briefly with cap open at 37° C. until remaining traces of ethanol evaporates. Expect the pellet to be very small and almost invisible.
31) Dissolve DNA pellet in 130 µl of 1× Tris buffer (10 mM Tris-HCl pH 8.0). Make sure to elute any precipitated DNA from the sides of the tube. Incubate at 55° C. with 600 rpm shaking for at least 30 minutes to fully dissolve DNA.
32) Transfer the entire sample volume to a Pre-Slit Snap-Cap 6×16 mm glass microTUBE vial (Covaris, 520045).
33) To make the library suitable for Illumina high-throughput sequencing, which requires insert sizes of 300-500 base pairs (bp), shear DNA using the following parameters:
    Instrument: M220 Focused-ultrasonicator (Covaris)
    Peak Power: 50.0
    Duty Factor: 20.0
    Cycles/Burst: 200
    Duration: 105 seconds ("DNA_1m45s" program)
34) Transfer sheared DNA to a fresh 1.5-ml tube. Wash the Covaris microTUBE with 70 µl of 1× Tris buffer and add to the sample. Bring the volume of the sample to exactly 300 µl.
35) Incubate at 4° C. overnight, or continue directly to biotin pulldown.

Day 4: Biotin Pull-Down, End Repair, A-Tailing, and Adapter Ligation (7-9 Hours)

36) Prepare wash buffers:
    2× Binding Buffer (2× BB)
        23.52 ml of water
        16 ml of 5 M NaCl [final: 2 M]
        400 µl of 1 M Tris-HCl pH 8.0 [final: 10 mM]
        80 µl of 0.5 M EDTA [final: 1 mM]
    1× Tween Washing Buffer (1× TWB)
        19.8 ml of water
        20 ml of 2×BB
        200 µl of 10% Tween-20 [final: 0.05%]
37) Mix a bottle of 10 mg/ml Dynabeads MyOne Streptavidin T1 beads (Life Technologies, 65602) by vortexing to resuspend the beads in the buffer.
38) In a fresh 1.5 ml tube, aliquot 100 µl of the T1 beads, pulse centrifuge, and separate on a magnet. Discard the supernatant.
39) Wash the beads twice with 400 µl of 1× TWB, pipetting to mix. Separate on a magnet and discard the supernatant.
40) Resuspend the beads in 300 µl of 2×BB and add to the sample. Incubate at room temperature for 15 minutes with rotation to bind biotinylated DNA to the streptavidin-coated beads. Separate on a magnet and discard the supernatant.
41) Wash the beads sequentially in the following buffers by resuspending in the buffer, transferring to a fresh 1.5 ml tube if indicated, mixing on a heated shaker at 600 rpm for 2 minutes at the indicated temperature, pulse centrifuging, separating on a magnet, and discarding the supernatant:
   a) 600 µl of 1× TWB at 55° C.
   b) 600 µl of 1× TWB at 55° C.
   c) 100 µl of 1× Tris buffer at 25° C. (fresh tube)
42) Resuspend the beads in 100 µl of end repair master mix:
   88 µl of 1× T4 DNA ligase reaction buffer, diluted from 10× stock (NEB, B0202S)
   2 µl of 25 mM dNTP mix (all 4 nucleotides)
   5 µl of 10 U/µl T4 polynucleotide kinase (NEB, M0201L)
   4 µl of 3 U/µl T4 DNA polymerase I (NEB, M0203L)
   1 µl of 5 U/µl DNA polymerase I, large (Klenow) fragment (NEB, M0210L)
43) Pulse centrifuge and incubate at room temperature for 30 minutes. Separate on a magnet and discard the supernatant.
44) Wash the beads as before:
   a) 600 µl of 1× TWB at 55° C. (fresh tube)
   b) 600 µl of 1× TWB at 55° C.
   c) 100 µl of 1× Tris buffer at 25° C.
45) Resuspend the beads in 100 µl of A-tailing master mix:
   90 µl of 1× NEBuffer 2, diluted from 10× stock (NEB, B7002S)
   5 µl of 10 mM dATP
   5 µl of 5 U/µl Klenow fragment (3'→5' exo-) (NEB, M0212L)
46) Pulse centrifuge and incubate at 37° C. for 30 minutes. Separate on a magnet and discard the supernatant.
47) Wash the beads as before:
   a) 600 µl of 1× TWB at 55° C. (fresh tube)
   b) 600 µl of 1× TWB at 55° C.
   c) 100 µl of 1× Tris buffer at 25° C.
48) Resuspend the beads in 50 µl of 1× Quick ligation reaction buffer, diluted from 2× stock (NEB, M2200L).
49) Add 2 µl of Quick T4 DNA ligase (NEB, M2200L).
50) To enable multiplexing during sequencing, add 5 µl of an Illumina indexed adapter from array I96 and mix thoroughly by flicking the tube. Record the sample-index combination.
51) Pulse centrifuge and incubate at room temperature for 15 minutes. Separate on a magnet and discard the supernatant.
52) Wash the beads as before:
   a) 600 µl of 1× TWB at 55° C. (fresh tube)
   b) 600 µl of 1× TWB at 55° C.
   c) 100 µl of 1× Tris buffer at 25° C.
53) Resuspend the beads in 51 µl of 1× Tris buffer.
54) To detach DNA from streptavidin-coated beads, pulse centrifuge and incubate at 98° C. for 10 minutes. Separate on a magnet, transfer the supernatant to a fresh 1.5-ml tube, and discard the beads.
55) Quantify DNA yield by the Qubit dsDNA High Sensitivity Assay (Life Technologies, Q32854) using 1 µl of sample. Use this reading to determine the number of PCR cycles needed for amplification of the library to at least 10 nM.
56) Incubate at 4° C. overnight, or continue directly to PCR amplification.

Day 5: Final Amplification, SPRI Purification, and qPCR (5-7 Hours)
57) Working on ice, add 200 µl of PCR master mix:
   100 µl of 2× Phusion High-Fidelity PCR Master Mix with HF Buffer (NEB, M0531S)
   90 µl of water
   10 µl of Illumina indexing primers, F&R mix (Integrated DNA Technologies)
58) To amplify the Hi-C library, aliquot 50 µl into each of 4 fresh 0.2 ml PCR tubes and run the following PCR protocol:
   98° C. for 30 sec
   [98° C. for 10 sec
   55° C. for 30 sec
   72° C. for 30 sec] cycle 8 times
   2° C. for 7 min
   4° C. indefinitely
59) After 8 cycles of PCR, remove 1 PCR tube and place on ice.
60) Separate on a magnet and use 1 µl of PCR reaction mix to run a 1.2% agarose gel to verify successful PCR. In a successful PCR without prior size selection, you should see a range of DNA between 100 bp and 1 kb. If no DNA is visible, run another cycle of PCR and repeat gel. Repeat until band is visible.
61) Once PCR has been deemed successful, move onto final cleanup and size selection.
62) Pool the PCR aliquots into a fresh 1.5-ml tube. Some loss of volume is expected, so wash the PCR tubes with ~20 µl of 1× Tris buffer and add to the sample, bringing the total reaction volume to exactly 250 µl.
63) Separate on a magnet. Transfer the solution to a fresh tube and discard the beads.
64) Warm a bottle of AMPure XP beads to room temperature. Gently shake to resuspend the magnetic beads. Add 113 µl of beads to the PCR reaction (0.45× volumes). Mix by pipetting and incubate at room temperature for 5 minutes.
65) Separate on a magnet. Transfer the clear solution to a fresh tube, avoiding any beads. The supernatant will contain fragments shorter than ~650 bp.
66) Add exactly 62 µl of fresh AMPure XP beads to the solution. Mix by pipetting and incubate at room temperature for 5 minutes.
67) Keeping the beads on the magnet, wash once with 700 µl of 80% ethanol without mixing.
68) Remove ethanol completely. To remove traces of short products, resuspend in 100 µl of 1× Tris buffer and add another 70 µl of AMPure XP beads or SPRI solution (0.7× to retain fragments longer than 400 bp).
69) This extra purification step guarantees complete removal of adapter-dimers prior sequencing and retaining on the beads library with final size 400-700 bp.
70) Separate on a magnet and remove the clear solution.
71) Keeping the beads on the magnet, wash twice with 700 µl of freshly prepared 80% ethanol without mixing. Leave the beads on the magnet for 5 minutes to allow the remaining ethanol to evaporate.
72) Resuspend the beads in 25 µl of 1× Tris buffer to elute DNA. Incubate at room temperature for 5 minutes, separate on a magnet, and transfer the supernatant to a fresh 1.5-ml tube labeled with the HIC# and "Final Library." Store the libraries at −20° C. indefinitely.
73) Measure the DNA concentration of each final Hi-C library using a qPCR Illumina Library Quantification Kit (KAPA Biosystems, KK4824). Use an Agilent Bioanalyzer to estimate the average fragment size in bp, and calculate the final molarity of each library. The Hi-C final libraries are now ready for Illumina paired end sequencing.

Example 6—7 h Cells-to-Sequencing Native Hi-C Protocol

This protocol uses fresh or cryopreserved cells. The library prep can be completed in about 7 hours only if all buffers etc. are prepared in advance and all instruments are ready for use. Set centrifuge to 4° C. and thermomixer at 58° C. while thawing cells and reagents on ice. Have all reagents thawed on ice and start preparing master-mixes 2-5 minutes prior using them. It is also easier to use a library prep kit such as Kapa library preparation kit for Illumina Platforms. Mix reactions by flicking the tubes or by low-speed touch vortex.

Preparation of Cells (~15 Minutes)
1) Grow mammalian cells under recommended culture conditions to about 80% confluence. Pellet suspension cells or detached adherent cells by centrifugation at 500×G for 3 minutes.
2) Resuspend cells in 1×PBS at expected concentration of approximately 0.5-3 million cells/ml and count them using Countess cell counter. Distribute cells for each library (~1 M cells per tube) in 1.5-ml tubes.
3) Centrifuge for 3 minutes at 500×G at room temperature. Discard supernatant. Either proceed with library prep or resuspend the cells in 100 µl 1×PBS 10% DMSO and freeze at −80° C. for long term storage.

Lysis and Restriction Digest (~45 Minutes)
4) Prepare in advance lysis buffer: 20 mM Tris pH 7.5, 1 mM EDTA, 5 mM EGTA, 100 mM NaCl, 100 µg/ml BSA, 0.2% Igepal CA360 with added protease inhibitor cocktail (Roche, 11836170001) to final 1× concentration. Keep on ice. Buffer can be stored for 2 weeks at 4° C.
5) Gently resuspend ~1 million cells in 100 µl of ice-cold lysis buffer. Keep on ice for 3 minutes.
6) Centrifuge for 3 minutes at 750×G at 4° C. Carefully pipet out the supernatant and resuspend the nuclear pellet in 100 µl 1×NEB Cutsmart buffer (or DpnII buffer if restricting with DpnII) and add Triton X-100 to 0.5% final concentration.
7) Heat nuclear suspension at 58° C. for 15 min to heat-inactivate endogenous nucleases.
8) Cool down on ice and add 100 U of MseI restriction enzyme (NEB, R0525) and mix well. Alternatively, 50 U of DpnII (NEB, R0543T) can be used. Note that MboI does not produce good quality libraries with the current protocol.
9) Restrict chromatin for 15 minutes at 37° C. without mixing.

Marking of DNA Ends and Proximity Ligation (~60 Minutes)

The 5' overhangs produced during restriction digest (TA for MseI) are blunted incorporating biotin-dUTP and dATP. If using other restriction enzymes, other combination of biotinylated and regular dNTPs may be needed.
10) Centrifuge for 3 minutes at 750×G at 4° C. Resuspend pellet in 25 µl 1× Ligase buffer (NEB, B0202)
11) Incubate at 58° C. for 10 minutes then cool on ice. This heating step is normally included to inactivate traces of restriction enzymes like DpnII and although inactivation of MseI is not strictly needed as its recognition site is lost during blunting, having this step greatly improves library quality probably due to melting the restricted DNA ends and mixing them before fill-in and ligation.
12) Prepare 50 µl master mix to fill in the restriction fragment overhangs and mark the DNA ends with biotin
   18.5 µl of water (or 15.5 µl if using DpnII)
   5 µl of 10×NEB T4 DNA ligase buffer (NEB, B0202)
   4 µl of 10% Triton X-100
   1 µl of 10 mg/ml Bovine Serum Albumin (100×BSA)
   15 µl of 1 mM biotin-11-dUTP (Thermo Fisher, R0081)
   1.5 µl of 10 mM dATP (or 4.5 µl mix of 10 mM each dATP, dCTP, dGTP if using DpnII)
   5 µl of 5 U/µl DNA Polymerase I, Large (Klenow) Fragment (NEB, M0210)
13) Mix well and incubate at 37° C. for 15 minutes without mixing.
14) Add 5 µl DNA Quick Ligase (NEB, M2200). Mix well and incubate at room temperature for 30 minutes without mixing.

Purification and DNA Shearing (~45 Minutes)
15) After ligation is over, pellet nuclei by spinning at 750×G for 3 minutes. Discard the supernatant.
16) Resuspend nuclear pellet in 23 µl 1× Tris buffer (10 mM Tris pH 8) and add:
   1 µl 10% SDS
   1 µl of 5 M NaCl
   5 µl of 20 mg/ml proteinase K (NEB, P8102)
17) Incubate at 55° C. for 10 min.
18) Cool tubes at room temperature. Dilute library with 100 µl 1× Tris buffer bringing final volume to 130 µl and transfer to Covaris micro-tube.
19) To make the biotinylated DNA suitable for high-throughput sequencing using Illumina sequencers, shear to a size of 300-500 bp using Covaris instrument. Note that shearing parameters may need to be adjusted for the current buffer composition and may be different from the conditions used for regular in situ Hi-C protocol. All fragments must be shorter than 700 bp with a peak around 400 bp. 20) Remove the cap of the Covaris tube and transfer solution to a 1.5-ml tube containing 90 µl AMPure XP (SPRI) beads (~0.7× ratio). Mix well and incubate at room temperature for several minutes. Reclaim the beads using a magnet. Discard supernatant.
21) Keeping the beads on the magnet, wash once with 300 µl of 70% ethanol.
22) Elute beads in 25 µl of 1× Tris buffer Biotin Pull-Down (~15 Minutes)
23) Prepare in advance Tween Binding and Washing Buffer (TWB): 5 mM Tris-HCl (pH 7.5); 0.5 mM EDTA; 1 M NaCl; 0.05% Tween 20. Pre-heat the buffer to 55° C. Perform all the following steps in low-binding tubes. Keep TWB buffer aliquots pre-heated at 55° C. during the library preparation steps. Buffer can be stored at 4° C. for one month.
24) Take 30 µl of 10 mg/ml Dynabeads MyOne Streptavidin T1 beads (Thermo Fisher, 65602) per Hi-C library and separate on a magnet discarding the storage solution.
25) Resuspend the beads in 300 µl of TWB and add to the tube with library from step 22. Incubate at 55° C. for 10 minutes mixing at 650 RPM to bind biotinylated DNA to the streptavidin beads.
26) Separate on a magnet and discard the solution.

27) Wash the beads by adding 300 µl of pre-heated 1× TWB. Heat the tubes on a Thermomixer at 55° C. for 1 min with mixing. Reclaim the beads using a magnet. Discard supernatant.
28) Resuspend beads in 100 µl 1× Tris buffer and transfer to a new tube.

Preparation for Illumina Sequencing (~180 Minutes)

The steps of end repair, A-tailing and adapter ligation could be done using Kapa library preparation kit for Illumina Platforms (Kapa Biosystems, KK8201) as well as the master mixes as described in the in situ Hi-C protocol.

29) Reclaim beads and discard the buffer. To repair ends of sheared DNA, resuspend beads in 70 µl of master mix:
   58 µl of water
   7 µl of 10×KAPA End Repair Buffer
   5 µl of KAPA End Repair Enzyme
30) Incubate at room temperature for 30 minutes. Separate on a magnet and discard the solution.
31) Wash the beads by adding 300 µl of pre-heated 1× TWB. Heat the tubes on a Thermomixer at 55° C. for 1 min with mixing. Reclaim the beads using a magnet. Discard supernatant.
32) Resuspend beads in 100 µl 1× Tris buffer and transfer to a new tube. Reclaim beads and discard the buffer.
33) Resuspend beads in 50 µl of dATP attachment master mix:
   42 µl of water
   5 µl of 10×KAPA A-tailing Buffer
   3 µl of KAPA A-tailing Enzyme
34) Incubate at 30° C. for 30 minutes. Separate on a magnet and discard the solution.
35) Wash the beads by adding 300 µl of pre-heated 1× TWB. Heat the tubes on a Thermomixer at 55° C. for 1 min with mixing. Reclaim the beads using a magnet. Discard supernatant.
36) Resuspend beads in 100 µl 1× Tris buffer and transfer to a new tube. Reclaim beads and discard the buffer.
37) Spin briefly adapter plate before using it to ensure that all liquid is on the bottom. Add 5 µl of an Illumina indexed adapter. Record the sample-index combination.
38) Resuspend beads and adapter in 45 µl of ligation reaction mix:
   30 µl of water
   10 µl of 5×KAPA Ligation Buffer
   5 µl of KAPA T4 DNA Ligase
39) Incubate at room temperature for 15 minutes. Separate on a magnet and discard the solution.
40) Wash the beads by adding 300 µl of pre-heated 1× TWB. Heat the tubes on a Thermomixer at 55° C. for 1 min with mixing. Reclaim the beads using a magnet. Discard supernatant.
41) Resuspend beads in 100 µl 1× Tris buffer and transfer to a new tube. Reclaim beads and discard the buffer.
42) Resuspend in 50 µl of amplification mix:
   25 µl of 2×KAPA HiFi HotStart ReadyMix (or 2×NEB Phusion Master Mix with HF Buffer)
   20 µl of water
   5 µl of Broad Institute Illumina indexed PE primer mix
43) Amplify the Hi-C library directly off of the T1 beads with 8-12 cycles:
   98° C. for 30 sec
   Cycles 4-12:
   [98° C. for 10 sec
   55° C. for 30 sec
   72° C. for 30 sec]
   72° C. for 7 min
   4° C. indefinitely
Note that annealing temperature for Broad Institute adapters is 55° C., which is different than the temperature for most Illumina adapters.
44) After amplification is complete, separate reaction on a magnet. Transfer the solution to a fresh tube/strip with 40 µl SPRI beads. Mix well and incubate at room temperature for several minutes.
45) Keeping the beads on the magnet, wash once with 200 µl of 70% ethanol without mixing.
46) Remove ethanol completely. To remove traces of short products, resuspend in 100 µl of 1× Tris buffer and add 60 µl of SPRI solution. Mix by pipetting and incubate at room temperature for several minutes.
47) Separate on a magnet and remove the clear solution. Keeping the beads on the magnet, wash twice with 200 µl 70% ethanol without mixing. Leave the beads on the magnet for couple of minutes to allow the remaining ethanol to evaporate.
48) Add 30 µl of 1× Tris buffer to elute DNA. Mix by pipetting, incubate at room temperature for few minutes.
49) Separate on a magnet, and transfer the solution to a fresh labeled tube. The result is a final native in situ Hi-C library.
50) Run library on Agilent TapeStation or Bioanalyzer to verify size and concentration prior sequencing on Illumina sequencing platform.

Example 7—Nuclei Pellet Preparation from Fresh Plant Samples and Hi-C Protocol

Fresh Sample

1) Put 5-10 g of chopped up plant tissue into a food processor.
2) Pulse thrice at 5-second intervals with the food processor's chopping blade.
3) Transfer sample to 50 mL tube.

Crosslinking

1) Crosslink in 1% formaldehyde in 1× Homogenization Buffer pH 9.2 (10 mM Trizma, 80 mM KCl, 10 mM EDTA, 1 mM spermidine trihydrochloride, 1 mM spermine tetrahydrochloride, 0.5 M sucrose) for 30 min with mixing in a 50-mL tube.
2) Quench formaldehyde with 0.2 M Glycine and incubate for 5 min with mixing.
3) Remove solution and resuspend sample in 1×PBS. Mix thoroughly for 5 min.
4) Remove solution and store in −80° C.

Nuclei Extraction and Purification (2-4 Hours)

5) Grind frozen plant sample into a fine powder in liquid nitrogen with a pre-chilled mortar and pestle for ~5-10 minutes.
6) Transfer powder into beaker and add 40-50 ml of ice-cold Nuclear Isolation Buffer pH 9.2 (10 mM Trizma, 80 mM KCl, 10 mM EDTA, 1 mM spermidine trihydrochloride, 1 mM spermine tetrahydrochloride, 0.5 M sucrose, 0.5% Triton X-100, 0.15% beta-mercaptoethanol)
7) Incubate beaker on ice with shaking for 30 minutes.
8) Filter suspension through 2 layers of Miracloth into 50-ml tubes. Gently squeeze Miracloth to collect remaining suspension. Discard the solids.
9) Centrifuge at 200 g, 4° C. for 2 minutes. Transfer the supernatant to another 50-ml tube and discard the pellet.

10) Centrifuge supernatant at 2,000 g-3,800 g, 4° C. for 5 minutes (speed may vary based on the size of the genome). Discard the supernatant.
11) Resuspend pellet in 30 ml of cold NIB buffer and repeat steps 10-12 until the pellet is white or a pale shade (Usually 1-4 washes are necessary).
12) Resuspend in 1 ml of ice-cold Hi-C lysis buffer (10 mM Tris-HCl pH 8.0, 10 mM NaCl, 0.2% Igepal CA630) and transfer to 1.5-ml tubes (resuspend in a larger volume and split appropriately for larger amounts of starting material.).
13) Centrifuge at 2,000-3,800 g, 4° C. for 5 minutes. Discard the supernatant. Optionally repeat steps 12 and 13.
14) Store pellet(s) at −80° C. or move on to restriction digest.

Restriction Digest (1-2 Hours)
15) To permeabilize the nuclear membrane and solubilize proteins, gently resuspend pellet in 50 µl of 0.5% sodium dodecyl sulfate (SDS) and incubate at 62° C. for 10 minutes.
16) Add 146 µl of water and 25 µl of 10% Triton X-100 to quench SDS. Mix well by pipetting, avoiding excessive foaming. Incubate at 37° C. for 15 minutes.
17) Add 25 µl of 10× NEBuffer 2 (New England BioLabs [NEB], B7002S).
18) Add 4 µl of 25 U/µl MboI restriction enzyme (NEB, R0147M) and digest chromatin overnight at 37° C. with rotation.

Fill-in, Proximity Ligation, and Crosslink Reversal (7-8 Hours)
19) To inactivate MboI, incubate at 62° C. for 20 minutes, then cool to room temperature.
20) To fill in the 5' restriction fragment overhangs and mark the DNA ends with biotin, add 50 µl of fill-in master mix (note that a different biotinylated base may be used in place of biotin-14-dATP, as long as all four dNTPs are present at equimolar concentration):
  37.5 µl of 0.4 mM biotin-14-dATP (Life Technologies, 19524-016)
  1.5 µl of 10 mM dCTP
  1.5 µl of 10 mM dGTP
  1.5 µl of 10 mM dTTP
  8 µl of 5 U/µl DNA polymerase I, large (Klenow) fragment (NEB, M0210L)
21) Mix by pipetting and incubate at 37° C. for 1.5 hours with rotation.
22) To catalyze proximity ligation, add 900 µl of ligation master mix:
  669 µl of water
  120 µl of 10× T4 DNA ligase reaction buffer (NEB, B0202S)
  100 µl of 10% Triton X-100
  6 µl of 20 mg/ml bovine serum albumin (BSA) (NEB, B9000S)
  5 µl of 400 U/µl T4 DNA ligase (NEB, M0202L)
23) Mix by inverting and incubate at room temperature for 4 hours with slow rotation.
24) Centrifuge at 2500×G, 25° C. for 5 minutes. Discard the supernatant.
25) Resuspend pelleted nuclei in 330 µl of 1% SDS. Gently mix by flicking the tube.
26) To degrade proteins and reverse crosslinks, add 12.5 µl of 0.8 U/µl proteinase K (NEB, P8107S) and 32.5 µl of 5 M NaCl. Mix by pipetting and pulse centrifuge. Incubate at 55° C. for 30 minutes.
27) Raise the temperature to 68° C. and incubate overnight.

DNA Precipitation, Shearing, and Size Selection (4-7 Hours)
28) Cool sample to room temperature, not on ice.
29) To precipitate DNA, add 875 µl of pure 100% ethanol (70% final concentration) and 3.13 µl of 20 mg/ml glycogen (50 µg/ml final concentration).
30) Mix well by inverting and incubate at −80° C. for at least 1 hour or at −20° C. overnight.
31) Centrifuge at maximum speed, 2° C. for 15 minutes.
32) Immediately after centrifugation, keeping the sample on ice, discard the supernatant by pipetting.
33) Resuspend in 800 µl of freshly prepared 70% ethanol to remove traces of salt. Centrifuge at maximum speed for 5 minutes.
34) Discard the supernatant by pipetting and incubate briefly with cap open at 37° C. until remaining traces of ethanol evaporate. Expect the pellet to be very small and almost invisible.
35) Dissolve DNA pellet in 130 µl of 1× Tris buffer (10 mM Tris-HCl pH 8.0). Make sure to elute any precipitated DNA from the sides of the tube. Incubate at 37° C. with 600 rpm shaking for at least 15 minutes to fully dissolve DNA.
36) Transfer the entire sample volume to a Pre-Slit Snap-Cap 6×16 mm glass microTUBE vial (Covaris, 520045).
37) To make the library suitable for Illumina high-throughput sequencing, shear DNA to 300-500 bp. Example parameters for MM220 Covaris instrument listed below:
  Instrument: M220 Focused-ultrasonicator (Covaris)
  Peak Power: 50.0
  Duty Factor: 20.0
  Cycles/Burst: 200
  Duration: 105 seconds
38) Transfer sheared DNA to a fresh 1.5-ml tube. Wash the Covaris microTUBE with 70 µl of 1× Tris buffer and add to the sample. Bring the volume of the sample to exactly 200 µl.
39) Optionally, to perform a quality control, run a 1:5 dilution of DNA on a 2.2% agarose gel, verifying successful shearing. Incubate at 4° C. overnight, or continue directly to size selection.
40) Warm a bottle of AMPure XP solid-phase reversible immobilization (SPRI) beads (Beckman Coulter, A63881) to room temperature. Gently shake to resuspend the magnetic beads and draw a 1ml aliquot of the bead suspension for every 2 samples.
41) Concentrate the beads in each aliquot using a magnet and discard 700 µl of the clear solution.
42) Resuspend the beads in the remaining 300 µl of bead suspension and label as "concentrated SPRI beads."
43) Add exactly 110 µl of concentrated SPRI beads to the sample. Mix by pipetting 10 times and incubate at room temperature for 5 minutes.
44) Separate on a magnet. Transfer the clear supernatant to a fresh 1.5-ml tube, avoiding any beads. This supernatant will contain DNA fragments shorter than ~500 bp. The remaining beads can be discarded or kept as a backup.
45) Add exactly 30 µl of concentrated SPRI beads to the sample. Mix by pipetting 10 times and incubate at room temperature for 5 minutes.

46) Separate on a magnet. Discard the supernatant or keep it as a backup. The sample, precipitated on beads, will now contain DNA fragments longer than 300 bp but shorter than 500 bp.
47) Keeping the beads on the magnet, wash twice for 30 seconds with 700 µl of freshly prepared 70% ethanol without mixing. Do not pipet the ethanol directly onto the beads—target the opposite side of the tube.
48) Leave the beads on the magnet for 5 minutes to allow remaining ethanol to evaporate.
49) To elute DNA, add 306 µl of 1× Tris buffer, gently mix by pipetting, incubate at room temperature for 5 minutes, separate on a magnet, and transfer the supernatant to a fresh 1.5-ml tube. The remaining beads can be discarded or combined with the previous backups.
50) Quantify DNA yield by the Qubit dsDNA High Sensitivity Assay (Life Technologies, Q32854) using 1 µl of sample, and run 5 µl of sample (undiluted) on a 2.2% agarose gel to verify successful size selection.
51) Incubate at 4° C. overnight, or continue directly to biotin pulldown.

Biotin Pull-Down, End Repair, A-Tailing, and Adapter Ligation (7-9 Hours)

[Note that the downstream steps can be adjusted to fit into strips or plates for high throughput preparations.]

52) Prepare wash buffers:
   2× Binding Buffer (2×BB)
      23.52 ml of water
      16 ml of 5 M NaCl [final: 2 M]
      400 µl of 1 M Tris-HCl pH 8.0 [final: 10 mM]
      80 µl of 0.5 M EDTA [final: 1 mM]
   1× Tween Washing Buffer (1× TWB)
      19.8 ml of water
      20 ml of 2×BB
      200 µl of 10% Tween-20 [final: 0.05%]
53) Mix a bottle of 10 mg/ml Dynabeads MyOne Streptavidin T1 beads (Life Technologies, 65602) by vortexing to resuspend the beads in the buffer.
54) In a fresh 1.5-ml tube, aliquot 100 µl of the T1 beads, pulse centrifuge, and separate on a magnet. Discard the supernatant.
55) Wash the beads twice with 400 µl of 1× TWB, pipetting to mix. Separate on a magnet and discard the supernatant.
56) Resuspend the beads in 300 µl of 2×BB and add to the sample. Incubate at room temperature for 15 minutes with rotation to bind biotinylated DNA to the streptavidin-coated beads. Separate on a magnet and discard the supernatant.
57) Wash the beads sequentially in the following buffers by resuspending in the buffer, transferring to a fresh 1.5-ml tube if indicated, mixing on a heated shaker at 600 rpm for 2 minutes at the indicated temperature, pulse centrifuging, separating on a magnet, and discarding the supernatant:
   a) 600 µl of 1× TWB at 55° C.
   b) 600 µl of 1× TWB at 55° C.
   c) 100 µl of 1× Tris buffer at 25° C. (fresh tube)
58) Resuspend the beads in 100 µl of end repair master mix:
   88 µl of 1× T4 DNA ligase reaction buffer, diluted from 10× stock (NEB, B0202S)
   2 µl of 25 mM dNTP mix (all 4 nucleotides)
   5 µl of 10 U/µl T4 polynucleotide kinase (NEB, M0201L)
   4 µl of 3 U/µl T4 DNA polymerase I (NEB, M0203L)
   1 µl of 5 U/µl DNA polymerase I, large (Klenow) fragment (NEB, M0210L)
59) Pulse centrifuge and incubate at room temperature for 30 minutes. Separate on a magnet and discard the supernatant.
60) Wash the beads as before:
   a) 600 µl of 1× TWB at 55° C. (fresh tube)
   b) 600 µl of 1× TWB at 55° C.
   c) 100 µl of 1× Tris buffer at 25° C.
61) Resuspend the beads in 100 µl of A-tailing master mix:
   90 µl of 1× NEBuffer 2, diluted from 10× stock (NEB, B7002S)
   5 µl of 10 mM dATP
   5 µl of 5 U/µl Klenow fragment (3'→5' exo-) (NEB, M0212L)
62) Pulse centrifuge and incubate at 37° C. for 30 minutes. Separate on a magnet and discard the supernatant.
63) Wash the beads as before:
   a) 600 µl of 1× TWB at 55° C. (fresh tube)
   b) 600 µl of 1× TWB at 55° C.
   c) 100 µl of 1× Tris buffer at 25° C.
64) Resuspend the beads in 50 µl of 1× Quick ligation reaction buffer, diluted from 2× stock (NEB, M2200L).
65) Add 2 µl of Quick T4 DNA ligase (NEB, M2200L).
66) To enable multiplexing during sequencing, add 5 µl of an Illumina indexed adapter from array 196 and mix thoroughly by flicking the tube. Record the sample-index combination.
67) Pulse centrifuge and incubate at room temperature for 15 minutes. Separate on a magnet and discard the supernatant.
68) Wash the beads as before:
   a) 600 µl of 1× TWB at 55° C. (fresh tube)
   b) 600 µl of 1× TWB at 55° C.
   c) 100 µl of 1× Tris buffer at 25° C.
69) Resuspend the beads in 50 µl of 1× Tris buffer. Keep at 4° C. until proceeding to next step.

Final Amplification, SPRI Purification, and qPCR (5-7 Hours)

70) Working on ice, add 150 µl of PCR master mix to the beads in Tris buffer:
   100 µl of 2× Phusion High-Fidelity PCR Master Mix with HF Buffer (NEB, M0531S)
   40 µl of water
   10 µl of Illumina indexing primers, F&R mix (Integrated DNA Technologies)
71) To amplify the Hi-C library, aliquot 50 µl into each of 4 fresh 0.2-ml PCR tubes and run the following PCR protocol:
   98° C. for 30 sec
   [98° C. for 10 sec
   55° C. for 30 sec
   72° C. for 30 sec] cycle 6-16 times depending on the expected yield
   72° C. for 7 min
   4° C. indefinitely
72) Separate the beads on a magnet and move the supernatant into a fresh 1.5-ml tube. Optionally run 1 µl a 2.2% agarose gel to confirm amplification. Discard the beads.
73) Some loss of volume is expected, so wash the PCR tubes with ~20 µl of 1× Tris buffer and add to the sample, bringing the total reaction volume to 200 µl.

74) Warm a bottle of AMPure XP solid-phase reversible immobilization (SPRI) beads (Beckman Coulter, A63881) to room temperature. Gently shake to resuspend the magnetic beads.
75) Add exactly 140 µl of the beads to the sample. Mix by pipetting 10 times and incubate at room temperature for 5 minutes.
76) Separate on a magnet and discard the supernatant.
77) Keeping the beads on the magnet, wash once for 30 seconds with 700 µl of freshly prepared 70% ethanol without mixing. Do not pipet the ethanol directly onto the beads—target the opposite side of the tube. Remove the ethanol completely.
78) To thoroughly clean the final Hi-C library, resuspend the beads again in 100 µl of 1× Tris buffer and add another 70 µl of fresh SPRI beads. Mix by pipetting 10 times and incubate at room temperature for 5 minutes.
79) Separate on a magnet and discard the supernatant.
80) Keeping the beads on the magnet, wash twice for 30 seconds with 700 µl of freshly prepared 70% ethanol without mixing. Leave the beads on the magnet for 5 minutes to allow remaining ethanol to evaporate.
81) Resuspend the beads in 25 µl of 1× Tris buffer to elute DNA. Incubate at room temperature for 5 minutes, separate on a magnet, and transfer the supernatant to a fresh 1.5-ml tube. This is the final library.
82) Optionally elute once more, as above, with another 15 µl of 1× Tris buffer. Add the supernatant to the same final library tube. Discard the beads. Store libraries at −20° C. indefinitely.
83) Measure the DNA concentration of each final Hi-C library using a qPCR Illumina Library Quantification Kit (KAPA Biosystems, KK4824). Use an Agilent Bioanalyzer to estimate the average fragment size in bp, and calculate the final molarity of each library. The Hi-C final libraries are now ready for Illumina paired end sequencing.

Example 8—Plant Nuclei Pellet Preparation and Hi-C Protocol

Crosslinking

1) Crosslink 5-10 g of chopped up plant tissue in 1% formaldehyde in 1× Homogenization Buffer pH 9.2 (10 mM Trizma, 80 mM KCl, 10 mM EDTA, 1 mM spermidine trihydrochloride, 1 mM spermine tetrahydrochloride, 0.5 M sucrose) for 30 min with mixing in a 50-mL tube.
2) Quench formaldehyde with 0.2 M Glycine and incubate for 5 min with mixing.
3) Remove solution and resuspend sample in 1×PBS. Mix thoroughly for 5 min.
4) Remove solution and blot sample dry on a paper towel.
5) Transfer sample to a new 50-mL tube and store in −80° C.

Nuclei Extraction and Purification (2-4 Hours)

6) Grind frozen plant sample into a fine powder in liquid nitrogen with a pre-chilled mortar and pestle for ~5-10 minutes.
7) Transfer powder into beaker and add 40-50 ml of ice-cold Nuclear Isolation Buffer pH 9.2 (10 mM Trizma, 80 mM KCl, 10 mM EDTA, 1 mM spermidine trihydrochloride, 1 mM spermine tetrahydrochloride, 0.5 M sucrose, 0.5% Triton X-100, 0.15% beta-mercaptoethanol)
8) Incubate beaker on ice with shaking for 30 minutes.
9) Filter suspension through 2 layers of Miracloth into 50-ml tubes. Gently squeeze Miracloth to collect remaining suspension. Discard the solids.
10) Centrifuge at 200 g, 4° C. for 2 minutes. Transfer the supernatant to another 50-ml tube and discard the pellet.
11) Centrifuge supernatant from step 10 at 2,000 g-3,800 g, 4° C. for 5 minutes (speed may vary based on the size of the genome). Discard the supernatant.
12) Resuspend pellet in 30 ml of cold NIB buffer and repeat steps 10-12 until the pellet is white or a pale shade. (Usually 1-4 washes are necessary).
13) Resuspend in 1 ml of ice-cold Hi-C lysis buffer (10 mM Tris-HCl pH 8.0, 10 mM NaCl, 0.2% Igepal CA630) and transfer to 1.5-ml tubes (resuspend in a larger volume and split appropriately for larger amounts of starting material.).
14) Centrifuge at 2,000-3,800 g, 4° C. for 5 minutes. Discard the supernatant. Optionally repeat steps 13-14.
15) Store pellet(s) at −80° C. or move on to restriction digest.

Restriction Digest (1-2 Hours)

16) To permeabilize the nuclear membrane and solubilize proteins, gently resuspend pellet in 50 µl of 0.5% sodium dodecyl sulfate (SDS) and incubate at 62° C. for 10 minutes.
17) Add 146 µl of water and 25 µl of 10% Triton X-100 to quench SDS. Mix well by pipetting, avoiding excessive foaming. Incubate at 37° C. for 15 minutes.
18) Add 25 µl of 10× NEBuffer 2 (New England BioLabs [NEB], B7002S).
19) Add 4 µl of 25 U/µl MboI restriction enzyme (NEB, R0147M) and digest chromatin overnight at 37° C. with rotation.

Fill-in, Proximity Ligation, and Crosslink Reversal (7-8 Hours)

20) To inactivate MboI, incubate at 62° C. for 20 minutes, then cool to room temperature.
21) To fill in the 5' restriction fragment overhangs and mark the DNA ends with biotin, add 50 µl of fill-in master mix (note that a different biotinylated base may be used in place of biotin-14-dATP, as long as all four dNTPs are present at equimolar concentration):
   37.5 µl of 0.4 mM biotin-14-dATP (Life Technologies, 19524-016)
   1.5 µl of 10 mM dCTP
   1.5 µl of 10 mM dGTP
   1.5 µl of 10 mM dTTP
   8 µl of 5 U/µl DNA polymerase I, large (Klenow) fragment (NEB, M0210L)
22) Mix by pipetting and incubate at 37° C. for 1.5 hours with rotation.
23) To catalyze proximity ligation, add 900 µl of ligation master mix:
   669 µl of water
   120 µl of 10× T4 DNA ligase reaction buffer (NEB, B0202S)
   100 µl of 10% Triton X-100
   6 µl of 20 mg/ml bovine serum albumin (BSA) (NEB, B9000S)
   5 µl of 400 U/µl T4 DNA ligase (NEB, M0202L)
24) Mix by inverting and incubate at room temperature for 4 hours with slow rotation.
25) Centrifuge at 2500×G, 25° C. for 5 minutes. Discard the supernatant.
26) Resuspend pelleted nuclei in 330 µl of 1% SDS. Gently mix by flicking the tube.

27) To degrade proteins and reverse crosslinks, add 12.5 µl of 0.8 U/µl proteinase K (NEB, P8107S) and 32.5 µl of 5 M NaCl. Mix by pipetting and pulse centrifuge. Incubate at 55° C. for 30 minutes.
28) Raise the temperature to 68° C. and incubate overnight.

DNA Precipitation, Shearing, and Size Selection (4-7 Hours)

29) Cool sample to room temperature, not on ice.
30) To precipitate DNA, add 875 µl of pure 100% ethanol (70% final concentration) and 3.13 µl of 20 mg/ml glycogen (50 µg/ml final concentration).
31) Mix well by inverting and incubate at −80° C. for at least 1 hour or at −20° C. overnight.
32) Centrifuge at maximum speed, 2° C. for 15 minutes.
33) Immediately after centrifugation, keeping the sample on ice, discard the supernatant by pipetting.
34) Resuspend in 800 µl of freshly prepared 70% ethanol to remove traces of salt. Centrifuge at maximum speed for 5 minutes.
35) Discard the supernatant by pipetting and incubate briefly with cap open at 37° C. until remaining traces of ethanol evaporate. Expect the pellet to be very small and almost invisible.
36) Dissolve DNA pellet in 130 µl of 1× Tris buffer (10 mM Tris-HCl pH 8.0). Make sure to elute any precipitated DNA from the sides of the tube. Incubate at 37° C. with 600 rpm shaking for at least 15 minutes to fully dissolve DNA.
37) Transfer the entire sample volume to a Pre-Slit Snap-Cap 6×16 mm glass microTUBE vial (Covaris, 520045).
38) To make the library suitable for Illumina high-throughput sequencing, shear DNA to 300-500 bp. Example parameters for MM220 Covaris instrument listed below:
Instrument: M220 Focused-ultrasonicator (Covaris)
Peak Power: 50.0
Duty Factor: 20.0
Cycles/Burst: 200
Duration: 105 seconds
39) Transfer sheared DNA to a fresh 1.5-ml tube. Wash the Covaris microTUBE with 70 µl of 1× Tris buffer and add to the sample. Bring the volume of the sample to exactly 200 µl.
40) Optionally, to perform a quality control, run a 1:5 dilution of DNA on a 2.2% agarose gel, verifying successful shearing. Incubate at 4° C. overnight, or continue directly to size selection.
41) Warm a bottle of AMPure XP solid-phase reversible immobilization (SPRI) beads (Beckman Coulter, A63881) to room temperature. Gently shake to resuspend the magnetic beads and draw a 1-ml aliquot of the bead suspension for every 2 samples.
42) Concentrate the beads in each aliquot using a magnet and discard 700 µl of the clear solution.
43) Resuspend the beads in the remaining 300 µl of bead suspension and label as "concentrated SPRI beads."
44) Add exactly 110 µl of concentrated SPRI beads to the sample. Mix by pipetting 10 times and incubate at room temperature for 5 minutes.
45) Separate on a magnet. Transfer the clear supernatant to a fresh 1.5-ml tube, avoiding any beads. This supernatant will contain DNA fragments shorter than ~500 bp. The remaining beads can be discarded or kept as a backup.
46) Add exactly 30 µl of concentrated SPRI beads to the sample. Mix by pipetting 10 times and incubate at room temperature for 5 minutes.
47) Separate on a magnet. Discard the supernatant or keep it as a backup. The sample, precipitated on beads, will now contain DNA fragments longer than 300 bp but shorter than 500 bp.
48) Keeping the beads on the magnet, wash twice for 30 seconds with 700 µl of freshly prepared 70% ethanol without mixing. Do not pipet the ethanol directly onto the beads—target the opposite side of the tube.
49) Leave the beads on the magnet for 5 minutes to allow remaining ethanol to evaporate.
50) To elute DNA, add 306 µl of 1× Tris buffer, gently mix by pipetting, incubate at room temperature for 5 minutes, separate on a magnet, and transfer the supernatant to a fresh 1.5-ml tube. The remaining beads can be discarded or combined with the previous backups.
51) Quantify DNA yield by the Qubit dsDNA High Sensitivity Assay (Life Technologies, Q32854) using 1 µl of sample, and run 5 µl of sample (undiluted) on a 2.2% agarose gel to verify successful size selection.
52) Incubate at 4° C. overnight, or continue directly to biotin pulldown.

Biotin Pull-Down, End Repair, A-Tailing, and Adapter Ligation (7-9 Hours)

[Note that the downstream steps can be adjusted to fit into strips or plates for high throughput preparations.]

53) Prepare wash buffers:
2× Binding Buffer (2×BB)
23.52 ml of water
16 ml of 5 M NaCl [final: 2M]
400 µl of 1 M Tris-HCl pH 8.0 [final: 10 mM]
80 µl of 0.5 M EDTA [final: 1 mM]
1× Tween Washing Buffer (1× TWB)
19.8 ml of water
20 ml of 2×BB
200 µl of 10% Tween-20 [final: 0.05%]
54) Mix a bottle of 10 mg/ml Dynabeads MyOne Streptavidin T1 beads (Life Technologies, 65602) by vortexing to resuspend the beads in the buffer.
55) In a fresh 1.5-ml tube, aliquot 100 µl of the T1 beads, pulse centrifuge, and separate on a magnet. Discard the supernatant.
56) Wash the beads twice with 400 µl of 1× TWB, pipetting to mix. Separate on a magnet and discard the supernatant.
57) Resuspend the beads in 300 µl of 2×BB and add to the sample. Incubate at room temperature for 15 minutes with rotation to bind biotinylated DNA to the streptavidin-coated beads. Separate on a magnet and discard the supernatant.
58) Wash the beads sequentially in the following buffers by resuspending in the buffer, transferring to a fresh 1.5-ml tube if indicated, mixing on a heated shaker at 600 rpm for 2 minutes at the indicated temperature, pulse centrifuging, separating on a magnet, and discarding the supernatant:
a) 600 µl of 1× TWB at 55° C.
b) 600 µl of 1× TWB at 55° C.
c) 100 µl of 1× Tris buffer at 25° C. (fresh tube)
59) Resuspend the beads in 100 µl of end repair master mix:
88 µl of 1× T4 DNA ligase reaction buffer, diluted from 10× stock (NEB, B0202S)
2 µl of 25 mM dNTP mix (all 4 nucleotides)

5 µl of 10 U/µl T4 polynucleotide kinase (NEB, M0201L)
4 µl of 3 U/µl T4 DNA polymerase I (NEB, M0203L)
1 µl of 5 U/µl DNA polymerase I, large (Klenow) fragment (NEB, M0210L)
60) Pulse centrifuge and incubate at room temperature for 30 minutes. Separate on a magnet and discard the supernatant.
61) Wash the beads as before:
a) 600 µl of 1× TWB at 55° C. (fresh tube)
b) 600 µl of 1× TWB at 55° C.
c) 100 µl of 1× Tris buffer at 25° C.
62) Resuspend the beads in 100 µl of A-tailing master mix:
90 µl of 1× NEBuffer 2, diluted from 10× stock (NEB, B7002S)
5 µl of 10 mM dATP
5 µl of 5 U/µl Klenow fragment (3'→5' exo-) (NEB, M0212L)
63) Pulse centrifuge and incubate at 37° C. for 30 minutes. Separate on a magnet and discard the supernatant.
64) Wash the beads as before:
a) 600 µl of 1× TWB at 55° C. (fresh tube)
b) 600 µl of 1× TWB at 55° C.
c) 100 µl of 1× Tris buffer at 25° C.
65) Resuspend the beads in 50 µl of 1× Quick ligation reaction buffer, diluted from 2× stock (NEB, M2200L).
66) Add 2 µl of Quick T4 DNA ligase (NEB, M2200L).
67) To enable multiplexing during sequencing, add 5 µl of an Illumina indexed adapter from array I96 and mix thoroughly by flicking the tube. Record the sample-index combination.
68) Pulse centrifuge and incubate at room temperature for 15 minutes. Separate on a magnet and discard the supernatant.
69) Wash the beads as before:
a) 600 µl of 1× TWB at 55° C. (fresh tube)
b) 600 µl of 1× TWB at 55° C.
c) 100 µl of 1× Tris buffer at 25° C.
70) Resuspend the beads in 50 µl of 1× Tris buffer. Keep at 4 C if one needs a break for a few hours.

Final Amplification, SPRI Purification, and qPCR (5-7 Hours)
71) Working on ice, add 150 µl of PCR master mix to the beads in Tris buffer:
100 µl of 2× Phusion High-Fidelity PCR Master Mix with HF Buffer (NEB, M0531S)
40 µl of water
10 µl of Illumina indexing primers, F&R mix (Integrated DNA Technologies)
72) To amplify the Hi-C library, aliquot 50 µl into each of 4 fresh 0.2-ml PCR tubes and run the following PCR protocol:
98° C. for 30 sec
[98° C. for 10 sec
55° C. for 30 sec
72° C. for 30 sec] cycle 6-16 times depending on the expected yield
72° C. for 7 min
4° C. indefinitely
73) Separate the beads on a magnet and move the supernatant into a fresh 1.5-ml tube. Optionally run 1 µl a 2.2% agarose gel to confirm amplification. Discard the beads.
74) Some loss of volume is expected, so wash the PCR tubes with ~20 µl of 1× Tris buffer and add to the sample, bringing the total reaction volume to 200 µl.
75) Warm a bottle of AMPure XP solid-phase reversible immobilization (SPRI) beads (Beckman Coulter, A63881) to room temperature. Gently shake to resuspend the magnetic beads.
76) Add exactly 140 µl of the beads to the sample. Mix by pipetting 10 times and incubate at room temperature for 5 minutes.
77) Separate on a magnet and discard the supernatant.
78) Keeping the beads on the magnet, wash once for 30 seconds with 700 µl of freshly prepared 70% ethanol without mixing. Do not pipet the ethanol directly onto the beads—target the opposite side of the tube. Remove the ethanol completely.
79) To thoroughly clean the final Hi-C library, resuspend the beads again in 100 µl of 1× Tris buffer and add another 70 µl of fresh SPRI beads. Mix by pipetting 10 times and incubate at room temperature for 5 minutes.
80) Separate on a magnet and discard the supernatant.
81) Keeping the beads on the magnet, wash twice for 30 seconds with 700 µl of freshly prepared 70% ethanol without mixing. Leave the beads on the magnet for 5 minutes to allow remaining ethanol to evaporate.
82) Resuspend the beads in 25 µl of 1× Tris buffer to elute DNA. Incubate at room temperature for 5 minutes, separate on a magnet, and transfer the supernatant to a fresh 1.5-ml tube. This is the final library.
83) Optionally elute once more, as above, with another 15 µl of 1× Tris buffer. Add the supernatant to the same final library tube. Discard the beads. Store libraries at −20° C. indefinitely.
84) Measure the DNA concentration of each final Hi-C library using a qPCR Illumina Library Quantification Kit (KAPA Biosystems, KK4824). Use an Agilent Bioanalyzer to estimate the average fragment size in bp, and calculate the final molarity of each library. The Hi-C final libraries are now ready for Illumina paired end sequencing.

Example 9—Nuclei Pellet Preparation and Plant Juice Hi-C Protocol

Crosslinking
1) Transfer juice to 50-mL tube.
2) Add 1× Homogenization Buffer pH 9.2 (10 mM Trizma, 80 mM KCl, 10 mM EDTA, 1 mM spermidine trihydrochloride, 1 mM spermine tetrahydrochloride, 0.5 M sucrose) so that the ratio of juice to 1× Homogenization Buffer is 1:1.
3) Crosslink in 1% formaldehyde for 30 min with mixing.
4) Quench formaldehyde with 0.2 M Glycine and incubate for 5 min with mixing.
5) Centrifuge at 2,000-3,800 g, 4° C. for 5 minutes. Discard the supernatant.
6) Resuspend sample in 1×PBS. Mix thoroughly for 5 min.
7) Centrifuge at 2,000-3,800 g, 4° C. for 5 minutes. Discard the supernatant.
8) Store in −80° C.

Nuclei Extraction and Purification (2-4 Hours)
9) Add 40-50 ml of ice-cold Nuclear Isolation Buffer pH 9.2 (10 mM Trizma, 80 mM KCl, 10 mM EDTA, 1 mM spermidine trihydrochloride, 0.5 M sucrose, 0.5% Triton X-100, 0.15% beta-mercaptoethanol)
10) Incubate beaker on ice with shaking for 30 minutes.

11) Filter suspension through 2 layers of Miracloth into 50-ml tubes. Gently squeeze Miracloth to collect remaining suspension. Discard the solids.
12) Centrifuge at 200 g, 4° C. for 2 minutes. Transfer the supernatant to another 50-ml tube and discard the pellet.
13) Centrifuge supernatant at 2,000 g-3,800 g, 4° C. for 5 minutes (speed may vary based on the size of the genome). Discard the supernatant.
14) Resuspend pellet in 30 ml of cold NIB buffer and repeat wash steps until the pellet is white or a pale shade (usually 1-4 washes are necessary).
15) Resuspend in 1 ml of ice-cold Hi-C lysis buffer (10 mM Tris-HCl pH 8.0, 10 mM NaCl, 0.2% Igepal CA630) and transfer to 1.5-ml tubes (resuspend in a larger volume and split appropriately for larger amounts of starting material.).
16) Centrifuge at 2,000-3,800 g, 4° C. for 5 minutes. Discard the supernatant. Optionally repeat steps 15-16.
17) Store pellet(s) at −80° C. or move on to restriction digest.

Restriction Digest (1-2 Hours)
18) To permeabilize the nuclear membrane and solubilize proteins, gently resuspend pellet in 50 µl of 0.5% sodium dodecyl sulfate (SDS) and incubate at 62° C. for 10 minutes.
19) Add 146 µl of water and 25 µl of 10% Triton X-100 to quench SDS. Mix well by pipetting, avoiding excessive foaming. Incubate at 37° C. for 15 minutes.
20) Add 25 µl of 10× NEBuffer 2 (New England BioLabs [NEB], B7002S).
21) Add 4 µl of 25 U/µl MboI restriction enzyme (NEB, R0147M) and digest chromatin overnight at 37° C. with rotation.

Fill-in, Proximity Ligation, and Crosslink Reversal (7-8 Hours)
22) To inactivate MboI, incubate at 62° C. for 20 minutes, then cool to room temperature.
23) To fill in the 5' restriction fragment overhangs and mark the DNA ends with biotin, add 50 µl of fill-in master mix (note that a different biotinylated base may be used in place of biotin-14-dATP, as long as all four dNTPs are present at equimolar concentration):
   37.5 µl of 0.4 mM biotin-14-dATP (Life Technologies, 19524-016)
   1.5 µl of 10 mM dCTP
   1.5 µl of 10 mM dGTP
   1.5 µl of 10 mM dTTP
   8 µl of 5 U/µl DNA polymerase I, large (Klenow) fragment (NEB, M0210L)
24) Mix by pipetting and incubate at 37° C. for 1.5 hours with rotation.
25) To catalyze proximity ligation, add 900 µl of ligation master mix:
   669 µl of water
   120 µl of 10× T4 DNA ligase reaction buffer (NEB, B0202S)
   100 µl of 10% Triton X-100
   6 µl of 20 mg/ml bovine serum albumin (BSA) (NEB, B9000S)
   5 µl of 400 U/µl T4 DNA ligase (NEB, M0202L)
26) Mix by inverting and incubate at room temperature for 4 hours with slow rotation.
27) Centrifuge at 2500×G, 25° C. for 5 minutes. Discard the supernatant.
28) Resuspend pelleted nuclei in 330 µl of 1% SDS. Gently mix by flicking the tube.
29) To degrade proteins and reverse crosslinks, add 12.5 µl of 0.8 U/µl proteinase K (NEB, P8107S) and 32.5 µl of 5 M NaCl. Mix by pipetting and pulse centrifuge. Incubate at 55° C. for 30 minutes.
30) Raise the temperature to 68° C. and incubate overnight.

DNA Precipitation, Shearing, and Size Selection (4-7 Hours)
31) Cool sample to room temperature, not on ice.
32) To precipitate DNA, add 875 µl of pure 100% ethanol (70% final concentration) and 3.13 µl of 20 mg/ml glycogen (50 µg/ml final concentration).
33) Mix well by inverting and incubate at −80° C. for at least 1 hour or at −20° C. overnight.
34) Centrifuge at maximum speed, 2° C. for 15 minutes.
35) Immediately after centrifugation, keeping the sample on ice, discard the supernatant by pipetting.
36) Resuspend in 800 µl of freshly prepared 70% ethanol to remove traces of salt. Centrifuge at maximum speed for 5 minutes.
37) Discard the supernatant by pipetting and incubate briefly with cap open at 37° C. until remaining traces of ethanol evaporate. Expect the pellet to be very small and almost invisible.
38) Dissolve DNA pellet in 130 µl of 1× Tris buffer (10 mM Tris-HCl pH 8.0). Make sure to elute any precipitated DNA from the sides of the tube. Incubate at 37° C. with 600 rpm shaking for at least 15 minutes to fully dissolve DNA.
39) Transfer the entire sample volume to a Pre-Slit Snap-Cap 6×16 mm glass microTUBE vial (Covaris, 520045).
40) To make the library suitable for Illumina high-throughput sequencing, shear DNA to 300-500 bp. Example parameters for MM220 Covaris instrument listed below:
   Instrument: M220 Focused-ultrasonicator (Covaris)
   Peak Power: 50.0
   Duty Factor: 20.0
   Cycles/Burst: 200
   Duration: 105 seconds
41) Transfer sheared DNA to a fresh 1.5-ml tube. Wash the Covaris microTUBE with 70 µl of 1× Tris buffer and add to the sample. Bring the volume of the sample to exactly 200
42) Optionally, to perform a quality control, run a 1:5 dilution of DNA on a 2.2% agarose gel, verifying successful shearing. Incubate at 4° C. overnight, or continue directly to size selection.
43) Warm a bottle of AMPure XP solid-phase reversible immobilization (SPRI) beads (Beckman Coulter, A63881) to room temperature. Gently shake to resuspend the magnetic beads and draw a 1 ml aliquot of the bead suspension for every 2 samples.
44) Concentrate the beads in each aliquot using a magnet and discard 700 µl of the clear solution.
45) Resuspend the beads in the remaining 300 µl of bead suspension and label as "concentrated SPRI beads."
46) Add exactly 110 µl of concentrated SPRI beads to the sample. Mix by pipetting 10 times and incubate at room temperature for 5 minutes.
47) Separate on a magnet. Transfer the clear supernatant to a fresh 1.5-ml tube, avoiding any beads. This supernatant will contain DNA fragments shorter than ~500 bp. The remaining beads can be discarded or kept as a backup.

48) Add exactly 30 µl of concentrated SPRI beads to the sample. Mix by pipetting 10 times and incubate at room temperature for 5 minutes.
49) Separate on a magnet. Discard the supernatant or keep it as a backup. The sample, precipitated on beads, will now contain DNA fragments longer than 300 bp but shorter than 500 bp.
50) Keeping the beads on the magnet, wash twice for 30 seconds with 700 µl of freshly prepared 70% ethanol without mixing. Do not pipet the ethanol directly onto the beads—target the opposite side of the tube.
51) Leave the beads on the magnet for 5 minutes to allow remaining ethanol to evaporate.
52) To elute DNA, add 306 µl of 1× Tris buffer, gently mix by pipetting, incubate at room temperature for 5 minutes, separate on a magnet, and transfer the supernatant to a fresh 1.5-ml tube. The remaining beads can be discarded or combined with the previous backups.
53) Quantify DNA yield by the Qubit dsDNA High Sensitivity Assay (Life Technologies, Q32854) using 1 µl of sample, and run 5 µl of sample (undiluted) on a 2.2% agarose gel to verify successful size selection.
54) Incubate at 4° C. overnight, or continue directly to biotin pulldown.

Biotin Pull-Down, End Repair, A-Tailing, and Adapter Ligation (7-9 Hours)

[Note that the downstream steps can be adjusted to fit into strips or plates for high throughput preparations.]

55) Prepare wash buffers:
    2× Binding Buffer (2×BB)
        23.52 ml of water
        16 ml of 5 M NaCl [final: 2 M]
        400 µl of 1 M Tris-HCl pH 8.0 [final: 10 mM]
        80 µl of 0.5 M EDTA [final: 1 mM]
    1× Tween Washing Buffer (1× TWB)
        19.8 ml of water
        20 ml of 2×BB
        200 µl of 10% Tween-20 [final: 0.05%]
56) Mix a bottle of 10 mg/ml Dynabeads MyOne Streptavidin T1 beads (Life Technologies, 65602) by vortexing to resuspend the beads in the buffer.
57) In a fresh 1.5-ml tube, aliquot 100 µl of the T1 beads, pulse centrifuge, and separate on a magnet. Discard the supernatant.
58) Wash the beads twice with 400 µl of 1× TWB, pipetting to mix. Separate on a magnet and discard the supernatant.
59) Resuspend the beads in 300 µl of 2×BB and add to the sample. Incubate at room temperature for 15 minutes with rotation to bind biotinylated DNA to the streptavidin-coated beads. Separate on a magnet and discard the supernatant.
60) Wash the beads sequentially in the following buffers by resuspending in the buffer, transferring to a fresh 1.5-ml tube if indicated, mixing on a heated shaker at 600 rpm for 2 minutes at the indicated temperature, pulse centrifuging, separating on a magnet, and discarding the supernatant:
    a) 600 µl of 1× TWB at 55° C.
    b) 600 µl of 1× TWB at 55° C.
    c) 100 µl of 1× Tris buffer at 25° C. (fresh tube)
61) Resuspend the beads in 100 µl of end repair master mix:
    88 µl of 1× T4 DNA ligase reaction buffer, diluted from 10× stock (NEB, B0202S)
    2 µl of 25 mM dNTP mix (all 4 nucleotides)
    5 µl of 10 U/µl T4 polynucleotide kinase (NEB, M0201L)
    4 µl of 3 U/µl T4 DNA polymerase I (NEB, M0203L)
    1 µl of 5 U/µl DNA polymerase I, large (Klenow) fragment (NEB, M0210L)
62) Pulse centrifuge and incubate at room temperature for 30 minutes. Separate on a magnet and discard the supernatant.
63) Wash the beads as before:
    a) 600 µl of 1× TWB at 55° C. (fresh tube)
    b) 600 µl of 1× TWB at 55° C.
    c) 100 µl of 1× Tris buffer at 25° C.
64) Resuspend the beads in 100 µl of A-tailing master mix:
    90 µl of 1× NEBuffer 2, diluted from 10× stock (NEB, B7002S)
    5 µl of 10 mM dATP
    5 µl of 5 U/µl Klenow fragment (3'→5' exo-) (NEB, M0212L)
65) Pulse centrifuge and incubate at 37° C. for 30 minutes. Separate on a magnet and discard the supernatant.
66) Wash the beads as before:
    a) 600 µl of 1× TWB at 55° C. (fresh tube)
    b) 600 µl of 1× TWB at 55° C.
    c) 100 µl of 1× Tris buffer at 25° C.
67) Resuspend the beads in 50 µl of 1× Quick ligation reaction buffer, diluted from 2× stock (NEB, M2200L).
68) Add 2 µl of Quick T4 DNA ligase (NEB, M2200L).
69) To enable multiplexing during sequencing, add 5 µl of an Illumina indexed adapter from array I96 and mix thoroughly by flicking the tube. Record the sample-index combination.
70) Pulse centrifuge and incubate at room temperature for 15 minutes. Separate on a magnet and discard the supernatant.
71) Wash the beads as before:
    a) 600 µl of 1× TWB at 55° C. (fresh tube)
    b) 600 µl of 1× TWB at 55° C.
    c) 100 µl of 1× Tris buffer at 25° C.
72) Resuspend the beads in 50 µl of 1× Tris buffer. Keep at 4 C if one needs a break for a few hours.

Final Amplification, SPRI Purification, and qPCR (5-7 Hours)

73) Working on ice, add 150 µl of PCR master mix to the beads in Tris buffer:
    100 µl of 2× Phusion High-Fidelity PCR Master Mix with HF Buffer (NEB, M0531S)
    40 µl of water
    10 µl of Illumina indexing primers, F&R mix (Integrated DNA Technologies)
74) To amplify the Hi-C library, aliquot 50 µl into each of 4 fresh 0.2-ml PCR tubes and run the following PCR protocol:
    98° C. for 30 sec
    [98° C. for 10 sec
    55° C. for 30 sec
    72° C. for 30 sec] cycle 6-16 times depending on the expected yield
    72° C. for 7 min
    4° C. indefinitely
75) Separate the beads on a magnet and move the supernatant into a fresh 1.5-ml tube. Optionally run 1 µl a 2.2% agarose gel to confirm amplification. Discard the beads.
76) Some loss of volume is expected, so wash the PCR tubes with ~20 µl of 1× Tris buffer and add to the sample, bringing the total reaction volume to 200 µl.

77) Warm a bottle of AMPure XP solid-phase reversible immobilization (SPRI) beads (Beckman Coulter, A63881) to room temperature. Gently shake to resuspend the magnetic beads.
78) Add exactly 140 µl of the beads to the sample. Mix by pipetting 10 times and incubate at room temperature for 5 minutes.
79) Separate on a magnet and discard the supernatant.
80) Keeping the beads on the magnet, wash once for 30 seconds with 700 µl of freshly prepared 70% ethanol without mixing. Do not pipet the ethanol directly onto the beads—target the opposite side of the tube. Remove the ethanol completely.
81) To thoroughly clean the final Hi-C library, resuspend the beads again in 100 µl of 1× Tris buffer and add another 70 µl of fresh SPRI beads. Mix by pipetting 10 times and incubate at room temperature for 5 minutes.
82) Separate on a magnet and discard the supernatant.
83) Keeping the beads on the magnet, wash twice for 30 seconds with 700 µl of freshly prepared 70% ethanol without mixing. Leave the beads on the magnet for 5 minutes to allow remaining ethanol to evaporate.
84) Resuspend the beads in 25 µl of 1× Tris buffer to elute DNA. Incubate at room temperature for 5 minutes, separate on a magnet, and transfer the supernatant to a fresh 1.5-ml tube. This is the final library
85) Optionally elute once more, as above, with another 15 µl of 1× Tris buffer. Add the supernatant to the same final library tube. Discard the beads. Store the libraries at −20° C. indefinitely.
86) Measure the DNA concentration of each final Hi-C library using a qPCR Illumina Library Quantification Kit (KAPA Biosystems, KK4824). Use an Agilent Bioanalyzer to estimate the average fragment size in bp, and calculate the final molarity of each library. The Hi-C final libraries are now ready for Illumina paired end sequencing.

Example 10—Nuclei Pellet Preparation and Plant Seed Hi-C Protocol

Grinding
1) Hammer one seed 3 times.
2) Transfer sample to 1.5-mL tube.
Crosslinking
1) Crosslink in 1% formaldehyde in 1× Homogenization Buffer pH 9.2 (10 mM Trizma, 80 mM KCl, 10 mM EDTA, 1 mM spermidine trihydrochloride, 1 mM spermine tetrahydrochloride, 0.5 M sucrose) for 30 min with mixing in a 1.5-mL tube.
2) Quench formaldehyde with 0.2 M Glycine and incubate for 5 min with mixing.
3) Centrifuge at 2,000-3,800 g, 4° C. for 5 minutes. Discard the supernatant.
4) Resuspend sample in 1×PBS. Mix thoroughly for 5 min.
5) Centrifuge at 2,000-3,800 g, 4° C. for 5 minutes. Discard the supernatant.
6) Store in −80° C.
Nuclei Extraction and Purification (2-4 Hours)
7) Grind frozen seed sample into a fine powder in liquid nitrogen with a pre-chilled mortar and pestle for ~5-10 minutes.
8) Transfer powder into a 1.5-mL tube and add 1 ml of ice-cold Nuclear Isolation Buffer pH 9.2 (10 mM Trizma, 80 mM KCl, 10 mM EDTA, 1 mM spermidine trihydrochloride, 1 mM spermine tetrahydrochloride, 0.5 M sucrose, 0.5% Triton X-100, 0.15% beta-mercaptoethanol)
9) Incubate on ice with shaking for 30 minutes.
10) Centrifuge at 200 g, 4° C. for 2 minutes. Transfer the supernatant to another 1.5-ml tube and discard the pellet.
11) Centrifuge supernatant at 2,000 g-3,800 g, 4° C. for 5 minutes (speed may vary based on the size of the genome). Discard the supernatant.
12) Resuspend pellet in 1 ml of cold NIB buffer and repeat wash steps until the pellet is mostly white or a pale shade. (Usually 1-4 washes are necessary).
13) Resuspend in 1 ml of ice-cold Hi-C lysis buffer (10 mM Tris-HCl pH 8.0, 10 mM NaCl, 0.2% Igepal CA630) and transfer to 1.5-ml tubes (resuspend in a larger volume and split appropriately for larger amounts of starting material.).
14) Centrifuge at 2,000-3,800 g, 4° C. for 5 minutes. Discard the supernatant. Optionally repeat steps 13-14.
15) Store pellet(s) at −80° C. or move on to restriction digest.
Restriction Digest (1-2 Hours)
16) To permeabilize the nuclear membrane and solubilize proteins, gently resuspend pellet in 50 µl of 0.5% sodium dodecyl sulfate (SDS) and incubate at 62° C. for 10 minutes.
17) Add 146 µl of water and 25 µl of 10% Triton X-100 to quench SDS. Mix well by pipetting, avoiding excessive foaming. Incubate at 37° C. for 15 minutes.
18) Add 25 µl of 10× NEBuffer 2 (New England BioLabs [NEB], B7002S).
19) Add 4 µl of 25 U/µl MboI restriction enzyme (NEB, R0147M) and digest chromatin overnight at 37° C. with rotation.
Fill-in, Proximity Ligation, and Crosslink Reversal (7-8 Hours)
20) To inactivate MboI, incubate at 62° C. for 20 minutes, then cool to room temperature.
21) To fill in the 5' restriction fragment overhangs and mark the DNA ends with biotin, add 50 µl of fill-in master mix (note that a different biotinylated base may be used in place of biotin-14-dATP, as long as all four dNTPs are present at equimolar concentration):
    37.5 µl of 0.4 mM biotin-14-dATP (Life Technologies, 19524-016)
    1.5 µl of 10 mM dCTP
    1.5 µl of 10 mM dGTP
    1.5 µl of 10 mM dTTP
    8 µl of 5 U/µl DNA polymerase I, large (Klenow) fragment (NEB, M0210L)
22) Mix by pipetting and incubate at 37° C. for 1.5 hours with rotation.
23) To catalyze proximity ligation, add 900 µl of ligation master mix:
    669 µl of water
    120 µl of 10× T4 DNA ligase reaction buffer (NEB, B0202S)
    100 µl of 10% Triton X-100
    6 µl of 20 mg/ml bovine serum albumin (BSA) (NEB, B9000S)
    5 µl of 400 U/µl T4 DNA ligase (NEB, M0202L)
24) Mix by inverting and incubate at room temperature for 4 hours with slow rotation.
25) Centrifuge at 2500×G, 25° C. for 5 minutes. Discard the supernatant.

26) Resuspend pelleted nuclei in 330 μl of 1% SDS. Gently mix by flicking the tube.
27) To degrade proteins and reverse crosslinks, add 12.5 μl of 0.8 U/μl proteinase K (NEB, P8107S) and 32.5 μl of 5 M NaCl. Mix by pipetting and pulse centrifuge. Incubate at 55° C. for 30 minutes.
28) Raise the temperature to 68° C. and incubate overnight.

DNA Precipitation, Shearing, and Size Selection (4-7 Hours)

29) Cool sample to room temperature, not on ice.
30) To precipitate DNA, add 875 μl of pure 100% ethanol (70% final concentration) and 3.13 μl of 20 mg/ml glycogen (50 μg/ml final concentration).
31) Mix well by inverting and incubate at −80° C. for at least 1 hour or at −20° C. overnight.
32) Centrifuge at maximum speed, 2° C. for 15 minutes.
33) Immediately after centrifugation, keeping the sample on ice, discard the supernatant by pipetting.
34) Resuspend in 800 μl of freshly prepared 70% ethanol to remove traces of salt. Centrifuge at maximum speed for 5 minutes.
35) Discard the supernatant by pipetting and incubate briefly with cap open at 37° C. until remaining traces of ethanol evaporate. Expect the pellet to be very small and almost invisible.
36) Dissolve DNA pellet in 130 μl of 1× Tris buffer (10 mM Tris-HCl pH 8.0). Make sure to elute any precipitated DNA from the sides of the tube. Incubate at 37° C. with 600 rpm shaking for at least 15 minutes to fully dissolve DNA.
37) Transfer the entire sample volume to a Pre-Slit Snap-Cap 6×16 mm glass microTUBE vial (Covaris, 520045).
38) To make the library suitable for Illumina high-throughput sequencing, shear DNA to 300-500 bp. Example parameters for MM220 Covaris instrument listed below:
Instrument: M220 Focused-ultrasonicator (Covaris)
Peak Power: 50.0
Duty Factor: 20.0
Cycles/Burst: 200
Duration: 105 seconds
39) Transfer sheared DNA to a fresh 1.5-ml tube. Wash the Covaris microTUBE with 70 μl of 1× Tris buffer and add to the sample. Bring the volume of the sample to exactly 200 μl.
40) Optionally, to perform a quality control, run a 1:5 dilution of DNA on a 2.2% agarose gel, verifying successful shearing. Incubate at 4° C. overnight, or continue directly to size selection.
41) Warm a bottle of AMPure XP solid-phase reversible immobilization (SPRI) beads (Beckman Coulter, A63881) to room temperature. Gently shake to resuspend the magnetic beads and draw a 1-ml aliquot of the bead suspension for every 2 samples.
42) Concentrate the beads in each aliquot using a magnet and discard 700 μl of the clear solution.
43) Resuspend the beads in the remaining 300 μl of bead suspension and label as "concentrated SPRI beads."
44) Add exactly 110 μl of concentrated SPRI beads to the sample. Mix by pipetting 10 times and incubate at room temperature for 5 minutes.
45) Separate on a magnet. Transfer the clear supernatant to a fresh 1.5-ml tube, avoiding any beads. This supernatant will contain DNA fragments shorter than ~500 bp. The remaining beads can be discarded or kept as a backup.
46) Add exactly 30 μl of concentrated SPRI beads to the sample. Mix by pipetting 10 times and incubate at room temperature for 5 minutes.
47) Separate on a magnet. Discard the supernatant or keep it as a backup. The sample, precipitated on beads, will now contain DNA fragments longer than 300 bp but shorter than 500 bp.
48) Keeping the beads on the magnet, wash twice for 30 seconds with 700 μl of freshly prepared 70% ethanol without mixing. Do not pipet the ethanol directly onto the beads—target the opposite side of the tube.
49) Leave the beads on the magnet for 5 minutes to allow remaining ethanol to evaporate.
50) To elute DNA, add 306 μl of 1× Tris buffer, gently mix by pipetting, incubate at room temperature for 5 minutes, separate on a magnet, and transfer the supernatant to a fresh 1.5-ml tube. The remaining beads can be discarded or combined with the previous backups.
51) Quantify DNA yield by the Qubit dsDNA High Sensitivity Assay (Life Technologies, Q32854) using 1 μl of sample, and run 5 μl of sample (undiluted) on a 2.2% agarose gel to verify successful size selection.
52) Incubate at 4° C. overnight, or continue directly to biotin pulldown.

Biotin Pull-Down, End Repair, A-Tailing, and Adapter Ligation (7-9 Hours)

[Note that the downstream steps can be adjusted to fit into strips or plates for high throughput preparations.]

53) Prepare wash buffers:
2× Binding Buffer (2×BB)
23.52 ml of water
16 ml of 5 M NaCl [final: 2 M]
400 μl of 1 M Tris-HCl pH 8.0 [final: 10 mM]
80 μl of 0.5 M EDTA [final: 1 mM]
1× Tween Washing Buffer (1× TWB)
19.8 ml of water
20 ml of 2×BB
200 μl of 10% Tween-20 [final: 0.05%]
54) Mix a bottle of 10 mg/ml Dynabeads MyOne Streptavidin T1 beads (Life Technologies, 65602) by vortexing to resuspend the beads in the buffer.
55) In a fresh 1.5-ml tube, aliquot 100 μl of the T1 beads, pulse centrifuge, and separate on a magnet. Discard the supernatant.
56) Wash the beads twice with 400 μl of 1× TWB, pipetting to mix. Separate on a magnet and discard the supernatant.
57) Resuspend the beads in 300 μl of 2×BB and add to the sample. Incubate at room temperature for 15 minutes with rotation to bind biotinylated DNA to the streptavidin-coated beads. Separate on a magnet and discard the supernatant.
58) Wash the beads sequentially in the following buffers by resuspending in the buffer, transferring to a fresh 1.5-ml tube if indicated, mixing on a heated shaker at 600 rpm for 2 minutes at the indicated temperature, pulse centrifuging, separating on a magnet, and discarding the supernatant:
a) 600 μl of 1× TWB at 55° C.
b) 600 μl of 1× TWB at 55° C.
c) 100 μl of 1× Tris buffer at 25° C. (fresh tube)
59) Resuspend the beads in 100 μl of end repair master mix:
88 μl of 1× T4 DNA ligase reaction buffer, diluted from 10× stock (NEB, B0202S)
2 μl of 25 mM dNTP mix (all 4 nucleotides)

5 µl of 10 U/µl T4 polynucleotide kinase (NEB, M0201L)

4 µl of 3 U/µl T4 DNA polymerase I (NEB, M0203L)

1 µl of 5 U/µl DNA polymerase I, large (Klenow) fragment (NEB, M0210L)

60) Pulse centrifuge and incubate at room temperature for 30 minutes. Separate on a magnet and discard the supernatant.
61) Wash the beads as before:
   a) 600 µl of 1× TWB at 55° C. (fresh tube)
   b) 600 µl of 1× TWB at 55° C.
   c) 100 µl of 1× Tris buffer at 25° C.
62) Resuspend the beads in 100 µl of A-tailing master mix:

90 µl of 1× NEBuffer 2, diluted from 10× stock (NEB, B7002S)

5 µl of 10 mM dATP

5 µl of 5 U/µl Klenow fragment (3'→5' exo-) (NEB, M0212L)

63) Pulse centrifuge and incubate at 37° C. for 30 minutes. Separate on a magnet and discard the supernatant.
64) Wash the beads as before:
   a) 600 µl of 1× TWB at 55° C. (fresh tube)
   b) 600 µl of 1× TWB at 55° C.
   c) 100 µl of 1× Tris buffer at 25° C.
65) Resuspend the beads in 50 µl of 1× Quick ligation reaction buffer, diluted from 2× stock (NEB, M2200L).
66) Add 2 µl of Quick T4 DNA ligase (NEB, M2200L).
67) To enable multiplexing during sequencing, add 5 µl of an Illumina indexed adapter from array I96 and mix thoroughly by flicking the tube. Record the sample-index combination.
68) Pulse centrifuge and incubate at room temperature for 15 minutes. Separate on a magnet and discard the supernatant.
69) Wash the beads as before:
   a) 600 µl of 1× TWB at 55° C. (fresh tube)
   b) 600 µl of 1× TWB at 55° C.
   c) 100 µl of 1× Tris buffer at 25° C.
70) Resuspend the beads in 50 µl of 1× Tris buffer. Keep at 4 C if one needs a break for a few hours.

Final Amplification, SPRI Purification, and qPCR (5-7 Hours)

71) Working on ice, add 150 µl of PCR master mix to the beads in Tris buffer:

100 µl of 2× Phusion High-Fidelity PCR Master Mix with HF Buffer (NEB, M0531S)

40 µl of water

10 µl of Illumina indexing primers, F&R mix (Integrated DNA Technologies)

72) To amplify the Hi-C library, aliquot 50 µl into each of 4 fresh 0.2-ml PCR tubes and run the following PCR protocol:

98° C. for 30 sec

[98° C. for 10 sec

55° C. for 30 sec

72° C. for 30 sec] cycle 6-16 times depending on the expected yield

72° C. for 7 min

4° C. indefinitely

73) Separate the beads on a magnet and move the supernatant into a fresh 1.5-ml tube. Optionally run 1 µl a 2.2% agarose gel to confirm amplification. Discard the beads.
74) Some loss of volume is expected, so wash the PCR tubes with ~20 µl of 1× Tris buffer and add to the sample, bringing the total reaction volume to 200 µl.
75) Warm a bottle of AMPure XP solid-phase reversible immobilization (SPRI) beads (Beckman Coulter, A63881) to room temperature. Gently shake to resuspend the magnetic beads.
76) Add exactly 140 µl of the beads to the sample. Mix by pipetting 10 times and incubate at room temperature for 5 minutes.
77) Separate on a magnet and discard the supernatant.
78) Keeping the beads on the magnet, wash once for 30 seconds with 700 µl of freshly prepared 70% ethanol without mixing. Do not pipet the ethanol directly onto the beads—target the opposite side of the tube. Remove the ethanol completely.
79) To thoroughly clean the final Hi-C library, resuspend the beads again in 100 µl of 1× Tris buffer and add another 70 µl of fresh SPRI beads. Mix by pipetting 10 times and incubate at room temperature for 5 minutes.
80) Separate on a magnet and discard the supernatant.
81) Keeping the beads on the magnet, wash twice for 30 seconds with 700 µl of freshly prepared 70% ethanol without mixing. Leave the beads on the magnet for 5 minutes to allow remaining ethanol to evaporate.
82) Resuspend the beads in 25 µl of 1× Tris buffer to elute DNA. Incubate at room temperature for 5 minutes, separate on a magnet, and transfer the supernatant to a fresh 1.5-ml tube. This is the final library.
83) Optionally elute once more, as above, with another 15 µl of 1× Tris buffer. Add the supernatant to the same final library tube. Discard the beads. Store libraries at −20° C. indefinitely.
84) Measure the DNA concentration of each final Hi-C library using a qPCR Illumina Library Quantification Kit (KAPA Biosystems, KK4824). Use an Agilent Bioanalyzer to estimate the average fragment size in bp, and calculate the final molarity of each library. The Hi-C final libraries are now ready for Illumina paired end sequencing.

Example 11—Hi-C Library Preparation Adapted for ¼ of a Single Mosquito Individual Sample Cell Crosslinking:

1) Resuspend ¼ mosquito cell homogenate in 10 ml RPMI 10% FBS, in 15 Falcon tube.
2) Add fresh 16% formaldehyde solution to final 1% (667 µl 16% FA).
3) Incubate 10 min at room temperature with occasional mixing.
4) Quench non reacted formaldehyde with 1.25 M glycine solution (2.1 ml of 1.25 M glycine)
5) Incubate 5 min at RT.
6) Spin suspension at 280 g for 6 min.
7) Discard formaldehyde-containing solution into designated formaldehyde waste container working in a chemical fume hood.
8) Wash cell pellet once with 10 ml ice cold PBS solution.
9) Spin cell suspension at 280 g for 6 min. Discard supernatant and immediately store crosslinked pellet directly in the 15-ml Falcon tube, at −80 C.

Day 1: Lysis and Restriction Digest (1-3 Hours)
1) Dissolve 1 protease inhibitor cocktail tablet (Roche, 11836170001) in 10 ml of ice-cold

| Hi-C lysis buffer: | 50 ml 1× buffer |
|---|---|
| 10 mM Tris-HCl pH 8.0 | 500 ul of 1M |
| 10 mM NaCl | 100 µl of 5M |
| 0.2% Igepal CA630 | 1 ml 10% |
| | 48.4 ml H$_2$O |

Resuspend cross-linked pellet of cells in 1000 µl of Hi-C buffer.
2) Incubate cell suspension on ice for at least 30 minutes.
3) Centrifuge at 300×g, 25° C. for 5 minutes. Discard the supernatant.
4) Resuspend pelleted nuclei in 1000 µl of ice-cold Hi-C lysis buffer. Centrifuge again at 300×g, 25° C. for 5 minutes. Discard the supernatant.
5) To facilitate complete cell lysis and solubilize proteins, gently resuspend pellet in 50 µl of 0.5% SDS and incubate at 62° C. for EXACTLY 10 minutes.
6) After heating is over, add 142 µl of water and 25 µl of 10% Triton X-100 to quench SDS. Mix well, avoiding excessive foaming. Incubate at 37° C. for 15 minutes.
7) Add 27 µl of 10× NEBuffer 2 (New England BioLabs [NEB], B7002S).
8) Add 8 µl of 25 U/µl MboI restriction enzyme (NEB, R0147M) and digest chromatin overnight at 37° C.

Day 2: Fill-in, Proximity Ligation, and Crosslink Reversal (7-9 Hours)
1) To inactivate MboI, incubate at 62° C. for 20 minutes, then cool to room temperature.
2) To fill in the 5' restriction fragment overhangs and mark the DNA ends with biotin, add
50 µl of fill-in master mix:
37.5 µl of 0.4 mM biotin-14-dCTP
1.5 µl of 10 mM dATP, dGTP, dTTP
3.5 µl of 10× NEBuffer 2
8 µl of 5 U/µl DNA polymerase I, large (Klenow) fragment (NEB, M0210L)
3) Mix by pipetting and incubate at 37° C. for 1.5 hours.
4) To catalyze proximity ligation, add 804l of ligation master mix:
587 µl of water
110 µl of 10× T4 DNA ligase reaction buffer (NEB, B0202S)
92 µl of 10% Triton X-100
5.5 µl of 100× (10 mg/ml) bovine serum albumin (BSA)
7 µl of 400 U/µl T4 DNA ligase (NEB, M0202L)
5) Mix by inverting and incubate at room temperature for 4 hours with slow rotation.
6) Centrifuge at 300×g, 25° C. for 5 minutes. Discard 500 µl from the top part of supernatant.
7) Add 66 µl of 10% SDS
25 µl of proteinase K—to degrade proteins and reverse crosslinks
65 µl of 5 M NaCl—to remove tightly bound histones
8) Incubate at 55° C. overnight.

Day 3: DNA Purification, Shearing, and Size Selection (5-7 Hours)
1) Cool to room temperature, not on ice.
2) Add 4 µl of glycogen, 70 µl of 3 M sodium acetate pH 5.2. and 700 µl of isopropanol. Mix by inverting.
3) Incubate at −80° C. for 1-2 hours.
4) Centrifuge at maximum speed, 4° C. for 30 minutes.
5) To maximize DNA recovery, invert tubes, repeat centrifugation at maximum speed, 4° C. for 30 minutes.
6) Carefully remove the supernatant by pipetting.
7) Resuspend in 700 µl of 75% ethanol. Centrifuge at maximum speed, 4° C. for 5 minutes.
8) Remove all supernatant and briefly spin, remove traces of ethanol using P10.
9) Incubate at room temperature for 10 minutes to allow remaining ethanol to evaporate.
10) Dissolve pellet in 130 µl of 1× Tris buffer (10 mM Tris-HCl pH 8.0) and incubate at 56° C. for 15 minutes to fully dissolve DNA. Transfer the entire sample volume to a Pre-Slit Snap-Cap 6×16 mm glass microTUBE (Covaris, 520045).
11) To make the biotinylated DNA suitable for Illumina high-throughput sequencing, shear to a size of 300-500 base pairs (bp) using the following parameters:
Instrument: M220 Focused-ultrasonicator (Covaris)
Peak Power: 50.0
Duty Factor: 10.0
Cycles/Burst: 200
Duration: 1':45"
12) Transfer sheared DNA to a fresh 1.5-ml tube. Wash the Covaris microTUBE with ~75 µl of 10 mM Tris buffer.
13) Add 100 µl of 10 mM TRIS buffer to bring the total volume to 300 µl.
Skip completely the SPRI selection and go directly to:

Day 4: Biotin Pull-Down, End Repair, A-Tailing, and Adapter Ligation (7-9 Hours)
Prepare Wash Buffers:
2× Binding Buffer (2×BB)
24 ml of water
16 ml of 5 M NaCl [final: 2 M]
400 µl of 1 M Tris-HCl pH 8.0 [final: 10 mM]
80 µl of 0.5 M EDTA [final: 1 mM]
1× Tween Washing Buffer (1× TWB)
20 ml of water
20 ml of 2×BB
200 µl of 10% Tween-20 [final: 0.05%]
To prepare for biotin pull-down, (remove the BSA-blocking reagent and remove non-covalently attached streptavidin that may leak during subsequent stringent washes) for each sample, wash 100 µl of 10 mg/ml Dynabeads as follows:
MyOne Streptavidin T1 beads (Life Technologies, 65602)
1. for N samples aliquot N×100 µl T1 beads
2. bind to magnet, discard solution
3. add 8 ml of TWB, rotate to mix, spin to collect solution from the tube cap
4. repeat steps 2 and 3.
5. repeat step 2.
6. Add 8 ml of Tris 10 mM, rotate to mix, spin to collect solution from the tube cap.
7. Bind to magnet, discard solution.
8. repeat steps 6 and 7.
9. Add 5 ml 2×BB buffer. Rotate to mix, spin to collect solution from the tube cap.
10. Bind to magnet, discard solution.
11. Resuspend beads in (N×300) µl of 2×BB buffer. Mix, aliquot mixed beads into each tube containing DNA sample.
12. Incubate beads 15 min at RT with rotation to bind biotinylated DNA to the streptavidin coated beads. Separate on a magnet and discard the supernatant.

13. Wash the beads sequentially in the following buffers by resuspending in the buffer,
mixing, separating on a magnet, and discarding the supernatant:
  a) 700 µl of 1× TWB at 56° C., 2 min precisely
  b) 700 µl of Tris 10 mM
  c) 700 µl of Tris 10 mM
14) Resuspend the beads in 100 µl of end repair master mix:
  78 µl H$_2$O
  10 µl of 1× T4 DNA ligase reaction buffer (NEB, B0202S)
  2 µl of 25 mM dNTP mix
  5 µl of 10 U/µl T4 polynucleotide kinase (NEB, M0201L)
  4 µl of 3 U/µl T4 DNA polymerase I (NEB, M0203L)
  1 µl of 5 U/µl DNA polymerase I, large (Klenow) fragment (NEB, M0210L)
  Incubate at room temperature for 30 minutes. Separate on a magnet and discard the supernatant.
  Wash the beads as before:
  a) 700 µl of 1× TWB at 56° C., 2 min precisely
  b) 700 µl of Tris 10 mM
  c) 700 µl of Tris 10 mM
15) Resuspend the beads in 100 µl of A-tailing master mix:
  80 µl H$_2$O
  10 µl of 1× NEBuffer 2
  5 µl of 10 mM dATP
  5 µl of 5 U/µl Klenow fragment (3'→5' exo-) (NEB, M0212L)
16) Incubate at 37° C. for 30 minutes. Separate on a magnet and discard the supernatant.
17) Wash the beads as before:
  a) 700 µl of 1× TWB at 56° C., 2 min precisely
  b) 700 µl of Tris 10 mM
  c) 700 µl of Tris 10 mM
18) Add 7 µl of an Illumina indexed adapter from array I96 and mix thoroughly. Record the sample-index combination.
19) Make mix: add 25 µl 2× quick ligation buffer
  16 µl H$_2$O
  2 µl of Quick T4 DNA ligase (NEB, M2200L)
20) Incubate at room temperature for 20-30 minutes. Separate on a magnet and discard the supernatant.
21) Wash the beads as before:
  a) 600 µl of 1× TWB at 56° C., 2 min precisely
  b) 700 µl of Tris 10 mM
  c) 700 µl of Tris 10 mM
22) Resuspend the beads in 140 µl of Tris buffer 10 mM.
23) Incubate at 4° C. overnight.

Day 5: Final Amplification, SPRI Purification, and qPCR (5-7 Hours)
  58) Working on ice, to each reaction add 160 µl of PCR master mix: 150 µl of 2× Phusion mix
  10 µl of Illumina indexing primers, F&R mix (Integrated DNA Technologies) aliquot 100 µl/PCR tube.
  Amplify N cycles: 98° C. for 2 min; N cycles of: 98° C. for 10 sec, 55° C. for 15 sec;
  72° C. for 20 sec; 72° C. for 7 min. Usually 14 cycles for ¼ of a mosquito.
Final Cleanup of the library:
  Prepare 3×SPRI solution from Stock SPRI bottle.
  Shake bottle, aspirate SPRI bead stock multiple times to mix.
  Pipette out 1 ml of SPRI beads into a new eppendorf tube. Set on magnet for 5 minute until solution is completely clear.
  Once solution is clear, remove 700 µl (PEG+NaCl).
  Save this solution is a separate tube to prepare 0.7× wash solution. For this purpose, add 1 ml H$_2$O per every 700 µl clear SPRI solution. Label "0.7×SPRI"
  The remaining beads are resuspended in the 300 µl leftover clear solution.
  This concentrates the SPRI beads from 1× to 3×. Label as "3×SPRI"
  Mix 3×SPRI beads.
  Add 100 µ3×SPRI beads per 200 µl PCR sample volume.
  Or depending on the measured PCR reaction volume, add 0.5× of the (3×SPRI mix).
  Cap tube and flick tube to mix sample and beads. Do not use pipetting up and down to prevent loss of sample.
  Place tube on magnet for 10 minutes, well mixed.
  (This step is used to remove fragments larger than 650 nucleotides from the library)
  Keep Supernatant. Supernatant will contain the library, that is ~650 bp in size and below. Beads will contain fragments larger than ~650 bp and are to be put aside, (Label Waste but do not yet discard)
  Transfer all of the clear solution (library) to new tube using P200 pipette, spin in microfuge and bind to magnet again, and then collect the remainder of supernatant with a P20 pipette. Be sure to collect all of the supernatant. Set aside beads and label.
  Add 30 µl of 3×SPRI bead solution (or 0.15× of the initial PCR reaction measured volume if this was different than 200 µl). Cap tube, mix vigorously, Let the solution sit for 15-30 minutes on the magnet.
  This step binds shorter fragments to the beads. Smaller fragments including PCR primers and adaptor dimers remain in solution.
  Place mix on magnet and let the solution become fully clear. Remove supernatant (containing fragments of ~200 and lower) and add it to the previous "waste" tube (Tube with beads containing greater than 650-bp fragments).
  Wash beads with 250 µl (0.7×SPRI/200 µl PCR sample) by adding the solution, cap tube mix vigorously, spin to collect from cap, place on magnet 15 min. Remove clear solution, add to waste tube.
  Use 700 µl freshly made 75% ethanol (EtOH) solution to wash beads that contain bound library. Let beads in EtOH 1 min. Do not remove from magnet. Remove the 700 µl EtOH by slowly aspirating and avoiding touching the beads. To completely remove ethanol traces, cap tube and spin briefly in microfuge for 5 sec. Replace on magnet and remove ethanol using P10. Let the tube dry while open for 5 minutes. Resuspend beads in 50 µl Tris 10 mM. Vortex to resuspend and elute library.

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth

REFERENCES AND NOTES

1) A. Harmon, Team of Rival Scientists Comes Together to Fight Zika. *N. Y. Times* (2016).
2) S. Gnerre et al., High-quality draft assemblies of mammalian genomes from massively parallel sequence data. *Proc. Natl. Acad. Sci.* 108, 1513-1518 (2011).
3) L. J. S. Williams et al., Paired-end sequencing of Fosmid libraries by Illumina. *Genome Res.* 22, 2241-2249 (2012).
4) E. Lieberman-Aiden et al., Comprehensive mapping of long-range interactions reveals folding principles of the human genome. *Science.* 326, 289-293 (2009).
5) S. S. P. Rao et al., A 3D map of the human genome at kilobase resolution reveals principles of chromatin looping. *Cell.* 159, 1665-1680 (2014).
6) N. Kaplan, J. Dekker, High-throughput genome scaffolding from in vivo DNA interaction frequency. *Nat. Biotechnol.* 31, 1143-1147 (2013).
7) H. Marie-Nelly et al., High-quality genome (re)assembly using chromosomal contact data. *Nat. Commun.* 5, 5695 (2014).
8) C. L. Peichel, S. T. Sullivan, I. Liachko, M. A. White, Improvement of the threespine stickleback (*Gasterosteus aculeatus*) genome using a Hi-C-based Proximity-Guided Assembly method. *bioRxiv,* 068528 (2016).
9) N. H. Putnam et al., Chromosome-scale shotgun assembly using an in vitro method for long-range linkage. *Genome Res.* (2016), doi:10.1101/gr.193474.115.
10) J. N. Burton et al., Chromosome-scale scaffolding of de novo genome assemblies based on chromatin interactions. *Nat. Biotechnol.* 31, 1119-1125 (2013).
11) D. M. Bickhart et al., Single-molecule sequencing and conformational capture enable de novo mammalian reference genomes. *bioRxiv,* 064352 (2016).
12) A. M. Session et al., Genome evolution in the allotetraploid frog *Xenopus laevis. Nature.* 538, 336-343 (2016).
13) R. R. Love, N. I. Weisenfeld, D. B. Jaffe, N. J. Besansky, D. E. Neafsey, Evaluation of DISCOVAR de novo using a mosquito sample for cost-effective short-read genome assembly. *BMC Genomics.* 17, 187 (2016).
14) E. S. Lander et al., Initial sequencing and analysis of the human genome. *Nature.* 409, 860-921 (2001).
15) J. C. Venter et al., The Sequence of the Human Genome. *Science.* 291, 1304-1351 (2001).
16) M. Pendleton et al., Assembly and diploid architecture of an individual human genome via single-molecule technologies. *Nat. Methods.* 12, 780-786 (2015).
17) D. B. Jaffe et al., Whole-genome sequence assembly for mammalian genomes: Arachne 2. *Genome Res.* 13, 91-96 (2003).
18) V. Nene et al., Genome sequence of *Aedes aegypti*, a major arbovirus vector. *Science.* 316, 1718-1723 (2007).
19) P. Juneja et al., Assembly of the genome of the disease vector *Aedes aegypti* onto a genetic linkage map allows mapping of genes affecting disease transmission. *PLoS Negl. Trop. Dis.* 8, e2652 (2014).
20) P. Arensburger et al., Sequencing of *Culex quinquefasciatus* establishes a platform for mosquito comparative genomics. *Science.* 330, 86-88 (2010).
21) P. V. Hickner, A. Mori, D. D. Chadee, D. W. Severson, Composite linkage map and enhanced genome map for *Culex pipiens* complex mosquitoes. *J. Hered.* 104, 649-655 (2013).
22) N. C. Durand et al., Juicer Provides a One-Click System for Analyzing Loop-Resolution Hi-C Experiments. *Cell Syst.* 3, 95-98 (2016).
23) N. C. Durand et al., Juicebox Provides a Visualization System for Hi-C Contact Maps with Unlimited Zoom. *Cell Syst.* 3, 99-101 (2016).
24) M. R. Hübner, D. L. Spector, Chromatin Dynamics. *Annu. Rev. Biophys.* 39, 471-489 (2010).
25) M. A. Ferguson-Smith, V. Trifonov, Mammalian karyotype evolution. *Nat. Rev. Genet.* 8, 950-962 (2007).
26) A. L. Sanborn et al., Chromatin extrusion explains key features of loop and domain formation in wild-type and engineered genomes. *Proc. Natl. Acad. Sci.* 112, E6456-E6465 (2015).
27) O. Tange, GNU Parallel: The Command-Line Power Tool. *Login USENIX Mag.* 36 (2011), pp. 42-47.
28) Robert S. Harris, thesis, The Pennsylvania State University (2007).
29) J. B. Kruskal, On the Shortest Spanning Subtree of a Graph and the Traveling Salesman Problem. *Proc. Am. Math. Soc.* 7, 48-50 (1956).
30) J. P. Vinson et al., Assembly of polymorphic genomes: algorithms and application to Ciona savignyi. *Genome Res.* 15, 1127-1135 (2005).
24) C.-S. Chin et al., Phased diploid genome assembly with single-molecule real-time sequencing. *Nat. Methods.* 13, 1050-1054 (2016).
25) E. M. Darrow et al., Deletion of DXZ4 on the human inactive X chromosome alters higher-order genome architecture. *Proc. Natl. Acad. Sci.* 113, E4504-E4512 (2016).
26) N. I. Weisenfeld et al., Comprehensive variation discovery in single human genomes. *Nat. Genet.* 46, 1350-1355 (2014).
27) H. Li, R. Durbin, Fast and accurate short read alignment with Burrows-Wheeler transform. *Bioinformatics.* 25, 1754-1760 (2009).
28) H. Cao et al., Rapid detection of structural variation in a human genome using nanochannel-based genome mapping technology. *GigaScience.* 3, 34 (2014).
29) V. A. Timoshevskiy et al., Genomic composition and evolution of *Aedes aegypti* chromosomes revealed by the analysis of physically mapped supercontigs. *BMC Biol.* 12, 27 (2014).
30) M. F. Unger, M. V. Sharakhova, A. J. Harshbarger, P. Glass, F. H. Collins, A standard cytogenetic map of *Culex quinquefasciatus* polytene chromosomes in application for fine-scale physical mapping. *Parasit. Vectors.* 8, 307 (2015).
31) A. N. Naumenko et al., Correction: Mitotic-Chromosome-Based Physical Mapping of the *Culex quinquefasciatus* Genome. *PLoS One.* 10, e0127565 (2015).
32) G. I. Giraldo-Calderón et al., VectorBase: an updated bioinformatics resource for invertebrate vectors and other organisms related with human diseases. *Nucleic Acids Res.* 43, D707-713 (2015).
33) A. Yates et al., Ensembl 2016. *Nucleic Acids Res.* 44, D710-D716 (2016).
34) N. Varoquaux et al., Accurate identification of centromere locations in yeast genomes using Hi-C. *Nucleic Acids Res.* 43, 5331-5339 (2015).

What is claimed is:

1. A method for assembly of one or more long DNA molecules comprising:
   a) performing a DNA proximity ligation assay conducted on one or more samples;
   b) generating a draft assembly of contigs and scaffolds from input sequencing reads obtained, at least in part, from the DNA proximity ligation assay conducted on one or more samples;
   c) assembling larger sequences corresponding to one or more DNA molecules in the one or more samples by iteratively overlapping, ordering, orienting, and merging the contigs and scaffolds in the draft assembly, wherein assembling larger sequences is determined, at least in part, by application of a greedy algorithm, an optimization algorithm, or a manual annotation algorithm;
   d) performing misjoin correction on the scaffolds, wherein the misjoin correction uses contact frequency between sequences in the scaffolds generated from a contact matrix to determine one or more misjoins;
   e) generating one or more megascaffolds from the corrected scaffolds, wherein generating one or more megascaffolds comprises using a density graph to construct hemi-scaffolds from the corrected scaffolds and transforming the density graph into a confidence graph, the confidence graph constructs one or more megascaffolds from the hemi-scaffolds; and
   f) generating a final assembly from the megascaffolds.

2. The method of claim 1, wherein assembling the input sequencing reads, which forms a set, is determined, at least in part, based on a frequency at which all or part of a given sequence forms contact with other sequences and a given sequencing read forms contact with other sequencing reads in the set.

3. The method of claim 2 is wherein a part of a given se.

4. The method of claim 1, wherein assembling the input sequence is determined, at least in part, based on a relative orientation with which a given sequence forms contacts with other input sequences.

5. The method of claim 4, wherein the orientation is inner, outer, left, or right.

6. The method of claim 1, wherein;
   the input sequencing reads are:
   contigs, scaffolds, or a combination thereof;
   generated using short-read sequencing technology, long-read sequencing technology, insert clones, linkage mapping data, physical mapping data, optical mapping data, or a combination thereof;
   from a single organism or multiple organisms; or
   from multiple organisms, and the multiple organisms are from a same or different species; or
   a combination thereof;
   the one or more DNA molecules are chromosomes, portions of chromosomes, plasmids, or other nucleotide sequences;
   consecutive sequences in the assembly are merged to increase contiguity of the assembly;
   the DNA proximity ligation assay is Hi-C; or
   a combination thereof.

7. The method of claim 1, wherein assembling the input sequences is performed, at least in part, based on analyzing the sequences of the contigs and scaffolds.

8. The method of claim 7, wherein flanking sequences of the sequences of the contigs and scaffolds are analyzed.

9. The method of claim 1, further comprising assembling a draft assembly prior to generating the final assembly.

10. The method of claim 9, further comprising identifying neighboring contigs in the draft assembly, wherein the neighboring contig is a contig and/or scaffold located within a given linear genomic distance according to the draft assembly.

11. The method of claim 1, further comprising identifying different sub-compartments with different distance scaling and long range contact pattern based on massively multiplex single cell DNA-DNA proximity ligation assay.

12. The method of claim 11, wherein:
   DNA-DNA proximity ligation data from different subsets is used for different assembly related tasks, optionally wherein the assembly related tasks comprise of misassembly detection or contig ordering;
   DNA-DNA proximity ligation data from different subsets is used to perform tasks at different scales, optionally wherein the scales comprise of kilobase or megabase; or
   a Hi-C ligation protocol is performed on synchronized populations of cells.

13. The method of claim 1, wherein a Hi-C ligation protocol is performed on one or more cells that have been treated to modify genome folding.

14. The method of claim 13, where the treatment to modify genome folding is gene editing.

15. The method of claim 14, where the gene editing method is CRISPR or TALEN.

16. The method of claim 1, to assemble transcriptomes, thus generating a draft assembly.

17. The method of claim 16, wherein the draft assembly spans sequences of genes associated with RNA transcripts found in a cell.

18. The method of claim 17, wherein the final assembly performs one or more following tasks:
   assigning genes to chromosomes;
   determining the order and orientation of the genes; and
   estimating distances between genes.

19. The method of claim 1, wherein the one or more DNA molecules do not correspond to genes.

20. The method of claim 1, where bisulfite treatment is applied to ligation products derived from a proximity ligation experiment.

21. The method of claim 20, wherein the final assembly is used to:
   analyze proximity between DNA loci in a sample;
   determine a frequency of methylation for one or more bases in a sample; or
   determine whether one or more loci tend to be methylated simultaneously.

22. The method of claim 1, wherein the DNA proximity ligation assay is used to generate a 3D contact map, the 3D contact map defines one or more contact domains.

23. The method of claim 22, wherein the 3D contact map defines:
   one or more loops;
   one or more compartments;
   one or more superloops;
   one or more compartment interactions;
   other 3D features;
   centromere and telomere regions; or
   a combination thereof.

24. A method for genome assembly comprising:
   a) performing a DNA proximity ligation assay;
   b) generating a draft assembly of contigs and scaffolds from input sequencing reads obtained, at least in part, the DNA proximity ligation assay conducted on one or more samples;

c) assembling larger sequences corresponding to one or more DNA molecules in the one or more samples by iteratively overlapping, ordering, orienting, and merging the contigs and scaffolds in the draft assembly, wherein a proper orientation of contigs and/or scaffolds is determined, at least in part, by 3D contact features, wherein the features in question are centromere-to-centromere interactions, telomere-to-telomere interactions and centromere-to-telomere interactions or a combination thereof;

d) performing misjoin correction on the scaffolds, wherein the misjoin correction uses contact frequency between sequences in the scaffolds generated from a contact matrix to determine one or more misjoin; and e) generating one or more megascaffolds from the corrected scaffolds, wherein generating one or more megascaffolds comprises using a density graph to construct hemi-scaffolds from the corrected scaffolds and transforming the density graph into a confidence graph, the confidence graph constructs one or more megascaffolds from the hemi-scaffolds, the contact features are determined, at least in part, by data from the DNA proximity ligation assay.

25. The method of claim 24, wherein:

contacts associated with the reads correspond to one or more pixels in a contact map; or a combination thereof.

* * * * *